(12) United States Patent
Raboisson et al.

(10) Patent No.: US 9,334,282 B2
(45) Date of Patent: May 10, 2016

(54) MACROCYCLIC INDOLES AS HEPATITIS C VIRUS INHIBITORS

(71) Applicant: Janssen R&D Ireland, Co Cork (IE)

(72) Inventors: Pierre Jean-Marie Bernard Raboisson, Rosieres (BE); Lili Hu, Mechelen (BE); Sandrine Marie Helene Vendeville, Woluwe-Saint-Pierre (BE); Origéne Nyanguile, Grimisuat (CH); Abdellah Tahri, Anderlecht (BE)

(73) Assignee: Janssen Sciences Ireland UC, Little Island, Co. Cork. (IE)

( * ) Notice: Subject to any disclaimer, the term of this patent is extended or adjusted under 35 U.S.C. 154(b) by 0 days.

(21) Appl. No.: 13/908,705

(22) Filed: Jun. 3, 2013

(65) Prior Publication Data

US 2013/0267511 A1 Oct. 10, 2013

Related U.S. Application Data

(62) Division of application No. 12/809,160, filed as application No. PCT/EP2008/068280 on Dec. 23, 2008, now Pat. No. 8,524,716.

(30) Foreign Application Priority Data

Dec. 24, 2007 (EP) ..................................... 07150415

(51) Int. Cl.
| A61K 31/407 | (2006.01) |
| C07D 487/06 | (2006.01) |
| C07D 487/08 | (2006.01) |
| C07D 513/08 | (2006.01) |
| C07D 513/06 | (2006.01) |

(52) U.S. Cl.
CPC ............ *C07D 487/06* (2013.01); *C07D 487/08* (2013.01); *C07D 513/06* (2013.01); *C07D 513/08* (2013.01)

(58) Field of Classification Search
CPC ............................. A61K 31/407; C07D 487/06
USPC .................. 540/450, 451, 454; 548/469, 491; 514/183, 185, 411
See application file for complete search history.

(56) References Cited

U.S. PATENT DOCUMENTS

| 5,807,876 | A | 9/1998 | Armistead et al. |
| 6,054,472 | A | 4/2000 | Armistead et al. |
| 6,344,465 | B1 | 2/2002 | Armistead et al. |
| 6,498,178 | B2 | 12/2002 | Stamos et al. |
| 6,828,327 | B2 | 12/2004 | Kuo et al. |
| 8,357,687 | B2 * | 1/2013 | Mc Gowan et al. .......... 514/250 |
| 8,524,716 | B2 * | 9/2013 | Raboisson et al. ....... 514/254.01 |
| 8,921,355 | B2 | 12/2014 | Vendeville et al. |
| 2007/0184024 | A1 | 8/2007 | Meanwell et al. |
| 2007/0270405 | A1 | 11/2007 | Bender et al. |
| 2007/0270406 | A1 | 11/2007 | Gentles et al. |
| 2008/0146537 | A1 | 6/2008 | Bender et al. |
| 2014/0107101 | A1 | 4/2014 | Vendeville et al. |

FOREIGN PATENT DOCUMENTS

| WO | 9740028 A1 | 10/1997 |
| WO | 9840381 A1 | 9/1998 |
| WO | 0056331 A1 | 9/2000 |
| WO | 0219369 A2 | 3/2002 |
| WO | 03/010140 A2 | 2/2003 |
| WO | 2004065367 A1 | 8/2004 |
| WO | 2004087714 A1 | 10/2004 |
| WO | 2005095403 A2 | 10/2005 |
| WO | 2006/020082 A1 | 2/2006 |
| WO | 2006/029912 A2 | 3/2006 |
| WO | 2006029912 A1 | 3/2006 |
| WO | 2006076529 A1 | 7/2006 |

(Continued)

OTHER PUBLICATIONS

Chazalette, et al., Carbonic Anydrase Inhibitors: Allysulfonamide, Styrene Sulfonamide, N-ally Sulfonamides and Some of Their Si, Ge and B Derivatives, Journal of Enzyme Derivatives, 2001, pp. 475-489, vol. 16, No. 6.

Consensus Development Panel, National Institutes of Health Consensus Development Conference Statement: Management of Hepatitis C: 2002, Hepatology, Jun. 2002, S3-S20, vol. 36, No. 5.

Greene, et al., Protective Groups in Organic Synthesis, 1981.

Huang, et al., Olefin Metathesis-Active Ruthenium Complexes Bearing a Nucleophilic Carbene Ligand, The Journal of the American Chemical Society, 1999, p. 2674-2678, vol. 121.

Kim et al, The Burden of Hepatitis C in the United States, Hepatology, 2002, S30-S34, vol. 36, No. 5, s1.

Kingsbury et al, A Recyclable Ru-Based Metathesis Catalyst, The Journal of the American Chemical Society, 1999, p. 791-799, vol. 121.

Krchnak et al, Polymer-Supported Mitsunobu Ether Formation and its Use in Combinatorial Chemistry, Tetrahedron Letters, 1995, p. 6193-6196, vol. 36, No. 35.

(Continued)

*Primary Examiner* — Golam M M Shameem
(74) *Attorney, Agent, or Firm* — Andrea Jo Kamage

(57) ABSTRACT

The present invention relates to inhibitors of HCV replication of formula (I), the N-oxide forms, the pharmaceutically acceptable addition salts, the quaternary amines and the stereochemically isomeric forms thereof,

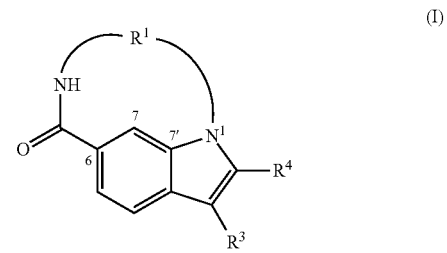

(I)

wherein $R^1$; $R^3$; and $R^4$ have the meaning defined in the claims.

The present invention also relates to processes for preparing said compounds, pharmaceutical compositions containing them and their use in HCV therapy.

9 Claims, No Drawings

(56) References Cited

FOREIGN PATENT DOCUMENTS

| WO | 2007001406 A2 | 1/2007 |
|---|---|---|
| WO | 2007/026024 A2 | 3/2007 |
| WO | 2007/033032 A1 | 3/2007 |
| WO | 2007026024 A2 | 3/2007 |
| WO | 2007/054741 A1 | 5/2007 |
| WO | 2009/010785 A1 | 7/2007 |
| WO | 2007/092000 A1 | 8/2007 |
| WO | 2007/140200 A2 | 12/2007 |
| WO | 2008/075103 A1 | 6/2008 |
| WO | 2008/112473 A1 | 9/2008 |
| WO | 2009/010783 A1 | 1/2009 |
| WO | 2010/003658 A1 | 1/2010 |

OTHER PUBLICATIONS

Krieger, et al, Enhancement of Hepatitis C Virus RNA Replication by Cell Culture, Journal of Virology, May 1, 2001, 4614-1624, 75-10, DE.

Lohmann, et al., Replication of Subgenomic Hepatitis C Virus RNAs in a Hepatoma Cell Line, Science, 1999, pp. 110-113, vol. 285.

Miller et al, Application of Ring-Closing Metathesis to the Synthesis of Rigidified Amino Acids and Peptides, The Journal of the American Chemical Society, 1996, p. 9606-9614, vol. 118.

Mitsunobu, et al., The Use of Diethyl Azodicarboxylate and Triphenylphosphine in Synthesis and Transformation of Natural Products, Synthesis, 1981, pp. 1-28, 0039-7881/81/0132-0001.

Rano, et al., Solid Phase Synthesis of Aryl Ethers Via The Mitsunobu Reaction, Tetrahedron Letters, 1995, p. 3789-3792, vol. 36, No. 22.

Richter, et al., A surprising Observation about Mitsunobu Reactions in Solid Phase Synthesis, Tetrahedron Letters, 1994, p. 4705-4706, vol. 35, No. 27.

Stansfield, et al., Development of Carboxylic Acid Replacements in Indole-N-Acetamide Inhibitors of Hepatitis C Virus NS5B Polymerase, Bioorganic & Medicinal Chemistry Letters, 2007, pp. 5143-5149, vol. 17.

Kazutaka et al., "Discovery of Confirmationally Constrained Tetracyclic Compounds as Potent Hepatitis C Virus NS5B RNA Polymerase Inhibitors", Journal of Med. Chemistry, vol. 49, pp. 6950-6953, 2006.

Dierynck et al., Binding Kinetics of Darunavir to Human Immunodeficiency Virus Type 1 Protease Explain the Potent Antiviral Activity and High Genetic Barrier, Journal of Virology, Dec. 15, 2007, pp. 13845-13851, vol. 81, No. 24.

Pauwels et al., "Binding-Site Identification and Genotypic Profiling of Hepatitis C Virus Polymerase Inhibitors", Journal of Virology, 2007, pp. 6909-6919, vol. 81, No. 13.

Harper et al., "Development and Preliminary Optimization of Indole-N-Acetamide Inhibitors of Hepatitis C Virus NS5B Polymerase", Journal of Medicinal Chemistry, vol. 48, No. 5, pp. 1314-1317, 2005.

Koutsoudakis et al., "The Level of CD81 Cell Surface Expression is a Key Determinant for Productive Entry of Hepatitis C Virus into Host Cells", Journal of Virology, vol. 81, No. 2, pp. 588-598, Jan. 2007.

* cited by examiner

MACROCYCLIC INDOLES AS HEPATITIS C VIRUS INHIBITORS

This application is a divisional application of U.S. application Ser. No. 12/809,160, filed Jun. 18, 2010, which is a national stage application of PCT/EP2008/068280, filed Dec. 23, 2008, which claims priority benefit of Application No. EP07150415.3 filed Dec. 24, 2007. The complete disclosures of the aforementioned related patent applications are hereby incorporated herein by reference for all purposes.

FIELD OF THE INVENTION

The present invention is concerned with macrocyclic indoles having inhibitory activity on the replication of the hepatitis C virus (HCV). It further concerns compositions comprising these compounds as active ingredients as well as processes for preparing these compounds and compositions.

BACKGROUND OF THE INVENTION

Hepatitis C virus is the leading cause of chronic liver disease worldwide and has become a focus of considerable medical research. HCV is a member of the Flaviviridae family of viruses in the hepacivirus genus, and is closely related to the *flavivirus* genus, which includes a number of viruses implicated in human disease, such as dengue virus and yellow fever virus, and to the animal pestivirus family, which includes bovine viral diarrhoea virus (BVDV). HCV is a positive-sense, single-stranded RNA virus, with a genome of around 9,600 bases. The genome comprises both 5' and 3' untranslated regions which adopt RNA secondary structures, and a central open reading frame that encodes a single polyprotein of around 3,010-3,030 amino acids. The polyprotein encodes ten gene products which are generated from the precursor polyprotein by an orchestrated series of co- and posttranslational endoproteolytic cleavages mediated by both host and viral proteases. The viral structural proteins include the core nucleocapsid protein, and two envelope glycoproteins E1 and E2. The non-structural (NS) proteins encode some essential viral enzymatic functions (helicase, polymerase, protease), as well as proteins of unknown function. Replication of the viral genome is mediated by an RNA-dependent RNA polymerase, encoded by non-structural protein 5b (NS5B). In addition to the polymerase, the viral helicase and protease functions, both encoded in the bifunctional NS3 protein, have been shown to be essential for replication of HCV RNA. HCV also encodes a metalloproteinase in the NS2 region.

HCV replicates preferentially in hepatocytes but is not directly cytopathic, leading to persistent infection. In particular, the lack of a vigorous T-lymphocyte response and the high propensity of the virus to mutate appear to promote a high rate of chronic infection. There are 6 major HCV genotypes and more than 50 subtypes, which are differently distributed geographically. HCV type 1 is the predominant genotype in the US and Europe. For instance, HCV type 1 accounts for 70 to 75 percent of all HCV infections in the United States. The extensive genetic heterogeneity of HCV has important diagnostic and clinical implications, perhaps explaining difficulties in vaccine development and the lack of response to therapy. An estimated 170 million persons worldwide are infected with hepatitis C virus (HCV). Following the initial acute infection, a majority of infected individuals develop chronic hepatitis, which can progress to liver fibrosis leading to cirrhosis, end-stage liver disease, and HCC (hepatocellular carcinoma) (National Institutes of Health Consensus Development Conference Statement: Management of Hepatitis C. *Hepatology*, 36, 5 Suppl. S3-S20, 2002). Liver cirrhosis due to HCV infection is responsible for about 10,000 deaths per year in the U.S.A. alone, and is the leading cause for liver transplantations. Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades (Kim, W. R. *Hepatology*, 36, 5 Suppl. S30-S34, 2002).

Current HCV therapies are based on (pegylated) interferon-alpha (IFN-α) in combination with ribavirin. This combination therapy yields a sustained virologic response in more than 40% of patients infected by genotype 1 viruses and about 80% of those infected by genotypes 2 and 3. Beside the limited efficacy on HCV type 1, combination therapy has significant side effects and is poorly tolerated in many patients. For instance, in registration trials of pegylated interferon and ribavirin, significant side effects resulted in discontinuation of treatment in approximately 10 to 14 percent of patients. Major side effects of combination therapy include influenza-like symptoms, hematologic abnormalities, and neuropsychiatric symptoms. The development of more effective, convenient and tolerated treatments is a major public health objective. Thus, the treatment of this chronic disease is an unmet clinical need, since current therapy is only partially effective and limited by undesirable side effects.

One area of particular focus has been the search for inhibitors of the NS5b RNA-dependent RNA polymerase. Close structural homologs of this polymerase do not exist within the uninfected host cell and the finding of inhibitors of said polymerase would provide a more specific mode of action Inhibitors which are currently under investigation can be classified as either nucleoside inhibitors (NIs) or non-nucleoside inhibitors (NNIs). NIs directly compete with nucleotide substrates for binding to highly conserved active sites. Greater specificity may be achieved by NNIs, which interact outside of the highly conserved active site at a unique allosteric site common only to structurally related polymerases. Preliminary clinical trials have resulted in a high failure rate, thereby highlighting the need to pursue the search for novel NS5b inhibitors.

SUMMARY OF THE INVENTION

It has been found that certain macrocyclic indole derivatives exhibit antiviral activity in mammals infected with HCV. These compounds are therefore useful in treating or combating HCV infections.

The present invention concerns inhibitors of HCV replication, which can be represented by formula (I):

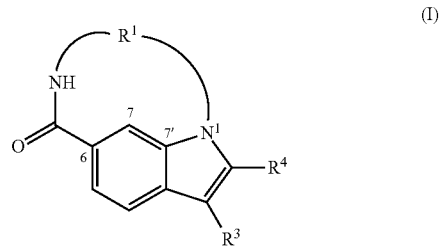

and the stereoisomers, tautomers, racemics, salts, hydrates or solvates thereof, wherein $R^1$ is a bivalent chain selected from

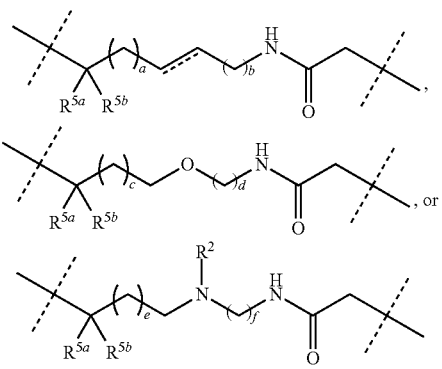

wherein the carbon atom carrying the $R^{5a}$ and $R^{5b}$ substituents is attached to the remainder of the molecule via the nitrogen atom of the amide group, and the carbon atom of the acetamide moiety is attached to the remainder of the molecule via the nitrogen of the indole ring of the compound of formula (I); or
$R^1$ is a bivalent chain selected from

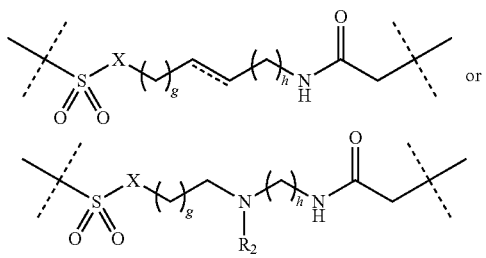

wherein the sulfonyl group is attached to the remainder of the molecule via the nitrogen atom of the amide group, and the carbon atom of the acetamide moiety is attached to the remainder of the molecule via the nitrogen of the indole ring of the compound of formula (I);
X is selected from $-CR^{5a}R^{5b}-$ or $-NR^{5a}-$;
each of a, b, c, d, e, f, g, and h, is, independently, an integer selected from 0, 1, 2, 3, 4, or 5, with the proviso that the macrocycle formed by the bivalent chain $R^1$, the $-C(=O)-NH-$ moiety to which $R^1$ is attached and the nitrogen and carbon atoms N1, C6, C7, and C7' of the indole ring, has from 14 to 17 member atoms;
each parallel dashed line (represented by =====) represents an optional double bond;
$R^2$ is hydrogen or $C_{1-6}$alkyl;
$R^3$ is $C_{3-7}$cycloalkyl;
$R^4$ is a group selected from:

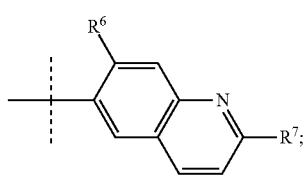

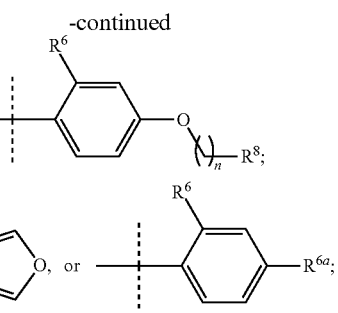

$R^{5a}$ and $R^{5b}$ are each independently selected from hydrogen; $C_{1-6}$alkyl; or halo$C_{1-6}$alkyl;
n is 0, 1, or 2;
$R^6$ is selected from hydrogen, halo, $C_{1-6}$alkyl, or $C_{3-7}$cycloalkyl;
$R^{6a}$ is selected from hydrogen, halo, $C_{1-6}$alkyl, or $C_{3-7}$cycloalkyl;
$R^7$ is phenyl or thiazolyl, wherein each phenyl is optionally substituted with one, two, or three substituents, wherein each thiazolyl is optionally substituted with one or two substituents; wherein the substituents on both phenyl and thiazolyl are each independently selected from halo; cyano; nitro; $C_{1-6}$alkyl; $-OR^{12}$; $-C(=O)OR^{12}$; $-C(=O)R^{13}$; $-C(=O)NR^{9a}R^{9b}$; $-NR^{9a}R^{9b}$; $-NR^{9a}C(=O)R^{13}$; $-NR^{9a}C(=O)-CH_2-NR^{9a}R^{9b}$; $-SR^{10}$; $-SO_2R^{11}$; $-SO_2NR^{9a}R^{9b}$; phenyl optionally substituted with one, two or three substituents each independently selected from halo, trifluoromethyl, cyano, $C_{1-6}$alkyl, $C_{1-6}$alkoxy, and $-C(=O)NR^{9a}R^{9b}$; and Het optionally substituted with one or two substituents each independently selected from oxo, $C_{1-6}$alkylsulfonyl, and $C_{1-6}$alkyl;
$R^8$ is hydrogen, phenyl, or thiazolyl, wherein each phenyl is optionally substituted with one, two, or three substituents, wherein each thiazolyl is optionally substituted with one or two substituents; wherein the substituents on both phenyl and thiazolyl are each independently selected from halo; cyano; nitro; $C_{1-6}$alkyl; $-OR^{12}$; $-C(=O)OR^{12}$; $-C(=O)R^{13}$; $-C(=O)NR^{9a}R^{9b}$; $-NR^{9a}R^{9b}$; $-NR^{9a}C(=O)R^{13}$; $-NR^{9a}C(=O)-CH_2-NR^{9a}R^{9b}$; $-SR^{10}$; $-SO_2R^{11}$; $-SO_2NR^{9a}R^{9b}$; phenyl optionally substituted with one, two or three substituents each independently selected from halo, trifluoromethyl, cyano, $C_{1-6}$alkyl, $C_{1-6}$alkoxy, and $-C(=O)NR^{9a}R^{9b}$; and Het optionally substituted with one or two substituents each independently selected from oxo, $C_{1-6}$alkylsulfonyl, and $C_{1-6}$alkyl;
$R^{9a}$ and $R^{9b}$ are each independently selected from hydrogen, $C_{1-6}$alkyl, or aryl$C_{1-6}$alkyl; or $R^{9a}$ and $R^{9b}$, together with the nitrogen to which they are attached, form a saturated, partially unsaturated, or completely unsaturated 5-8 membered monocycle, wherein said monocycle optionally contains one additional heteroatom selected from the group consisting of oxygen, sulfur and nitrogen, and wherein the remaining monocycle members are carbon atoms; wherein said monocycle is optionally substituted on any carbon atom with one or two substituents each independently selected from halo, $C_{1-6}$alkyl, hydroxy, or oxo, wherein aryl is phenyl or naphthyl;
$R^{10}$ is $C_{1-6}$alkyl or $C_{3-7}$cycloalkyl;
$R^{11}$ is $C_{1-6}$alkyl or $C_{3-7}$cycloalkyl;
$R^{12}$ is hydrogen, $C_{1-6}$alkyl, or benzyl;
$R^{13}$ is $C_{1-6}$alkyl;

Het is pyrrolidinyl, piperidinyl, morpholinyl, or piperazinyl.

In one embodiment, the invention concerns as subgroup of the compounds of formula (I), said subgroup hereinafter designated as compounds of formula (I'), wherein the compounds of formula (I') are those compounds of formula (I) and the stereoisomers, tautomers, racemics, salts, hydrates or solvates thereof, wherein
$R^1$ is a bivalent chain selected from

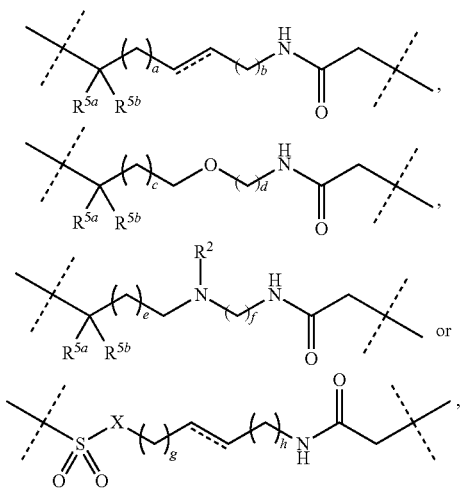

wherein the carbon atom carrying the $R^{5a}$ and $R^{5b}$ substituents (the left side of the depicted $R^1$ chains) is attached to the remainder of the molecule via the nitrogen atom of the amide group, and the carbon atom of the acetamide moiety (the right side of the depicted $R^1$ chains) is attached to the remainder of the molecule via the nitrogen of the indole ring of the compound of formula (I);
each parallel dashed line (represented by ----- ) represents an optional double bond;
$R^4$ is a group selected from:

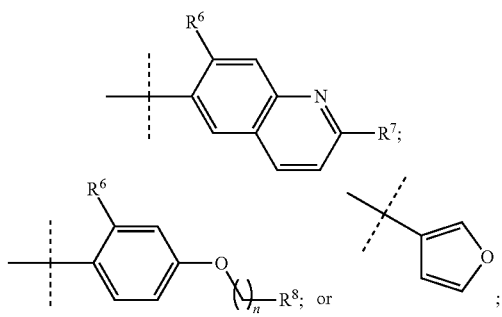

X, a, b, c, d, e, f, g, h, $R^2$, $R^3$, $R^{5a}$, $R^{5b}$, n, $R^6$, $R^7$, $R^8$, $R^{9a}$, $R^{9b}$, $R^{10}$, $R^{11}$, $R^{12}$, $R^{13}$ and Het have the same meanings as defined above.

The invention further relates to methods for the preparation of the compounds of formula (I) or any subgroup thereof, the N-oxides, quaternary amines, metal complexes, and stereochemically isomeric forms thereof, their intermediates, and the use of the intermediates in the preparation of the compounds of formula (I).

The invention relates to the compounds of formula (I) per se or any subgroup thereof, the N-oxides, salts, quaternary amines, metal complexes, and stereochemically isomeric forms thereof, for use as a medicament. The invention relates to the compounds of formula (I) per se or any subgroup thereof, the N-oxides, salts, quaternary amines, metal complexes, and stereochemically isomeric forms thereof, for treating hepatitis C. The invention further relates to pharmaceutical compositions comprising a carrier and an anti-virally effective amount of a compound of formula (I) or any subgroup thereof as specified herein. The pharmaceutical compositions may comprise combinations of the aforementioned compounds with other anti-HCV agents. The pharmaceutical compositions may comprise combinations of the aforementioned compounds with anti-HIV agents. The invention further relates to the aforementioned pharmaceutical compositions for administration to a subject suffering from HCV infection.

The invention also relates to the use of a compound of formula (I) or any subgroup thereof, or an N-oxide, salt, quaternary amine, metal complex, or stereochemically isomeric forms thereof, for the manufacture of a medicament for inhibiting HCV replication. Or the invention relates to a method of inhibiting HCV replication in a warm-blooded animal said method comprising the administration of an effective amount of a compound of formula (I) or any subgroup thereof, or an N-oxide, salt, quaternary amine, metal complex, or stereochemically isomeric forms thereof.

DETAILED DESCRIPTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

In a particular embodiment, the present invention provides a compound of formula (I) or (I') having one of the structural Formula (II), (III), or (IV), or a stereoisomer, tautomer, racemic, metabolite, salt, hydrate, or solvate thereof,

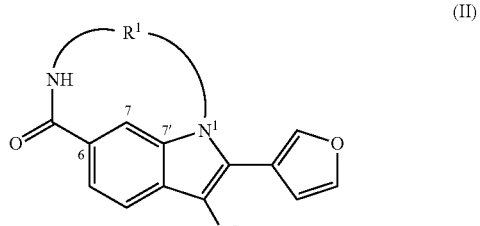

(II)

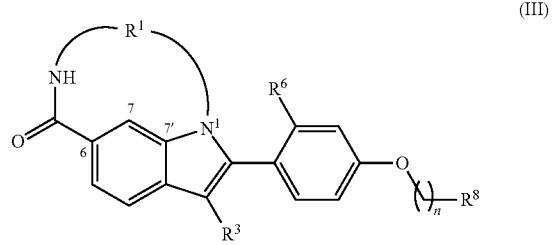

(III)

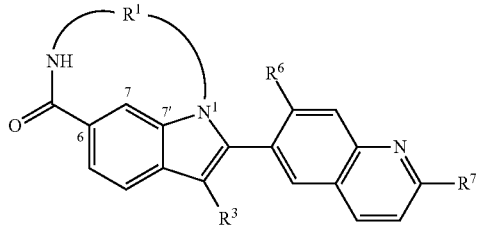

(IV)

wherein $R^1$, $R^3$, $R^6$, $R^7$, $R^8$ and n have the same meaning as that defined above.

Another particular embodiment of the present invention relates to a compound of formula (I) having the structural Formula (V), or a stereoisomer, tautomer, racemic, metabolite, salt, hydrate, or solvate thereof,

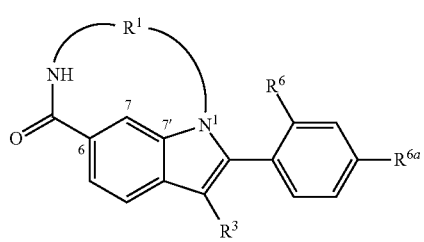

(V)

wherein $R^1$, $R^3$, $R^6$ and $R^{6a}$ have the same meaning as that defined above.

When describing the compounds of the invention, the terms used are to be construed in accordance with the following definitions, unless the context dictates otherwise.

Whenever the term "substituted" is used in the present invention, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

The term halo is generic to fluoro, chloro, bromo and iodo.

As used herein "$C_{1-4}$alkyl" as a group or part of a group defines straight or branched chain saturated hydrocarbon radicals having from 1 to 4 carbon atoms such as for example methyl, ethyl, prop-1-yl, prop-2-yl, but-1-yl, but-2-yl, isobutyl, 2-methyl-prop-1-yl; "$C_{1-6}$alkyl" encompasses $C_{1-4}$alkyl radicals and the higher homologues thereof having 5 or 6 carbon atoms such as, for example, pent-1-yl, pent-2-yl, pent-3-yl, hex-1-yl, hex-2-yl, 2-methyl-but-1-yl, 2-methyl-pent-1-yl, 2-ethyl-but-1-yl, 3-methyl-pent-2-yl, and the like. Of interest amongst $C_{1-6}$alkyl is $C_{1-4}$alkyl.

The term "halo$C_{1-6}$alkyl" alone or in combination, refers to a $C_{1-6}$alkyl radical having the meaning as defined above wherein one or more hydrogens are replaced with a halogen as defined above. Non-limiting examples of such halo$C_{1-6}$ alkyl radicals include chloromethyl, 1-bromoethyl, fluoromethyl, difluoromethyl, trifluoromethyl, and 1,1,1-trifluoroethyl.

The term "$C_{3-7}$cycloalkyl as used herein is a cyclic alkyl group, that is to say, a monovalent, saturated, or unsaturated hydrocarbyl group. $C_{3-7}$cycloalkyl groups may comprise 3 or more carbon atoms in the ring and generally, according to this invention comprise from 3 to 7, more preferably from 3 to 6 carbons. Examples of $C_{3-7}$cycloalkyl groups include cyclopropyl, cyclobutyl, cyclopentyl, cyclohexyl and cycloheptyl.

The term "$C_{1-6}$alkoxy" or "$C_{1-6}$alkyloxy" as used herein refers to a radical having the Formula —$OR^a$ wherein $R^a$ is $C_{1-6}$alkyl as defined above. Non-limiting examples of suitable $C_{1-6}$alkoxy include methoxy, ethoxy, propoxy, isopropoxy, butoxy, isobutoxy, sec-butoxy, tert-butoxy, pentyloxy and hexyloxy. Suitable $C_{1-4}$alkoxy include methoxy, ethoxy, propoxy, isopropoxy, butoxy, isobutoxy, sec-butoxy, and tert-butoxy.

The term "aryl" as a group or part of a group is meant to include phenyl, naphth-1-yl, or naphth-2-yl.

As used herein before, the term (═O) or oxo forms a carbonyl moiety when attached to a carbon atom, a sulfoxide moiety when attached to a sulfur atom and a sulfonyl moiety when two of said terms are attached to a sulfur atom. Whenever a ring or ring system is substituted with an oxo group, the carbon atom to which the oxo is linked is a saturated carbon.

The term "$C_{1-6}$alkylsulfonyl" alone or in combination refers to a group of Formula —$SO_2$—$R^b$ wherein $R^b$ is $C_{1-6}$alkyl as defined herein. Non-limiting examples of $C_{1-6}$alkylsulfonyl groups include methylsulfonyl, ethylsulfonyl, butylsulfonyl, n-propylsulfonyl, n-pentylsulfonyl, and hexylsulfonyl.

It should be noted that the radical positions on any molecular moiety used in the definitions may be anywhere on such moiety as long as it is chemically stable.

Radicals used in the definitions of the variables include all possible isomers unless otherwise indicated. For instance, piperidinyl includes piperidin-1-yl, piperidin-2-yl, piperidin-3-yl, and piperidin-4-yl; pentyl includes pent-1-yl, pent-2-yl and pent-3-yl.

When any variable occurs more than one time in any constituent, each definition is independent.

As used in the specification and the appended claims, the singular forms "a", "an," and "the" include plural referents unless the context clearly dictates otherwise. By way of example, "a compound" means one compound or more than one compound.

Whenever used hereinafter, the term "compounds of formula (I)", "the present compounds" or "the compounds of formula (I) or any subgroup thereof" or similar terms, it is meant to include the compounds of formula (I) and any subgroup thereof, their N-oxides, salts, quaternary amines, metal complexes, solvates, hydrates, and stereochemically isomeric forms. One embodiment comprises the compounds of formula (I) or any subgroup of compounds of formula (I) specified herein, as well as the N-oxides, salts, as the possible stereoisomeric forms thereof. Another embodiment comprises the compounds of formula (I) or any subgroup of compounds of formula (I) specified herein, as well as the salts as the possible stereoisomeric forms thereof.

The compounds of formula (I) and any subgroup thereof may have several centers of chirality and may exist as stereochemically isomeric forms. The term "stereochemically isomeric forms" as used herein defines all the possible compounds made up of the same atoms bonded by the same sequence of bonds but having different three-dimensional structures, which the compounds of formula (I) may possess.

With reference to the instances where (R) or (S) is used to designate the absolute configuration of a chiral atom within a substituent, the designation is done taking into consideration the whole compound and not the substituent in isolation.

Unless otherwise mentioned or indicated, the chemical designation of a compound encompasses the mixture of all possible stereochemically isomeric forms, which said compound may possess. Said mixture may contain all diastereomers and/or enantiomers of the basic molecular structure of said compound. All stereochemically isomeric forms of the compounds of the present invention both in pure form or mixed with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of the compounds of formula (I) can be obtained separately by conventional methods. Appropriate physical separation methods that may advantageously be employed are, for example, selective crystallization and chromatography, e.g. column chromatography.

For some of the compounds of formula (I), their N-oxides, salts, quaternary amines, or metal complexes, and the intermediates used in the preparation thereof, the absolute stereochemical configuration was not experimentally determined. A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

For therapeutic use, salts of the compounds of formula (I) are those wherein the counter-ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely, said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several nitrogen atoms are oxidized to the so-called N-oxide.

It will be appreciated that the compounds of formula (I) may have metal binding, chelating, complex forming properties and therefore may exist as metal complexes or metal chelates. Such metalated derivatives of the compounds of formula (I) are intended to be included within the scope of the present invention.

Some of the compounds of formula (I) or any subgroup thereof may also exist in their tautomeric form. Such forms although not explicitly indicated in the above formula are intended to be included within the scope of the present invention.

An embodiment of the present invention concerns compounds of formula (I), (II), (III), (IV) or of any subgroup thereof, wherein one or more of the following restrictions apply:

(a) $R^1$ is the bivalent chain selected from the group consisting of

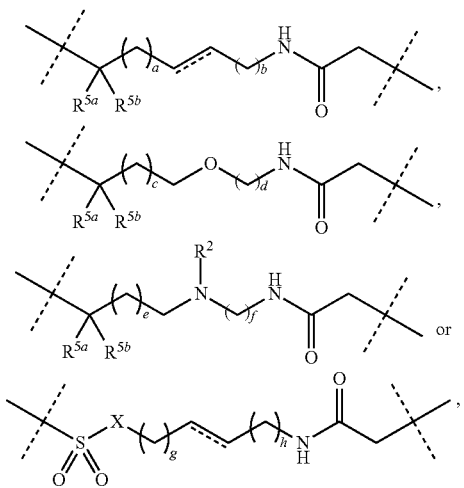

wherein the carbon atom carrying the $R^{5a}$ and $R^{5b}$ substituents is attached to the remainder of the molecule via the nitrogen atom of the amide group, and the carbon atom of the acetamide moiety is attached to the remainder of the molecule via the nitrogen atom of the indole ring of the compound of formula (I);

(b) each of a, b, c, d, e, f, g, and h is, independently, 0, 1, 2, or 3, with the proviso that the macrocycle formed by the bivalent chain $R^1$, the —C(=O)—NH— moiety to which $R^1$ is attached and the nitrogen and carbon atoms N1, C6, C7, and C7' of the indole ring, has from 14 to 17 member atoms;

(c) each parallel dashed line (represented by ≡≡≡) represents an optional double bond;

(d) $R^2$ is hydrogen or $C_{1-4}$alkyl;

(e) $R^3$ is cyclopropyl, cyclobutyl, cyclopentyl or cyclohexyl;

(f) X is selected from —$CR^{5a}R^{5b}$— or —$NR^{5a}$—;

(g) $R^{5a}$ and $R^{5b}$ are each independently selected from hydrogen; $C_{1-4}$alkyl; halo$C_{1-4}$alkyl;

(h) $R^6$ is hydrogen, $C_{1-6}$alkyl, or fluoro;

(i) n is 1, or 2;

(j) $R^7$ is phenyl or thiazolyl, wherein each phenyl is optionally substituted with one, two, or three substituents, wherein each thiazolyl is optionally substituted with one or two substituents; wherein the substituents on both phenyl and thiazolyl are each independently selected from halo; cyano; nitro; $C_{1-6}$alkyl; —$OR^{12}$; —C(=O)$OR^{12}$; —C(=O)$R^{13}$; —C(=O)$NR^{9a}R^{9b}$; —$NR^{9a}R^{9b}$; —$NR^{9a}C$(=O)$R^{13}$; —$NR^{9a}C$(=O)—$CH_2$—$NR^{9a}R^{9b}$; —$SR^{10}$; —$SO_2R^{11}$; —$SO_2NR^{9a}R^{9b}$; phenyl optionally substituted with one, two or three substituents each independently selected from halo, trifluoromethyl, cyano, $C_{1-6}$alkyl, $C_{1-6}$alkoxy, and —C(=O)$NR^{9a}R^{9b}$; and Het optionally substituted with one or two substituents each independently selected from oxo, $C_{1-6}$alkylsulfonyl, and $C_{1-6}$alkyl;

(k) $R^8$ is hydrogen, or phenyl, wherein said phenyl is optionally substituted with one, two, or three substituents each independently selected from halo; cyano; nitro; $C_{1-6}$alkyl; —$OR^{12}$; —C(=O)$OR^{12}$; —C(=O)$R^{13}$; —C(=O)$NR^{9a}R^{9b}$; —$NR^{9a}R^{9b}$; —$NR^{9a}C$(=O)$R^{13}$; —$NR^{9a}C$(=O)—$CH_2$—$NR^{9a}R^{9b}$; —$SR^{10}$; —$SO_2R^{11}$; —$SO_2NR^{9a}R^{9b}$; phenyl optionally substituted with one, two or three substituents each independently selected from halo, trifluoromethyl, cyano, $C_{1-6}$alkyl, $C_{1-6}$alkoxy, and —C(=O)$NR^{9a}R^{9b}$; and Het optionally substituted with one or two substituents each independently selected from oxo, $C_{1-6}$alkylsulfonyl, and $C_{1-6}$alkyl;

(l) $R^{9a}$ and $R^{9b}$ are each independently selected from hydrogen, $C_{1-6}$alkyl, or aryl$C_{1-6}$alkyl; or $R^{9a}$ and $R^{9b}$, together with the nitrogen to which they are attached, form a saturated, partially unsaturated, or completely unsaturated 5-8 membered monocycle, wherein said monocycle optionally contains one additional heteroatom selected from the group consisting of oxygen, sulfur and nitrogen, and wherein the remaining monocycle members are carbon atoms; wherein said monocycle is optionally substituted on any carbon atom with one or two substituents each independently selected from halo, $C_{1-6}$alkyl, hydroxy, or oxo;

(m) $R^{10}$ is $C_{1-6}$alkyl or $C_{3-7}$cycloalkyl;

(n) $R^{11}$ is $C_{1-6}$alkyl or $C_{3-7}$cycloalkyl;

(o) $R^{12}$ is hydrogen or $C_{1-6}$alkyl;

(p) $R^{13}$ is $C_{1-6}$alkyl;

(q) Het is pyrrolidinyl, piperidinyl, morpholinyl, or piperazinyl.

One embodiment of the present invention concerns compounds of formula (I), (II), (III), (IV) or of any subgroup thereof, wherein one or more of the following restrictions apply:

(a) $R^1$ is the bivalent chain selected from the group consisting of

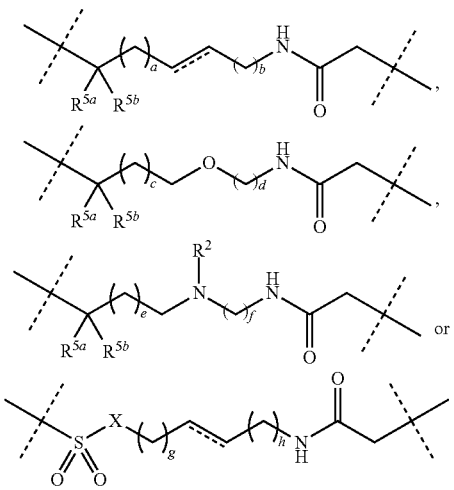

wherein the carbon atom carrying the $R^{5a}$ and $R^{5b}$ substituents is attached to the remainder of the molecule via the nitrogen atom of the amide group, and the carbon atom of the acetamide moiety is attached to the remainder of the molecule via the nitrogen atom of the indole ring of the compound of formula (I);

(b) each of a, b, c, d, e, f, g, and h is, independently, 0 1, 2, or 3, with the proviso that the macrocycle formed by the bivalent chain $R^1$, the —C(=O)—NH— moiety to which $R^1$ is attached and the nitrogen and carbon atoms N1, C6, C7, and C7' of the indole ring, has from 14 to 16 member atoms;

(c) each parallel dashed line (represented by ≡≡≡) represents an optional double bond;

(d) $R^2$ is hydrogen or $C_{1-4}$alkyl;

(e) $R^3$ is cyclopentyl or cyclohexyl;

(f) X is selected from —$CR^{5a}R^{5b}$— or —$NR^{5a}$—;

(g) $R^{5a}$ and $R^{5b}$ are each independently selected from hydrogen; $C_{1-3}$alkyl; halo$C_{1-3}$alkyl;

(h) $R^6$ is hydrogen, $C_{1-6}$alkyl, or fluoro;

(i) n is 1, or 2;

(j) $R^7$ is phenyl or thiazolyl, wherein said phenyl and thiazolyl are each independently optionally substituted with one, two or three substituents each independently selected from halo; cyano; nitro; $C_{1-6}$alkyl; —$OR^{12}$; —$C(=O)OR^{12}$; —$C(=O)R^{13}$; —$C(=O)NR^{9a}R^{9b}$; —$NR^{9a}R^{9b}$; —$NR^{9a}C(=O)R^{13}$; —$NR^{9a}C(=O)$—$CH_2$—$NR^{9a}R^{9b}$; —$SR^{10}$; —$SO_2R^{11}$; —$SO_2NR^{9a}R^{9b}$; phenyl optionally substituted with one or two substituents each independently selected from halo, trifluoromethyl, cyano, $C_{1-6}$alkyl, $C_{1-6}$alkoxy, and —$C(=O)NR^{9a}R^{9b}$; and Het optionally substituted with one or two substituents each independently selected from oxo, $C_{1-6}$alkylsulfonyl, and $C_{1-6}$alkyl;

(k) $R^8$ is hydrogen, or phenyl, wherein said phenyl is optionally substituted with one or two substituents each independently selected from halo; cyano; nitro; $C_{1-6}$alkyl; —$OR^{12}$; —$C(=O)OR^{12}$; —$C(=O)R^{13}$; —$C(=O)NR^{9a}R^{9b}$; —$NR^{9a}R^{9b}$; —$NR^{9a}C(=O)R^{13}$; phenyl optionally substituted with one or two substituents each independently selected from halo, trifluoromethyl, cyano, $C_{1-6}$alkyl, $C_{1-6}$alkoxy, and —$C(=O)NR^{9a}R^{9b}$; and Het optionally substituted with one or two substituents each independently selected from oxo, $C_{1-6}$alkylsulfonyl, and $C_{1-6}$alkyl;

(l) $R^{9a}$ and $R^{9b}$ are each independently selected from hydrogen or $C_{1-6}$alkyl;

(m) $R^{12}$ is hydrogen or $C_{1-6}$alkyl;

(n) $R^{13}$ is $C_{1-6}$alkyl;

(o) Het is pyrrolidinyl, piperidinyl, morpholinyl, or piperazinyl.

One embodiment of the present invention concerns compounds of formula (I), (I), (II), (III), (IV) or of any subgroup thereof, wherein one or more of the following restrictions apply:

(a) $R^1$ is the bivalent chain selected from the group consisting of

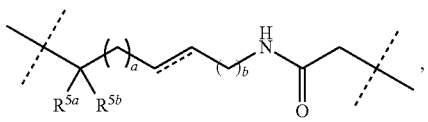

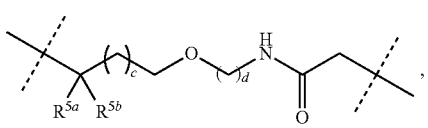

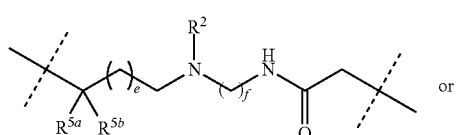

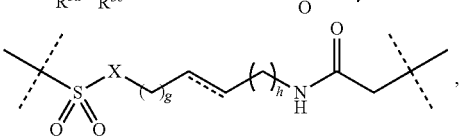

wherein the carbon atom carrying the $R^{5a}$ and $R^{5b}$ substituents is attached to the remainder of the molecule via the nitrogen atom of the amide group, and the carbon atom of the acetamide moiety is attached to the remainder of the molecule via the nitrogen atom of the indole ring of the compound of formula (I);

(b) each of a, b, c, d, e, f, g, and h is, independently, 0, 1, 2, or 3, with the proviso that the macrocycle formed by the bivalent chain $R^1$, the —$C(=O)$—NH— moiety to which $R^1$ is attached and the nitrogen and carbon atoms N1, C6, C7, and C7' of the indole ring, has from 14 to 16 member atoms;

(c) each parallel dashed line (represented by ═══ ) represents an optional double bond;

(d) $R^2$ is hydrogen;

(e) $R^3$ is cyclohexyl;

(f) X is selected from —$CR^{5a}R^{5b}$— or —$NR^{5a}$—;

(g) $R^{5a}$ and $R^{5b}$ are each independently selected from hydrogen; $C_{1-2}$alkyl; trifluoromethyl;

(h) $R^6$ is hydrogen or fluoro;

(i) n is 1;

(j) $R^7$ is phenyl or thiazolyl, wherein said phenyl and thiazolyl are each independently optionally substituted with one or two substituents each independently selected from halo; nitro; $C_{1-6}$alkyl; —$OR^{12}$; —$C(=O)OR^{12}$; —$C(=O)R^{13}$; —$C(=O)NR^{9a}R^{9b}$; —$NR^{9a}R^{9b}$; —$NR^{9a}C(=O)R^{13}$; —$NR^{9a}C(=O)$—$CH_2$—$NR^{9a}R^{9b}$; phenyl optionally substituted with one or two substituents each independently selected from halo, trifluoromethyl, $C_{1-6}$alkyl, and $C_{1-6}$alkoxy; and Het optionally substituted with $C_{1-6}$alkylsulfonyl;

(k) $R^8$ is hydrogen, or phenyl, wherein said phenyl is optionally substituted with one or two substituents each independently selected from halo; nitro; —$OR^{12}$; —$C(=O)OR^{12}$; —$C(=O)NR^{9a}R^{9b}$; —$NR^{9a}R^{9b}$; —$NR^{9a}C(=O)R^{13}$; phenyl optionally substituted with halo; and Het optionally substituted with one or two substituents each independently selected from oxo or $C_{1-6}$alkylsulfonyl;

(l) $R^{9a}$ and $R^{9b}$ are each independently selected from hydrogen or $C_{1-6}$alkyl;

(m) $R^{12}$ is hydrogen or $C_{1-6}$alkyl;

(n) $R^{13}$ is $C_{1-6}$alkyl;

(o) Het is pyrrolidinyl, morpholinyl, or piperazinyl.

One embodiment of the present invention concerns compounds of formula (I), (II), (III), (IV) or of any subgroup thereof, wherein $R^{9a}$ and $R^{9b}$, together with the nitrogen to which they are attached, form a morpholin-4-yl, 2-oxo-pyrrolidinyl, pyrrolidinyl, piperidinyl, or piperazinyl.

One embodiment of the present invention concerns compounds of formula (I), (I), (II), (III), (IV) or of any subgroup thereof, wherein a is 0 or 1, b is 1 or 2, g is 0 or 1, and h is 1 or 2:

One embodiment of the present invention concerns compounds of formula (I), (I), (II), (III), (IV) or of any subgroup thereof, wherein a is 1, b is 2, g is 0 or 1, and h is 1 or 2:

Particular subgroups of compounds of formula (I), (II), (III), or (IV) are those represented by the following structural formulae (II-a), (III-a), (IV-a), (II-b), (III-b), (IV-b) such as for example (II-aa), (III-aa), (IV-aa), (II-bb), (III-bb), (IV-bb), (II-bbb), (III-bbb), (IV-bbb),

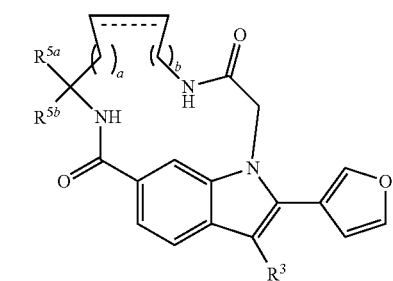
(II-a)
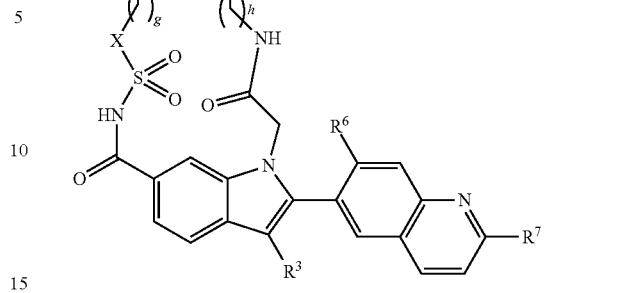
(IV-b)
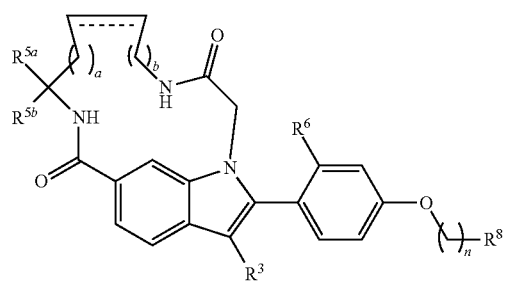
(III-a)
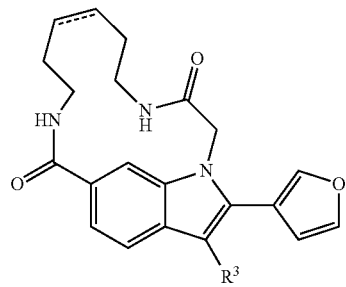
(II-aa)
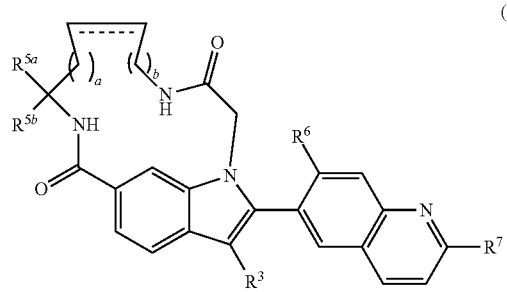
(IV-a)
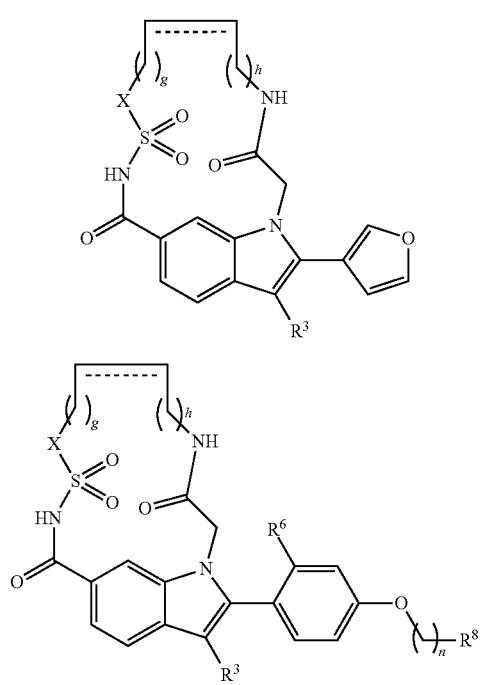
(II-b)
(III-aa)
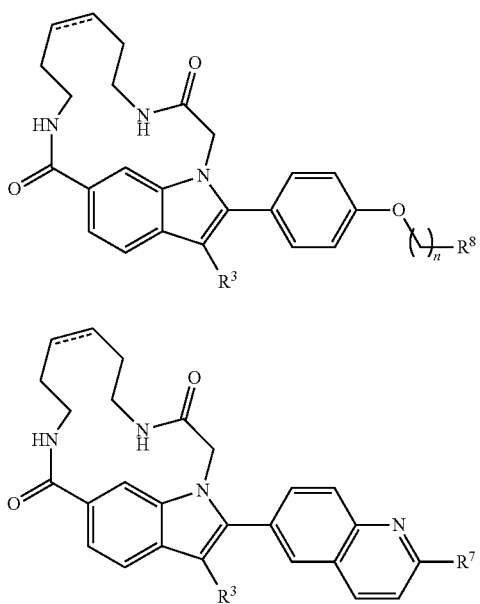
(IV-aa)
(III-b)
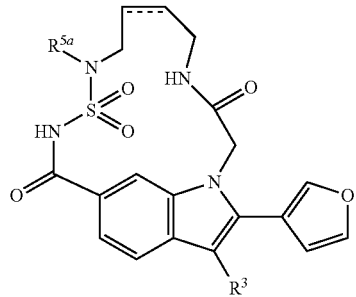
(II-bb)

-continued

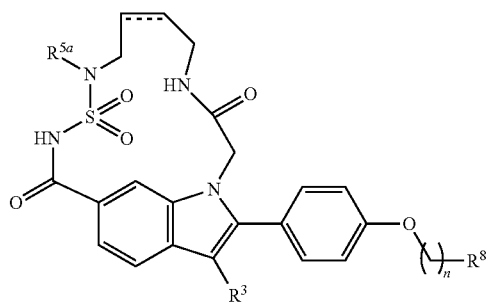
(III-bb)

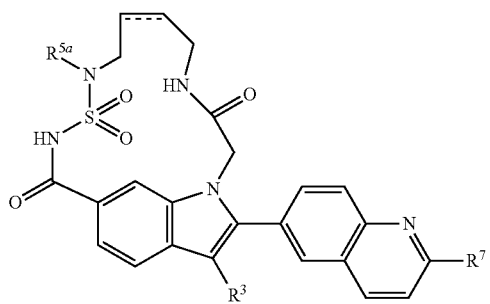
(IV-bb)

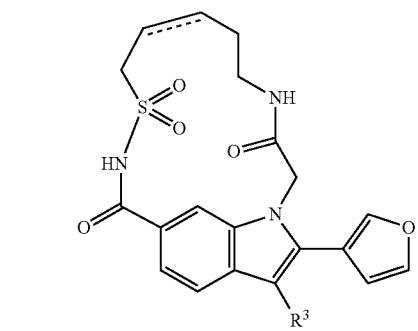
(II-bbb)

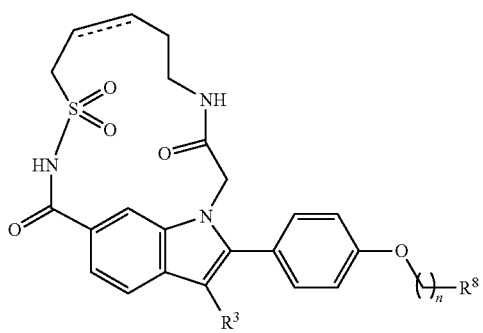
(III-bbb)

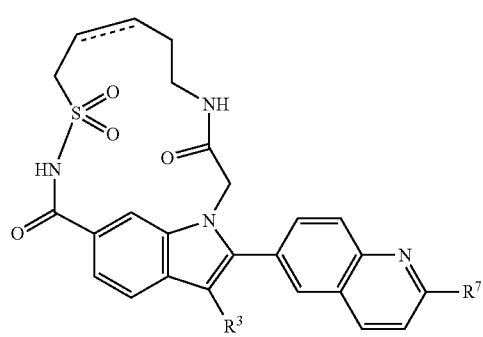
(IV-bbb)

wherein the parallel dashed line, a, b, g, h, $R^3$, $R^{5a}$, $R^{5b}$, $R^6$, $R^7$, X, n, and $R^8$, where appropriate, have the same meaning as that defined above or in any of the subgroups of compounds of formula (I) specified herein.

The parallel dashed line may represent a double bond. When such double bond is present in the compounds of formula (I), or in any subgroup of compounds of formula (I), it may be in a cis or in a trans configuration.

Preferably, such double bond is in a cis configuration, as depicted in formulae (II-1a), (III-1a), (IV-1a), (II-1b), (III-1b), (IV-1b) below. Examples of compounds of the invention have the formulae (II-1a1), (III-1a1), (IV-1a1), (II-1b1), (III-1b1), (IV-1b1), (II-1b2), (III-1b2), (IV-1b2).

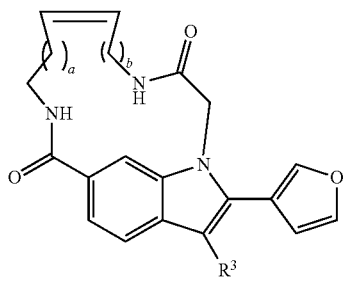
(II-1a)

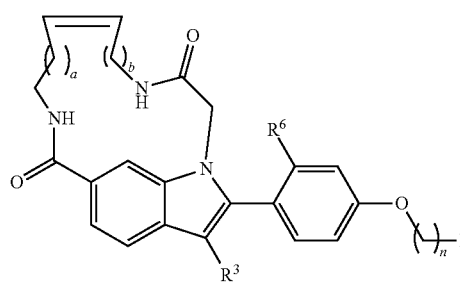
(III-1a)

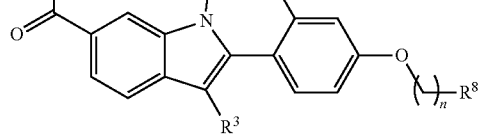

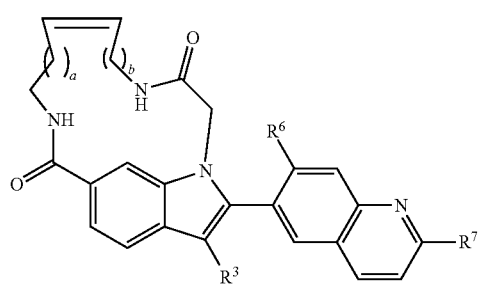
(IV-1a)

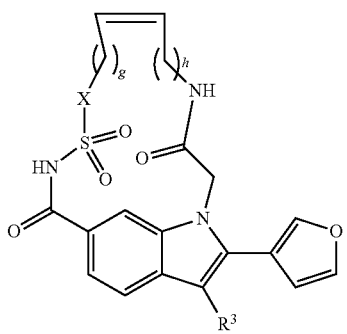
(II-1b)

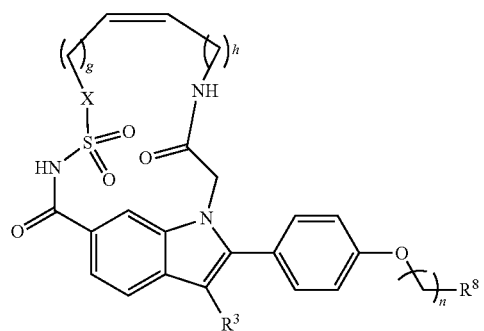
(III-1b)
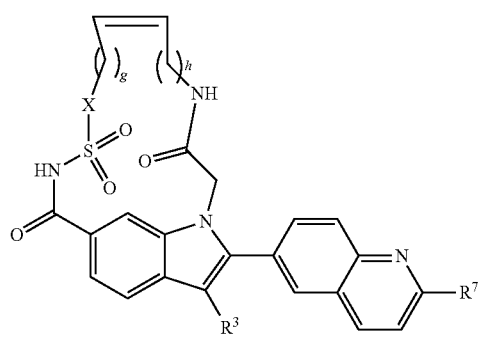
(IV-1b)
(II-1a1)
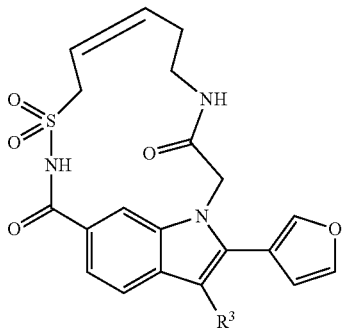
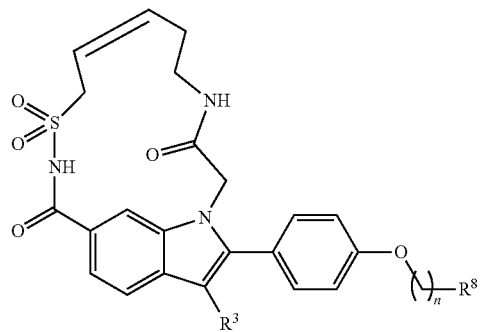
(III-1a1)
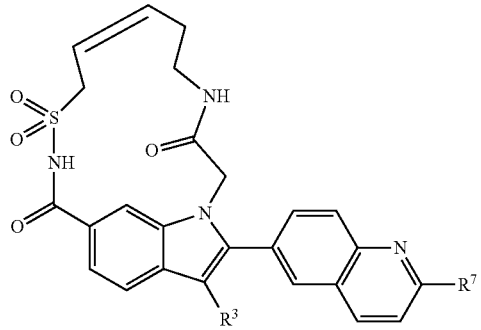
(IV-1a1)
(II-1b1)
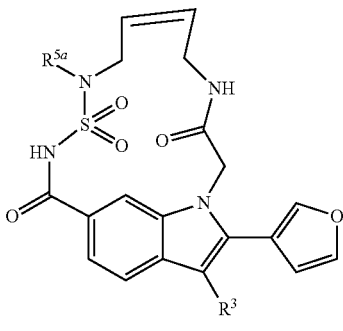
(III-1b1)
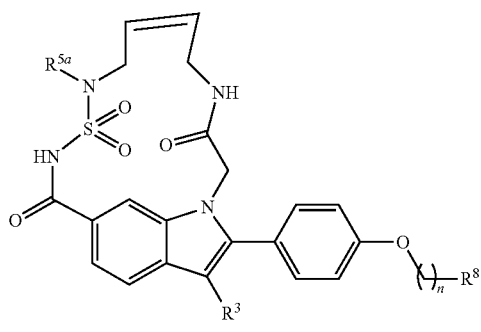
(IV-1b1)
(II-1b2)
(III-1b2)

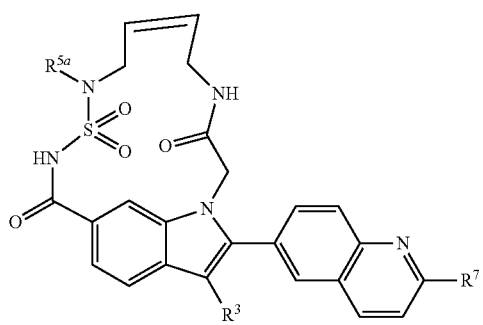

wherein a, b, g, h, $R^3$, n, $R^6$, $R^7$, X and $R^8$, where appropriate, have the same meaning as that defined above or in any of the subgroups of compounds of formula (I) specified herein.

A single bond may be present instead of the double bond in the macrocycle of the compounds of formula (I), or in any subgroup of compounds of formula (I), as depicted in formulae (II-2a), (III-2a), (IV-2a), (II-2b), (III-2b), (IV-2b), such as for example for compounds of formulae and (II-2a1), (III-2a1), (IV-2a1), (II-2b1), (III-2b1) or (IV-2b1) below.

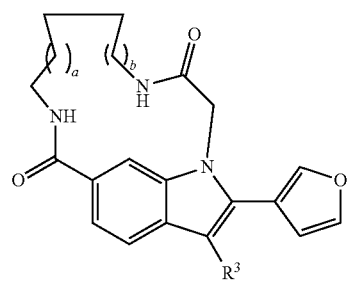

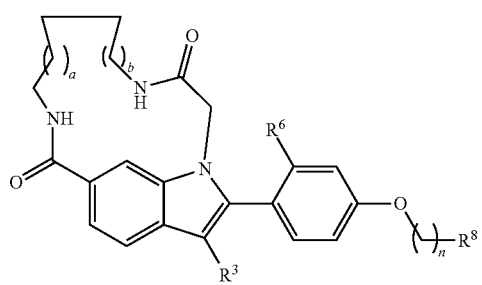

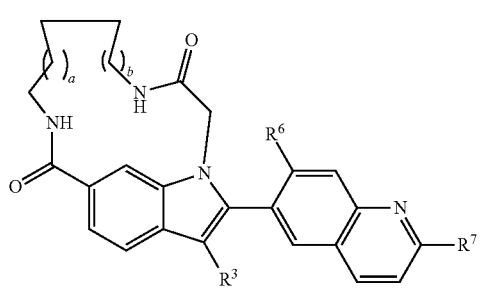

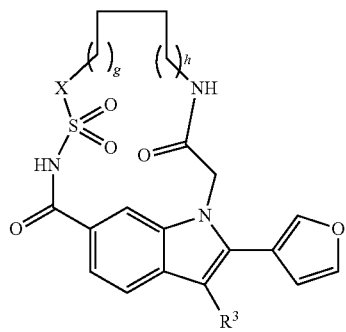

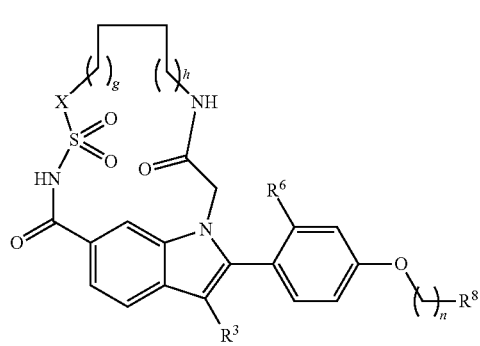

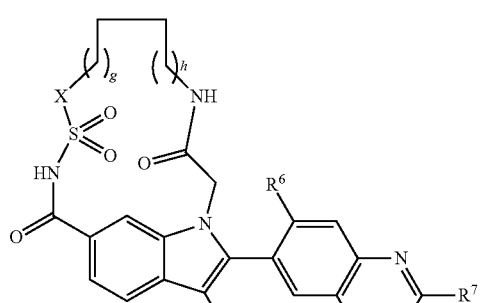

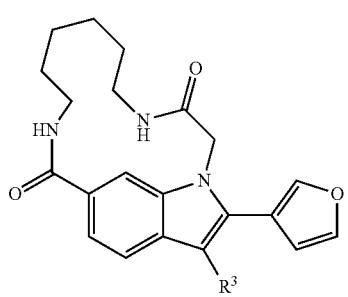

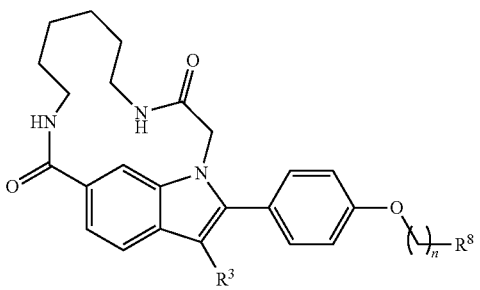

-continued

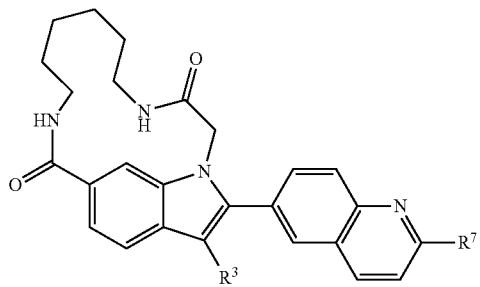
(IV-2a1)

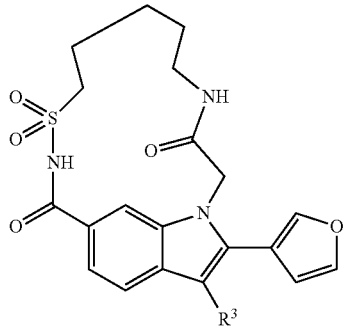
(II-2b1)

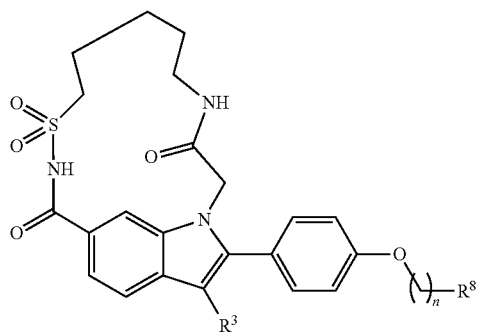
(III-2b1)

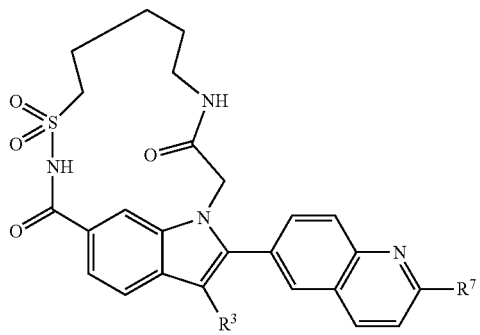
(IV-2b1)

wherein a, b, g, h, $R^3$, n, $R^6$, $R^7$, X and $R^8$, where appropriate, have the same meaning as that defined above or in any of the subgroups of compounds of formula (I) specified herein.

An embodiment of the present invention concerns compounds of formula (I), (II), (III), (IV), (II-a), (III-a), (IV-a), (II-b), (III-b), (IV-b), (II-aa), (III-aa), (IV-aa), (II-bb), (III-bb), (IV-bb), (II-bbb), (III-bbb), (IV-bbb), (II-1a), (III-1a), (IV-1a), (II-1b), (III-1b), (IV-1b), (II-1a1), (III-1a1), (IV-1a1), (II-1b1), (III-1b1), (IV-1b1), (II-1b2), (III-1b2), (IV-1b2), (II-2a), (III-2a), (IV-2a), (II-2b), (III-2b), (IV-2b), (II-2a1), (III-2a1), (IV-2a1), (II-2b1), (III-2b1) or (IV-2b1), or of any subgroup thereof, wherein each of a, b, c, d, e, f, g, and h, is, independently, 0, 1, 2, or 3, with the proviso that the macrocycle formed by the bivalent chain $R^1$, the —C(=O)—NH— moiety and the nitrogen and carbon atoms N1, C6, C7, and C7' of the indole ring, has from 14 to 16 member atoms.

An embodiment of the present invention concerns compounds of formula (I), (II), (III), (IV), (II-a), (III-a), (IV-a), (II-b), (III-b), (IV-b), (II-aa), (III-aa), (IV-aa), (II-bb), (III-bb), (IV-bb), (II-bbb), (III-bbb), (IV-bbb), (II-1a), (III-1a), (IV-1a), (II-1b), (III-1b), (IV-1b), (II-1a1), (III-1a1), (IV-1a1), (II-1b1), (III-1b1), (IV-1b1), (II-1b2), (III-1b2), (IV-1b2), (II-2a), (III-2a), (IV-2a), (II-2b), (III-2b), (IV-2b), (II-2a1), (III-2a1), (IV-2a1), (II-2b1), (III-2b1) or (IV-2b1), or of any subgroup thereof, wherein $R^2$ is hydrogen or $C_{1-4}$alkyl.

An embodiment of the present invention concerns compounds of formula (I), (II), (III), (IV), (II-a), (III-a), (IV-a), (II-b), (III-b), (IV-b), (II-aa), (III-aa), (IV-aa), (II-bb), (III-bb), (IV-bb), (II-bbb), (III-bbb), (IV-bbb), (II-1a), (III-1a), (IV-1a), (II-1b), (III-1b), (IV-1b), (II-1a1), (III-1a1), (IV-1a1), (II-1b1), (III-1b1), (IV-1b1), (II-1b2), (III-1b2), (IV-1b2), (II-2a), (III-2a), (IV-2a), (II-2b), (III-2b), (IV-2b), (II-2a1), (III-2a1), (IV-2a1), (II-2b1), (III-2b1) or (IV-2b1), or of any subgroup thereof, wherein $R^3$ is cyclopentyl or cyclohexyl.

An embodiment of the present invention concerns compounds of formula (I), (II), (III), (IV), (II-a), (III-a), (IV-a), (II-b), (III-b), (IV-b), (II-aa), (III-aa), (IV-aa), (II-bb), (III-bb), (IV-bb), (II-bbb), (III-bbb), (IV-bbb), (II-1a), (III-1a), (IV-1a), (II-1b), (III-1b), (IV-1b), (II-1a1), (III-1a1), (IV-1a1), (II-1b1), (III-1b1), (IV-1b1), (II-1b2), (III-1b2), (IV-1b2), (II-2a), (III-2a), (IV-2a), (II-2b), (III-2b), (IV-2b), (II-2a1), (III-2a1), (IV-2a1), (II-2b1), (III-2b1) or (IV-2b1), or of any subgroup thereof, wherein $R^7$ is phenyl or thiazolyl, wherein said phenyl and thiazolyl are each independently optionally substituted with one, two or three substituents each independently selected from halo; cyano; nitro; $C_{1-6}$alkyl; —$OR^{12}$; —C(=O)$OR^{12}$; —C(=O)$R^{13}$; —C(=O)$NR^{9a}R^{9b}$; —$NR^{9a}R^{9b}$; —$NR^{9a}$C(=O)$R^{13}$; —$NR^{9a}$C(=O)—$CH_2$—$NR^{9a}R^{9b}$; —$SR^{10}$; —$SO_2R^{11}$; —$SO_2NR^{9a}R^{9b}$;

phenyl optionally substituted with one, two or three substituents each independently selected from halo, trifluoromethyl, cyano, $C_{1-6}$alkyl, $C_{1-6}$alkoxy, and —C(=O)$NR^{9a}R^{9b}$; and Het optionally substituted with one or two substituents each independently selected from oxo, $C_{1-6}$alkylsulfonyl, and $C_{1-6}$alkyl; wherein $R^{9a}$ and $R^{9b}$ are each independently selected from hydrogen, $C_{1-6}$alkyl, or aryl$C_{1-6}$alkyl; or $R^{9a}$ and $R^{9b}$, together with the nitrogen to which they are attached, form a saturated, partially unsaturated, or completely unsaturated 5-8 membered monocycle, wherein said monocycle optionally contains one additional heteroatom selected from the group consisting of oxygen, sulfur and nitrogen, and wherein the remaining monocycle members are carbon atoms; wherein said monocycle is optionally substituted on any carbon atom with one or two substituents each independently selected from halo, $C_{1-6}$alkyl, hydroxy, or oxo; $R^{10}$ is $C_{1-6}$alkyl or $C_{3-7}$cycloalkyl; $R^{11}$ is $C_{1-6}$alkyl or $C_{3-7}$cycloalkyl; $R^{12}$ is hydrogen or $C_{1-6}$alkyl; $R^{13}$ is $C_{1-6}$alkyl; and Het is pyrrolidinyl, piperidinyl, morpholinyl, or piperazinyl.

An embodiment of the present invention concerns compounds of formula (I), (II), (III), (IV), (II-a), (III-a), (IV-a), (II-b), (III-b), (IV-b), (II-aa), (III-aa), (IV-aa), (II-bb), (III-bb), (IV-bb), (II-bbb), (III-bbb), (IV-bbb), (II-1a), (III-1a), (IV-1a), (II-1b), (III-1b), (IV-1b), (II-1a1), (III-1a1), (IV-1a1), (II-1b1), (III-1b1), (IV-1b1), (II-1b2), (III-1b2), (IV-1b2), (II-2a), (III-2a), (IV-2a), (II-2b), (III-2b), (IV-2b), (II-2a1), (III-2a1), (IV-2a1), (II-2b1), (III-2b1) or (IV-2b1), or of any subgroup thereof, wherein $R^8$ is hydrogen or phenyl, wherein said phenyl is optionally substituted with one, two, or three substituents each independently selected from halo; cyano; nitro; $C_{1-6}$alkyl; —$OR^{12}$; —$C(=O)OR^{12}$; —$C(=O)R^{13}$; —$C(=O)NR^{9a}R^{9b}$; —$NR^{9a}R^{9b}$; —$NR^{9a}C(=O)R^{13}$; —$NR^{9a}C(=O)$—$CH_2$—$NR^{9a}R^{9b}$; —$SR^{10}$; —$SO_2R^{11}$; —$SO_2NR^{9a}R^{9b}$; phenyl optionally substituted with one, two or three substituents each independently selected from halo, trifluoromethyl, cyano, $C_{1-6}$alkyl, $C_{1-6}$alkoxy, and —$C(=O)NR^{9a}R^{9b}$; and Het optionally substituted with one or two substituents each independently selected from oxo, $C_{1-6}$alkylsulfonyl, and $C_{1-6}$alkyl; wherein $R^{9a}$ and $R^{9b}$ are each independently selected from hydrogen, $C_{1-6}$alkyl, or aryl$C_{1-6}$alkyl; or $R^{9a}$ and $R^{9b}$, together with the nitrogen to which they are attached, form a saturated, partially unsaturated, or completely unsaturated 5-8 membered monocycle, wherein said monocycle optionally contains one additional heteroatom selected from the group consisting of oxygen, sulfur and nitrogen, and wherein the remaining monocycle members are carbon atoms; wherein said monocycle is optionally substituted on any carbon atom with one or two substituents each independently selected from halo, $C_{1-6}$alkyl, hydroxy, or oxo; $R^{10}$ is $C_{1-6}$alkyl or $C_{3-7}$cycloalkyl; $R^{11}$ is $C_{1-6}$alkyl or $C_{3-7}$cycloalkyl; $R^{12}$ is hydrogen or $C_{1-6}$alkyl; $R^{13}$ is $C_{1-6}$alkyl; and Het is pyrrolidinyl, piperidinyl, morpholinyl, or piperazinyl.

According to an embodiment, the present invention provides compounds having one of the structural Formula (I), (II), (III), (IV), (II-a), (III-a), (IV-a), (II-b), (III-b), (IV-b), (II-aa), (III-aa), (IV-aa), (II-bb), (III-bb), (IV-bb), (II-bbb), (III-bbb), (IV-bbb), (II-1a), (III-1a), (IV-1a), (II-1b), (III-1b), (IV-1b), (II-1a1), (III-1a1), (IV-1a1), (II-1b1), (III-1b1), (IV-1b1), (II-1b2), (III-1b2), (IV-1b2), (II-2a), (III-2a), (IV-2a), (II-2b), (III-2b), (IV-2b), (II-2a1), (III-2a1), (IV-2a1), (II-2b1), (III-2b1) or (IV-2b1), wherein $R^3$ is cyclopentyl or cyclohexyl;

X is selected from —$CR^{5a}R^{5b}$— or —$NR^{5a}$—;

$R^{5a}$ and $R^{5b}$ are each independently selected from hydrogen; $C_{1-2}$alkyl; halo$C_{1-4}$alkyl;

$R^6$ is hydrogen, $C_{1-6}$alkyl, or fluoro;

n is 1, or 2;

$R^7$ is phenyl or thiazolyl, wherein each phenyl is optionally substituted with one, two, or three substituents, wherein each thiazolyl is optionally substituted with one or two substituents; wherein the substituents on both phenyl and thiazolyl are each independently selected from halo; cyano; nitro; $C_{1-6}$alkyl; —$OR^{12}$; —$C(=O)OR^{12}$; —$C(=O)R^{13}$; —$C(=O)NR^{9a}R^{9b}$; —$NR^{9a}R^{9b}$; —$NR^{9a}C(=O)R^{13}$; —$NR^{9a}C(=O)$—$CH_2$—$NR^{9a}R^{9b}$; —$SR^{10}$; —$SO_2R^{11}$; —$SO_2NR^{9a}R^{9b}$; phenyl optionally substituted with one, two or three substituents each independently selected from halo, trifluoromethyl, cyano, $C_{1-6}$alkyl, $C_{1-6}$alkoxy, and —$C(=O)NR^{9a}R^{9b}$; and Het optionally substituted with one or two substituents each independently selected from oxo, $C_{1-6}$alkyl-sulfonyl, and $C_{1-6}$alkyl;

$R^8$ is hydrogen, or phenyl, wherein said phenyl is optionally substituted with one, two, or three substituents each independently selected from halo; cyano; nitro; $C_{1-6}$alkyl; —$OR^{12}$; —$C(=O)OR^{12}$; —$C(=O)R^{13}$; —$C(=O)NR^{9a}R^{9b}$; —$NR^{9a}R^{9b}$; —$NR^{9a}C(=O)R^{13}$; —$NR^{9a}C(=O)$—$CH_2$—$NR^{9a}R^{9b}$; —$SR^{10}$; —$SO_2R^{11}$; —$SO_2NR^{9a}R^{9b}$; phenyl optionally substituted with one, two or three substituents each independently selected from halo, trifluoromethyl, cyano, $C_{1-6}$alkyl, $C_{1-6}$alkoxy, and —$C(=O)NR^{9a}R^{9b}$; and Het optionally substituted with one or two substituents each independently selected from oxo, $C_{1-6}$alkylsulfonyl, and $C_{1-6}$alkyl;

$R^{9a}$ and $R^{9b}$ are each independently selected from hydrogen, $C_{1-6}$alkyl, or aryl$C_{1-6}$alkyl; or $R^{9a}$ and $R^{9b}$, together with the nitrogen to which they are attached, form a saturated, partially unsaturated, or completely unsaturated 5-8 membered monocycle, wherein said monocycle optionally contains one additional heteroatom selected from the group consisting of oxygen, sulfur and nitrogen, and wherein the remaining monocycle members are carbon atoms; wherein said monocycle is optionally substituted on any carbon atom with one or two substituents each independently selected from halo, $C_{1-6}$alkyl, hydroxy, or oxo;

$R^{10}$ is $C_{1-6}$alkyl or $C_{3-7}$cycloalkyl;

$R^{11}$ is $C_{1-6}$alkyl or $C_{3-7}$cycloalkyl;

$R^{12}$ is hydrogen or $C_{1-6}$alkyl;

$R^{13}$ is $C_{1-6}$alkyl;

Het is pyrrolidinyl, piperidinyl, morpholinyl, or piperazinyl.

According to another embodiment, the present invention provides compounds having one of the structural Formula (I), (II), (III), (IV), (II-a), (III-a), (IV-a), (II-b), (III-b), (IV-b), (II-aa), (III-aa), (IV-aa), (II-bb), (III-bb), (IV-bb), (II-bbb), (III-bbb), (IV-bbb), (II-1a), (III-1a), (IV-1a), (II-1b), (III-1b), (IV-1b), (II-1a1), (III-1a1), (IV-1a1), (II-1b1), (III-1b1), (IV-1b1), (II-1b2), (III-1b2), (IV-1b2), (II-2a), (III-2a), (IV-2a), (II-2b), (III-2b), (IV-2b), (II-2a1), (III-2a1), (IV-2a1), (II-2b1), (III-2b1) or (IV-2b1), wherein $R^3$ is cyclopentyl or cyclohexyl;

X is selected from —$CR^{5a}R^{5b}$— or —$NR^{5a}$—; $R^{5a}$ and $R^{5b}$ are each independently selected from hydrogen; methyl; ethyl; trifluoromethyl;

$R^6$ is hydrogen, $C_{1-4}$alkyl, or fluoro;

n is 1, or 2;

$R^7$ is phenyl or thiazolyl, wherein said phenyl and thiazolyl are each independently optionally substituted with one or two substituents each independently selected from halo; cyano; nitro; $C_{1-6}$alkyl; —$OR^{12}$; —$C(=O)OR^{12}$; —$C(=O)R^{13}$; —$C(=O)NR^{9a}R^{9b}$; —$NR^{9a}R^{9b}$; —$NR^{9a}C(=O)R^{13}$; —$NR^{9a}C(=O)$—$CH_2$—$NR^{9a}R^{9b}$; —$SR^{10}$; —$SO_2R^{11}$; —$SO_2NR^{9a}R^{9b}$; phenyl optionally substituted with one or two substituents each independently selected from halo, trifluoromethyl, cyano, $C_{1-6}$alkyl, $C_{1-6}$alkoxy, and —$C(=O)NR^{9a}R^{9b}$; and Het optionally substituted with one or two substituents each independently selected from oxo, $C_{1-6}$alkylsulfonyl, and $C_{1-6}$alkyl;

$R^8$ is hydrogen, or phenyl, wherein said phenyl is optionally substituted with one or two substituents each independently selected from halo; cyano; nitro; $C_{1-6}$alkyl; —$OR^{12}$; —$C(=O)OR^{12}$; —$C(=O)R^{13}$; —$C(=O)NR^{9a}R^{9b}$; —$NR^{9a}R^{9b}$; —$NR^{9a}C(=O)R^{13}$; phenyl optionally substituted with one or two substituents each independently selected from halo, trifluoromethyl, cyano, $C_{1-6}$alkyl, $C_{1-6}$alkoxy, and —$C(=O)NR^{9a}R^{9b}$; and Het optionally substituted with one or two substituents each independently selected from oxo, $C_{1-6}$alkylsulfonyl, and $C_{1-6}$alkyl;

$R^{9a}$ and $R^{9b}$ are each independently selected from hydrogen or $C_{1-6}$alkyl;

$R^{12}$ is hydrogen or $C_{1-6}$alkyl;

$R^{13}$ is $C_{1-6}$alkyl;

Het is pyrrolidinyl, piperidinyl, morpholinyl, or piperazinyl.

According to another embodiment, the present invention provides compounds having one of the structural Formula (I), (II), (III), (IV), (II-a), (III-a), (IV-a), (II-b), (III-b), (IV-b), (II-aa), (III-aa), (IV-aa), (II-bb), (III-bb), (IV-bb), (II-bbb), (III-bbb), (IV-bbb), (II-1a), (III-1a), (IV-1a), (II-1b), (III-1b), (IV-1b), (II-1a1), (III-1a1), (IV-1a1), (II-1b1), (III-1b1), (IV-1b1), (II-1b2), (III-1b2), (IV-1b2), (II-2a), (III-2a), (IV-2a), (II-2b), (III-2b), (IV-2b), (II-2a1), (III-2a1), (IV-2a1), (II-2b1), (III-2b1) or (IV-2b1), wherein R³ is cyclohexyl;
X is selected from —CR⁵ᵃR⁵ᵇ— or —NR⁵ᵃ—;
R⁵ᵃ and R⁵ᵇ are each independently selected from hydrogen; methyl, ethyl; or trifluoromethyl;
R⁶ is hydrogen or fluoro;
n is 1;
R⁷ is phenyl or thiazolyl, wherein said phenyl and thiazolyl are each independently optionally substituted with one or two substituents each independently selected from halo; nitro; $C_{1-6}$alkyl; —OR¹²; —C(=O)OR¹²; —C(=O)R¹³; —C(=O)NR⁹ᵃR⁹ᵇ; —NR⁹ᵃR⁹ᵇ; —NR⁹ᵃC(=O)R¹³; —NR⁹ᵃC(=O)—CH₂—NR⁹ᵃR⁹ᵇ; phenyl optionally substituted with one or two substituents each independently selected from halo, trifluoromethyl, $C_{1-6}$alkyl, and $C_{1-6}$alkoxy; and Het optionally substituted with $C_{1-6}$alkylsulfonyl;
R⁸ is hydrogen, or phenyl, wherein said phenyl is optionally substituted with one or two substituents each independently selected from halo; nitro; —OR¹²; —C(=O)OR¹²; —C(=O)NR⁹ᵃR⁹ᵇ; —NR⁹ᵃR⁹ᵇ; —NR⁹ᵃC(=O)R¹³; phenyl optionally substituted with halo; and Het optionally substituted with one or two substituents each independently selected from oxo or $C_{1-6}$alkylsulfonyl;
R⁹ᵃ and R⁹ᵇ are each independently selected from hydrogen or $C_{1-6}$alkyl;
R¹² is hydrogen or $C_{1-6}$alkyl;
R¹³ is $C_{1-6}$alkyl;
Het is pyrrolidinyl, morpholinyl, or piperazinyl.

According to an embodiment, the present invention provides compounds having one of the structural Formula (I), (II), (III), (IV), (II-a), (III-a), (IV-a), (II-b), (III-b), (IV-b), (II-aa), (III-aa), (IV-aa), (II-bb), (III-bb), (IV-bb), (II-bbb), (III-bbb), (IV-bbb), (II-1a), (III-1a), (IV-1a), (II-1b), (III-1b), (IV-1b), (II-1a1), (III-1a1), (IV-1a1), (II-1b1), (III-1b1), (IV-1b1), (II-1b2), (III-1b2), (IV-1b2), (II-2a), (III-2a), (IV-2a), (II-2b), (III-2b), (IV-2b), (II-2a1), (III-2a1), (IV-2a1), (II-2b1), (III-2b1) or (IV-2b1), wherein
X is selected from —CR⁵ᵃR⁵ᵇ— or —NR⁵ᵃ—;
R⁵ᵃ and R⁵ᵇ are each independently selected from hydrogen; methyl, or trifluoromethyl;
n is 1;
R⁶ is selected from hydrogen or fluoro;
R⁷ is phenyl or thiazolyl, wherein said phenyl and thiazolyl are each independently optionally substituted with one or two, preferably two substituents each independently selected from halo; nitro; $C_{1-6}$alkyl; —OR¹²; phenyl optionally substituted with one, two or three halo substituents;
R⁸ is hydrogen, or phenyl, wherein said phenyl is optionally substituted with one or two, preferably two substituents each independently selected from halo; nitro; $C_{1-3}$alkyl; —OR¹²; —NR⁹ᵃR⁹ᵇ; —NR⁹ᵃC(=O)R¹³; phenyl optionally substituted with halo; and Het optionally substituted with one or two substituents each independently selected from oxo, and $C_{1-3}$alkylsulfonyl;
R⁹ᵃ and R⁹ᵇ are each independently selected from hydrogen or $C_{1-3}$alkyl;
R¹² is hydrogen or $C_{1-3}$alkyl;
R¹³ is $C_{1-3}$alkyl;
Het is pyrrolidinyl, morpholinyl, or piperazinyl.

It is to be understood that the above defined subgroups of compounds of formulae (I), (II), (III), (IV), (II-a), (III-a), (IV-a), (II-b), (III-b), (IV-b), (II-aa), (III-aa), (IV-aa), (II-bb), (III-bb), (IV-bb), (II-bbb), (III-bbb), (IV-bbb), (II-1a), (III-1a), (IV-1a), (II-1b), (III-1b), (IV-1b), (II-1a1), (III-1a1), (IV-1a1), (II-1b1), (III-1b1), (IV-1b1), (II-1b2), (III-1b2), (IV-1b2), (II-2a), (III-2a), (IV-2a), (II-2b), (III-2b), (IV-2b), (II-2a1), (III-2a1), (IV-2a1), (II-2b1), (III-2b1) or (IV-2b1) as well as any other subgroup defined herein, are meant to also comprise any N-oxides, salts, quaternary amines, metal complexes and stereochemically isomeric forms of such compounds.

Yet another embodiment relates to the compounds of formula (V) wherein one or more of the following restrictions apply:
(a) R¹ is a bivalent chain of formula

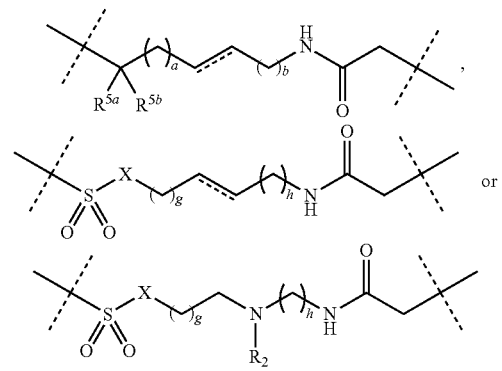

wherein the points of attachment are as defined above;
(b) R³ is cyclohexyl;
(c) R⁶ is hydrogen;
(d) R⁶ᵃ is halo or hydrogen.

One embodiment relates to the compounds of formula (I) or any subgroup thereof wherein R¹ is a bivalent chain of formula

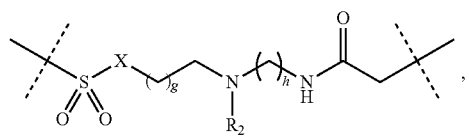

and wherein one or more of the following restrictions apply:
(a) X is NH or CH₂;
(b) g is 1;
(c) h is 2;
(d) R² is $C_{1-4}$alkyl, preferably methyl;
(e) R³ is cyclohexyl;
(f) R⁴ is a group selected from

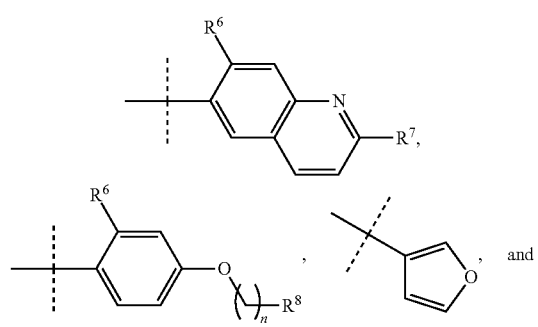

-continued

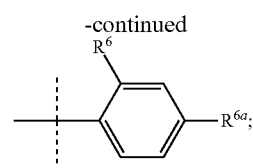

preferably a group selected from

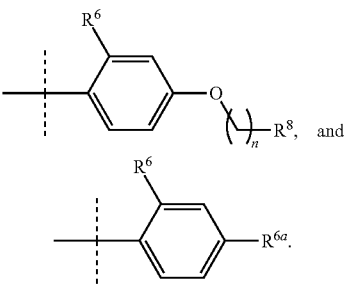

Another embodiment relates to the compounds of formula (I) or any subgroup thereof wherein $R^4$ is phenyl, p-methoxy-phenyl or p-halo-phenyl.

Preparation of the Compounds of Formula (I)

The compounds of formula (I) and the salts and stereoisomers thereof, wherein $R^1$ is the bivalent chain

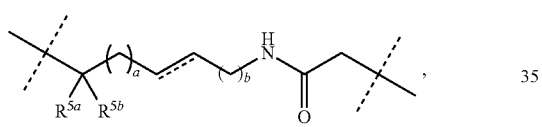

wherein the carbon atom carrying the $R^{5a}$ and $R^{5b}$ substituents is attached to the remainder of the molecule via the nitrogen atom of the amide group, and the carbon atom of the acetamide moiety is attached to the remainder of the molecule via the nitrogen atom of the indole ring of the compound of formula (I);

each of a, and b is, independently, 0, 1, 2, or 3, with the proviso that the macrocycle formed by the bivalent chain $R^1$, the —C(=O)—NH— moiety to which $R^1$ is attached and the nitrogen and carbon atoms N1, C6, C7, and C7' of the indole ring, has from 14 to 17 member atoms; and the parallel dashed line (represented by =====) represents an optional double bond;

may be prepared according to Scheme I, as depicted below, wherein i is an integer equal to a+1, and b, $R^3$ and $R^4$ have the same meaning as that defined above.

Scheme 1

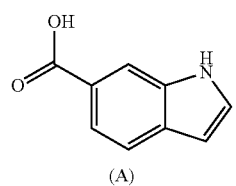

(A)

-continued

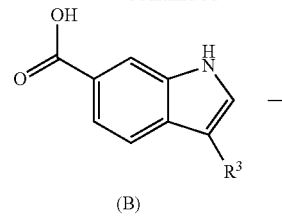

(B)

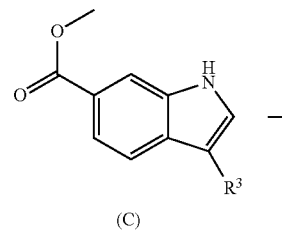

(C)

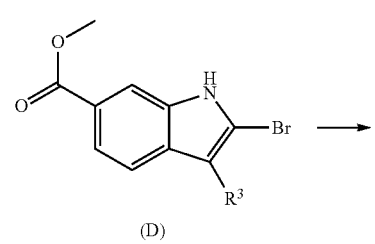

(D)

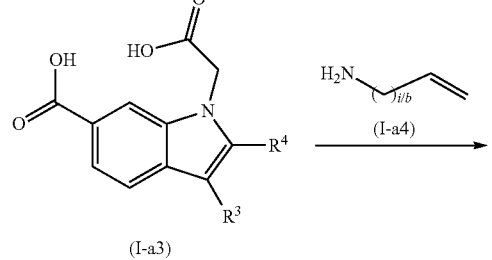

(I-a1)

(I-a2)

(I-a3)

(I-a4)

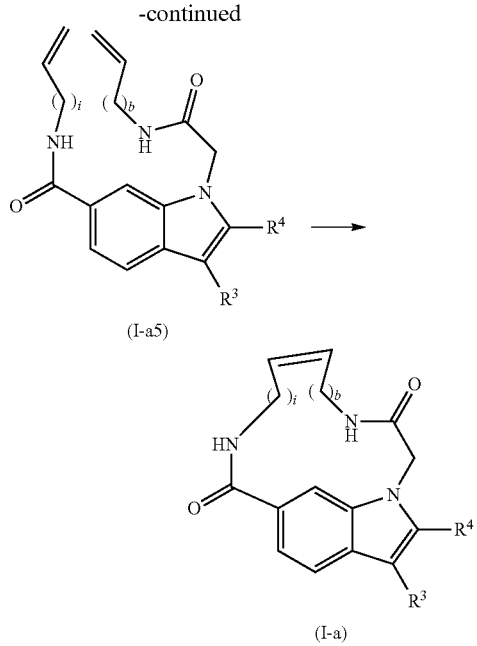

(I-a5)

(I-a)

The compound of formula (B), i.e. a 3-substituted indole, may be obtained by condensation of a $C_{4-7}$cycloalkanone with the indole of formula (A) followed by a reduction. $C_{4-7}$cycloalkanone is the precursor of the $R^3$ substituent: $C_{4-7}$cycloalkyl, as defined for the compounds of formula (I) or any subgroup thereof.

Condensation of the $C_{4-7}$cycloalkanone with the indole of formula (A) may be carried out in a suitable solvent such as methanol or ethanol, in the presence of a base such as sodium methanolate or potassium tert-butoxide. The $C_{4-7}$cycloalkanone, once introduced into compound of formula (B), is attached to the indole as a $C_{4-7}$cycloalkenyl. Both $C_{4-7}$cycloalkanone and the compound of formula (A) are commercially available. Reduction of the double bond in the $C_{4-7}$cycloalkenyl moiety may be achieved using an appropriate catalyst (Pd(OH)$_2$/C) in a suitable solvent such as methanol, ethanol, THF, or a mixture thereof, and by applying a pressure between atmospheric pressure and 80 psi.

Esterification of the acid in compound of formula (B) by standard procedures generates compound of formula (C). Standard procedures for esterification of an acid are known by the skilled in the art and include amongst other, adding thionyl chloride in a solution of the acid in methanol, or adding methanol in the presence of an acid such as sulfuric acid.

Compound of formula (D) may be obtained by brominating the indole of formula (C) with a bromination agent such as bromine or pyridine tribromide, in an appropriate solvent such as THF, chloroform, dichloromethane or carbon tetrachloride.

Compound of formula (I-a1) may be obtained by a palladium coupling reaction between the 2-bromoindole of formula (D) and a boronic acid derivative (including ester derivatives) carrying the $R^4$ group, in the presence of a palladium derivative at a temperature between 20° C. and 100° C., in an appropriate solvent such as ethanol, water, acetonitrile, toluene, or a mixture thereof.

Compound of formula (I-a2) may be obtained by alkylation at position 1 of the indole of formula (I-a1) using a haloacetate derivative in the presence of a base such as sodium hydride, potassium carbonate, cesium carbonate, and the like, in the presence of a suitable solvent such as DMF, THF, acetonitrile and the like.

Compound of formula (I-a3) may be obtained by carrying out a hydrolysis on compound of formula (I-a2) in acid media or via saponification using a hydroxide, for instance LiOH or NaOH, in polar solvents such as water, an alcohol such as methanol or ethanol, THF, or a mixture thereof.

Compound of formula (I-a5) may be prepared by an amide forming reaction starting from intermediate (I-a3) which is reacted with an alkenylamine (I-a4) as shown in Scheme I.

The formation of amide bonds can be carried out using standard procedures such as those used for coupling amino acids in peptide synthesis. The latter involves the dehydrative coupling of a carboxyl group of one reactant with an amino group of the other reactant to form a linking amide bond. The amide bond formation may be performed by reacting the starting materials in the presence of a coupling agent or by converting the carboxyl functionality into an active form such as an active ester, mixed anhydride or a carboxyl acid chloride or bromide. General descriptions of such coupling reactions and the reagents used therein can be found in general textbooks on peptide chemistry, for example, M. Bodanszky, "Peptide Chemistry", 2nd rev. ed., Springer-Verlag, Berlin, Germany, (1993).

Examples of coupling reactions with amide bond formation include the azide method, mixed carbonic-carboxylic acid anhydride (isobutyl chloroformate) method, the carbodiimide (dicyclohexylcarbodiimide, diisopropylcarbodiimide, or water-soluble carbodiimide such as N-ethyl-N'-[3-(dimethylamino)propyl]carbodiimide) method, the active ester method (e.g. p-nitrophenyl, p-chlorophenyl, trichlorophenyl, pentachloro-phenyl, pentafluorophenyl, N-hydroxysuccinic imido and the like esters), the Woodward reagent K-method, the 1,1-carbonyldiimidazole (CDI or N,N'-carbonyl-diimidazole) method, the phosphorus reagents or oxidation-reduction methods. Some of these methods can be enhanced by adding suitable catalysts, e.g. in the carbodiimide method by adding 1-hydroxybenzotriazole, or 4-DMAP. Further coupling agents are (benzotriazol-1-yloxy)-tris-(dimethylamino) phosphonium hexafluorophosphate, either by itself or in the presence of 1-hydroxy-benzotriazole or 4-DMAP; or 2-(1H-benzotriazol-1-yl)-N,N,N',N'-tetra-methyluronium tetrafluoroborate, or O-(7-azabenzotriazol-1-yl)-N,N,N',N'-tetramethyluronium hexafluorophosphate. These coupling reactions can be performed in either solution (liquid phase) or solid phase.

A preferred amide bond formation is performed employing N-ethyloxycarbonyl-2-ethyl-oxy-1,2-dihydroquinoline (EEDQ) or N-isobutyloxycarbonyl-2-isobutyloxy-1,2-dihydroquinoline (IIDQ). Unlike the classical anhydride procedure, EEDQ and IIDQ do not require base nor low reaction temperatures. Typically, the procedure involves reacting equimolar amounts of the carboxyl and amine components in an organic solvent (a wide variety of solvents can be used). Then EEDQ or IIDQ is added in excess and the mixture is allowed to stir at room temperature.

The coupling reactions preferably are conducted in an inert solvent, such as halogenated hydrocarbons, e.g. dichloromethane, chloroform, dipolar aprotic solvents such as acetonitrile, dimethylformamide, dimethylacetamide, DMSO, HMPT, ethers such as tetrahydrofuran (THF).

In many instances the coupling reactions are done in the presence of a suitable base such as a tertiary amine, e.g. triethylamine, diisopropylethylamine (DIPEA), N-methylmorpholine, N-methylpyrrolidine, 4-DMAP or 1,8-diazabicyclo[5.4.0]undec-7-ene (DBU). The reaction temperature may range between 0° C. and 50° C. and the reaction time may range between 15 min and 24 h.

Formation of the macrocycle, i.e. compound of formula (I-a) can be carried out via an olefin metathesis reaction in the presence of a suitable metal catalyst such as e.g. the Ru-based catalyst reported by Miller, S. J., Blackwell, H. E., Grubbs, R. H. J. Am. Chem. Soc. 118, (1996), 9606-9614; Kingsbury, J. S., Harrity, J. P. A., Bonitatebus, P. J., Hoveyda, A. H., J. Am. Chem. Soc. 121, (1999), 791-799; and Huang et al., J. Am. Chem. Soc. 121, (1999), 2674-2678; for example a Hoveyda-Grubbs catalyst.

Air-stable ruthenium catalysts such as bis(tricyclohexylphosphine)-3-phenyl-1H-inden-1-ylidene ruthenium chloride (Neolyst M1®) or bis(tricyclohexylphosphine)-[(phenylthio)methylene]ruthenium (IV) dichloride can be used. Other catalysts that can be used are Grubbs first and second generation catalysts, i.e. benzylidene-bis(tricyclo-hexylphosphine)dichlororuthenium and (1,3-bis-(2,4,6-trimethylphenyl)-2-imidazolidinylidene)dichloro(phenylmethylene)(tricyclohexylphosphine)ruthenium, respectively. Of particular interest are the Hoveyda-Grubbs first and second generation catalysts, which are dichloro(o-isopropoxyphenylmethylene)(tricyclohexylphosphine)-ruthenium(II) and 1,3-bis-(2,4,6-trimethylphenyl)-2-imidazolidinylidene) dichloro-(o-isopropoxyphenylmethylene)ruthenium respectively. Also, other catalysts containing other transition metals such as Mo can be used for this reaction.

The metathesis reactions may be conducted in a suitable solvent such as for example ethers, e.g. THF, dioxane; halogenated hydrocarbons, e.g. dichloromethane, $CHCl_3$, 1,2-dichloroethane and the like, hydrocarbons, e.g. toluene. These reactions are conducted at increased temperatures under nitrogen atmosphere.

Alternatively, compound of formula (I-a) may be obtained by coupling the diacid (I-a3) with a diamine using diluted conditions.

In an embodiment, compounds of formula (III-1a) can be prepared according to Scheme II, as depicted below, wherein i is an integer equal to a+1, and b, n, $R^3$, $R^6$ and $R^8$ have the same meaning as that defined above.

Scheme II

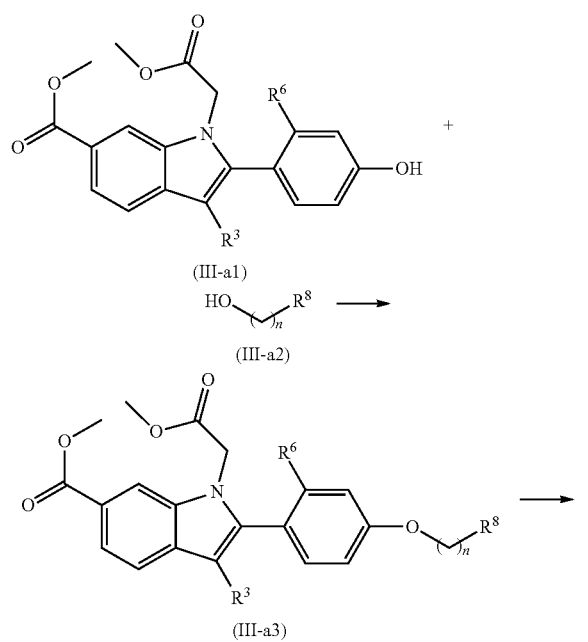

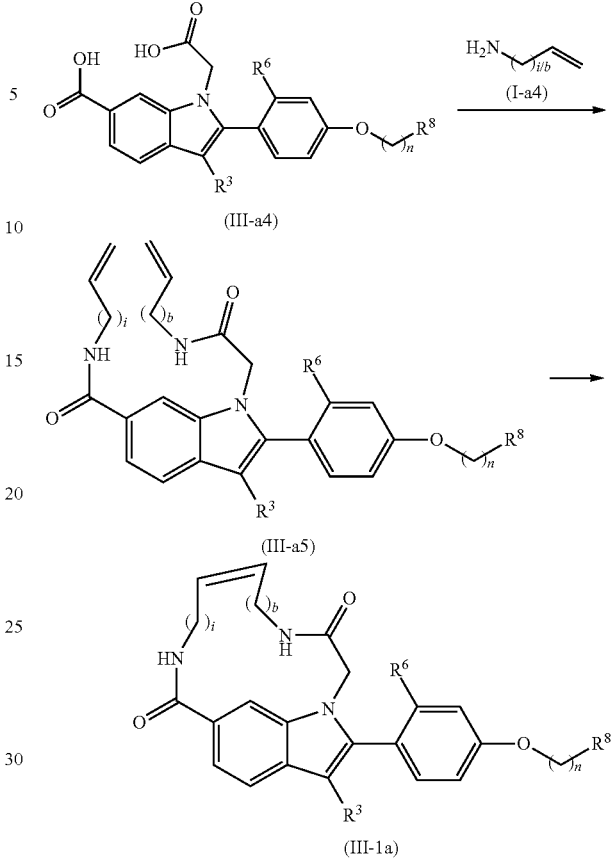

In Scheme II, compound of formula (III-a1) is reacted with compound of formula (III-a2) via a Mitsunobu reaction (Mitsunobu, 1981, Synthesis, January, 1-28; Rano et al., Tetrahedron Lett., 1995, 36, 22, 3779-3792; Krchnak et al., Tetrahedron Lett., 1995, 36, 5, 6193-6196; Richter et al., Tetrahedron Lett., 1994, 35, 27, 4705-4706) to obtain compound of formula (III-a3). This reaction comprises treatment of intermediate (III-a1) with intermediate (III-a2), in the presence of triphenylphosphine or tris(tert-butyl)phosphine and an activating agent such as a dialkyl azodicarboxylate, e.g. diethyl azodicarboxylate (DEAD), diisopropyl azodicarboxylate (DIAD) or the like. Suitable solvents for this reaction are dimethylformamide (DMF) or tetrahydrofuran (THF), and the temperature of the reaction may vary between −20° C. and +50° C.

Alternatively, the compound of formula (III-a3) can be generated by reacting the compound of formula (III-a1) with the halo-derivative of formula (III-a2), i.e. compound of formula (E) as depicted below wherein Z is halo, via an alkylation with a base such as potassium carbonate, cesium carbonate, sodium hydride, or potassium tert-butoxide, in the presence of a suitable solvent such as DMF, THF, or acetonitrile.

Compound of formula (III-a4) may be obtained by carrying out a hydrolysis on compound of formula (III-a3) in acid media or via saponification using a hydroxide, for instance LiOH or NaOH, in polar solvents such as water, an alcohol such as methanol or ethanol, THF, or a mixture thereof.

Compound of formula (III-a5) may be prepared by an amide forming reaction starting from intermediate (III-a4) which is reacted with an alkenylamine (I-a4) as shown in Scheme II.

The formation of amide bonds can be carried out using standard procedures such as those used for coupling amino acids in peptide synthesis described above for scheme I.

Formation of the macrocycle, i.e. compound of formula (III-1a), can be carried out via an olefin metathesis reaction in the presence of a suitable metal catalyst such as e.g. the Ru-based catalyst as reported above for the formation of the macrocycle of formula (I-a).

Alternatively, compound of formula (III-1a) may be obtained by coupling the diacid (III-a4) with a diamine using diluted conditions.

Compound of formula (III-a1) may be generated according to the procedure depicted in Scheme III, wherein $R^3$ and $R^6$ have the same meaning as that defined above and PG is a suitable protecting group.

Scheme III

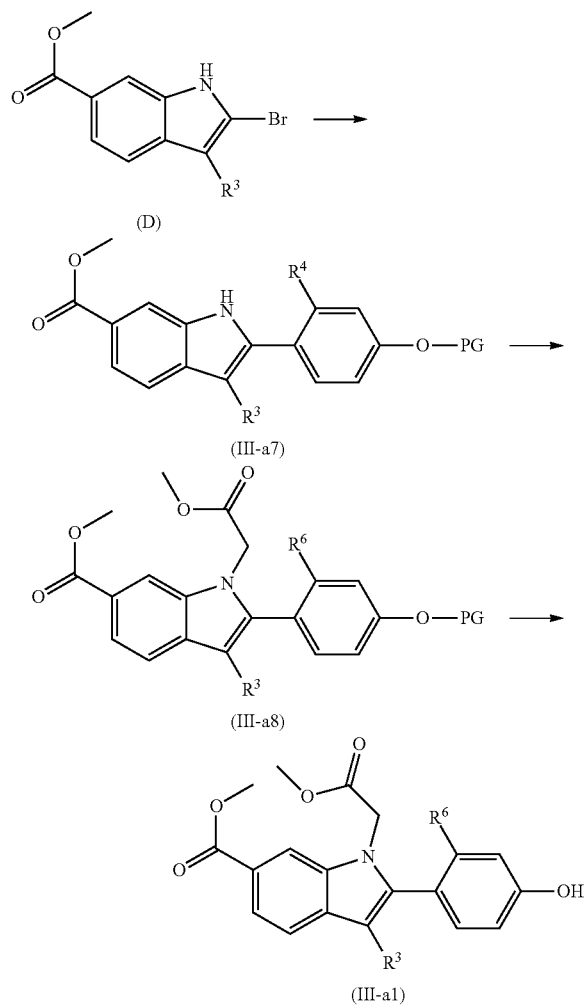

Compound of formula (III-a7) may be obtained by a palladium coupling reaction between the 2-bromoindole of formula (D) and a boronic acid derivative (including ester derivatives) carrying a $R^6$-substituted phenyl, in the presence of a palladium derivative at a temperature between 20° C. and 100° C., in an appropriate solvent such as ethanol, water, acetonitrile, toluene, or a mixture thereof. The $R^6$-substituted phenyl is optionally protected, as shown in Scheme III, wherein PG is a hydroxyl-protecting group. Hydroxyl groups may be protected as benzyl or substituted benzyl ethers, e.g. 4-methoxybenzyl ether, benzoyl or substituted benzoyl esters, e.g. 4-nitrobenzoyl ester, or with trialkylsilyl groups (e.g. trimethylsilyl or tert-butyldimethylsilyl). Further appropriate protecting groups that can be used are listed for example in Greene, "Protective Groups in Organic Chemistry", John Wiley & Sons, New York (1999) and "The Peptides: Analysis, Synthesis, Biology", Vol. 3, Academic Press, New York (1987).

Compound of formula (III-a8) may be obtained by alkylation at position 1 of the indole of formula (III-a7) using a haloacetate derivative in the presence of a base such as sodium hydride, potassium carbonate, cesium carbonate, and the like, in the presence of a suitable solvent such as DMF, THF, acetonitrile and the like.

Compound of formula (III-a1) may be obtained by unmasking or deprotecting the hydroxyl in compound of formula (III-a8), by using hydrogenation in the presence of a catalyst such as Pd/C in a suitable solvent such as methanol, ethanol, THF, or a mixture thereof, and the like, and by applying a pressure between atmospheric pressure and 80 psi. Other unmasking or deprotecting methods known in the art may be used.

In one embodiment of the present invention, in the compound of formula (III-a2)

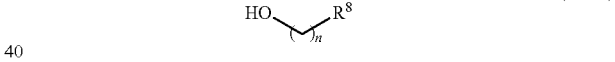

(III-a2)

n is 1;

$R^8$ is phenyl substituted with one Het that is optionally substituted with one or two substituents each independently selected from oxo, $C_{1-6}$alkylsulfonyl, and $C_{1-6}$alkyl; and said phenyl is as well optionally substituted with one or two $R^{15}$ substituents;

$R^{15}$ is halo; cyano; nitro; $C_{1-6}$alkyl; —$OR^{12}$; —$C(=O)OR^{12}$; —$C(=O)R^{13}$; —$C(=O)NR^{9a}R^{9b}$; —$NR^{9a}R^{9b}$; —$NR^{9a}C(=O)R^{13}$; —$NR^{9a}C(=O)$—$CH_2$—$NR^{9a}R^{9b}$; —$SR^{10}$; —$SO_2R^{11}$; —$SO_2NR^{9a}R^{9b}$; or phenyl optionally substituted with one, two or three substituents each independently selected from halo, trifluoromethyl, $C_{1-6}$alkyl, and $C_{1-6}$alkoxy;

Het is pyrrolidinyl, piperidinyl, morpholinyl, or piperazinyl, and $R^{9a}$, $R^{9b}$, $R^{10}$, $R^{11}$, $R^{12}$, and $R^{13}$, have the same meaning as that defined above.

Examples of compound of formula (III-a2), such as compound of formula (J), may be prepared according to the procedure depicted in Scheme IV below, wherein $R^{15}$ has the same meaning as that defined above, Y is a halo, and Het is pyrrolidinyl, piperidinyl, morpholinyl, or piperazinyl, wherein Het is optionally substituted with oxo, $C_{1-6}$alkylsulfonyl or $C_{1-6}$alkyl.

Scheme IV

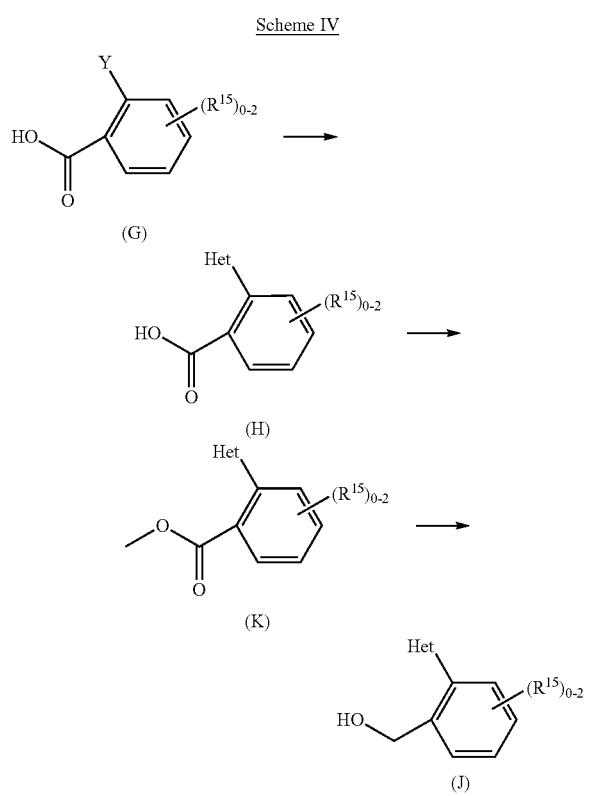

Introduction of an optionally substituted Het group into the compound of formula (G) to afford the benzoic acid derivative (H) may be performed by an aromatic nucleophilic substitution of the 2-halobenzoic acid derivative (G) with a nucleophilic amine, optionally in the presence of a base, in an appropriate solvent such as DMF, THF, or acetonitrile. Obviously, the nucleophilic amine refers to the optionally substituted Het group.

Compound of formula (G) is commercially available. Y represents a halo substituent in the compound of formula (G).

The Het compound, which may be a pyrrolidinyl, piperidinyl, morpholinyl, or piperazinyl, and is optionally substituted with oxo, $C_{1-6}$alkylsulfonyl, or $C_{1-6}$alkyl, is also commercially available.

The acid of compound of formula (H) is then esterified in order to produce the compound of formula (K). Esterification may be performed according to several methods known by the skilled in the art, including amongst other, the use of methyl iodide in the presence of a base in an appropriate solvent such as DMF, THF or acetonitrile.

Compound of formula (J), which is a particular embodiment of compound of formula (III-a2), may be then obtained by reduction of the ester of formula (K) using a hydride such as $LiAlH_4$ in an appropriate solvent such as THF.

Alternatively, a compound (G) may be esterified first to produce for example a methyl ester derivative, prior to the introduction of the Het group. Furthermore, before transforming (K) to (J), when $R^{15}$ is nitro, a catalytic hydrogenation may be performed to get a compound of formula (K) where $R^{15}$ is amino. This amino group may be further transformed into a group of formula $NR^{9a}R^{9b}$.

Compounds of formula (I) wherein the macrocycle contains no double bond, i.e. such as for example compounds of formula (II-2a), (III-2a), (IV-2a), can be prepared from the compounds of formula (I-a) by a reduction of the double bond. This reduction may be conducted by catalytic hydrogenation with hydrogen in the presence of a noble metal catalyst such as, for example, Pt, Pd, Rh, Ru or Raney nickel. Of interest is Rh on alumina. The hydrogenation reaction preferably is conducted in a solvent such as, e.g. an alcohol such as methanol, ethanol, or an ether such as THF, or mixtures thereof. Water can also be added to these solvents or solvent mixtures.

Alternative methods for the preparation of the compounds of the present invention encompass the procedure as depicted in Scheme V below, wherein i is an integer equal to a+1, and $R^3$, b, and $R^4$ have the same meaning as that defined above.

Scheme V

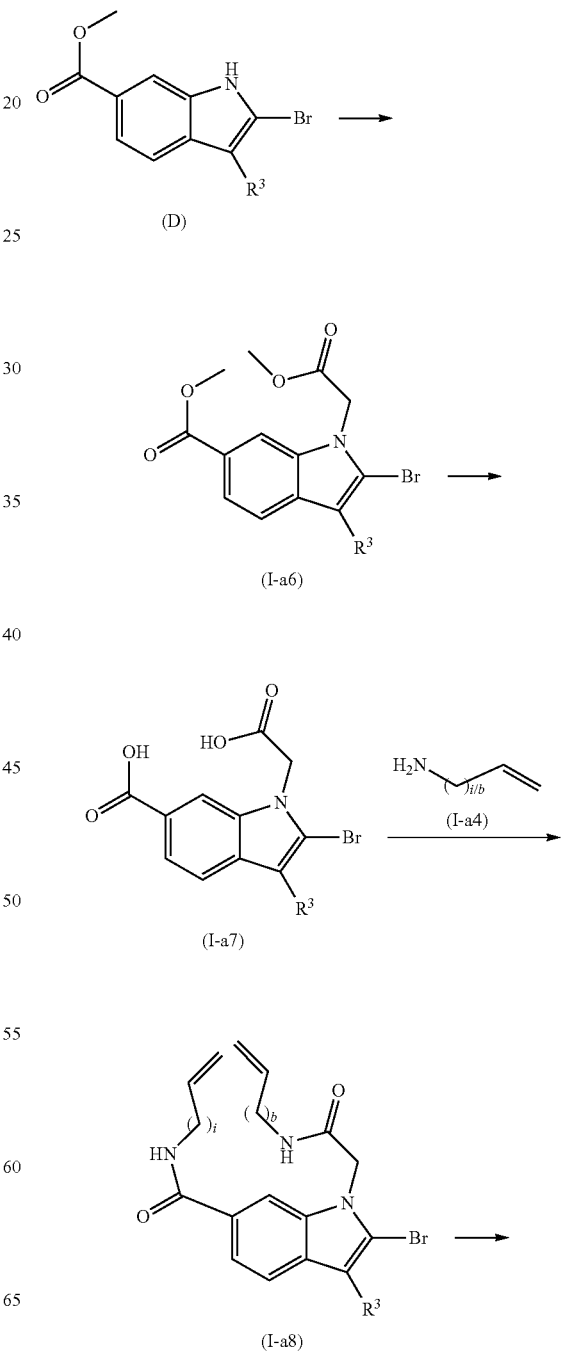

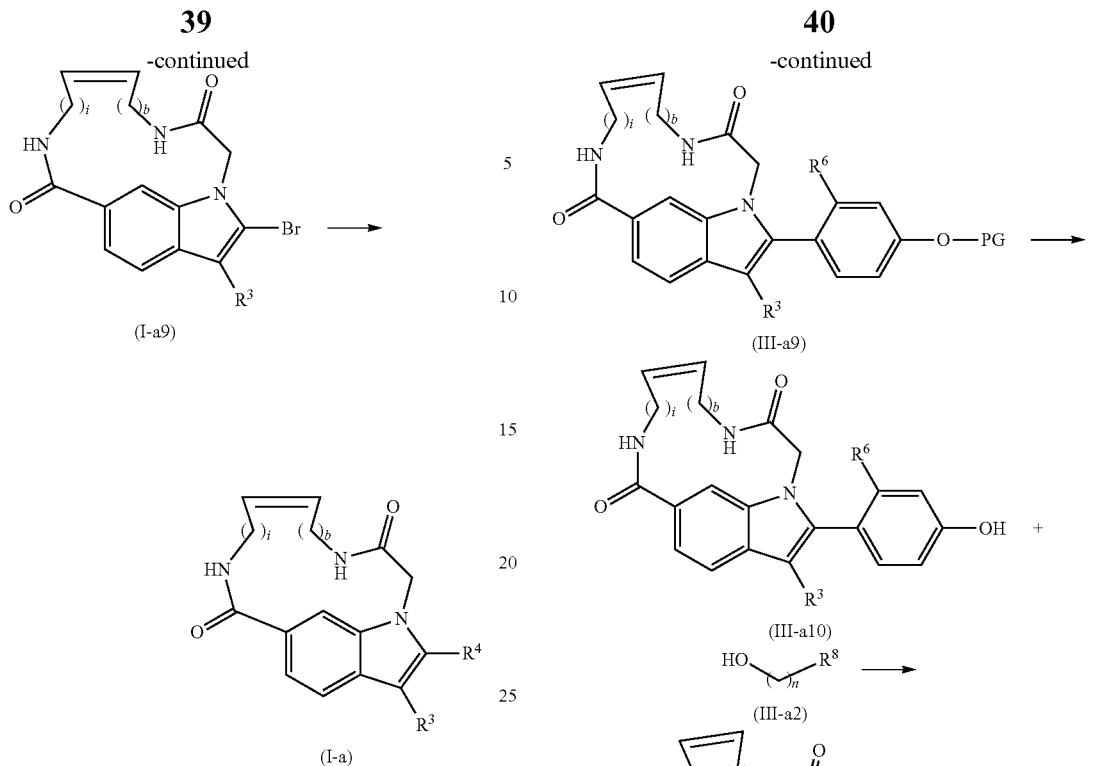

(I-a9)

(I-a)

(III-a9)

(III-a10)

(III-a2)

(III-1a)

The compound of formula (I-a6) may be obtained from intermediate (D) by the alkylation procedure as described for compound of formula (I-a2) above.

Compound of formula (I-a6) is then submitted to a hydrolysis in acid media or to a saponification as described for compound of formula (I-a2), in order to generate compound of formula (I-a7).

Compound of formula (I-a8) may be prepared by an amide forming reaction by reacting intermediate (I-a7) with an alkenylamine (I-a4), as described for compound of formula (I-a5).

Ring closure by an olefin metathesis reaction is then carried out in order to produce compound of formula (I-a9), which is then reacted with a boronic acid derivative (including ester derivatives) carrying the $R^4$ group, following the procedures described for compound of formula (I-a1) above. Compound of formula (I-a) is then obtained.

In an embodiment, compounds of formula (III-1a) can be prepared according to Scheme VI, as depicted below, wherein i is an integer equal to a+1, and $R^3$, b, n, $R^6$, PG and $R^8$ have the same meaning as that defined above.

Scheme VI

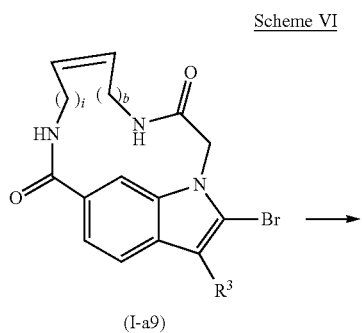

(I-a9)

Compound of formula (I-a9) is reacted with a boronic acid derivative (including ester derivatives) carrying a $R^6$-substituted phenyl, following the procedures described for compound of formula (III-a7) above. Compound of formula (III-a9) is then obtained.

Unmasking or deprotection of the hydroxyl in compound of formula (III-a9) leads to compound of formula (III-a10), which is then coupled to intermediate (III-a2) or (E) through a Mitsunobu or an alkylation reaction, respectively, as described above. Compound of formula (III-1a) is then obtained.

The compounds of formula (I) and the salts and stereoisomers thereof, wherein $R^1$ is the bivalent chain

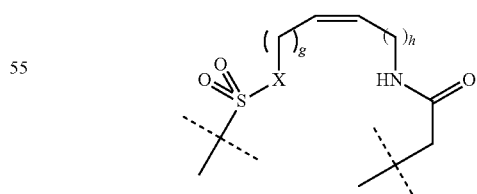

wherein the carbon atom carrying the $R^{5a}$ and $R^{5b}$ substituents is attached to the remainder of the molecule via the nitrogen atom of the amide group, and the carbon atom of the acetamide moiety is attached to the remainder of the molecule via the nitrogen atom of the indole ring of the compound of formula (I);

each of h, and g is, independently, 0, 1, 2, or 3, with the proviso that the macrocycle formed by the bivalent chain $R^1$, the —C(=O)—NH— moiety to which $R^1$ is attached and the nitrogen and carbon atoms N1, C6, C7, and C7' of the indole ring, has from 14 to 17 member atoms;

may be prepared according to Scheme VII, as depicted below, wherein $R^3$, $R^4$, and X have the same meaning as that defined above.

Scheme VII

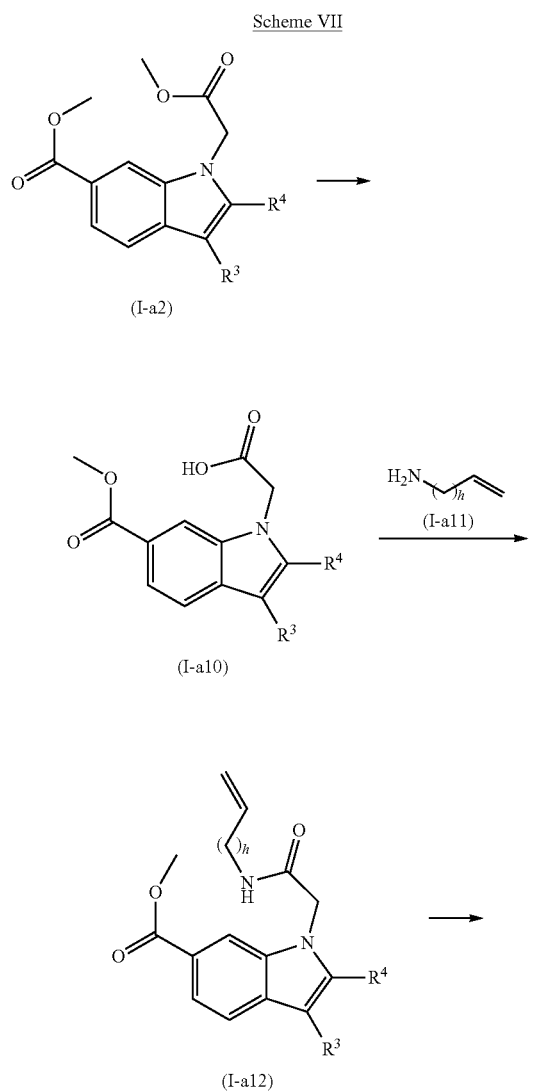

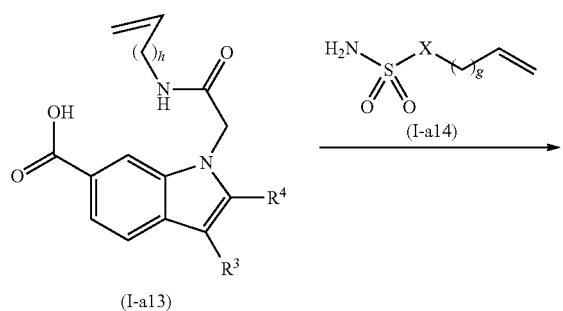

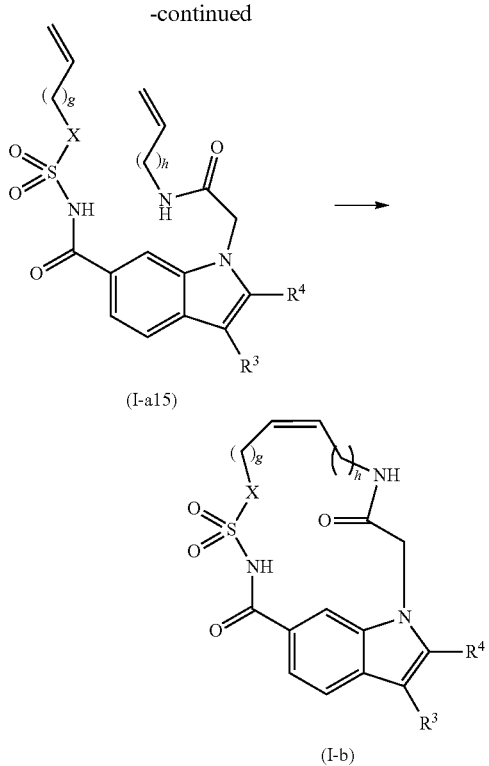

Sulfonamide compounds (I-b) may be obtained as described in scheme VII.

A compound of formula (I-a 10) may be obtained from an intermediate (I-a2) by regioselective cleavage of the acetic acid methylester moiety, for example by saponification at low temperature, such as 0° C.

A compound of formula (I-a12) may be prepared by an amide forming reaction by reacting intermediate (I-a 10) with an alkenylamine (I-a11), as described above for compound of formula (I-a5).

A compound of formula (I-a12) is then submitted to a hydrolysis in acid media or to a saponification as described for compound of formula (I-a3), in order to generate a compound of formula (I-a13).

A compound of formula (I-a15) may be obtained by coupling an intermediate (I-a13) with a sulfonamide (I-a14) in the presence of coupling agents, such as EDCI, in the presence of DMAP.

Ring closure by an olefin metathesis reaction is then carried out in order to produce a compound of formula (I-b).

Compounds of formula (I) may be converted into each other following art-known functional group transformation reactions. For example, amino groups may be N-alkylated, nitro groups reduced to amino groups, a halo atom may be exchanged for another halo.

In the previous scheme (I), an intermediate of formula (L) may be used as an alternative instead of an intermediate of formula (D). This compound (L) may be synthesized as described in US2007270405 A1. When using said alternative for an intermediate of formula (D), the methyl ester in the intermediates (I-a1), (I-a2), (III-a1), (III-a3), (III-a7), (III-a8), (I-a6), (I-a10) and (I-a12) as described in schemes (I), (II), (III), (V) and (VII), is replaced by the tertbutyl group. For the subsequent hydrolysis of this tertbutyl ester group, acidic conditions may be used, such as TFA in DCM, or HCl in isopropanol or another suitable organic solvent.

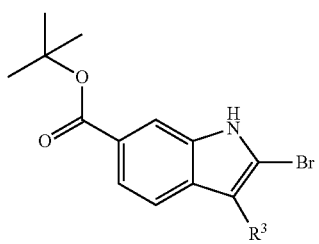

In schemes (VIII) and (IX), the group A is defined as the chain comprised between the carbonyl group and the sulfonyl group of the bivalent chains $R^1$ as shown below.

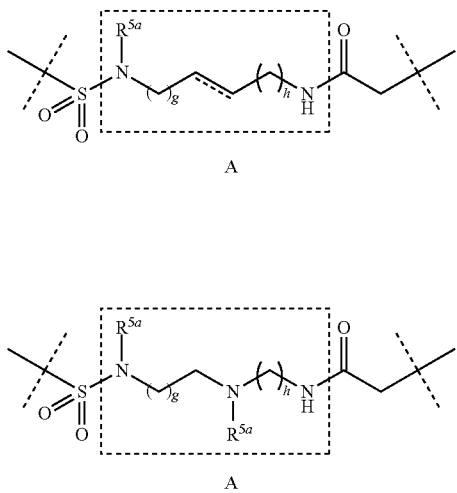

Such acylsulfonamide forming bivalent chains are generally depicted as follows:

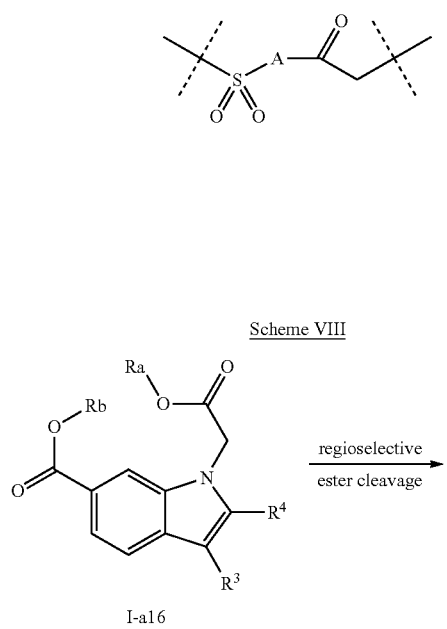

Scheme VIII

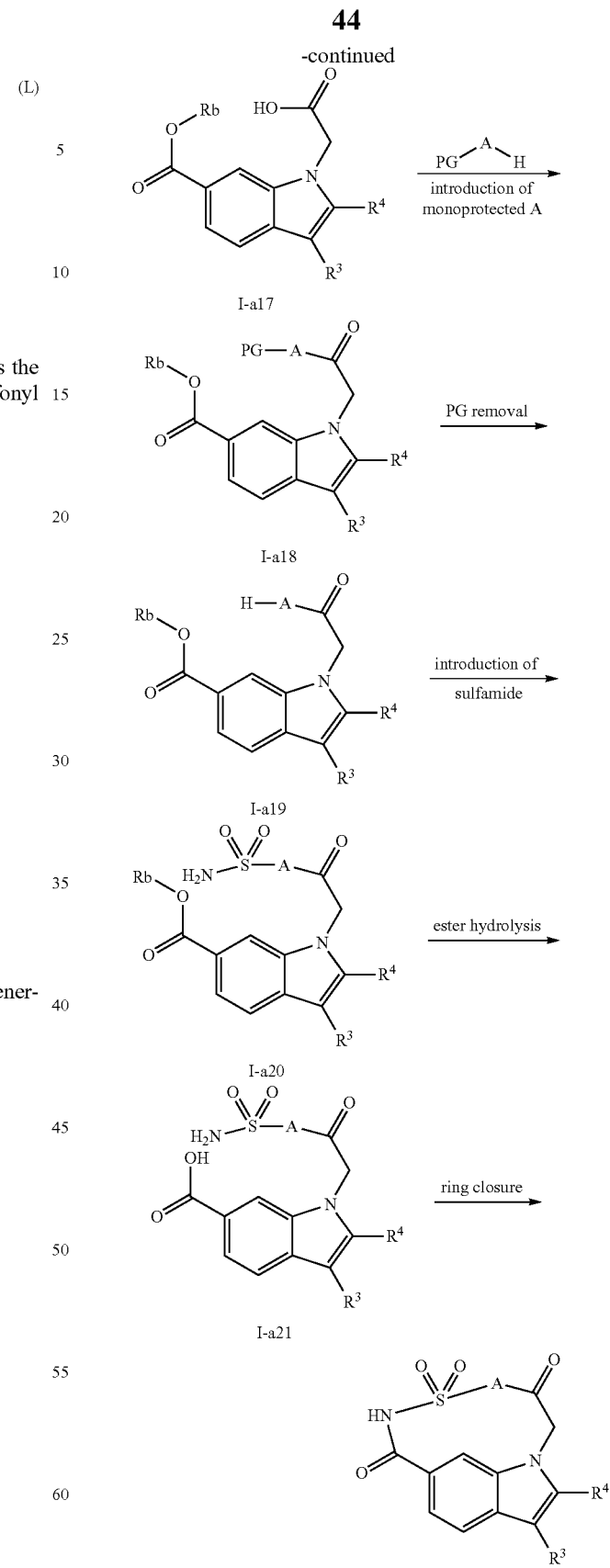

A schematic overview for the synthesis of the compounds of formula (I) bearing the acylsulfonamide chains described above is given in scheme (VIII). The method starts from a compound of formula (I-a16), where Ra and Rb may be a methyl group or a tertbutyl group, with the provisio that compounds (I-a16) have only one tertbutyl group (if Ra is tertbutyl then Rb is methyl, and vice-versa) and wherein $R^3$ and $R^4$ have the same meaning as that defined above or in any of the subgroups of compounds of formula (I) specified herein.

Compounds of formula I-a17 may be prepared by the regioselective hydrolysis of the ester bearing the Ra group, under basic conditions, using a hydroxide such as LiOH or NaOH, in polar solvents such as water, an alcohol such as methanol or ethanol, tetrahydrofurane (THF), or a mixture thereof, and at low temperature, for example 0° C. This method may be used when Ra is a methyl group. The regioselective hydrolysis of the ester bearing the Ra group may also be performed under acidic conditions when Ra is a tertbutyl group, using for example HCl in an appropriate organic solvent such as isopropanol, or TFA in DCM for example.

A monoprotected bifunctional derived reagent of formula PG-A-H wherein A is as defined above, may then be coupled to the carboxylic acid of compounds I-a17 to form an amide bond, leading to compounds I-a18. "PG", as used herein, is a suitable amine protecting group, chosen from the ones known in the art. Preferably PG is a tert-butyloxy carbonyl (Boc) protecting group or a 2-nitrobenzenesulfonyl (nosyl) group.

The formation of amide bonds can be carried out using standard procedures such as those used for coupling amino acids in peptide synthesis. The latter involves the dehydrative coupling of a carboxyl group of one reactant with an amino group of the other reactant to form a linking amide bond. The amide bond formation may be performed by reacting the starting materials in the presence of a coupling agent or by converting the carboxyl functionality into an active form such as an active ester, mixed anhydride or a carboxyl acid chloride or bromide. General descriptions of such coupling reactions and the reagents used therein can be found in general textbooks on peptide chemistry, for example, M. Bodanszky, "Peptide Chemistry", 2nd rev. ed., Springer-Verlag, Berlin, Germany, (1993).

Examples of coupling reactions with amide bond formation include the azide method, mixed carbonic-carboxylic acid anhydride (isobutyl chloroformate) method, the carbodiimide (dicyclohexylcarbodiimide (DCC), diisopropylcarbodiimide (DIC), or water-soluble carbodiimide such as N-ethyl-N'-[3-(dimethylamino)propyl]carbodiimide (EDC) method, the active ester method (e.g. p-nitrophenyl, p-chlorophenyl, trichlorophenyl, pentachlorophenyl, pentafluorophenyl, N-hydroxysuccinic imido and the like esters), the Woodward reagent K-method, the 1,1-carbonyldiimidazole (CDI or N,N'-carbonyldiimidazole) method, the phosphorus reagents or oxidation-reduction methods. Some of these methods can be enhanced by adding suitable catalysts, e.g. in the carbodiimide method by adding 1-hydroxybenzotriazole, or 4-dimethylamino-pyridine (4-DMAP). Further coupling agents are (benzotriazol-1-yloxy)-tris-(dimethylamino) phosphonium hexafluorophosphate, either by itself or in the presence of 1-hydroxy-benzotriazole or 4-DMAP; or 2-(1H-benzotriazol-1-yl)-N,N,N',R'-tetra-methyluronium tetrafluoroborate, or O-(7-azabenzotriazol-1-yl)-N,N,N',N'-tetramethyl-uronium hexafluorophosphate. These coupling reactions can be performed in either solution (liquid phase) or solid phase.

The coupling reactions preferably are conducted in an inert solvent, such as halogenated hydrocarbons, e.g. dichloromethane (DCM), chloroform, dipolar aprotic solvents such as acetonitrile, dimethylformamide (DMF), dimethylacetamide, DMSO, HMPT, ethers such as tetrahydrofuran (THF).

In many instances the coupling reactions are done in the presence of a suitable base such as a tertiary amine, e.g. triethylamine, diisopropylethylamine (DIPEA), N-methylmorpholine, N-methylpyrrolidine, 4-DMAP or 1,8-diazabicyclo[5.4.0]undec-7-ene (DBU). The reaction temperature may range between 0° C. and 50° C. and the reaction time may range between 15 min and 24 h.

Removal of the protecting group following methods known in the art may lead to compounds I-a19. These methods include the reaction of compounds I-a18 with trifluoro acetic acid (TFA) in a suitable solvent such as DCM, when PG is a Boc-protecting group, or the reaction of compounds I-a18 with a thiol like mercapto acetic acid or thiophenol, in solution or in solid phase, in the presence of a base, such as cesium carbonate or LiOH, in a suitable solvent, such as DMF, THF when PG is nosyl.

Compounds I-a19 are then reacted with sulfamide, in a suitable solvent, for example dioxane, under heating conditions, eg 100° C. This reaction may take place under microwave irradiation and lead to compounds I-a20. Another method to introduce the sulfamide moiety may consist of the reaction of compound I-a18 with aminosulfonyl-chloride, in the presence of a suitable base, such as triethylamine, DIPEA, or pyridine, in a suitable solvent, such as a chlorinated solvent like DCM, or DMF, THF.

The ester function of compounds I-a20 may then be hydrolyzed, using conditions known in the art, and including the saponification in basic media as described above, leading to compounds I-a21. Heating may be required to complete this reaction. Acidic conditions, such as TFA in DCM or HCl in isopropanol, may also be used when Rb is a tertbutyl group.

Compounds (I) bearing the acylsulfonamide chains may be obtained by macrocyclisation by forming the intramolecular acylsulfamide bond, in the presence of coupling agents, such as CDI which converts the carboxylic acid group to a reactive species acylimidazole, under heating. This acylimidazole may then be purified before adding a suitable base such as DBU, in order to perform the ring closure, which may take place under heating conditions. Solvents used for these reactions may include acetonitrile or THF. Other coupling agents, such as those known in the art, may also be used to achieve the ring closure.

Scheme IX

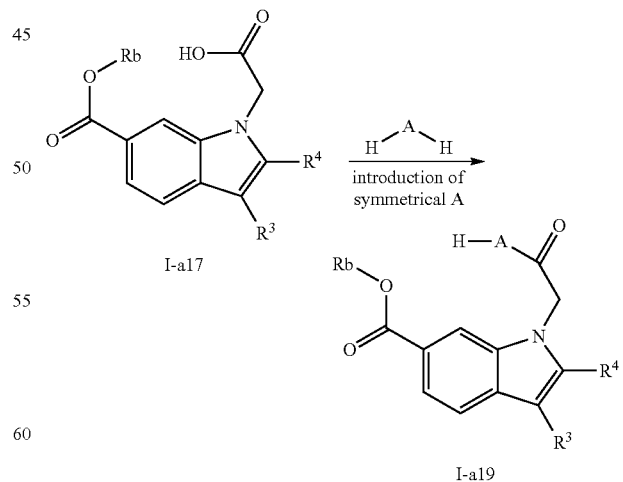

An alternative method leading to compounds I-a19 as illustrated in scheme (IX), may be the formation of an amide bond between compounds I-a17 and a symmetrical bivalent chain, used in excess compared to compounds I-a17. This amide bond may be synthesized as described above, in particular using a coupling agent such as [dimethylamino-([1,2,3]triazolo[4,5-b]pyridin-3-yloxy)-methylene]-dimethyl-ammonium hexafluorophosphate (HATU), in the presence of a base such as DIPEA and in a suitable solvent like DCM, DMF, or more preferably THF. Compounds I-a19 may then be reacted as described above in scheme (VIII) in order to prepare compounds (I) bearing the acylsulfonamide chains.

Compounds of formula (I), wherein $R^1$ are the bivalent chains

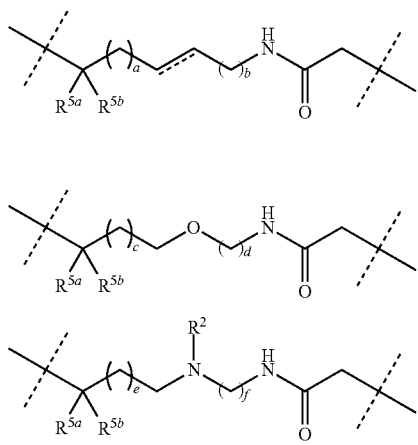

wherein $R^{5a}$, $R^{5b}$, a, b, c, d, e, f and $R^2$ have the same meaning as defined earlier, may be synthesized following scheme (X), wherein B stands for any one of the following chains

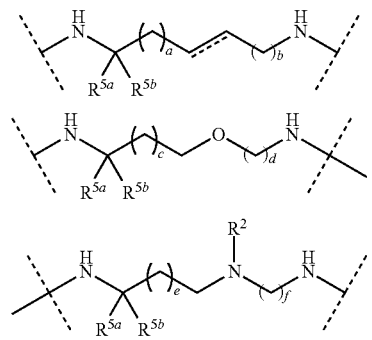

Scheme X

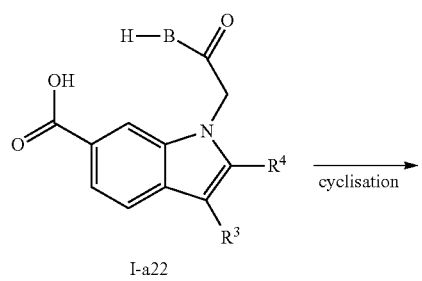

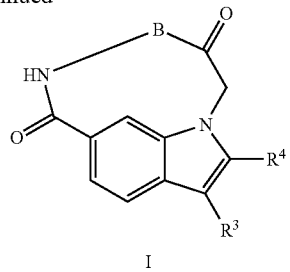

Compounds of formula (I-a22), obtained analogous to the route described in scheme (VIII) by replacing group A by group B, may be cyclized by forming an intramolecular amide bond using standard procedures such as those used for coupling amino acids in peptide synthesis described above for scheme (I). Preferably the macrocyclisation is performed with a coupling reagent such as HATU, in the presence of a base such as DIPEA, in a suitable organic solvent such as DMF, THF, CH3CN or DCM, under high dilution conditions. Those conditions may be obtained by adding dropwise a solution of compound (I-a22) to a solution of the above mentioned reagents.

Compounds of formula (I) wherein $R^1$ are the bivalent chains

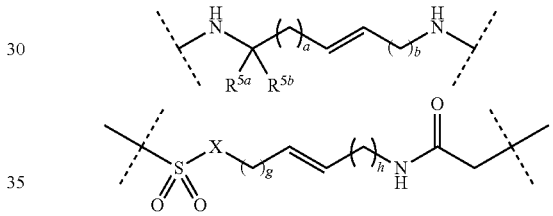

wherein $R^{5a}$, $R^{5b}$, a, b, g and h have the same meaning as defined earlier, may be reduced following methods known in the art, such as catalytic hydrogenation, using for example Pd/C as a catalyst, in a suitable solvent such as methanol, ethanol, THF, acetic acid or a mixture thereof, to yield compounds of formula I-2a or I-2b, where the alkene of the bivalent chain $R^1$ is reduced to the corresponding alkane.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarbo-peroxoic acid or halo substituted benzenecarboperoxoic acid, e.g. 3-chlorobenzene-carboperoxoic acid, peroxoalkanoic acids, e.g. peroxoacetic acid, alkylhydroperoxides, e.g. tert-butyl hydroperoxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) may be obtained as racemic mixtures of enantiomers which can be separated from one another following art-known resolution procedures. The racemic compounds of formula (I), which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound may be synthesized by stereospecific methods of preparation. These methods may advantageously employ enantiomerically pure starting materials.

In a further aspect, the present invention concerns a pharmaceutical composition comprising a therapeutically effective amount of a compound of formula (I) as specified herein, or a compound of any of the subgroups of compounds of formula (I) as specified herein, and a pharmaceutically acceptable carrier. A therapeutically effective amount in this context is an amount sufficient to prophylactically act against, to stabilize or to reduce viral infection, and in particular HCV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula (I), as specified herein, or of a compound of any of the subgroups of compounds of formula (I) as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula (I) show antiviral properties as shown in the experimental section below. Some of the compounds of formula (I) have also been tested in an in vivo rat model and showed favourable pharmacokinetic properties. In particular, compounds of formula (I) wherein $R^4$ is a phenyl or substituted phenyl group showed good pharmacokinetic properties.

Viral infections and their associated diseases treatable using the compounds and methods of the present invention include those infections brought on by HCV and other pathogenic flaviviruses such as Yellow fever, Dengue fever (types 1-4), St. Louis encephalitis, Japanese encephalitis, Murray valley encephalitis, West Nile virus and Kunjin virus. The diseases associated with HCV include progressive liver fibrosis, inflammation and necrosis leading to cirrhosis, end-stage liver disease, and HCC; and for the other pathogenic flaviviruses the diseases include yellow fever, dengue fever, hemorrhagic fever and encephalitis.

Due to their antiviral properties, particularly their anti-HCV properties, the compounds of formula (I) or any subgroup thereof, their N-oxides, salts, quaternary amines, metal complexes and stereochemically isomeric forms, are useful in the treatment of individuals experiencing a viral infection, particularly a HCV infection, and for the prophylaxis of these infections. In general, the compounds of the present invention may be useful in the treatment of warm-blooded animals infected with viruses, in particular flaviviruses such as HCV.

The compounds of the present invention or any subgroup thereof may therefore be used as medicines. Said use as a medicine or method of treatment comprises the systemic administration to viral infected subjects or to subjects susceptible to viral infections of an amount effective to combat the conditions associated with the viral infection, in particular the HCV infection.

The present invention also relates to the use of the present compounds or any subgroup thereof in the manufacture of a medicament for the treatment or the prevention of viral infections, particularly HCV infection.

The present invention furthermore relates to a method of treating a warm-blooded animal infected by a virus, or being at risk of infection by a virus, in particular by HCV, said method comprising the administration of an anti-virally effective amount of a compound of formula (I), as specified herein, or of a compound of any of the subgroups of compounds of formula (I), as specified herein.

The present invention also concerns combinations of a compound of formula (I) or any subgroup thereof, as specified herein with other anti-HCV agents.

The combination of previously known anti-HCV compound, such as, for instance, interferon-α (IFN-α), pegylated interferon-α, or ribavirin, and a compound of formula (I) can be used as a medicine in a combination therapy. The term "combination therapy" relates to a product containing mandatory (a) a compound of formula (I), and (b) at least one other anti-HCV compound, as a combined preparation for simultaneous, separate or sequential use in treatment of HCV infections, in particular, in the treatment of infections with HCV.

Anti-HCV compounds encompass agents selected from HCV polymerase inhibitors, R1626, R7128, MK-0608, VCH759, VCH916, PF-868554 and GS91-90; NM283, JTK109, JTK003, HCV371, HCV086, HCV796, XTL2125, GSK625433, ANA598, IDX184, MK3281, MK1220, A831, A689, ABT333, HCV proteases (NS2-NS3 and NS3-NS4A) inhibitors, the compounds of WO02/18369 (see, e.g., page 273, lines 9-22 and page 274, line 4 to page 276, line 11), BI-1335, TMC435350, VX-950, SCH 503034, MK70009 and ITMN-191; GS9132, TMC493706, BILN-2065, BMS605339, R7227, VX500, inhibitors of other targets in the HCV life cycle, including helicase, NS5A like BMS790052 and metalloprotease inhibitors, ISIS-14803; immunomodulatory agents such as, α-, β-, and γ-interferons, pegylated derivatized interferon-α compounds, compounds that stimulate the synthesis of interferon in cells, interleukins, Toll like receptor (TLR) agonists, compounds that enhance the development of type 1 helper T cell response, and thymosin; other antiviral agents such as ribavirin, amantadine, and telbivudine, inhibitors of internal ribosome entry, broad-spectrum viral inhibitors, such as IMPDH inhibitors (e.g., compounds of U.S. Pat. No. 5,807,876, U.S. Pat. No. 6,498,178, U.S. Pat. No. 6,344,465, U.S. Pat. No. 6,054,472, WO97/40028, WO98/40381, WO00/56331, and mycophenolic acid and derivatives thereof, and including, but not limited to VX-950, VX-497, VX-148, and/or VX-944); or combinations of any of the above.

Thus, to combat or treat HCV infections, the compounds of formula (I) may be co-administered in combination with for instance, interferon-α (IFN-α), pegylated interferon-α, ribavirin or a combination thereof, as well as therapeutics based on antibodies targeted against HCV epitopes, small interfering RNA (Si RNA), ribozymes, DNAzymes, antisense RNA, small molecule antagonists of for instance NS3 protease, NS3 helicase and NS5B polymerase.

The combinations of the present invention may be used as medicaments. Accordingly, the present invention relates to the use of a compound of formula (I) or any subgroup thereof as defined above for the manufacture of a medicament useful for inhibiting HCV activity in a mammal infected with HCV viruses, wherein said medicament is used in a combination therapy, said combination therapy preferably comprising a compound of formula (I) and at least one other HCV inhibitory compound, e.g. IFN-α, pegylated IFN-α, or ribavirin.

Furthermore, it is known that a large percentage of patients infected with human immunodeficiency virus 1 (HIV) are also infected with HCV, i.e. they are HCV/HIV co-infected. HIV infection appears to adversely affect all stages of HCV infection, leading to increased viral persistence and accelerated progression of HCV-related liver disease. In turn, HCV infection may affect the management of HIV infection, increasing the incidence of liver toxicity caused by antiviral medications.

The present invention therefore also concerns combinations of a compound of formula (I) or any subgroup thereof with anti-HIV agents. Also, the combination of one or more additional anti-HIV compounds and a compound of formula (I) can be used as a medicine.

The term "combination therapy" also encompasses a product comprising (a) a compound of formula (I), and (b) an anti-HIV compound, and (c) optionally another anti-HCV compound, as a combined preparation for simultaneous, separate or sequential use in treatment of HCV and HIV infections, in particular, in the treatment of infections with HCV and HIV.

Thus, the present invention also relates to a product containing (a) a compound of formula (I) or any subgroup thereof, and (b) one or more additional anti-HIV compounds, as a combined preparation for simultaneous, separate or sequential use in anti-HCV and anti-HIV treatment. The different drugs may be combined in a single preparation together with pharmaceutically acceptable carriers. Said other anti-HIV compounds may be any known antiretroviral compounds such as suramine, pentamidine, thymopentin, castanospermine, dextran (dextran sulfate), foscarnet-sodium (trisodium phosphono formate); nucleoside reverse transcriptase inhibitors (NRTIs), e.g. zidovudine (AZT), didanosine (ddI), zalcitabine (ddC), lamivudine (3TC), stavudine (d4T), emtricitabine (FTC), abacavir (ABC), amdoxovir (DAPD), elvucitabine (ACH-126,443), AVX 754 ((−)-dOTC), fozivudine tidoxil (FZT), phosphazide, HDP-990003, KP-1461, MIV-210, racivir (PSI-5004), UC-781 and the like; non-nucleoside reverse transcriptase inhibitors (NNRTIs) such as delavirdine (DLV), efavirenz (EFV), nevirapine (NVP), dapivirine (TMC120), etravirine (TMC125), rilpivirine (TMC278), DPC-082, (+)-Calanolide A, BILR-355, and the like; nucleotide reverse transcriptase inhibitors (NtRTIs), e.g. tenofovir ((R)-PMPA) and tenofovir disoproxil fumarate (TDF), and the like; nucleotide-competing reverse transcriptase inhibitors (NcRTIs), e.g. NcRTI-1 and the like; inhibitors of trans-activating proteins, such as TAT-inhibitors, e.g. RO-5-3335, BI-201, and the like; REV inhibitors; protease inhibitors e.g. ritonavir (RTV), saquinavir (SQV), lopinavir (ABT-378 or LPV), indinavir (IDV), amprenavir (VX-478), TMC126, nelfinavir (AG-1343), atazanavir (BMS 232, 632), darunavir (TMC114), fosamprenavir (GW433908 or VX-175), brecanavir (GW-640385, VX-385), P-1946, PL-337, PL-100, tipranavir (PNU-140690), AG-1859, AG-1776, Ro-0334649 and the like; entry inhibitors, which comprise fusion inhibitors (e.g. enfuvirtide (T-20)), attachment inhibitors and co-receptor inhibitors, the latter comprise the CCR5 antagonists (e.g. ancriviroc, CCR5 mAb004, maraviroc (UK-427,857), PRO-140, TAK-220, TAK-652, vicriviroc (SCH-D, SCH-417,690)) and CXR4 antagonists (e.g. AMD-070, KRH-27315), examples of entry inhibitors are PRO-542, TNX-355, BMS-488,043, BlockAide/CR™, FP 21399, hNM01, nonakine, VGV-1; a maturation inhibitor for example is PA-457; inhibitors of the viral integrase e.g. raltegravir (MK-0518), elvitegravir (JTK-303, GS-9137), BMS-538,158; ribozymes; immunomodulators; monoclonal antibodies; gene therapy; vaccines; siRNAs; antisense RNAs; microbicides; Zinc-finger inhibitors.

Therefore, HCV infected patients also suffering from conditions associated with HIV or even other pathogenic retroviruses, such as AIDS, AIDS-related complex (ARC), progressive generalized lymphadenopathy (PGL), as well as chronic CNS diseases caused by retroviruses, such as, for example HIV mediated dementia and multiple sclerosis, can conveniently be treated with the present composition.

The compositions may be formulated into suitable pharmaceutical dosage forms such as the dosage forms described above. Each of the active ingredients may be formulated separately and the formulations may be co-administered or one formulation containing both and if desired further active ingredients may be provided.

As used herein, the term "composition" is intended to encompass a product comprising the specified ingredients, as well as any product which results, directly or indirectly, from the combination of the specified ingredients.

The term "therapeutically effective amount" as used herein means that amount of active compound or component or pharmaceutical agent that elicits the biological or medicinal response in a tissue, system, animal or human that is being sought, in the light of the present invention, by a researcher, veterinarian, medical doctor or other clinician, which includes alleviation of the symptoms of the disease being treated. Since the instant invention refers as well to combinations comprising two or more agents, the "therapeutically effective amount" in the context of combinations is also that amount of the agents taken together so that the combined effect elicits the desired biological or medicinal response. For example, the therapeutically effective amount of a composition comprising (a) the compound of formula (I) and (b) another anti-HCV agent, would be the amount of the compound of formula (I) and the amount of the other anti-HCV agent that when taken together have a combined effect that is therapeutically effective.

In general, it is contemplated that an antiviral effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

In one embodiment of the present invention there is provided an article of manufacture comprising a composition effective to treat an HCV infection or to inhibit the NS5B polymerase of HCV; and packaging material comprising a label which indicates that the composition can be used to treat infection by the hepatitis C virus; wherein the composition comprises a compound of the formula (I) or any subgroup thereof, or the combination as described herein.

Another embodiment of the present invention concerns a kit or container comprising a compound of the formula (I) or any subgroup thereof, in an amount effective for use as a standard or reagent in a test or assay for determining the ability of potential pharmaceuticals to inhibit HCV NS5B polymerase, HCV growth, or both. This aspect of the invention may find its use in pharmaceutical research programs.

The compounds and combinations of the present invention can be used in high-throughput target-analyte assays such as those for measuring the efficacy of said combination in HCV treatment.

EXAMPLES

The following examples are intended to illustrate the present invention and not to limit it thereto.

Example 1

Synthesis of 17-cyclohexyl-18-(furan-3-yl)-1,4,11-triaza-tricyclo-[11.5.2.0$^{16,19}$]icosa-7,13(20),14,16 (19),17-pentaene-3,12-dione (1)

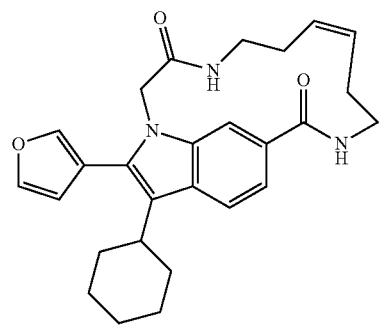

Step A.

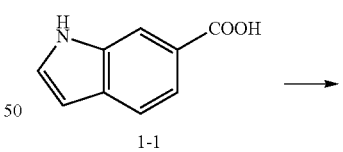

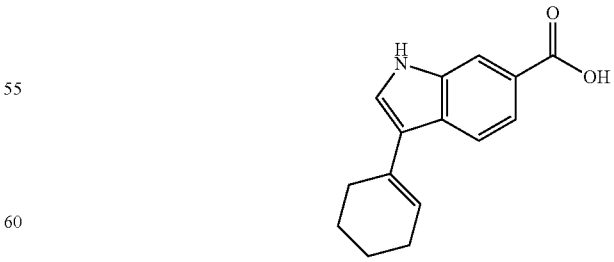

Cyclohexanone (18.2 g, 186 mmol) was added to a solution of indole-6-carboxylic acid 1-1 (10.0 g, 62.0 mmol) in methanol (100 mL). Then, a solution of sodium methoxide (20.4 g, 378.5 mmol) in methanol (50 mL) was added dropwise. The resulting solution was heated to reflux. After 5 days, the reaction mixture was evaporated and ice-cold water (250 mL) was added. The precipitate was filtered off, washed with water and dried under vacuum to give 12.0 g (80.1%) of the target compound I-2: m/z=242 (M+H)$^+$.

Step B.

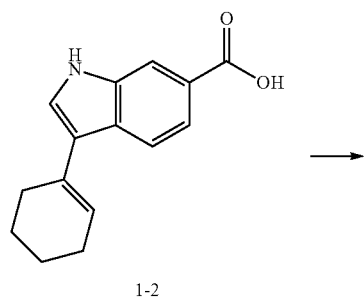

1-2

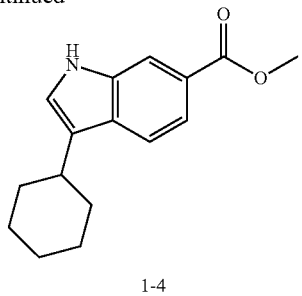

1-4

Thionyl chloride (135 μL, 1.85 mmol) was added to a solution of 3-cyclohexylindole-6-carboxylic acid (1-3, 1.80 g, 7.4 mmol) in methanol (20 mL). The resulting solution was heated to reflux for 1 h, then allowed to cool down to room temperature. The reaction mixture was concentrated under vacuum. Then, the residue was partitioned between CH$_2$Cl$_2$ and ice-cold water, dried and evaporated to give 1.05 g (55.2%) of the target product 1-4: m/z=258 (M+H)$^+$.

Step D.

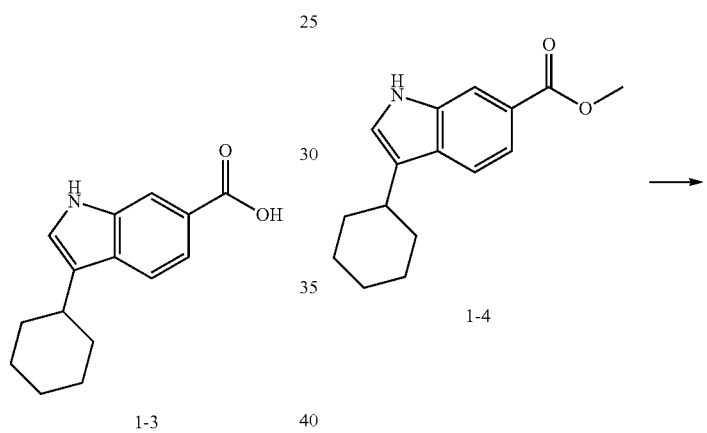

1-3     1-4

A mixture of 1-2 (14.0 g, 58 mmol) and 20% Pd(OH)$_2$/C (600 mg) in methanol (50 mL) and THF (50 mL) was shaken in a hydrogenation apparatus under 55 psi pressure at room temperature for 3 h. The catalyst was removed by filtration and washed with methanol. The filtrate was concentrated to dryness. The residue was triturated in hexane, then the beige solid was collected by filtration, washed with hexane and dried under vacuum to give 12.3 g (87%) of the target product 1-3: m/z=244 (M+H)$^+$.

Step C.

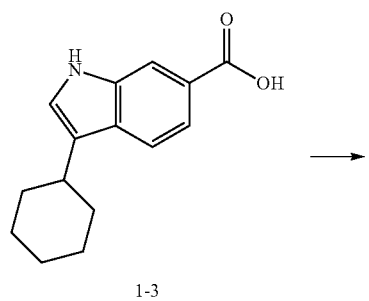

1-3

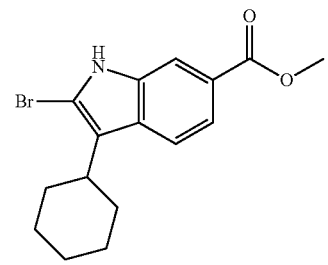

1-5

Methyl 3-cyclohexyl-6-indole carboxylate (1-4, 8.00 g, 31.1 mmol) was dissolved in a mixture of THF (20 mL) and CHCl$_3$ (20 mL). Then, the solution was cooled at 0° C. and pyridine tribromide (8.00 g, 31.1 mmol) was added. After 1.5 h at 0° C., the reaction mixture was diluted with CHCl$_3$ (40 mL), washed with 1N NaHSO$_3$, saturated NaHCO$_3$ and brine. The organic layer was dried (Na$_2$SO$_4$) and evaporated to dryness. Purification by column chromatography (ethyl acetate/hexane 1:1) afforded 7.70 g (73.7%) of the target compound 1-5: m/z=337 (M+H)$^+$.

Step E.

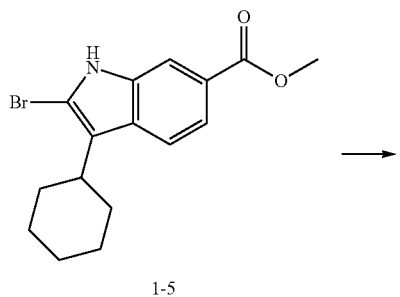

1-5

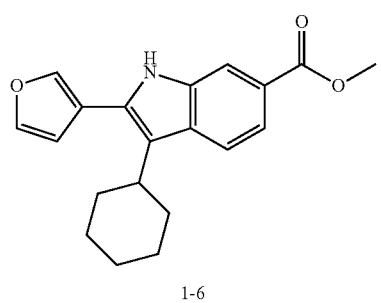

1-6

A solution of Na$_2$CO$_3$ (1M, 31.2 mmol) was added to a solution of the 2-bromoindole 1-5 (5.00 g, 14.8 mmol), 3-furanboronic acid (2.50 g, 22.3 mmol), and LiCl (1.26 g, 29.7 mmol) in a mixture of ethanol (50 mL) and toluene (50 mL). The reaction mixture was degassed with nitrogen. Then, tetrakis(triphenylphosphine)palladium(0) (1.72 g, 1.49 mmol) was added. The resulting reaction mixture was stirred at 80° C. under inert atmosphere. After 12 h, the reaction mixture was allowed to cool down to room temperature and volatiles were removed under reduced pressure. The residue was partitioned between NaHCO$_3$ 0.5 N and ethyl acetate. The organic layer was dried (Na$_2$SO$_4$), evaporated and purified by column chromatography (gradient of ethyl acetate/CH$_2$Cl$_2$ 1:9 to 1:1). Crystallization from isopropanol yielded 4.12 g (85.6%) of the target product 1-6: m/z=324 (M+H)$^+$.

Step F.

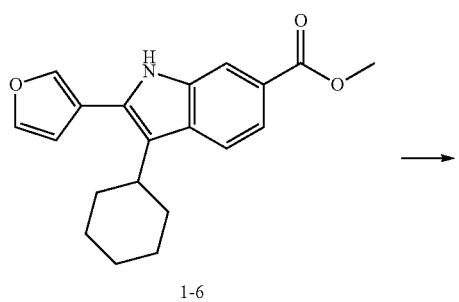

1-6

-continued

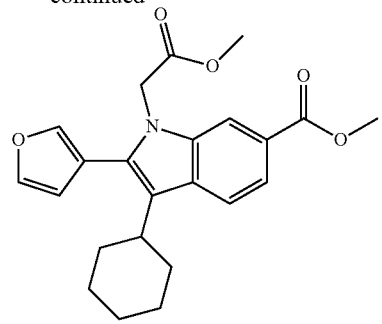

1-7

A dispersion of NaH in mineral oil was added at 0° C. to a solution of the ester 1-6 and bromoacetic acid methyl ester (615 mg, 4.02 mmol) in dry dimethylformamide (DMF; 5 mL). After 10 min at 0° C., the reaction mixture was warmed up to room temperature for 1 h. Then, the solution was poured into ice-cold water and extracted with ethyl acetate, dried (Na$_2$SO$_4$) and evaporated. The crude material was purified by column chromatography (ethyl acetate/CH$_2$Cl$_2$/heptane, 1:4:5) to give the target product 1-7, which was triturated in ether, filtered and washed with petroleum ether. The target product 1-7 (1.0 g, 82%) was obtained as a yellowish powder: m/z=396 (M+H)$^+$.

Step G.

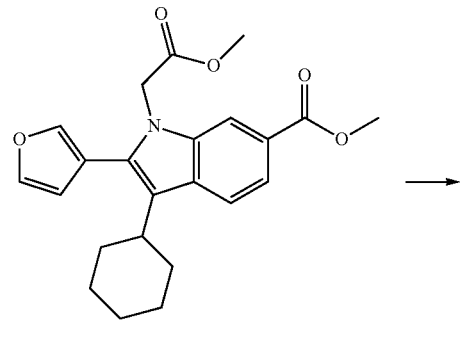

1-7

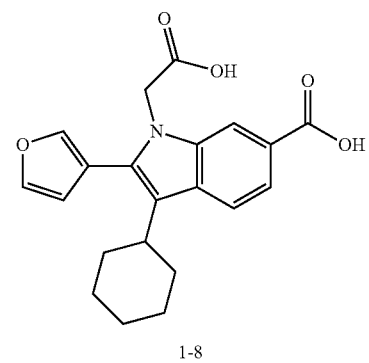

1-8

A solution of lithium hydroxide (1.54 g, 63.1 mmol) in water (50 mL) was added to a solution of the diester 1-7 (1.0 g, 2.53 mmol) in methanol (100 mL) and tetrahydro-furan (THF; 50 mL). The resulting solution was stirred at room temperature for 48 h. Then, volatiles were evaporated under reduced pressure. The residue was dissolved in water (100 mL) and the pH of the solution was adjusted to 3 with a 1N aqueous solution of HCl. The resulting solution was successively extracted with ethyl acetate, dried (Na$_2$SO$_4$) and evaporated. The residue was triturated in ether, then filtered off to afford 680 mg (73.2%) of the target diacid 1-8 as a yellowish powder: m/z=368 (M+H)$^+$.

Step H.

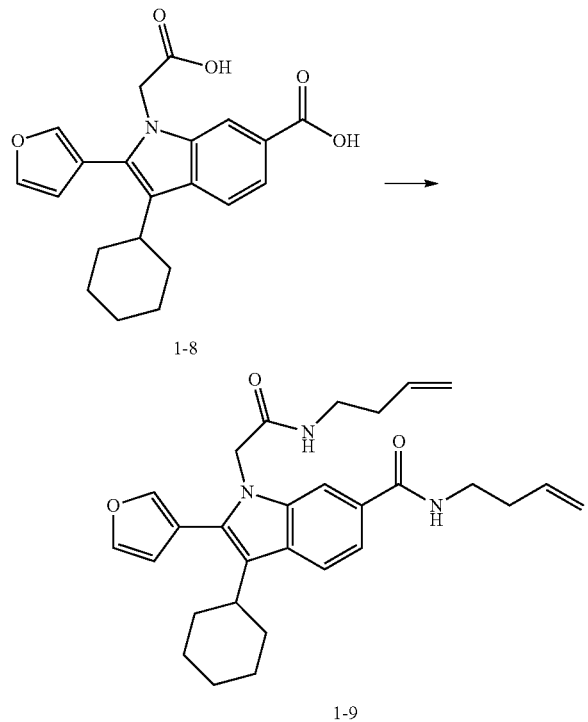

1-8

1-9

2-(1H-7-azabenzotriazol-1-yl)-1,1,3,3-tetramethyl uronium hexafluorophosphate methanaminium (HATU) (466 mg, 1.22 mmol) was added to a stirred solution of the diacid 1-8 (150 mg, 0.408 mmol) and but-3-enylamine (116 mg, 1.63 mmol) in DMF (5 mL). Then, diisopropylethylamine (284 µL, 1.63 mmol) was added dropwise. After 12 h, the reaction mixture was successively partitioned between ethyl acetate and ice-cold water, dried (Na$_2$SO$_4$) and evaporated. The residue was purified by column chromatography (ethyl acetate/hexane 1:1) to give 161 mg (83.3%) of the target product 1-9 as a white powder: m/z=474 (M+H)$^+$.

Step I.

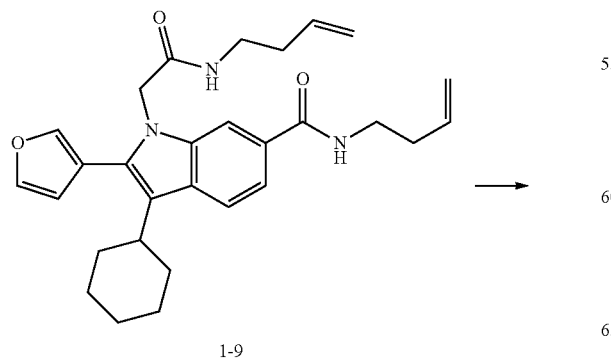

1-9

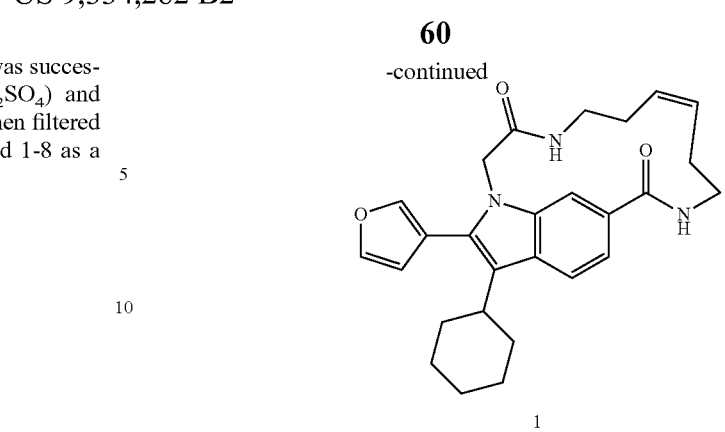

1

A solution of 1-9 (150 mg, 0.317 mmol) and Hoveyda-Grubbs 1$^{st}$ generation catalyst (19 mg, 0.032 mmol) in degassed dichloroethane (200 mL) was heated at 80° C. for 12 h. Then, additional catalyst (20 mg, 0.034 mmol) was added and the reaction mixture was heated for another 3 h at 80° C. Then, the reaction mixture was concentrated under vacuum and the residue was purified by column chromatography (gradient CH$_2$Cl$_2$/ethyl acetate/heptane, 2:2:1 to 0:1:0). Crystallization from ethyl acetate provided 35 mg (22%) of the target product 1 as a white powder: m/z=446 (M+H)$^+$.

Example 2

17-Cyclohexyl-18-(furan-3-yl)-1,4,11-triaza-tricyclo[11.5.2.0$^{16,19}$]icosa-13(20),14,16(19),17-tetraene-3,12-dione (2)

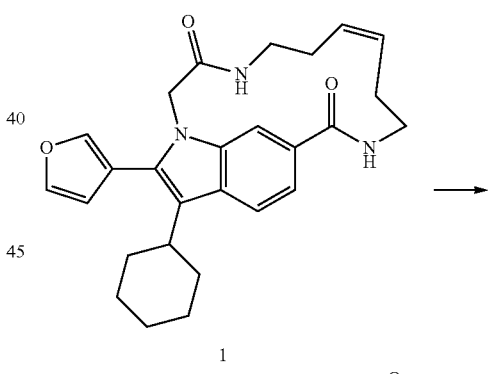

1

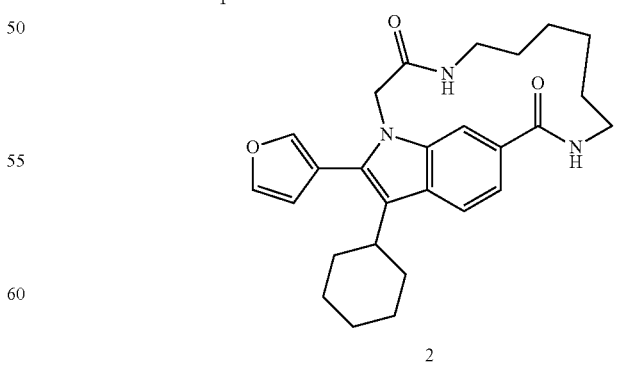

2

A mixture of 1 (30 mg, 0.067 mmol) and 10% Pd/C (20 mg) in methanol (10 mL) and THF (10 mL) was shaken in a hydrogenation apparatus under 55 psi pressure at room temperature for 1 h. The catalyst was removed by filtration and washed with methanol. The filtrate was concentrated to dryness. Filtration on silica gel afforded 24 mg (80%) of the target product 2: m/z=448 (M+H)$^+$.

Example 3

Preparation of 17-cyclohexyl-18-[4-[2-(4 methanesulfonylpiperazin-1-yl)-5-nitrobenzyloxy]phenyl]-1,4,11-triazatricyclo[11.5.2.0$^{16,19}$]icosa-7,13(20),14,16(19),17-pentaene-3,12-dione (3)

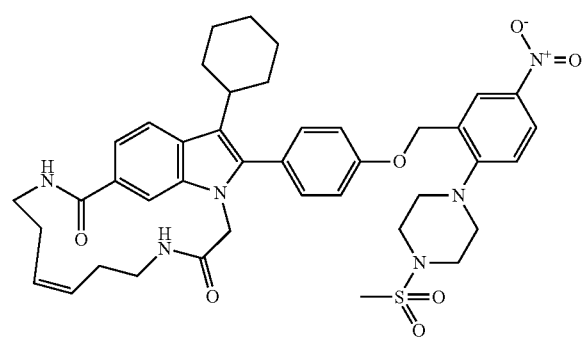

Step A.

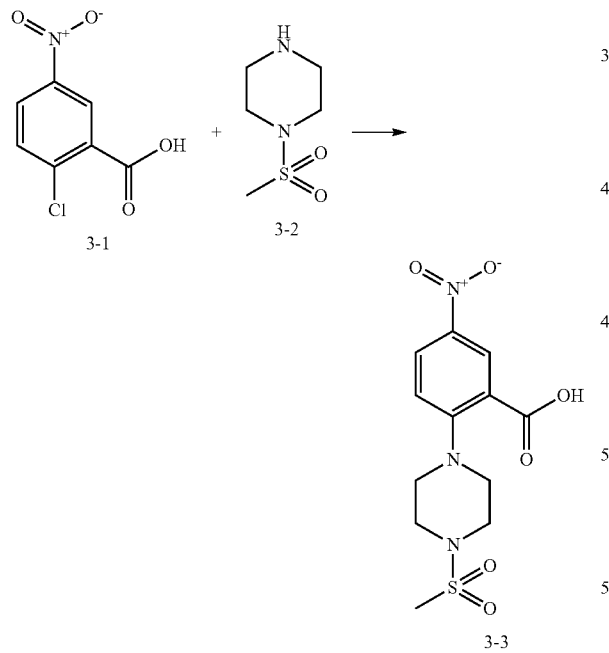

A solution of 2-chloro-5-nitrobenzoic acid 3-1 (101 mg, 0.503 mmol), N-methyl-sulfonylpiperazine 3-2 (110 mg, 0.673 mmol) and cesium carbonate (335 mg, 1.03 mmol) in DMF (5 mL) was heated at 100° C. under nitrogen. After 12 h, the reaction mixture was successively cooled down at room temperature and acidified to pH 5 with an aqueous 6 N solution of HCl. The precipitate was collected by filtration to give 75 mg (45.3%) of the target product 3-3: m/z=330 (M+H)$^+$.

On larger scale (4.53 g of 3 1) the target product 3-3 was obtained with a yield of 87.1%.

Step B.

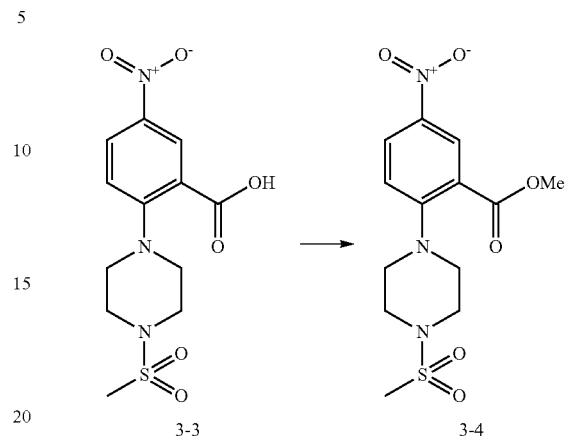

A solution of acid 3-3 (508 mg, 1.54 mmol), methyliodide (120 μL, 1.93 mmol) and NaHCO$_3$ (220 mg, 2.61 mmol) in dry DMF (10 mL) was stirred at room temperature for 12 h. Then, the reaction mixture was diluted with water (400 mL). The precipitate was collected by filtration, washed with water and isopropylether, then dried under vacuum to give 491 mg (93%) of the target product 3-4: m/z=344 (M+H)$^+$.

Step C.

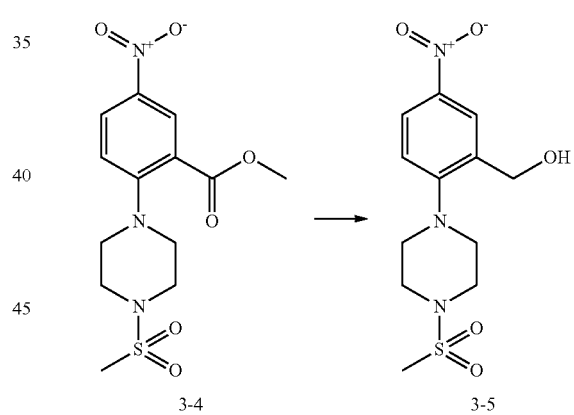

LiAlH$_4$ (113 mg, 2.99 mmol) was added at 0° C. under nitrogen to a suspension of the nitro derivative 3-4 (491 mg, 1.43 mmol) in dry THF (20 mL). The resulting orange suspension was stirred at room temperature for 3 days. Then, LiAlH$_4$ (57 mg, 1.45 mmol) was added. The resulting reaction mixture was stirred for an additional 12 h at room temperature. Then, the reaction mixture was successively diluted with ice-cold water, and the pH was adjusted to 5 with acetic acid. The resulting solution was extracted with ethyl acetate, dried (Na$_2$SO$_4$) and evaporated to dryness. The residue was purified by column chromatography (ethyl acetate/CH$_2$Cl$_2$, 15:85) to give the target product 3-5: m/z=316 (M+H)$^+$.

Step D.

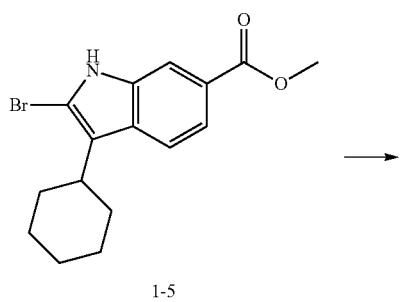

1-5

A 1 M solution of K₂CO₃ (10 mL) was added to a solution of bromoindole 1-5 (1.83 g, 5.43 mmol), 4-benzyloxybenzeneboronic acid (1.86 g, 8.15 mmol) and bis(triphenylphosphine)palladium (II) chloride (420 mg, 0.599 mmol) in ethanol (20 mL) and toluene (20 mL). The resulting reaction mixture was heated at 80° C. for 12 h. Then, volatiles were evaporated under vacuum. The residue was successively partitioned between ethyl acetate and diluted NaHCO₃, washed with brine, dried (Na₂SO₄) and evaporated. The residue was triturated in methanol, then filtered off to give 1.55 g (65%) of the target product 3-6: m/z=440 (M+H)⁺.

Step E.

A dispersion of NaH in mineral oil (60%, 180 mg, 4.50 mmol) was added at 0° C. to a solution of the ester 3-6 and bromoacetic acid methyl ester (703 mg, 4.59 mmol) in dry DMF (12 mL). After 20 min at 0° C., the reaction mixture was warmed up to room temperature for 1 h. Then, the solution was poured into ice-cold water (200 mL). The precipitate was filtered off, washed with water and petroleum ether to give 1.45 g (80.5%) of the target product 3-7 as a yellow powder: m/z=512 (M+H)⁺.

Step F.

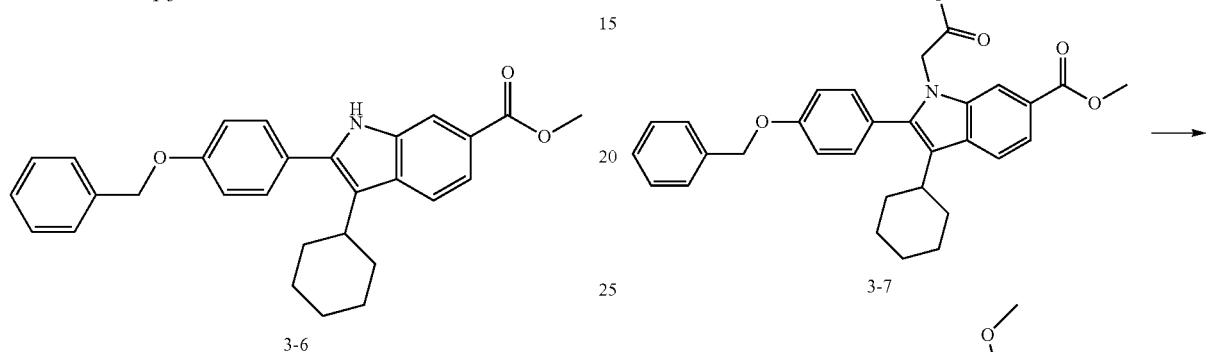

A mixture of 3-7 (1.45 g, 2.84 mmol) and 10% Pd/C (200 mg) in methanol (100 mL) and THF (100 mL) was shaken in a hydrogenation apparatus under 55 psi pressure at room temperature for 2 h. The catalyst was removed by filtration and washed with methanol. The filtrate was concentrated to dryness. Filtration on silica gel afforded 1.11 g (92%) of the target product 3-8: m/z=422 (M+H)⁺.

Step G.

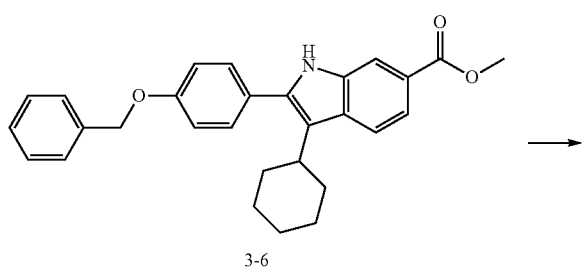

3-6

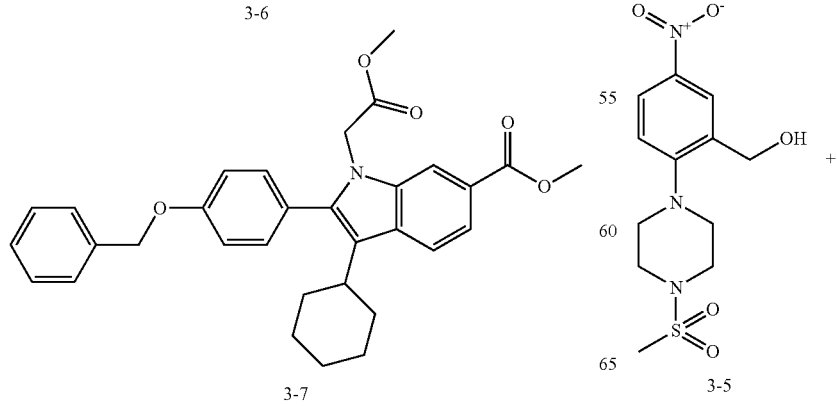

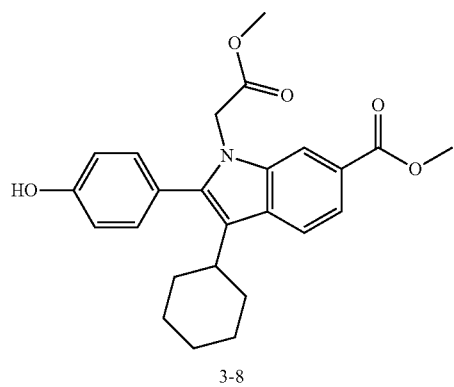

3-8

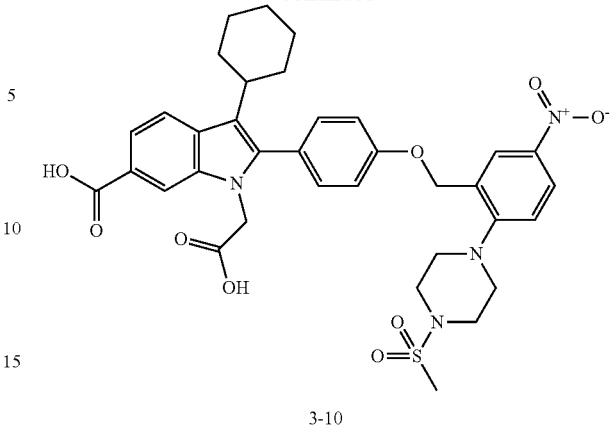

3-10

Intermediate 3-10 was prepared in 99.9% yield by adding a solution of lithium hydroxide in water to 3-9 in methanol and THF. The resulting solution was stirred at room temperature for 48 h. Then, volatiles were evaporated under reduced pressure. The residue was dissolved in water and the pH of the solution was adjusted to 3 with a 1 N aqueous solution of HCl. The resulting solution was successively extracted with ethyl acetate, dried ($Na_2SO_4$) and evaporated. The residue was triturated in ether, then filtered off to afford the target diacid 3-10: m/z=691 (M+H)$^+$.

Step I.

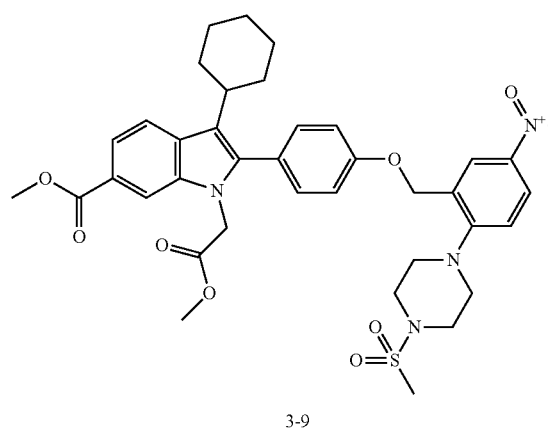

3-9

DIAD (100 µL, 0.507 mmol) was added at 0° C. under nitrogen to a stirred solution of sulfonamide 3-5 (107 mg, 0.338 mmol), indole 3-8 (139 mg, 0.328 mmol) and triphenylphosphine (162 mg, 0.618 mmol) in dry THF (10 mL). Then, the reaction mixture was allowed to warm up to room temperature. After 12 h, volatiles were evaporated and the residue was purified by column chromatography (ethyl acetate/$CH_2Cl_2$, 15:85) to give 138 mg of the desired product 3-9: m/z=719 (M+H)$^+$.

Step H.

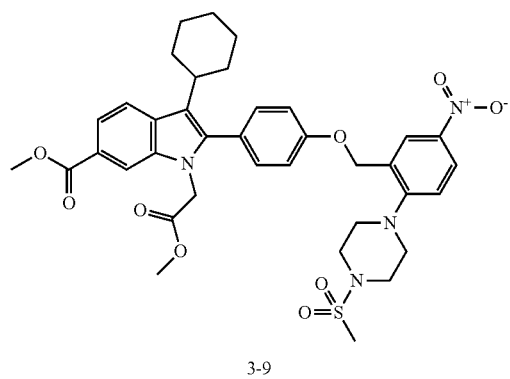

3-9

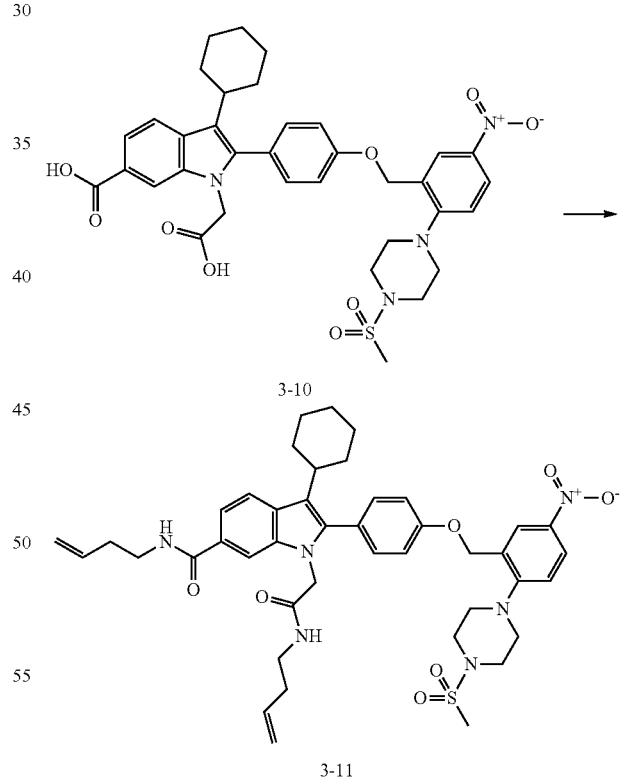

Intermediate 3-11 was prepared in 69.7% yield by adding HATU to a stirred solution of the diacid 3-10 and but-3-enylamine in DMF. Then, diisopropylethylamine was added dropwise. After 12 h, the reaction mixture was successively partitioned between ethyl acetate and ice-cold water, dried ($Na_2SO_4$) and evaporated. The residue was purified by column chromatography (ethyl acetate/hexane 1:1) to give the target product 3-11: m/z=797 (M+H)$^+$.

Step J.

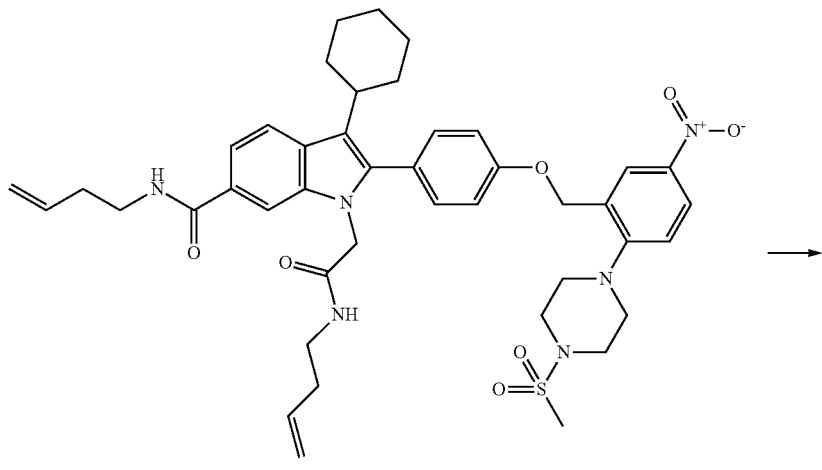

Intermediate 3 was prepared in 70% yield by heating a solution of 3-11 and Hoveyda-Grubbs 1$^{st}$ generation catalyst in degassed dichloroethane at 80° C. for 12 h. Then, additional catalyst was added and the reaction mixture was heated for another 3 h at 80° C. Next, the reaction mixture was concentrated under vacuum and the residue was purified by column chromatography (gradient CH$_2$Cl$_2$/ethyl acetate/heptane, 2:2:1 to 0:1:0). Crystallization from ethyl acetate provided the target product 3: m/z=769 (M+H)$^+$.

Example 4

17-cyclohexyl-18-[4-[2-(4 methanesulfonylpiperazin-1-yl)-5-amino-benzyloxy]phenyl]-1,4,11-triazatricyclo[11.5.2.0$^{16,19}$]icosa-7,13(20),14,16(19),17-pentaene-3,12-dione (4)

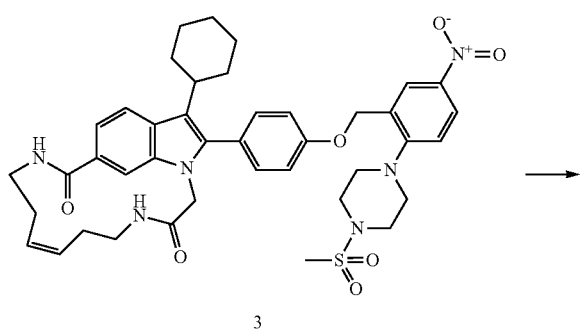

Tin(II) chloride dihydrate (400 mg, 1.77 mmol) was added to a solution of 3 (55 mg, 0.0715 mmol) in THF (1 mL) and ethanol (1.5 mL). The reaction mixture was heated at reflux for 3 days, then allowed to cool down to room temperature. Then, volatiles were evaporated under vacuum and the residue was successively partitioned between a diluted solution of NaHCO$_3$ and ethyl acetate, dried (Na$_2$SO$_4$) and evaporated. Purification by column chromatography (CH$_2$Cl$_2$/ methanol, 97.5:2.5) afforded the title compound 4 as a yellowish powder: m/z=740 (M+H)⁺.

Example 5

17-cyclohexyl-18-[4-[2-(4 methanesulfonylpiperazin-1-yl)-5-acetylamino-benzyloxy]phenyl]-1,4,11-triazatricyclo[11.5.2.0$^{16,19}$]icosa-7,13(20),14,16(19),17-pentaene-3,12-dione (5)

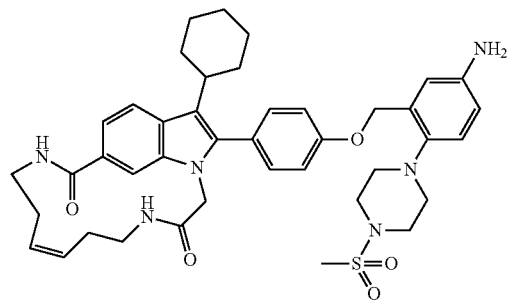

4

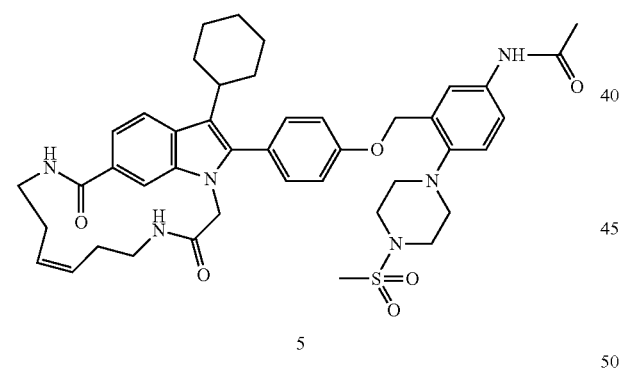

5

Acetyl chloride (4 μL, 0.057 mmol) was added under nitrogen to a solution of 4 (38 mg, 0.051 mmol) and N,N'-diisopropylethylamine (DIPEA; 8.7 μL, 0.062 mmol) in CHCl₃ (2 mL). After 12 h, the reaction mixture was successively partitioned between CHCl₃ and diluted NaHCO₃, dried (Na₂SO₄) and evaporated. The residue was purified by column chromatography to give 25 mg (61.7%) of the title product 5 as a white powder: m/z=782 (M+H)⁺. NMR (DMSO-d6): δ (ppm) 1.19-1.35 (m, 4H), 1.68-1.77 (m, 4H), 1.90 (m, 2H), 2.02 (s, 3H, COCH₃), 2.18 (m, 2H), 2.33 (m, 2H), 2.50 (m, 1H), 2.75 (m, 2H), 2.92 (s, 3H, SO₂CH₃), 2.96 (m, 2H), 3.33 (m, 8H), 4.43 (s, 2H, CH₂CONH), 5.22 (s, 2H, OCH₂), 5.35 (m, 1H), 5.53 (m, 1H), 7.17-7.20 (m, 3H), 7.39-7.60 (m, 5H), 7.69-7.79 (m, 2H), 7.86 (broad s, 1H, NH), 8.33+8.56 (m, 1H, NH), 9.95 (s, 1H, NH).

Example 6

N-[3-[4-(17-cyclohexyl-3,12-dioxo-1,4,11-triazatricyclo[11.5.2.0$^{16,19}$]icosa-13 (20),14,16(19),17-tetraen-18-yl)phenoxymethyl]-4-(4-methanesulfonylpiperazin-1-yl)-phenyl]acetamide (6)

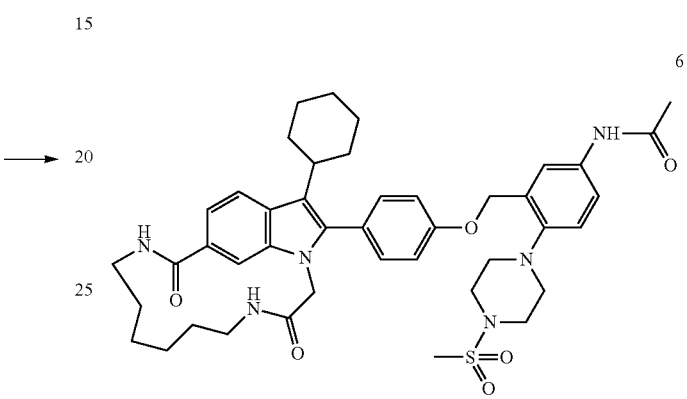

6

The title product 6 was prepared by shaking a mixture of 5, 10% Pd/C in methanol, and THF in a hydrogenation apparatus under 55 psi pressure at room temperature for 1 h. The catalyst was removed by filtration and washed with methanol. The filtrate was concentrated to dryness. Filtration on silica gel afforded the target product 6: m/z=784 (M+H)⁺.

Example 7

18-(4-benzyloxyphenyl)-17-cyclohexyl-1,4,11-triazatricyclo[11.5.2.0$^{16,19}$]-icosa-7,13(20),14,16(19),17-pentaene-3,12-dione (7)

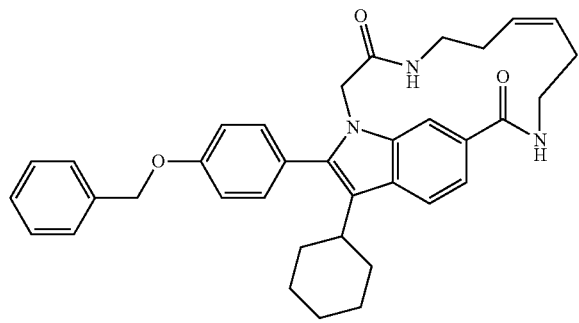

7

Step A.

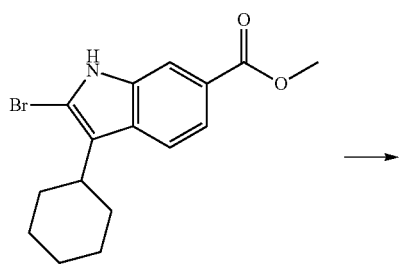

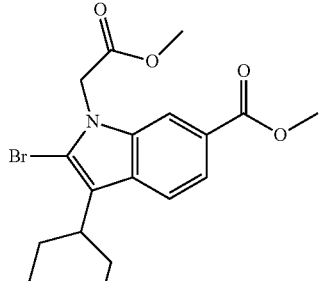

Intermediate 7-1 was prepared in 90% yield from 1-5 by adding a dispersion of NaH in mineral oil at 0° C. to a solution of the ester 1-5 and bromoacetic acid methyl ester in dry DMF. After 10 min at 0° C., the reaction mixture was warmed up to room temperature for 1 h. Then, the solution was poured into ice-cold water and extracted with ethyl acetate, dried (Na$_2$SO$_4$) and evaporated. The crude material was purified by column chromatography (ethyl acetate/CH$_2$Cl$_2$/heptane, 1:4:5) to give the target product 7-1 which was triturated in ether, filtered and washed with petroleum ether: m/z=409 (M+H)$^+$.

Step B.

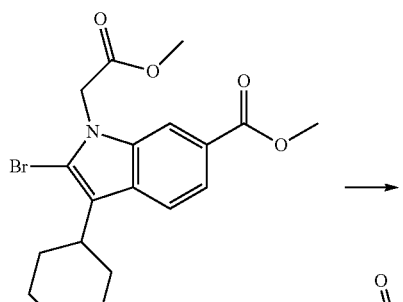

Intermediate 7-2 was prepared in 88% yield from 7-1 by adding a solution of lithium hydroxide in water to a solution of diester 7-1 in methanol and THF. The resulting solution was stirred at room temperature for 48 h. Then, volatiles were evaporated under reduced pressure. The residue was dissolved in water and the pH of the solution was adjusted to 3 with a 1N aqueous solution of HCl. The resulting solution was successively extracted with ethyl acetate, dried (Na$_2$SO$_4$) and evaporated. The residue was triturated in ether, then filtered off to afford the target diacid 7-2: m/z=381 (M+H)$^+$.

Step C.

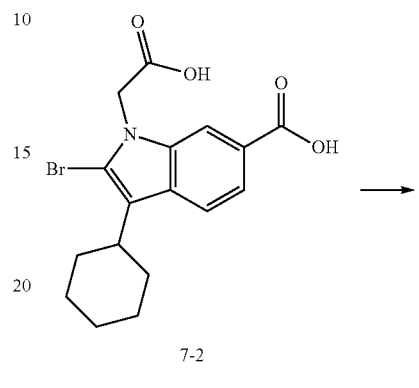

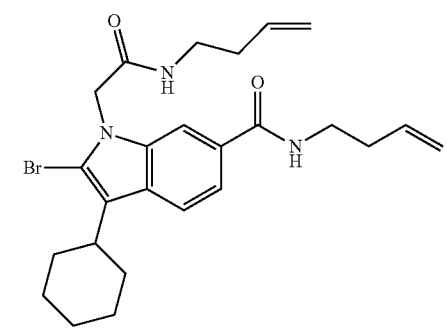

Intermediate 7-3 was prepared in 78% yield from 7-2 by adding HATU to a stirred solution of the diacid 7-2 and but-3-enylamine in DMF. Then, diisopropylethylamine was added dropwise. After 12 h, the reaction mixture was successively partitioned between ethyl acetate and ice-cold water, dried (Na$_2$SO$_4$) and evaporated. The residue was purified by column chromatography (ethyl acetate/hexane 1:1) to give the target product 7-3: m/z=487 (M+H)$^+$.

Step D.

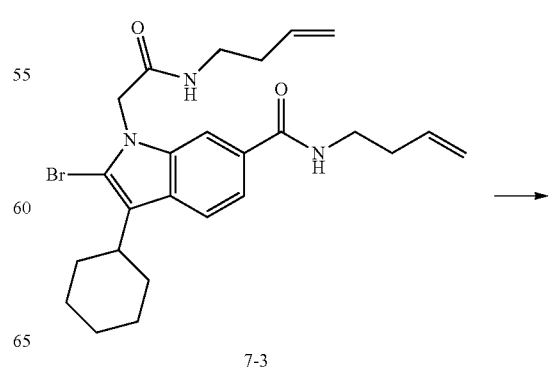

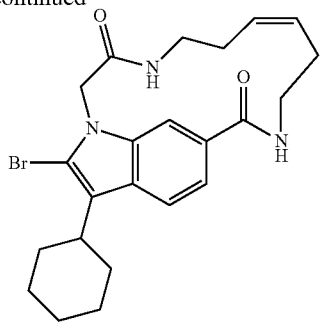

7-4

Intermediate 7-4 was prepared in 58% yield from 7-3 by heating a solution of 7-3 and Hoveyda-Grubbs $1^{st}$ generation catalyst in degassed dichloroethane at 80° C. for 12 h.

Then, additional catalyst was added and the reaction mixture was heated for another 3 h at 80° C. Next, the reaction mixture was concentrated under vacuum and the residue was purified by column chromatography (gradient CH$_2$Cl$_2$/ethyl acetate/heptane, 2:2:1 to 0:1:0). Crystallization from ethyl acetate provided the target product 7-4: m/z=459 (M+H)$^+$.

Step E.

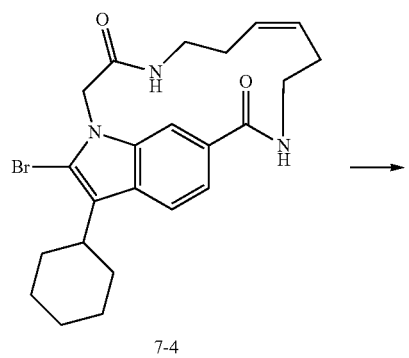

7-4

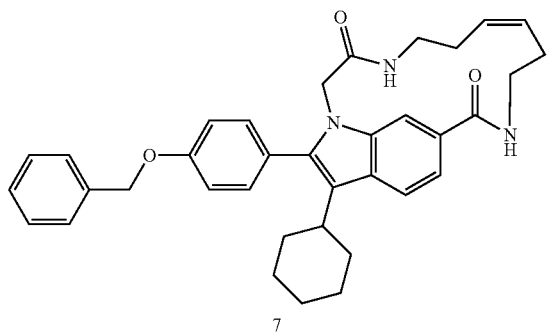

7

The target product 7 was prepared in 54% yield from 7-4 following the procedure reported for the synthesis of intermediate 3-6: m/z=562 (M+H)$^+$.

Example 8

18-[4-(2-bromo-5-methoxybenzyloxy)phenyl]-17-cyclohexyl-1,4,11-triaza-tricyclo[11.5.2.0$^{16,19}$]icosa-13(20),14,16(19),17-tetraene-3,12-dione (9)

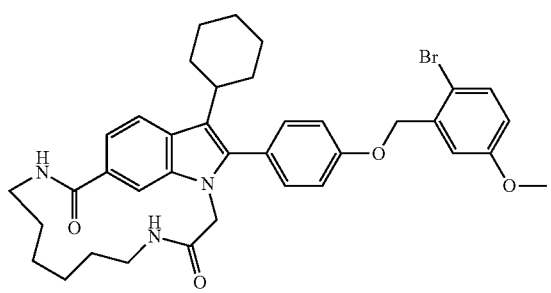

9

Step A.

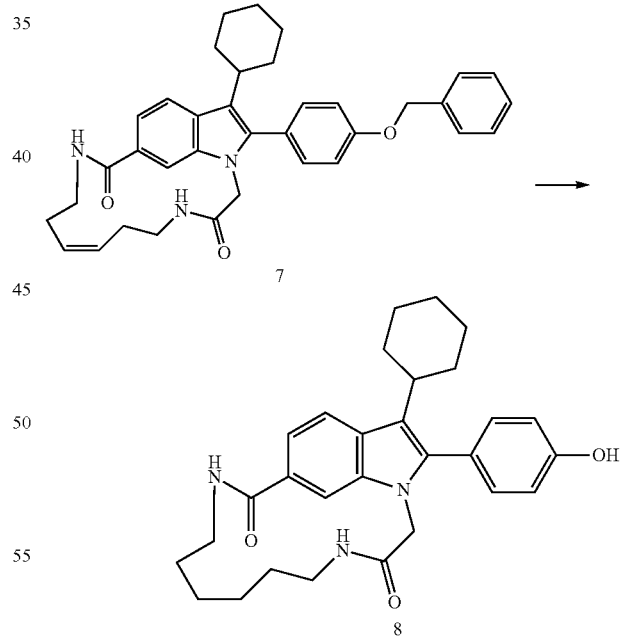

7

8

Intermediate 8 was prepared in 95% yield from 7 by shaking a mixture of 7, 10% Pd/C (20 mg) in methanol, and THF in a hydrogenation apparatus under 55 psi pressure at room temperature for 1 h. The catalyst was removed by filtration and washed with methanol. The filtrate was concentrated to dryness. Filtration on silica gel afforded the target product 8: m/z=474 (M+H)$^+$.

Step B.

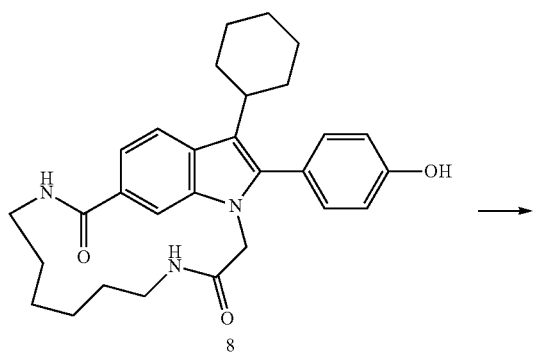
8

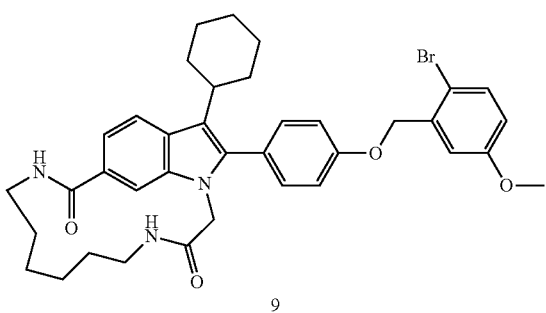
9

A solution of the phenol 8 (20 mg, 0.042 mmol), 2-bromo-5-methoxybenzylbromide (13 mg, 0.0465 mmol) and potassium carbonate (6.42 mg, 0.0465 mmol) in DMF (2 mL) was heated under nitrogen at 80° C. After 12 h, the reaction mixture was allowed to cool down to room temperature. The resulting solution was acidified to pH 4 with a 1 N aqueous solution of HCl and the precipitate was collected by filtration, then dried under high vacuum pump. Purification by column chromatography (CH$_2$Cl$_2$, methanol, 96.5:3.5) afforded 93 mg (51%) of the target product 9 as a white powder: m/z=673 (M+H)$^+$.

Example 9

18-[4-(4'-chloro-4-methoxybiphenyl-2-ylmethoxy)phenyl]-17-cyclohexyl-1,4,11-triazatricyclo[11.5.2.0$^{16,19}$]icosa-13(20),14,16(19),17-tetraene-3,12-dione (10)

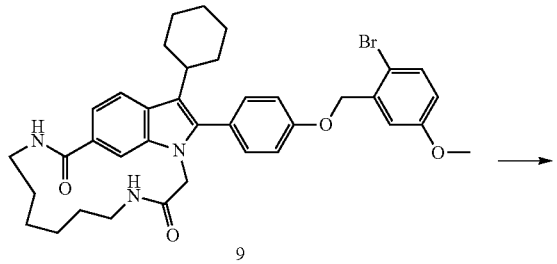
9

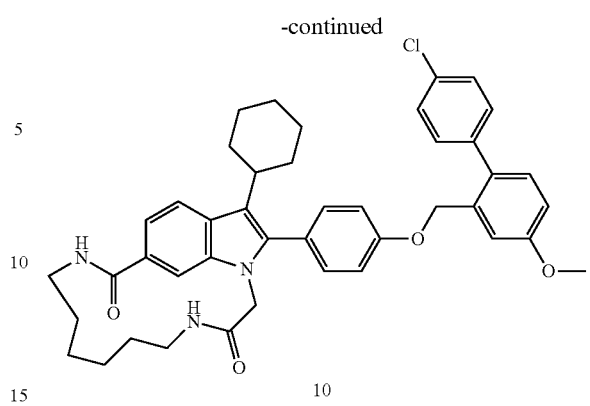
10

A saturated solution of NaHCO$_3$ (1 mL) was added to a solution of 9 (20 mg, 0.029 mmol), 4-chlorobenzeneboronic acid (11 mg, 0.068 mmol) and bis(triphenyl-phosphine)palladium (II) chloride (4 mg, 0.0063 mmol) in dimethoxyethane (DME; 6 mL). The resulting solution was heated at 73° C. for 8 h. Then, the reaction mixture was successively cooled down to room temperature, partitioned between water and ethyl acetate, dried (Na$_2$SO$_4$) and evaporated. Purification by column chromatography (CH$_2$Cl$_2$/methanol, 97:3) afforded the target product contaminated with impurities. The product was further purified by trituration in methanol, then filtered off to give the target product 10: m/z=704 (M+H)$^+$. NMR (DMSO-d6): δ (ppm) 1.23-1.33 (m, 6H), 1.42-1.53 (m, 8H), 1.67-1.77 (m, 2H), 1.87-2.02 (m, 2H), 2.80 (m, 1H, CH cyclohexyl), 3.15 (m, 4H, 2×C$\underline{H}_2$NHCO), 3.83 (s, 3H, OCH$_3$), 4.44 (s, 2H, C$\underline{H}_2$CONH), 5.00 (s, 2H, CH$_2$O), 7.04-7.09 (m, 3H), 7.23 (d, J=2.6 Hz, 1H), 7.29 (d, J=8.5 Hz, 1H), 7.40-7.47 (m, 7H), 7.76 (d, J=8.4 Hz, 1H), 7.93 (s, 1H), 8.30 (broad s, 1H, NH), 8.51 (broad s, 1H, NH).

Example 10

17-Cyclohexyl-18-[4-[2-morpholin-4-yl-5-(2-oxo-pyrrolidin-1-yl)-benzyloxy]-phenyl]-1,4,11-triazatricyclo[11.5.2.0$^{16,19}$]icosa-7,13 (20),14,16(19),17-pentaene-3,12-dione (11)

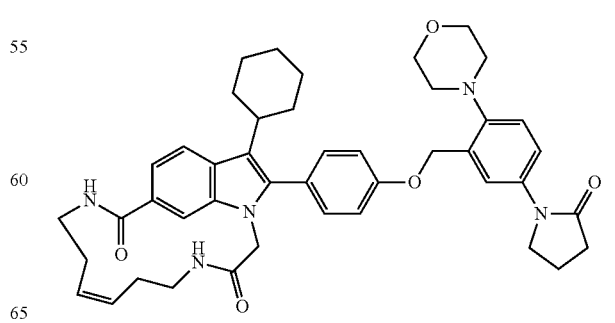
11

Step A.

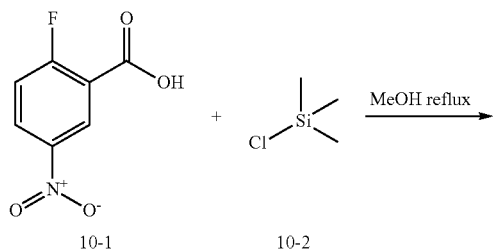

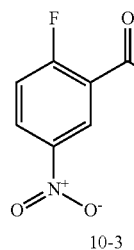

To a solution of 2-fluoro-5-nitrobenzoic acid 10-1 (5.22 g, 28.2 mmol) in methanol (30 mL) was added chlorotrimethylsilane 10-2 (6.00 g, 1.96 eq.). The reaction mixture was stirred under reflux during 16 h, then cooled down to room temperature, concentrated and the resulting precipitate was filtered off, washed with a small quantity of methanol, then heptane, to provide 4.36 g (78% yield) of 2-fluoro-5-nitrobenzoic acid methyl ester 10-3 as a white powder; m/z=200 (M+H)⁺.

Step B.

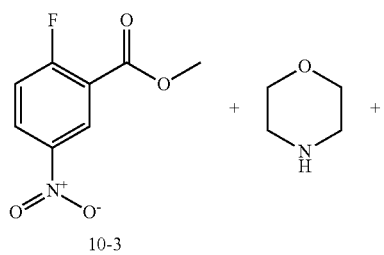

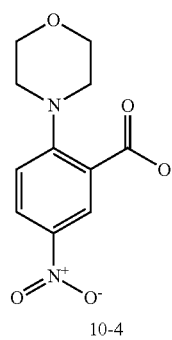

To a solution of 10-3 (4.36 g, 22 mmol) in dimethylsulfoxide (DMSO; 30 mL) were added morpholine (2.5 g, 1.3 eq) and potassium carbonate (3.98 g, 1.3 eq). The reaction mixture was heated at 80° C. during 1 h, then cooled down to room temperature, poured into 300 mL of water and the resulting yellow solid was filtered off, washed with a bit of water then petroleum ether, to afford 5.8 g (98% yield) of 2-morpholin-4-yl-5-nitro-benzoic acid methyl ester 10-4; m/z=267 (M+H)⁺.

Step C.

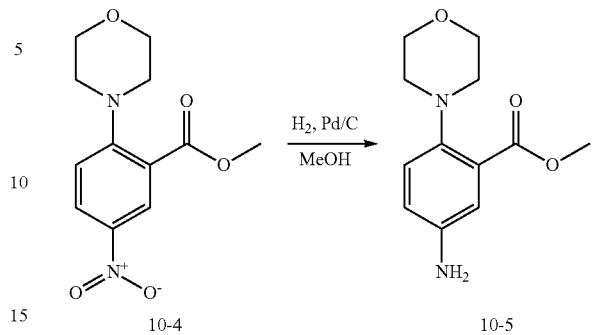

A solution of 10-4 (5.72 g, 21.5 mmol) in methanol was catalytically hydrogenated with Pd/C, then filtered and concentrated to dryness to afford the desired product 5-amino-2-morpholin-4-yl-benzoic acid methyl ester 10-5 (4.94 g, 97% yield); m/z=237 (M+H)⁺.

Step D.

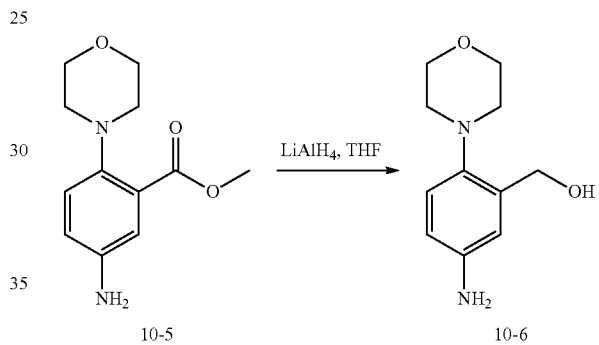

To an ice-cooled suspension of 10-5 (4.94 g, 21 mmol) in THF (100 mL), was added LiAlH₄ (4.0 g, 5 eq) in one portion under N₂. The reaction mixture was allowed to warm up to room temperature and was stirred during 16 h. The reaction mixture was then poured into ice-water and THF was evaporated under reduced pressure. The aqueous layer was acidified with acetic acid until pH 5 and extracted several times with ethyl acetate. The combined organic layers were then dried over sodium sulfate, filtered and concentrated to dryness, to afford 3.5 g (80% yield) of the desired product (5-amino-2-morpholin-4-yl-phenyl)-methanol 10-6; m/z=209 (M+H)⁺.

Step E.

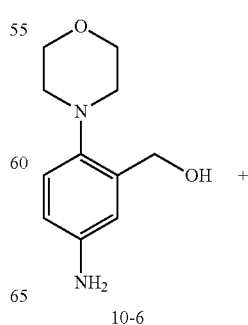 +

-continued

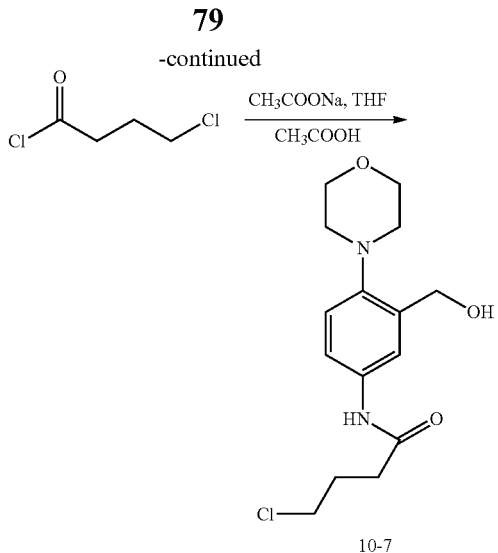

To a mixture of 10-6 (3.22 g, 15.5 mmol), sodium acetate (13.44 g, 10.6 eq) and acetic acid (7.80 g, 8.40 eq) in THF, at 0° C., was added slowly 4-chlorobutyryl chloride (5.04 g, 2.2 eq). The ice-bath was then removed and the reaction mixture was stirred at room temperature for 4 h, then diluted with water. The organic layer was separated, washed with a saturated NaHCO$_3$ aq. solution, dried with sodium sulfate, filtered and concentrated to dryness to give 4.84 g (quantitative yield) of the desired product 4-chloro-N-(3-hydroxymethyl-4-morpholin-4-yl-phenyl)-butyramide 10-7; m/z=313 (M+H)$^+$.

Step F.

To a solution of 10-7 (4.84 g, 15.47 mmol) in ethanol (50 mL) was added KOH (3.47 g, 4 eq) dissolved in water (50 mL). The reaction mixture was heated at 80° C. during 2 h, then ethanol was evaporated under reduced pressure. The aqueous layer was diluted with water (100 mL), acidified with HCl 1M until pH 3, and extracted with CH$_2$Cl$_2$ (3 times). The combined organic layers were dried over sodium sulfate, filtered and concentrated to dryness. The residue was redissolved in a minimum amount of CH$_2$Cl$_2$ and extracted with isopropylether to remove impurities. The isopropylether solution was then concentrated and the residue triturated in ether, then filtered off, to afford 2.27 g (53% yield) of the desired product 1-(3-hydroxymethyl-4-morpholin-4-yl-phenyl)-pyrrolidin-2-one 10-8 as a beige solid; m/z=277 (M+H)$^+$.

Step G.

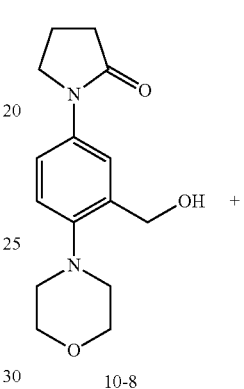

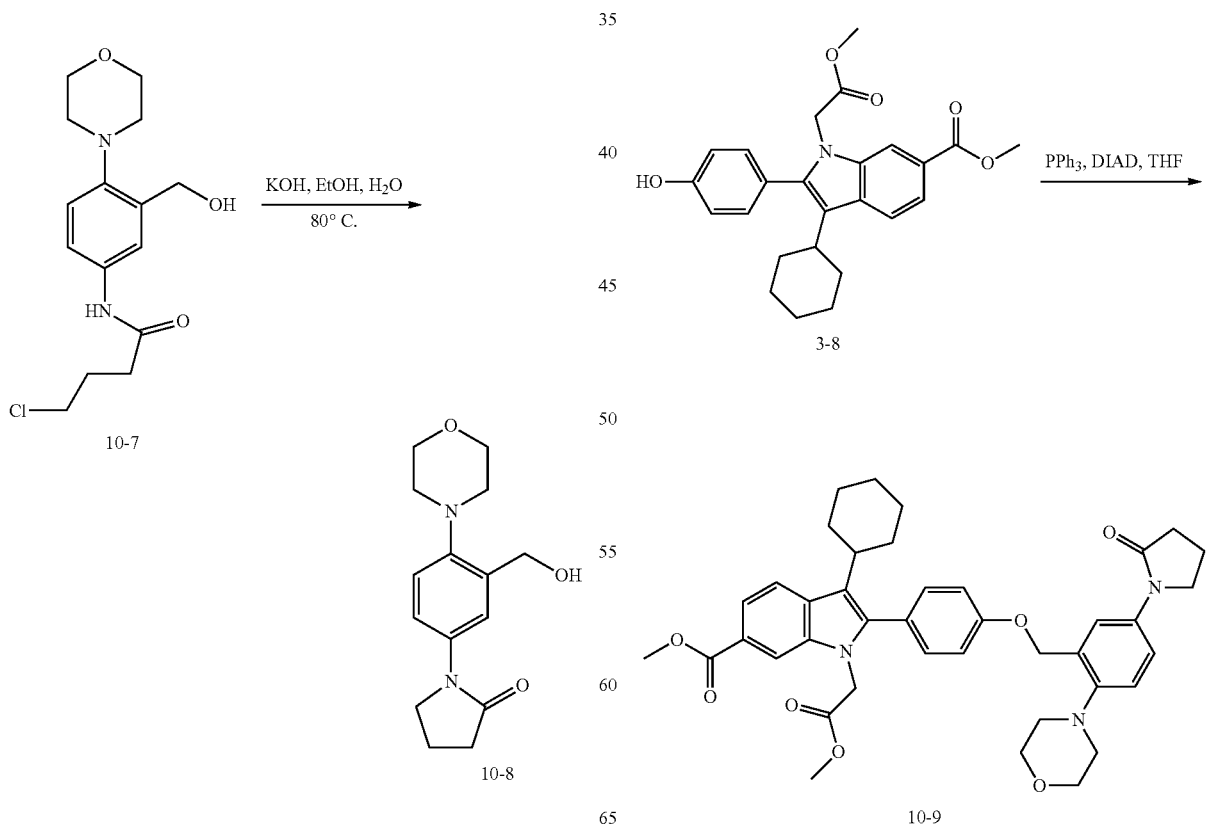

Intermediate 3-cyclohexyl-1-methoxycarbonylmethyl-2-[4-[2-morpholin-4-yl-5-(2-oxo-pyrrolidin-1-yl)-benzyloxy]-phenyl]-1H-indole-6-carboxylic acid methyl ester 10-9 was synthesized in 76% yield from intermediate 3-8, following the procedure reported for the synthesis of intermediate 3-9 and using 10-8 instead of intermediate 3-5; m/z=680 (M+H)⁺.

Step H.

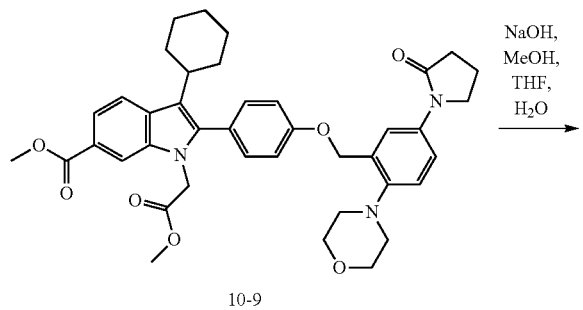

10-9

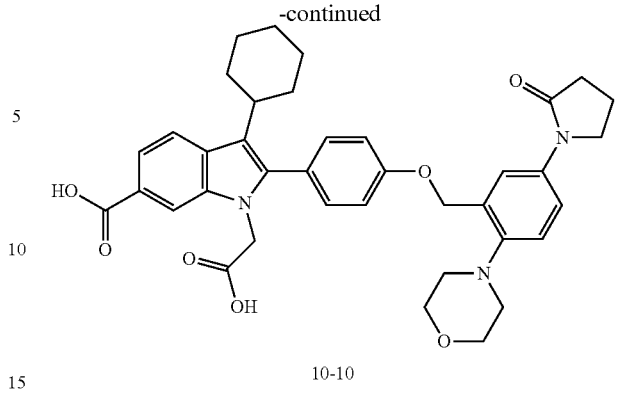

10-10

To a solution of intermediate 10-9 (260 mg, 0.191 mmol) in THF/methanol 1:1 (10 mL) was added NaOH (1.00 g, 131 eq) dissolved in water (2 mL). The reaction mixture was stirred at room temperature until completion, then acidified with HCl 3 M until pH 4, diluted with water and concentrated under reduced pressure to remove organic solvents. The resulting aqueous layer was subsequently extracted with THF and the organic layer was separated, dried with sodium sulfate, filtered and concentrated to dryness to afford 150 mg (60% yield) of the desired intermediate [1-carboxymethyl-3-cyclohexyl-2-[4-[2-morpholin-4-yl-5-(2-oxo-pyrrolidin-1-yl)-benzyloxy]-phenyl]-1H-indole]-6-carboxylic acid 10-10. This intermediate was used without further purification in the next step; m/z=652 (M+H)⁺.

Step I.

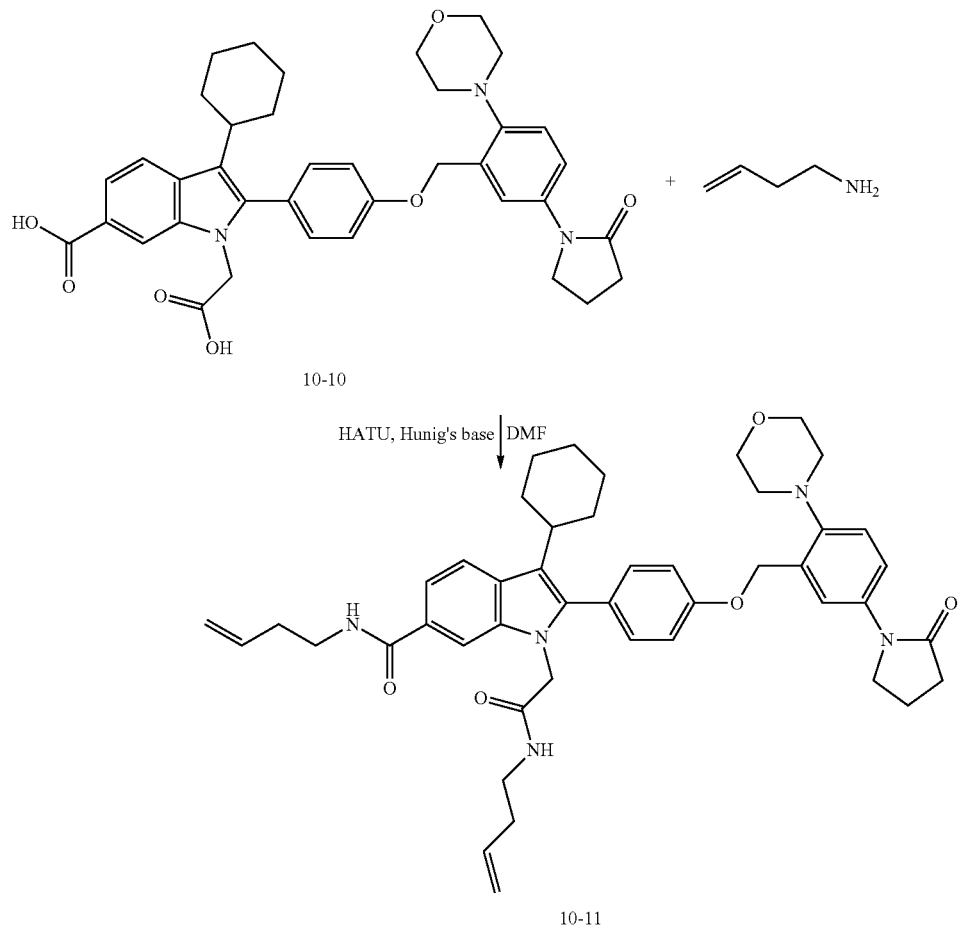

10-10

10-11

The target product 1-but-3-enylcarbamoylmethyl-3-cyclohexyl-2-[4-[2-morpholin-4-yl-5-(2-oxo-pyrrolidin-1-yl)-benzyloxy]-phenyl]-1H-indole-6-carboxylic acid but-3-enylamide 10-11 was synthesized in 38% yield, following the procedure reported for the synthesis of intermediate 3-11 and using intermediate 10-10 instead of intermediate 3-10; m/z=758 (M+H)+.

Step J.

following the procedure reported for the synthesis of compound 3 and using intermediate 10-11 instead of intermediate 3-11; m/z=730 (M+H)+.

Example 11

17-Cyclohexyl-18-[4-[2-(4 methanesulfonyl-piperazin-1-yl)-5-(2-oxo-pyrrolidin-1-yl)-benzyloxy]-phenyl]-1,4,11-triaza-tricyclo[11.5.2.0$^{16,19}$]icosa-7, 13 (20),14,16(19),17-pentaene-3,12-dione (12)

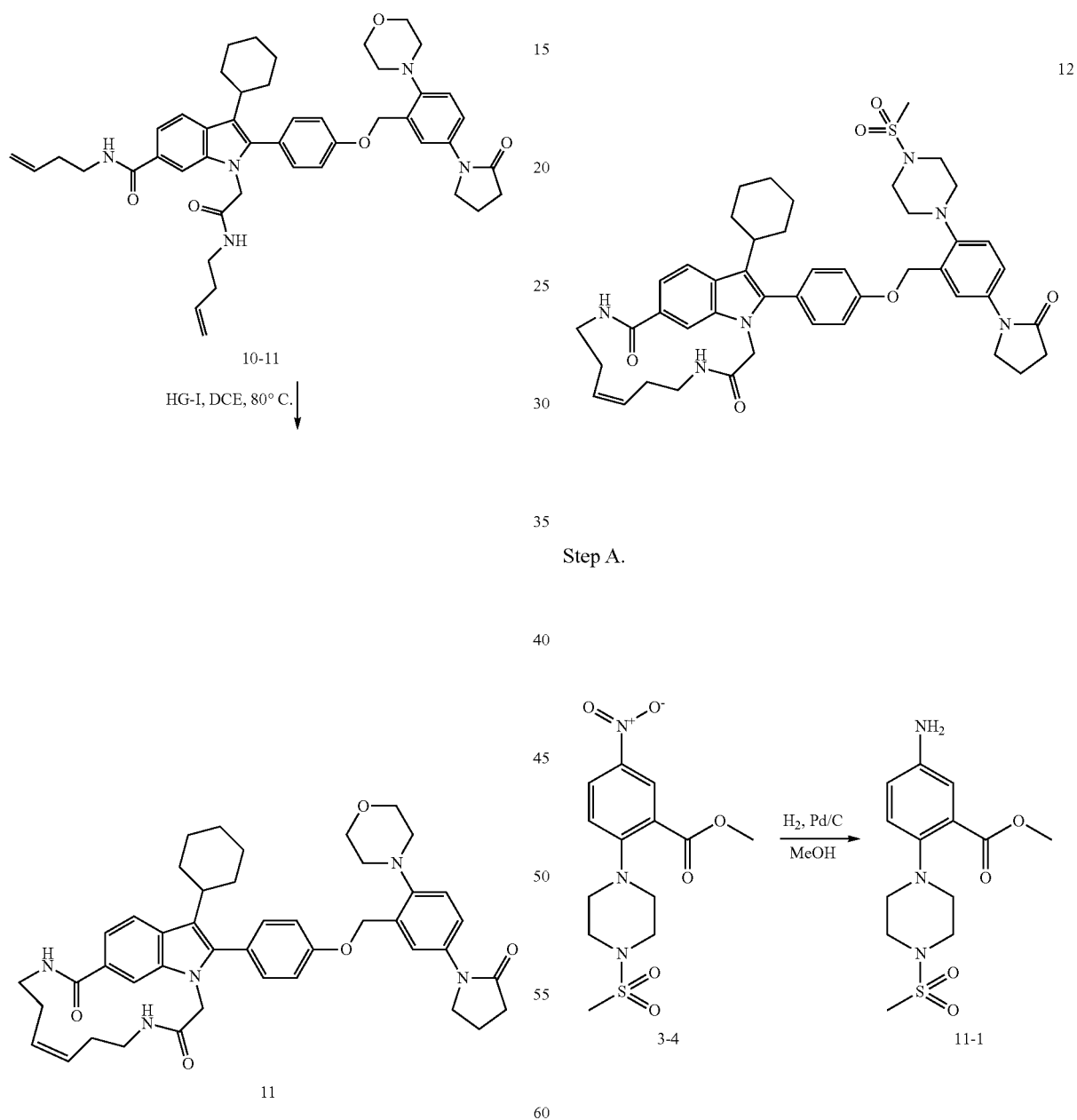

Step A.

The target product 17-cyclohexyl-18-[4-[2-morpholin-4-yl-5-(2-oxo-pyrrolidin-1-yl)-benzyloxy]-phenyl]-1,4,11-triaza-tricyclo[11.5.2.0$^{16,19}$]icosa-7,13 (20),14,16(19),17-pentaene-3,12-dione 11 was synthesized in 25% yield, A solution of 3-4 (5.72 g, 16.66 mmol) in methanol was catalytically hydrogenated with Pd/C, then filtered and concentrated to dryness to afford the desired product 5-amino-2-(4-methanesulfonyl-piperazin-1-yl)-benzoic acid methyl ester 11-1 (5.15 g, 99% yield); m/z=314 (M+H)+.

Step B.

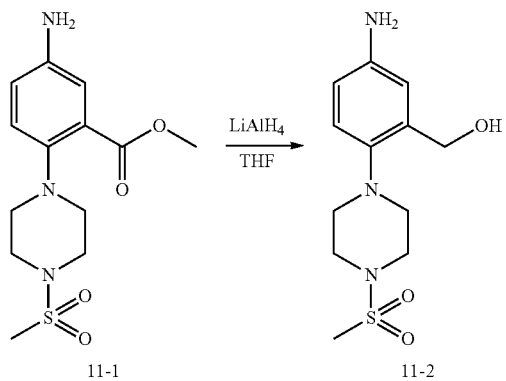

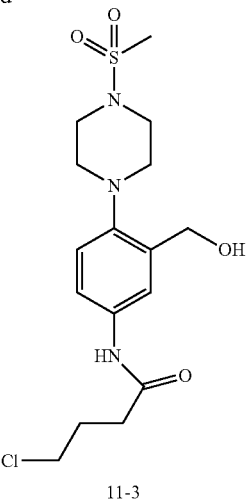

To an ice-cooled suspension of 5-amino-2-(4-methane-sulfonyl-piperazin-1-yl)-benzoic acid methyl ester 11-1 (4.63 g, 14.78 mmol) in THF (100 mL), was added LiAlH$_4$ (2.92 g, 5.2 eq) in one portion under N$_2$. The reaction mixture was allowed to warm up to room temperature and was stirred during 16 h. The reaction mixture was then poured into ice-water and THF was evaporated under reduced pressure. The aqueous layer was acidified with acetic acid until pH 5 and extracted several times with ethyl acetate. The combined organic layers were then dried over sodium sulfate, filtered and concentrated to dryness, to afford 4.22 g (57% yield) of the desired product [5-amino-2-(4-methane-sulfonyl-piperazin-1-yl)-phenyl]-methanol 11-2; m/z=286 (M+H)$^+$.

Step C.

To a mixture of 11-2 (1.0 g, 3.51 mmol), sodium acetate (2.14 g, 7.4 eq) and acetic acid (2.1 g, 10 eq) in dry THF (20 mL), at 0° C., was added slowly 4-chlorobutyryl chloride (1.07 g, 2.1 eq). The ice-bath was then removed and the reaction mixture was stirred at room temperature for 4 h, then diluted with water. The aqueous layer was several times extracted with CH$_2$Cl$_2$ and the combined organic layers were washed with a saturated NaHCO$_3$ aq. solution, dried with sodium sulfate, filtered and concentrated to dryness to give 1.36 g (quantitative yield) of the desired product 4-chloro-N-[3-hydroxymethyl-4-(4-methanesulfonyl-piperazin-1-yl)-phenyl]-butyramide 11-3; m/z=390 (M+H)$^+$.

Step D.

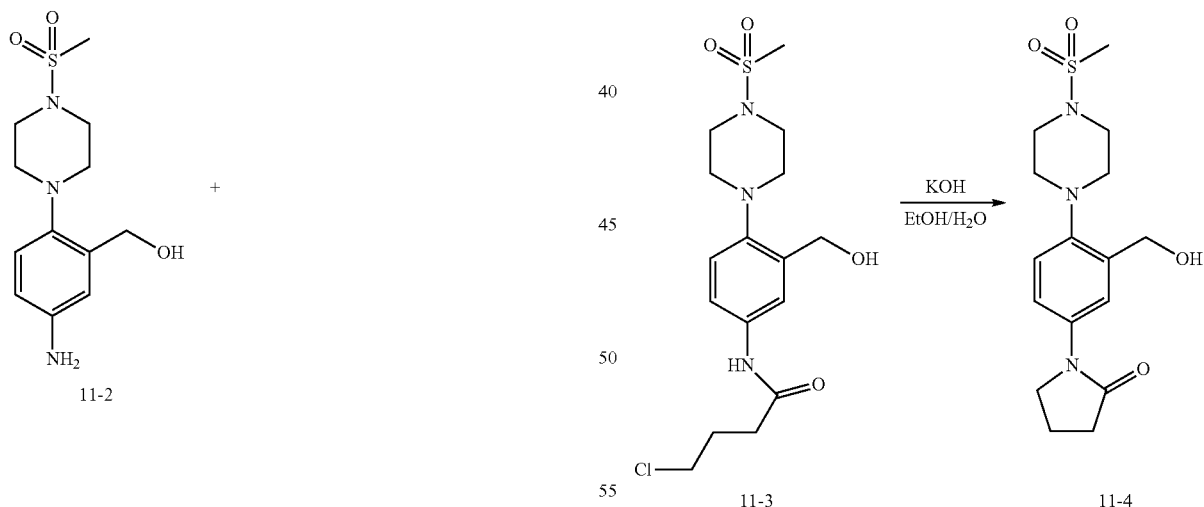

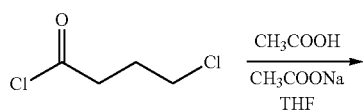

To a solution of 11-3 (1.37 g, 3.51 mmol) in ethanol (30 mL) was added KOH (0.804 g, 4 eq) dissolved in water (30 mL). The reaction mixture was heated at 80° C. for 2 h, then ethanol was evaporated under reduced pressure. The aqueous layer was diluted with water (100 mL) and acidified with HCl 1 M until pH 3. The resulting brown precipitate was filtered off, washed with water then petroleum ether and dried in vacuo to afford 873 mg (60% yield) of the desired product 1-[3-Hydroxymethyl-4-(4-methanesulfonyl-piperazin-1-yl)-phenyl]-pyrrolidin-2-one 11-4; m/z=354 (M+H)$^+$.

Step E.

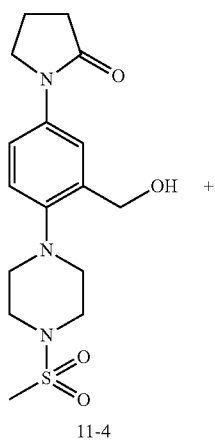

Step F.

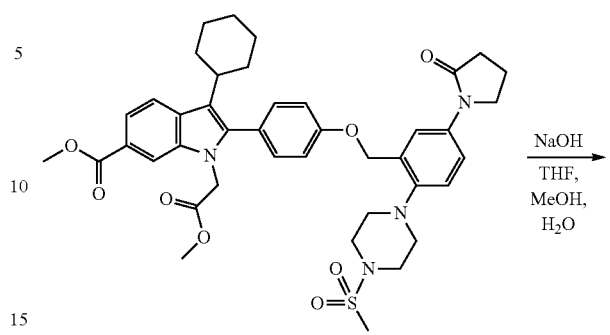

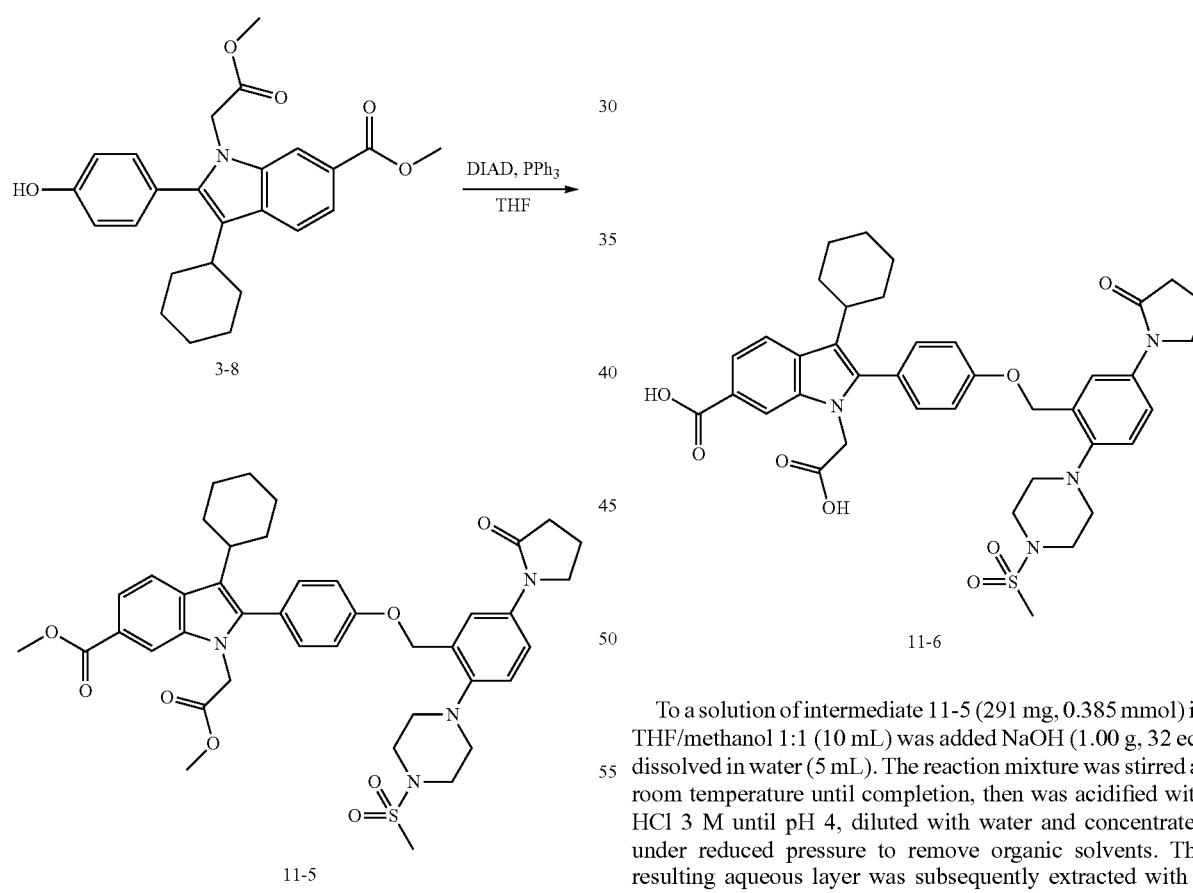

The target product 3-cyclohexyl-2-[4-[2-(4-methanesulfonyl-piperazin-1-yl)-5-(2-oxo-pyrrolidin-1-yl)-benzyloxy]-phenyl]-1-methoxycarbonylmethyl-1H-indole-6-carboxylic acid methyl ester 11-5 was synthesized in 57% yield from intermediate 3-8, following the procedure reported for the synthesis of intermediate 3-9 and using 11-4 instead of intermediate 1-16; m/z=757 (M+H)$^+$.

To a solution of intermediate 11-5 (291 mg, 0.385 mmol) in THF/methanol 1:1 (10 mL) was added NaOH (1.00 g, 32 eq) dissolved in water (5 mL). The reaction mixture was stirred at room temperature until completion, then was acidified with HCl 3 M until pH 4, diluted with water and concentrated under reduced pressure to remove organic solvents. The resulting aqueous layer was subsequently extracted with a mixture of ethyl acetate and THF and the organic layer was separated, dried with sodium sulfate, filtered and concentrated. The residue was triturated in petroleum ether and filtered off to afford 280 mg (99% yield) of the desired intermediate [1-carboxy-methyl-3-cyclohexyl-2-[4-[2-(4-methanesulfonyl-piperazin-1-yl)-5-(2-oxo-pyrrolidin-1-yl)-benzyloxy]-phenyl]-1H-indole]-6-carboxylic acid 11-6; m/z=729 (M+H)$^+$.

Step G.
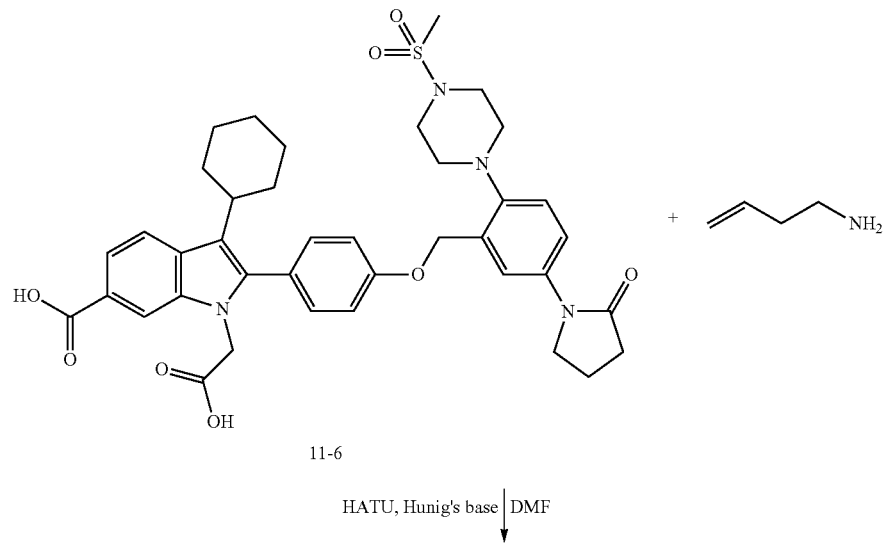
11-6
HATU, Hunig's base | DMF
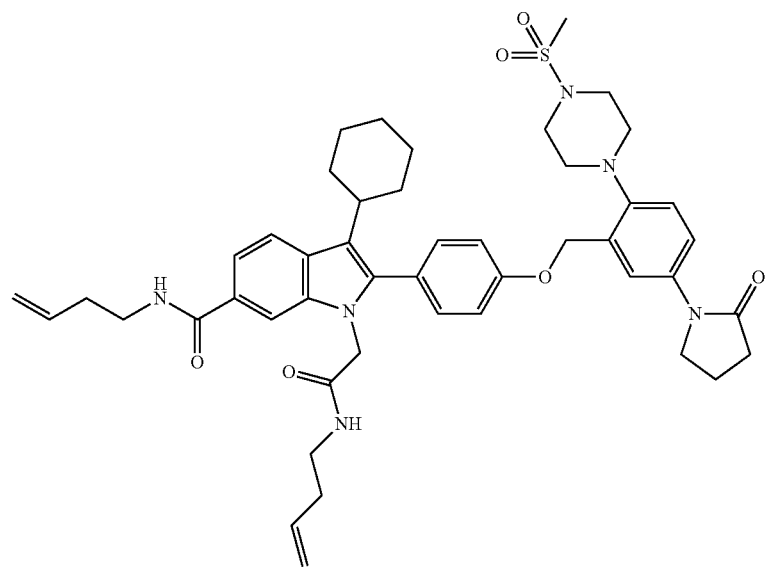
11-7

The target product 1-but-3-enylcarbamoylmethyl-3-cyclohexyl-2-[4-[2-(4-methane-sulfonyl-piperazin-1-yl)-5-(2-oxo-pyrrolidin-1-yl)-benzyloxy]-phenyl]-1H-indole-6-carboxylic acid but-3-enylamide 11-7 was synthesized in 87% yield, following the procedure reported for the synthesis of intermediate 3-11 and using intermediate 11-6 instead of intermediate 3-10; m/z=836 (M+H)+.

Step H.

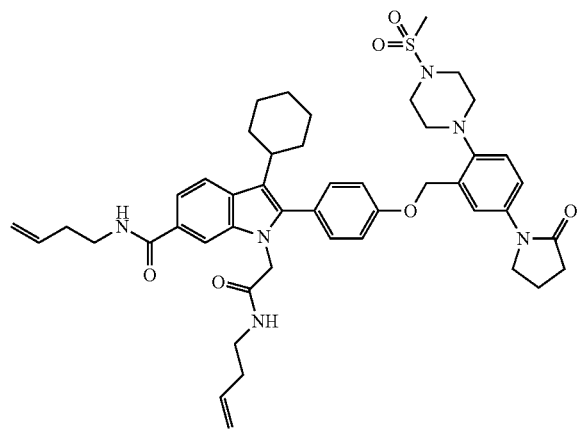

11-7

| HG-I, THF, 80° C.

12

The target product 17-cyclohexyl-18-[4-[2-(4-methane-sulfonyl-piperazin-1-yl)-5-(2-oxo-pyrrolidin-1-yl)-benzyloxy]-phenyl]-1,4,11-triaza-tricyclo[11.5.2.0$^{16,19}$]icosa-7,13(20),14,16(19),17-pentaene-3,12-dione 12 was synthesized in 32% yield, following the procedure reported for the synthesis of compound 3 and using intermediate 11-7 instead of intermediate 3-11; m/z=808 (M+H)+. NMR (DMSO-d6): δ (ppm) 1.21-1.27 (m, 4H, cyclohexyl), 1.66-1.94 (m, 6H, cyclohexyl), 2.06 (qt, J=7.6 Hz, 2H, CH$_2$ pyrrolidinone), 2.30 (m, 4H, 2×CH$_2$CH=CH), 2.48 (m, 2H, CH$_2$ pyrrolidinone), 2.60 (m, 1H, CH cyclohexyl), 2.92 (s, 3H, SO$_2$CH$_3$), 2.99 (m, 4H, piperidine), 3.28 (m, 4H, piperidine), 3.36 (m, 2H, CH$_2$NHCO), 3.43 (m, 2H, CH$_2$NHCO), 3.82 (t, J=7.1 Hz, 2H, CH$_2$ pyrrolidinone), 4.39 (s, 2H, CH$_2$CONH), 5.23 (s, 2H, CH$_2$O), 5.37 (m, 1H, CH=CH), 5.46 (m, 1H, CH=CH), 7.21 (d, J=8.7 Hz, 2H), 7.26 (d, J=8.7 Hz, 1H), 7.40 (d, J=8.4 Hz, 1H), 7.47 (d, J=8.6 Hz, 2H), 7.58 (dd, J=2.6 Hz, 8.7 Hz, 1H), 7.67 (s, 1H), 7.77 (d, J=8.3 Hz, 1H), 7.86 (d, J=2.6 Hz, 1H), 8.27 (m, 1H, NH), 8.46 (broad t, J=5.9 Hz, NH).

Example 12

17-Cyclohexyl-18-[4-[2-morpholin-4-yl-5-(2-oxo-pyrrolidin-1-yl)-benzyloxy]-phenyl]-10,10-dioxo-10λ$^6$-thia-1,4,11-triaza-tricyclo[11.5.2.0$^{16,19}$]icosa-7,13(20),14,16(19),17-pentaene-3,12-dione (13)

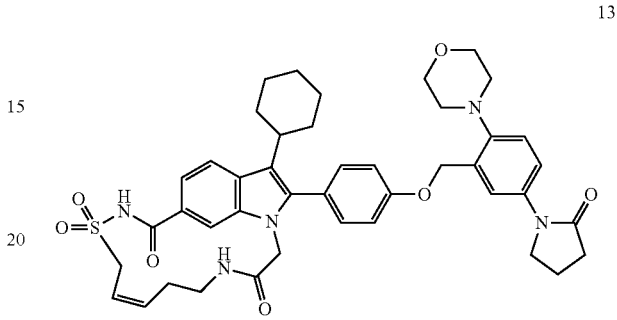

13

Step A.

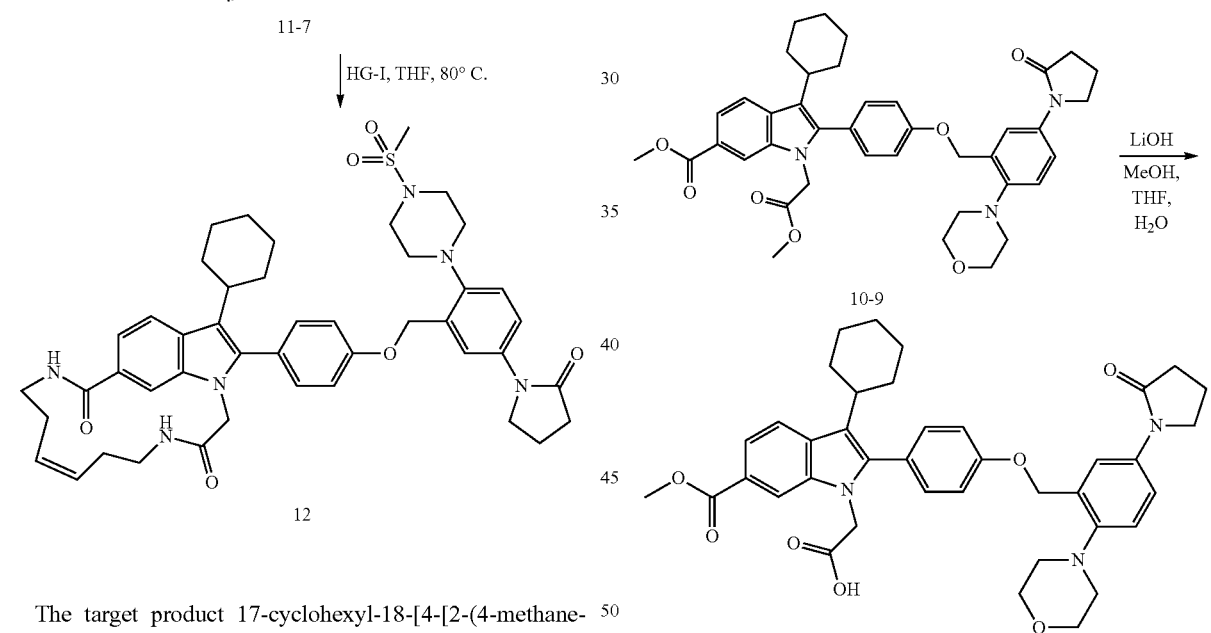

To an ice-cooled solution of intermediate 10-9 (1.02 g, 1.50 mmol) in THF/methanol 1:1 (20 mL) was added LiOH (40 mg, 1.1 eq) dissolved in water (2 mL). The reaction mixture was stirred at 0° C. during 5 h, then diluted with water, acidified with HCl 1 M until pH 4, concentrated under reduced pressure to remove organic solvents and extracted with a mixture of ethyl acetate and THF. The organic layer was separated, dried over sodium sulfate, filtered and concentrated. The obtained residue was triturated in petroleum ether to give 746 mg (73% yield) of the desired product [1-carboxymethyl-3-cyclohexyl-2-[4-[2-morpholin-4-yl-5-(2-oxo-pyrrolidin-1-yl)-benzyloxy]-phenyl]-1H-indole]-6-carboxylic acid methyl ester 12-2 as a slightly yellow powder; m/z=666 (M+H)+.

Step B.
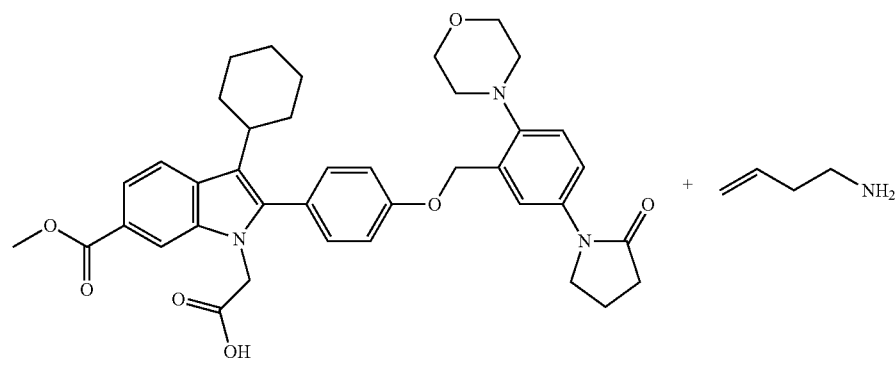
12-2
HATU, Hunig's base, DMF
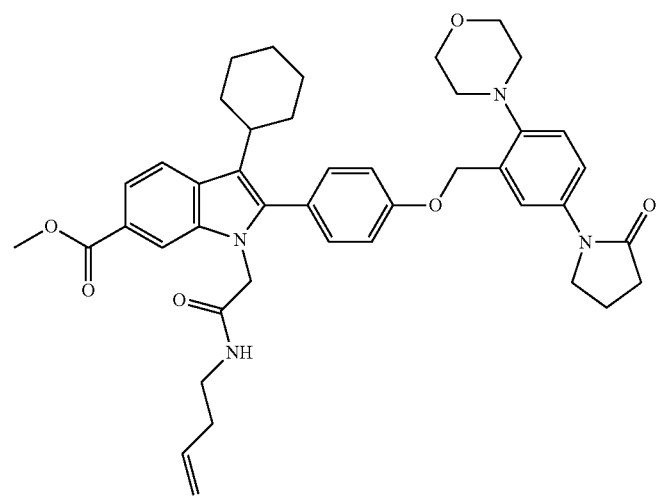
12-3

To a solution of intermediate 12-2 (476 mg, 0.716 mmol) and HATU (390 mg, 1.4 eq) in dry DMF (7 mL), under $N_2$, were added but-3-enylamine (68 mg, 1.35 eq) and Hunig's base (145 mg, 1.5 eq) at room temperature. The reaction mixture was stirred at room temperature until completion, then was poured into ice-water (150 mL) and the resulting white precipitate was filtered off, washed with a small amount of water then petroleum ether, to give 447 mg (87% yield) of the desired intermediate [1-(3-butenyl-carbamoylmethyl)-3-cyclohexyl-2-[4-[2-morpholin-4-yl-5-(2-oxo-pyrrolidin-1-yl)-benzyloxy]-phenyl]-1H-indole]-6-carboxylic acid methyl ester 12-3; m/z=719 $(M+H)^+$.

Step C.

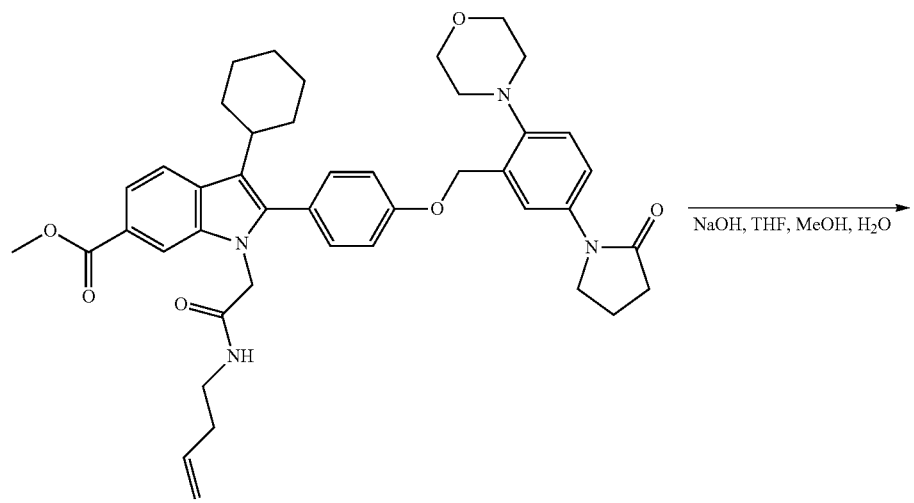

12-3

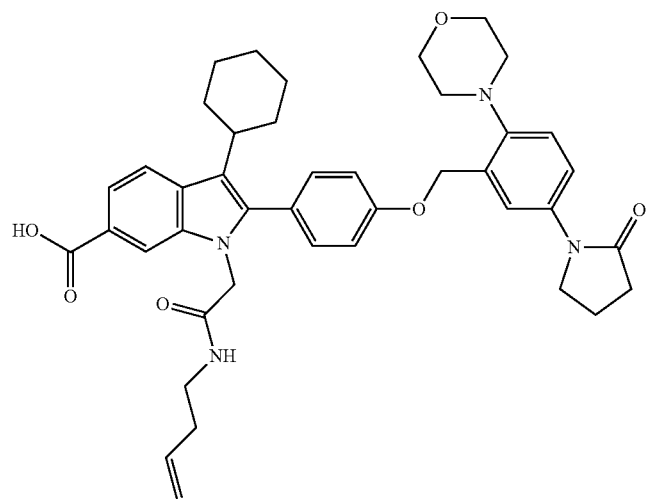

12-4

To a solution of intermediate 12-3 (447 mg, 0.622 mmol) in THF/methanol 1:1 (20 mL) was added NaOH (1.24 g, 50 eq) dissolved in water (10 mL). The reaction mixture was stirred at room temperature until completion, then was acidified with HCl 3 M until pH 4, diluted with water and concentrated under reduced pressure to get rid of the organic solvents. After vigorous stirring, a yellow precipitate appeared in the aqueous layer; this was filtered off and washed with a bit of petroleum ether to afford 438 mg (quantitative yield) of the desired intermediate [1-but-3-enylcarbamoylmethyl-3-cyclohexyl-2-[4-[2-morpholin-4-yl-5-(2-oxo-pyrrolidin-1-yl)-benzyloxy]-phenyl]-1H-indole]-6-carboxylic acid 12-4; m/z=705 (M+H)$^+$.

Step D.

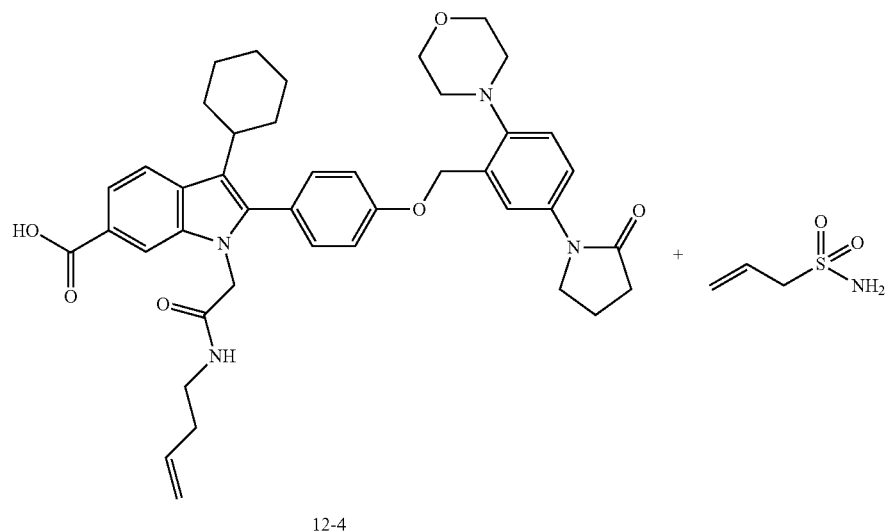

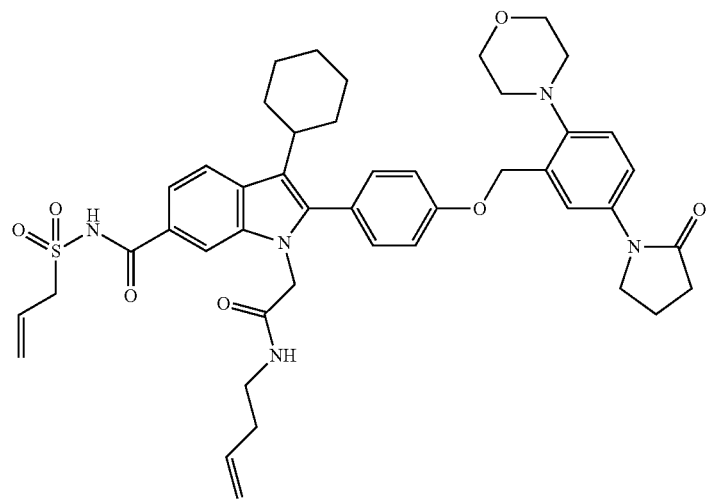

To a solution of intermediate 12-4 (438 mg, 0.622 mmol) and prop-2-ene-1-sulfon-amide (151 mg, 2 eq), synthesized as described in *Journal of Enzyme Inhibition,* 16(6), 475, 2001, in dry DMF (10 mL), were added 1-ethyl-3-(3-dimethylaminopropyl)-carbodiimide (EDCI; 193 mg, 2 eq) and 4-dimethylaminopyridine (DMAP; 152 mg, 2 eq) at room temperature, under $N_2$. After completion, the reaction mixture was poured into 200 mL of brine, and extracted with a mixture of ethyl acetate and THF (several times). The combined organic layers were dried over sodium sulfate, filtered and concentrated. The obtained residue was triturated in diethylether and filtered off to afford 436 mg (87% yield) of the desired product N-but-3-enyl-2-[3-cyclohexyl-2-[4-[2-morpholin-4-yl-5-(2-oxo-pyrrolidin-1-yl)-benzyloxy]-phenyl]-6-(prop-2-ene-1-sulfonylaminocarbonyl)-indol-1-yl]-acetamide 12-5 as an off-white solid; m/z=809 (M+H)$^+$.

Step E.

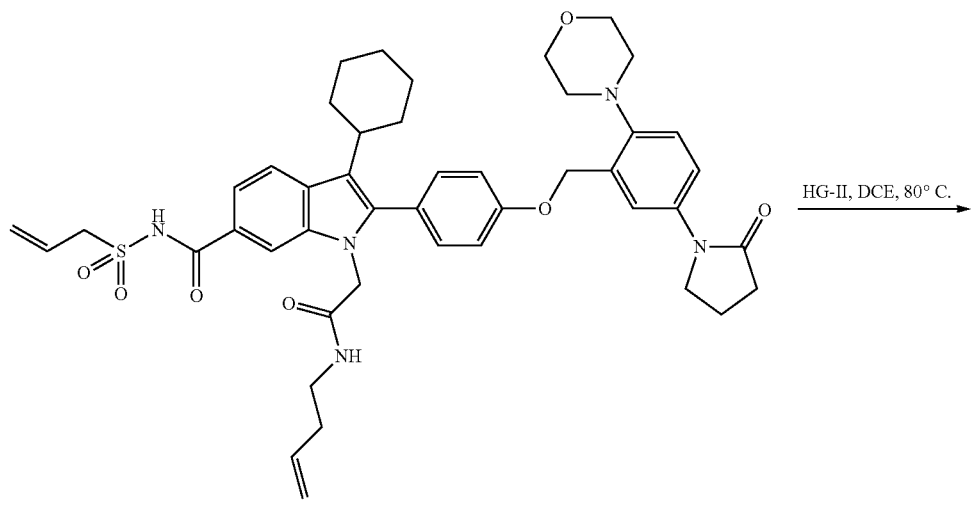

12-5

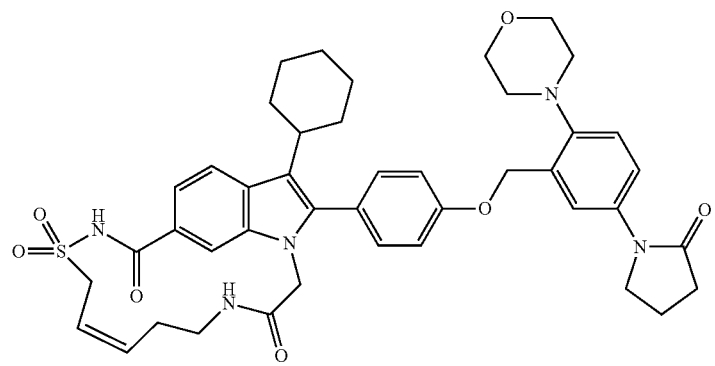

13

The target product 17-cyclohexyl-18-[4-[2-morpholin-4-yl-5-(2-oxo-pyrrolidin-1-yl)-benzyloxy]-phenyl]-10,10-dioxo-10λ$^6$-thia-1,4,11-triaza-tricyclo [11.5.2.0$^{16,19}$]icosa-7,13(20),14,16(19),17-pentaene-3,12-dione 13 was synthesized in 5% yield from intermediate 12-5, following the procedure reported for the synthesis of compound 3 and using Hoveyda-Grubbs 2$^{nd}$ generation catalyst instead of the 1$^{st}$ generation catalyst; m/z=780 (M+H)$^+$.

Example 13

17-Cyclohexyl-18-[4-[2-(4 methanesulfonyl-piperazin-1-yl)-5-(2-oxo-pyrrolidin-1-yl)-benzyloxy]-phenyl]-10,10-dioxo-10λ$^6$-thia-1,4,11-triaza-tricyclo-[11.5.2.0$^{16,19}$]icosa-7,13(20),14,16(19),17-pentaene-3,12-dione (14)

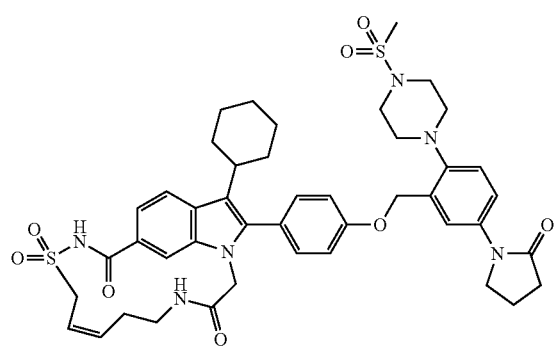

14

Step A.

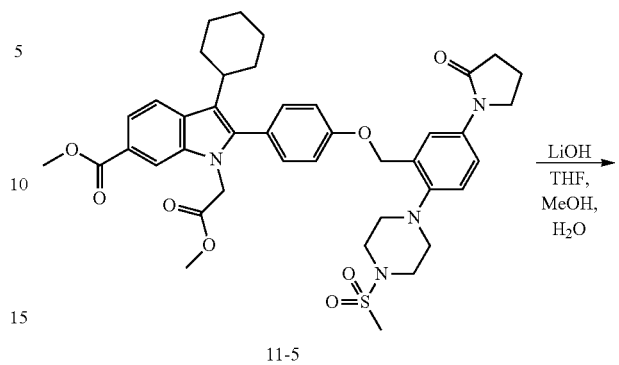

11-5

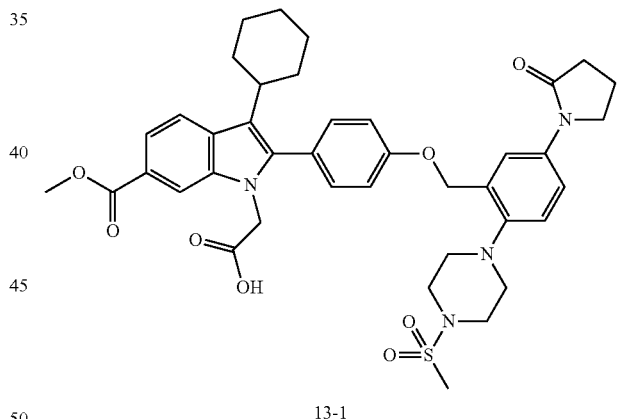

13-1

To an ice-cooled solution of intermediate 11-5 (0.606 g, 0.801 mmol) in THF/methanol 1:1 (20 mL) was added LiOH (21 mg, 1.1 eq) dissolved in water (2 mL). The reaction mixture was stirred at 0° C. during 5 h, then diluted with water, acidified with HCl 1 M until pH 4, and concentrated under reduced pressure to remove organic solvents. The resulting yellow precipitate was collected by filtration and washed with water and petroleum ether to give 575 mg (97% yield) of the desired product [1-carboxymethyl-3-cyclohexyl-2-[4-[2-(4-methanesulfonyl-piperazin-1-yl)-5-(2-oxo-pyrrolidin-1-yl)-benzyloxy]-phenyl]-1H-indole]-6-carboxylic acid methyl ester 13-1; m/z=743 (M+H)$^+$.

Step B.
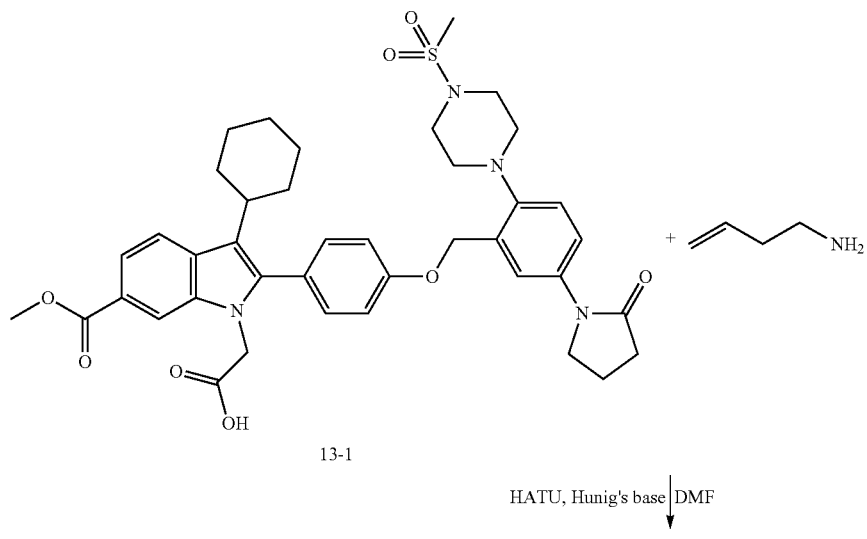
13-1
HATU, Hunig's base, DMF
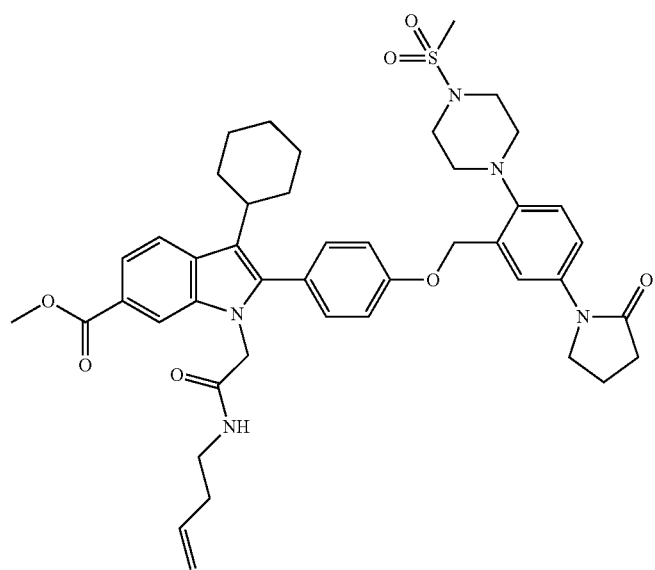
13-2

The target product 1-(but-3-enyl-carbamoyl-methyl)-3-cyclohexyl-2-[4-[2-(4-methane-sulfonyl-piperazin-1-yl)-5-(2-oxo-pyrrolidin-1-yl)-benzyloxy]-phenyl]-1H-indole-6-carboxylic acid methyl ester 13-2 was obtained in 83% yield as a white powder, following the procedure reported for the synthesis of compound 12-3 and using intermediate 13-1 instead of intermediate 12-2; m/z=796 (M+H)+.
Step C.

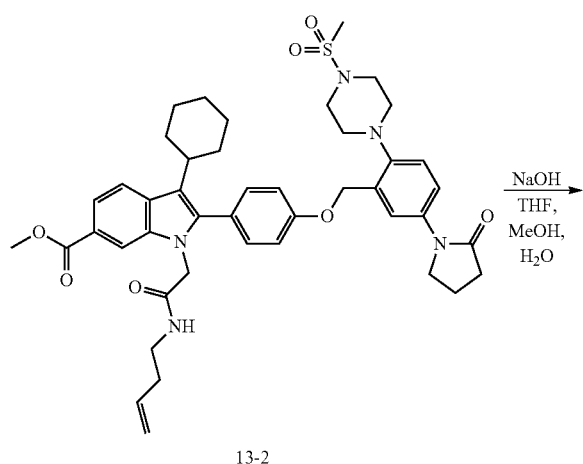

13-2

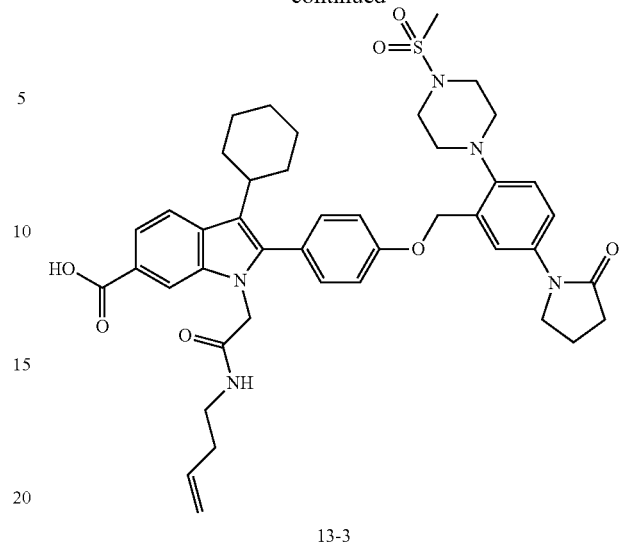

13-3

The target product 1-(but-3-enyl-carbamoyl-methyl)-3-cyclohexyl-2-[4-[2-(4-methane-sulfonyl-piperazin-1-yl)-5-(2-oxo-pyrrolidin-1-yl)-benzyloxy]-phenyl]-1H-indole-6-carboxylic acid 13-3 was obtained in 99% yield as a yellow powder, following the procedure reported for the synthesis of compound 12-4 and using intermediate 13-2 instead of intermediate 12-3; m/z=782 (M+H)+.
Step D.

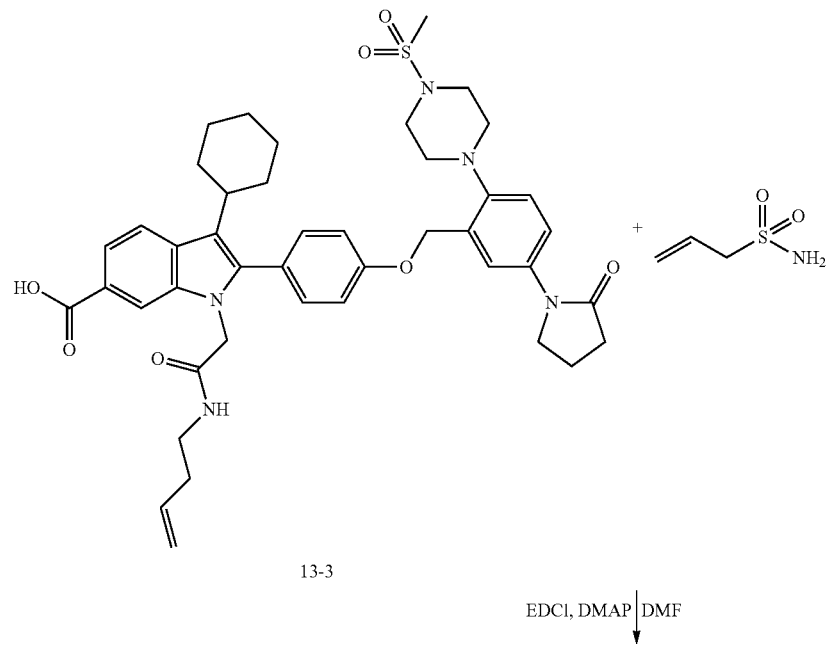

13-3

EDCl, DMAP | DMF

-continued

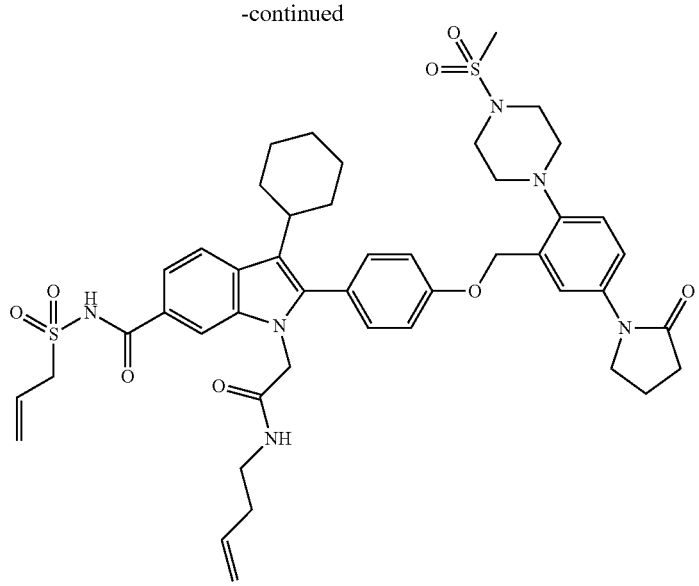

13-4

The target product N-but-3-enyl-2-[3-cyclohexyl-2-[4-[2-(4-methanesulfonyl-piperazin-1-yl)-5-(2-oxo-pyrrolidin-1-yl)-benzyloxy]-phenyl]-6-(prop-2-ene-1-sulfonylaminocarbonyl)-indol-1-yl]-acetamide 13-4 was obtained in 84% yield as a yellow powder, following the procedure reported for the synthesis of compound 12-5 and using intermediate 13-3 instead of intermediate 12-4; m/z=886 (M+H)$^+$.

Step E.

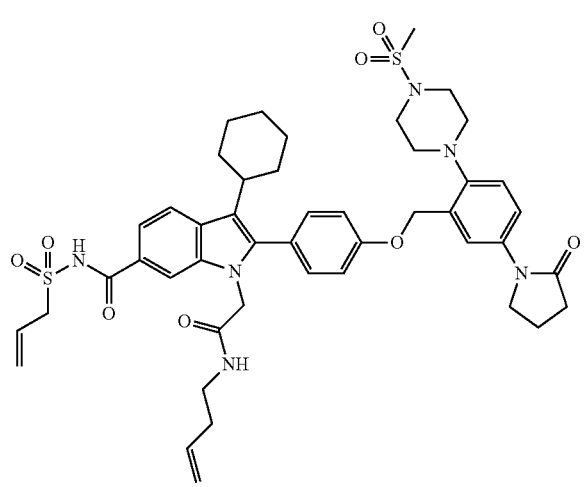

13-4

HG-II, DCE, 80° C.

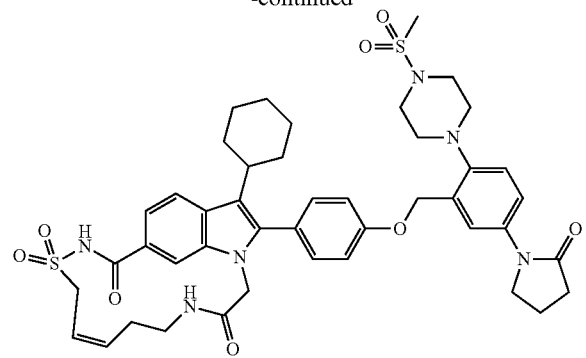

14

The target product 14 was obtained in 1% yield as a gray powder, following the procedure reported for the synthesis of compound 13 and using intermediate 13-4 instead of intermediate 12-5; m/z=858 (M+H)$^+$. NMR (DMSO-d6): δ (ppm) 1.12-1.35 (m, 4H, cyclohexyl), 1.65-1.77 (m, 4H, cyclohexyl), 1.86-1.95 (m, 2H, cyclohexyl), 2.06 (qt, J=7.4 Hz, 2H, CH$_2$-pyrrolidinone), 2.31 (m, 2H, CH$_2$CH=CH), 2.48 (m, 2H, CH$_2$-pyrrolidinone), 2.57 (m, 1H, CH cyclohexyl), 2.90 (s, 3H, SO$_2$CH$_3$), 2.99 (m, 4H, piperidine), 3.22 (m, 2H, CH$_2$NHCO), 3.29 (m, 4H, piperidine), 3.40 (m, 2H, CH$_2$SO$_2$), 3.82 (t, J=7.1 Hz, 2H, CH$_2$-pyrrolidinone), 4.38 (s, 2H, CH$_2$CONH), 5.22 (s, 2H, CH$_2$O), 5.61 (m, 2H, CH=CH), 7.18 (d, J=8.6 Hz, 2H), 7.26 (d, J=8.8 Hz, 1H), 7.44 (d, J=8.5 Hz, 2H), 7.50 (d, J=8.35 Hz, 1H), 7.59 (dd, J=2.5 Hz, 8.7 Hz, 1H), 7.63 (d, J=8.36 Hz, 1H), 7.84 (d, J=2.5 Hz, 1H), 7.96 (s, 1H), 8.53 (broad t, J=4.9 Hz, 1H, NHCO).

Example 14

17-Cyclohexyl-18-[2-fluoro-4-[2-(4-methanesulfonyl-piperazin-1-yl)-5-(2-oxo-pyrrolidin-1-yl)-benzyloxy]-phenyl]-1,4,11-triaza-tricyclo[11.5.2.0$^{16,19}$]icosa-7,13(20),14,16(19),17-pentaene-3,12-dione (15)

Step A:

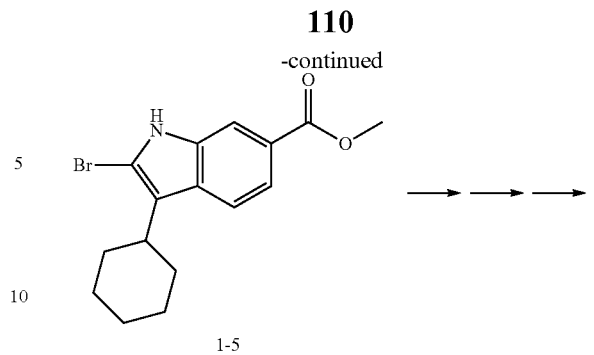

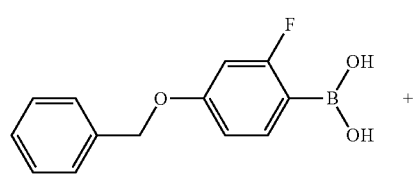

Intermediate 3-cyclohexyl-2-(2-fluoro-4-hydroxy-phenyl)-1-methoxycarbonylmethyl-1H-indole-6-carboxylic acid methyl ester 14-1 was synthesized following the steps D, E and F of example 3, starting from bromoindole 1-5 and 4-benzyloxy-2-fluorophenyl-boronic acid instead of 4-benzyloxybenzeneboronic acid and was obtained in 73% overall yield as a yellow solid; m/z=440 (M+H)$^+$.

Step B.

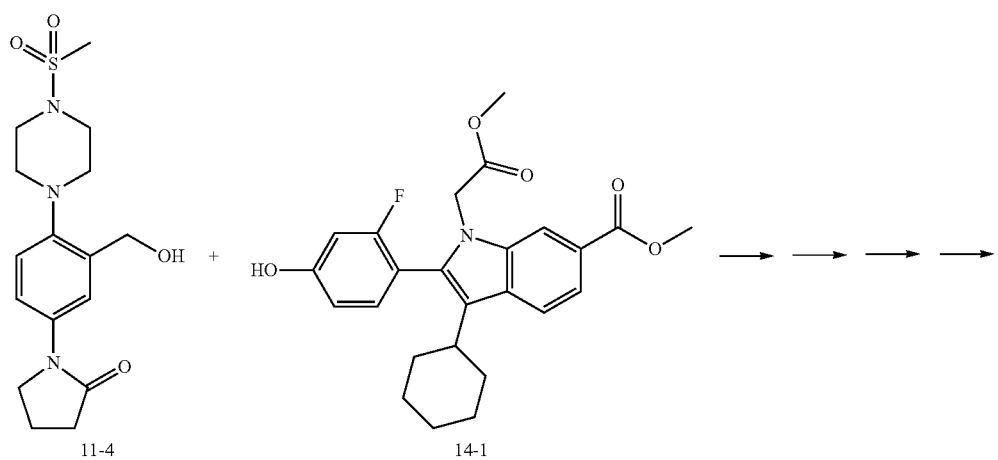

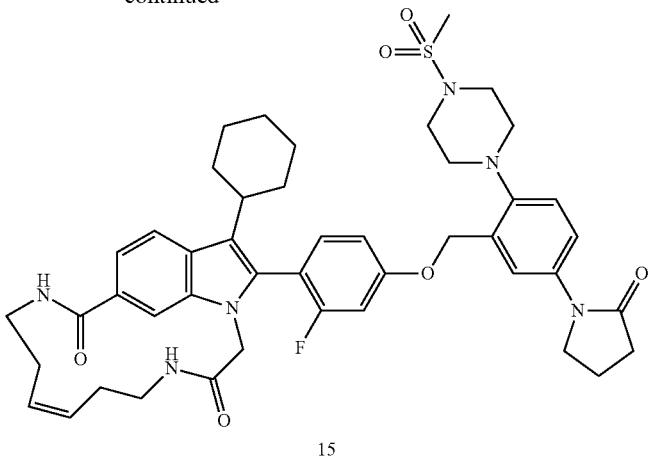

15

The target product 15 was synthesized following the steps E, F, G and H of example 11, starting from 11-4 and 14-1 instead of intermediate 3-8, and was obtained as an off-white solid; m/z=826 (M+H)+.

Example 15

Synthesis of 18-[2-(4'-Chloro-4-methoxy-biphenyl-2-yl)-quinolin-6-yl]-17-cyclohexyl-1,4,11-triazatricyclo[11.5.2.0^{16,19}]icosa-7,13(20),14,16(19),17-pentaene-3,12-dione (16)

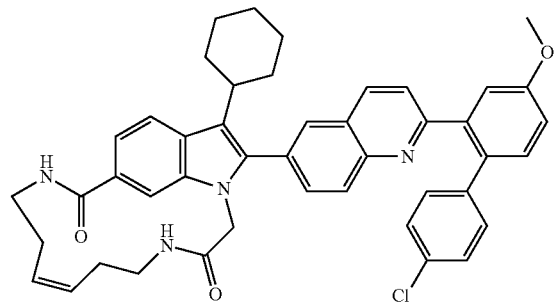

16

Step A.

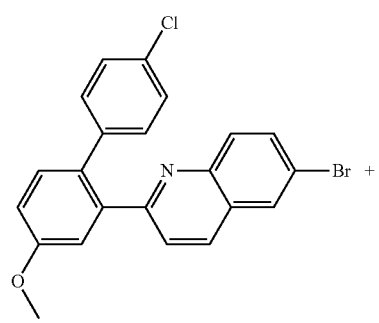

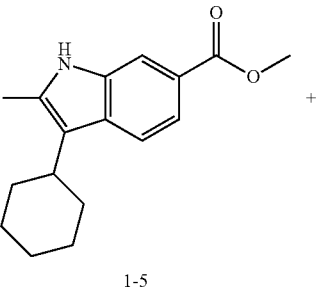

1-5

-continued

Pd(PPh3)4
NaHCO3, DMSO, 50° C.

15-1

A mixture of 6-bromo-2-(4'-chloro-4-methoxy-biphenyl-2-yl)-quinoline (200 mg, 0.473 mmol, synthesized as reported in WO2006/076529), bis(neopentylglycolato)-diboron (127 mg, 1.2 eq), potassium acetate (90 mg, 2 eq) and tetrakis(triphenylphosphine)palladium(0) (0.11 eq) in DMSO was stirred at 50° C. under N2 during 3 h. The reaction mixture was then diluted with ethyl acetate, washed with a NaHCO3 solution (5 M) and with brine, then dried over Na2SO4, filtered and concentrated. The residue was purified by preparative TLC to afford 150 mg (70%) of 2-(4'-chloro-4-methoxy-biphenyl-2-yl)-6-(5,5-dimethyl-[1,3,2]dioxaborinan-2-yl)-quinoline 15-1; m/z=458 (M+H+).

Step B.

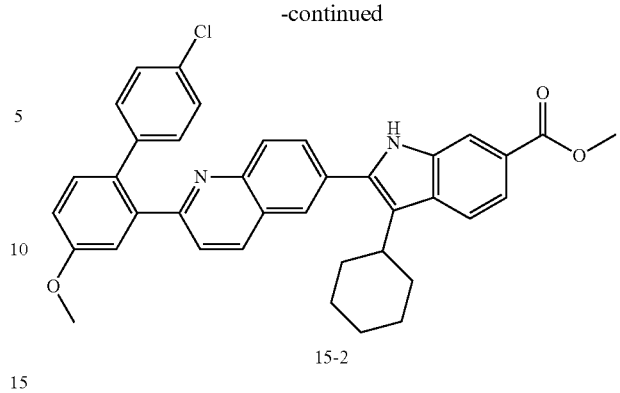

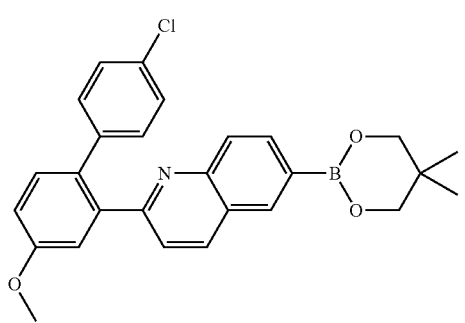

A mixture of intermediate 15-1 (150 mg, 0.328 mmol), intermediate 1-5 (110 mg, 1 eq), NaHCO₃ (55 mg, 2 eq) and Tetrakis(triphenylphosphine)palladium(0) (0.11 eq) in toluene was stirred at 80° C. under $N_2$ overnight. The reaction mixture was then concentrated, redissolved with ethyl acetate, washed with a NaHCO₃-solution (5 M) and with brine, then dried over $Na_2SO_4$, filtered and concentrated. The residue was purified by preparative TLC to afford 100 mg (50%) of 2-[2-(4'-Chloro-4-methoxy-biphenyl-2-yl)-quinolin-6-yl]-3-cyclohexyl-1H-indole-6-carboxylic acid methyl ester 15-2; m/z=601 (M+H⁺).

Step C.

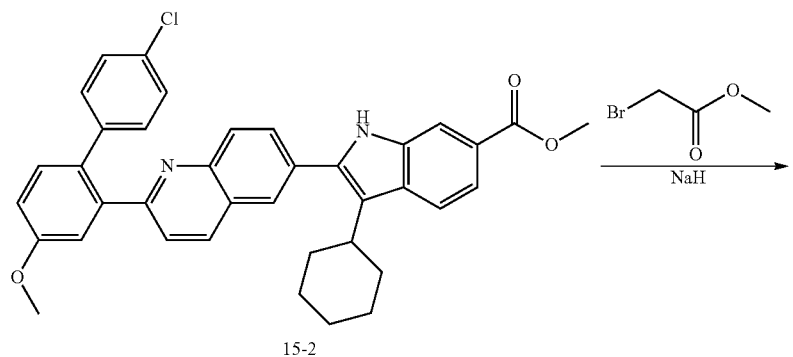

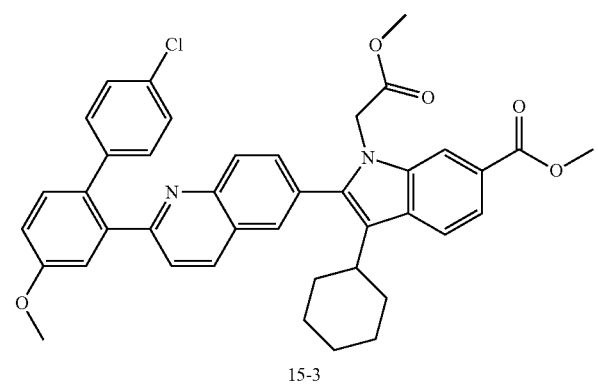

To a mixture of intermediate 15-2 (1.024 g, 1.7 mmol) and bromomethylacetate (388 mg, 1.5 eq) in dry DMF (30 mL) was added NaH (60% dispersion in mineral oil, 122 mg, 1.8 eq) at 0° C. After stirring for 20 min at this temperature, the reaction mixture was warmed up to room temperature. After 24 h, the reaction mixture was poured into 300 mL of ice-cold water. The formed yellow solid was filtered off, washed with petroleum ether and purified by column chromatography (CH$_2$Cl$_2$) to give 450 mg (39%) of 2-[2-(4'-Chloro-4-methoxy-biphenyl-2-yl)-quinolin-6-yl]-3-cyclohexyl-1-methoxycarbonylmethyl-1H-indole-6-carboxylic acid methyl ester 15-3; m/z=674 (M+H$^+$).

Step D.

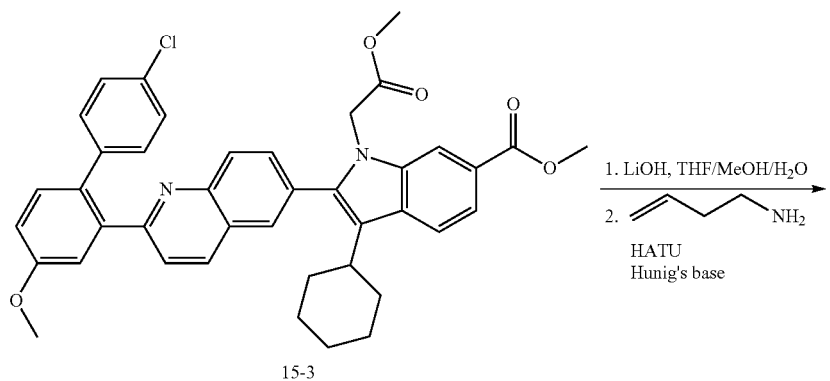

15-3

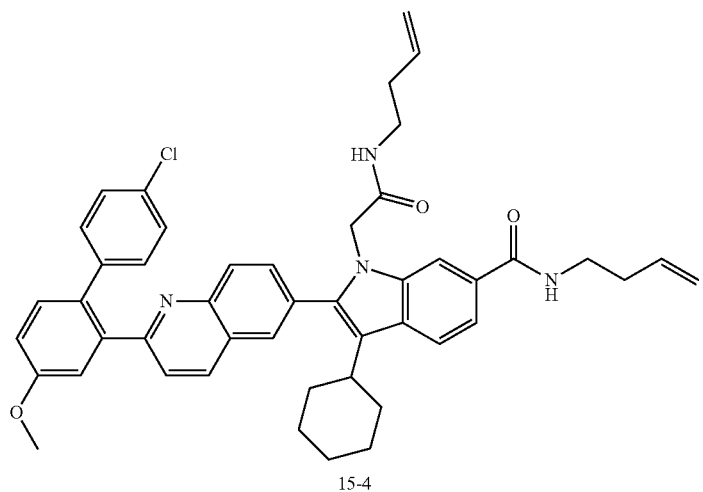

15-4

To a solution of intermediate 15-3 (450 mg, 0.669 mmol) in THF/methanol (1:1, 20 mL) was added a solution of LiOH (1.69 g, 59 eq) in water (10 mL) dropwise. The reaction mixture was stirred at room temperature until completion (48 h), then concentrated under reduced pressure, diluted with water, acidified with HCl 6 M until pH 3, extracted with ethyl acetate, dried over Na$_2$SO$_4$, filtered and evaporated to dryness to afford 429 mg (99%) of the desired bis-carboxylic acid intermediate as a yellow solid, which was used without any further purification in the next step; m/z=691 (M+H$^+$).

A mixture of the previous intermediate (350 mg, 0.544 mmol), HATU (641 mg, 3.1 eq), But-3-enylamine (86 mg, 2.23 eq) and Hunig's base (282 mg, 4 eq) in dry DMF (10 mL) was stirred at room temperature under N$_2$. After 18 h, the reaction mixture was poured into water and the yellow precipitate was filtered off, washed with a bit of water then petroleum ether, to afford 300 mg (73%) of 1-but-3-enylcarbamoyl-methyl-2-[2-(4'-chloro-4-methoxy-biphenyl-2-yl)-quinolin-6-yl]-3-cyclohexyl-1H-indole-6-carboxylic acid but-3-enylamide 15-4, which was used without any further purification in the next step; m/z=752 (M+H$^+$).

Step E.

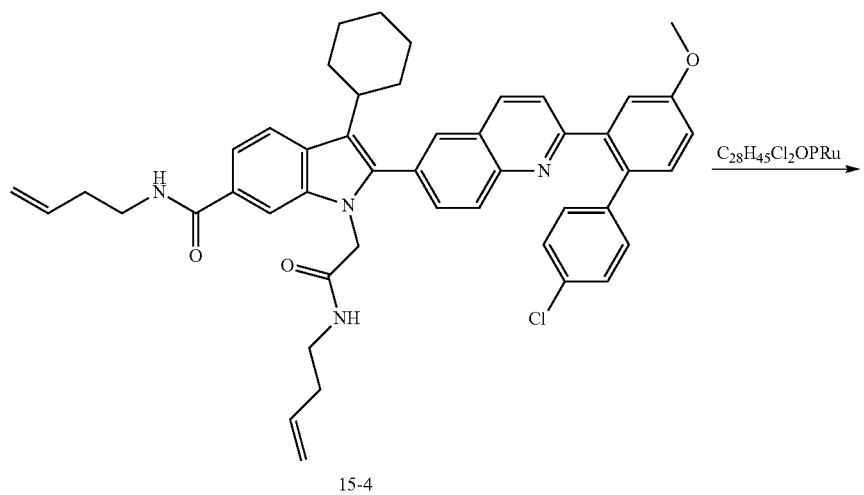

15-4

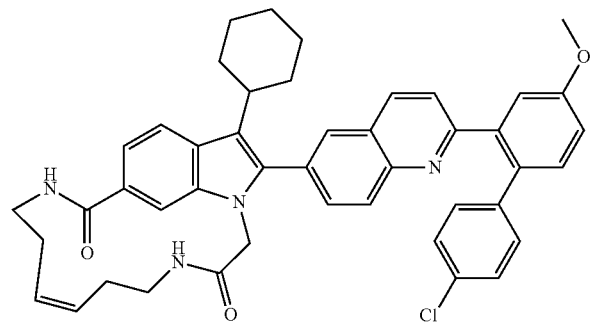

16

A solution of intermediate 15-4 (297 mg, 0.396 mmol) in dichloroethene (DCE; 300 mL) was bubbled through with $N_2$ during 2 h. Hoveyda-Grubbs $1^{st}$ generation catalyst (101 mg, 0.42 eq) was then added and the reaction mixture was heated at 80° C. under $N_2$ overnight. The reaction mixture was then concentrated under reduced pressure and purified by flash chromatography ($CH_2Cl_2$/methanol 97.5:2.5) to afford 87 mg (30%) of the desired product 16; m/z=724 (M+H$^+$), NMR (DMSO-d6): δ (ppm) 1.18-1.34 (m, 3H), 1.65 (m, 1H), 1.75 (m, 4H), 1.92 (m, 2H), 2.19 (m, 2H), 2.33 (m, 2H), 2.67 (m, 1H), 3.25 (m, 2H), 3.44 (m, 2H), 3.88 (s, 3H, OMe), 4.47+ 4.50 (s, 2H, 0.2/0.8), 5.36 (m, 1H), 5.53 (m, 1H), 7.10 (d, J=8.4 Hz, 1H), 7.16 (m, 2H), 7.19 (d, J=2.4 Hz, 1H), 7.30 (d, J=2.4 Hz, 1H), 7.32 (d, J=8.4 Hz, 1H), 7.42+7.57 (t, J=5.6 Hz, NH), 7.43 (d, J=8.4 Hz, 1H), 7.49 (d, J=8.4 Hz, 1H), 7.74+ 7.92 (s, 1H, 0.2/0.8), 7.84 (d, J=8.4 Hz, 1H), 7.96 (d, J=8.4 Hz, 1H), 8.08+8.143 (s, 1H, 0.2/0.8), 8.17 (d, J=8.4 Hz, 1H), 8.21 (d, J=8.4 Hz, 1H), 8.30+8.50 (m, 1H, NH).

Example 16

Synthesis of 17-Cyclohexyl-18-[2-(2,4-dimethyl-thiazol-5-yl)-quinolin-6-yl]-1,4,11-triaza-tricyclo[11.5.2.0$^{16,19}$]icosa-7,13 (20),14,16(19),17-pentaene-3,12-dione (17)

17

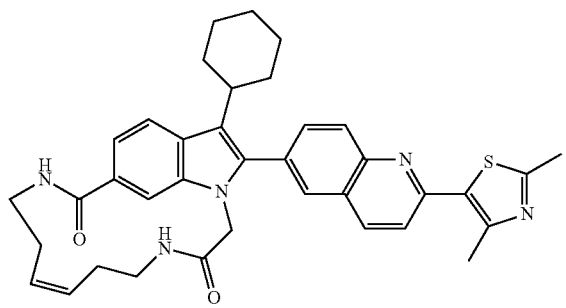

Step A.

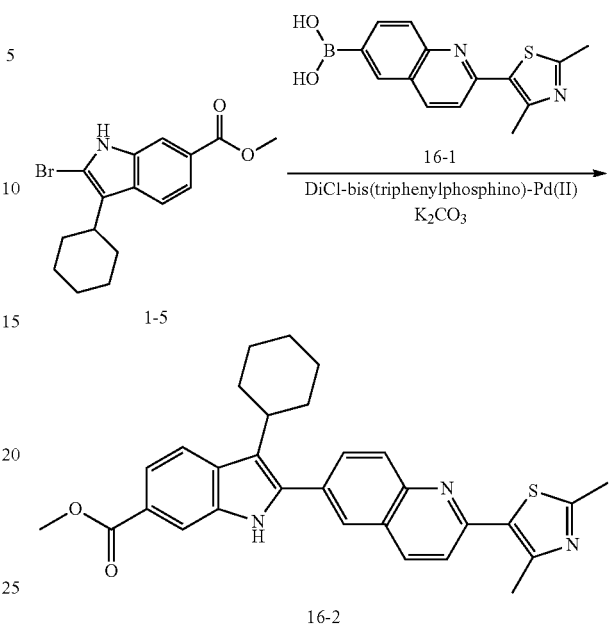

A mixture of intermediate 1-5 (4.02 g, 12 mmol), 2-(2,4-dimethyl-thiazol-5-yl)-quinoline-6-boronic acid 16-1 (4.58 g, 1.19 eq, synthesized as described in WO2006/076529), $K_2CO_3$ (5.13 g, 3.1 eq) and dichloro-bis(triphenylphosphino)-Pd(II) (0.86 g, 0.10 eq) in ethanol/toluene (1:1, 80 mL) was stirred at room temperature under $N_2$ overnight. After concentration under reduced pressure, the reaction mixture was redissolved in ethyl acetate and washed with a 5 M NaHCO$_3$ solution. The obtained yellow precipitate was filtered off, washed with water, then isopropanol to give 4.13 g (67%) of 3-Cyclohexyl-2-[2-(2,4-dimethyl-thiazol-5-yl)-quinolin-6-yl]-1H-indole-6-carboxylic acid methyl ester 16-2 as a yellow solid; m/z=496 (M+H$^+$).

Step B.

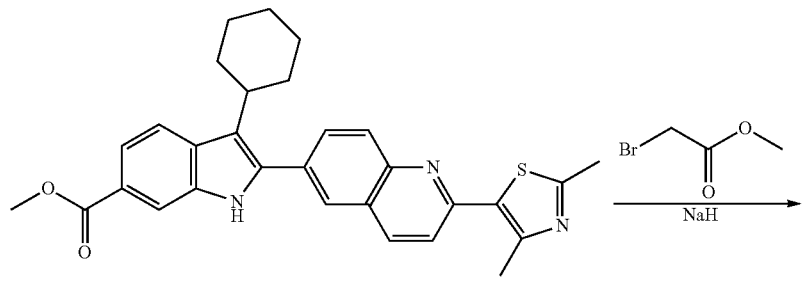

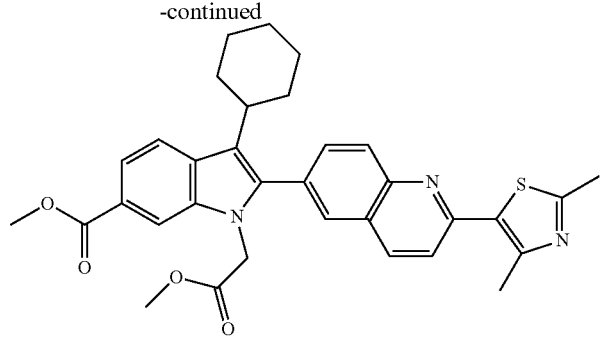
16-3
Intermediate 16-3 was synthesized following the procedure reported in the step C of the synthesis of example 15, starting from intermediate 16-2 (1.134 g, 2.29 mmol) instead of 15-2 and yielding 1.3 g (100%) of the pure product 3-cyclohexyl-2-[2-(2,4-dimethyl-thiazol-5-yl)-quinolin-6-yl]-1-methoxycarbonylmethyl-1H-indole-6-carboxylic acid methyl ester 16-3 as a white solid; m/z=568 (M+H⁺).
Step C.
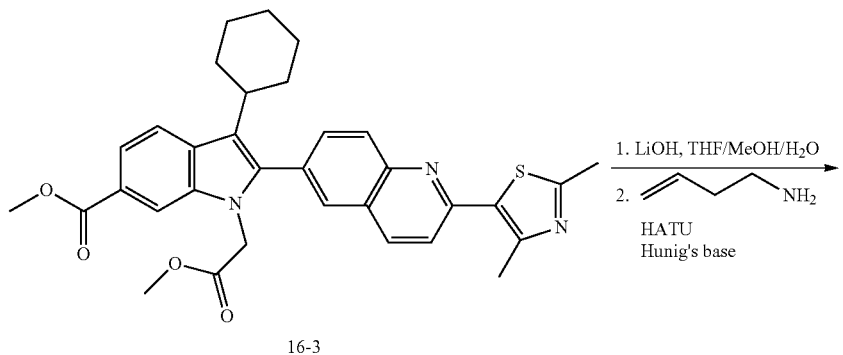
16-3
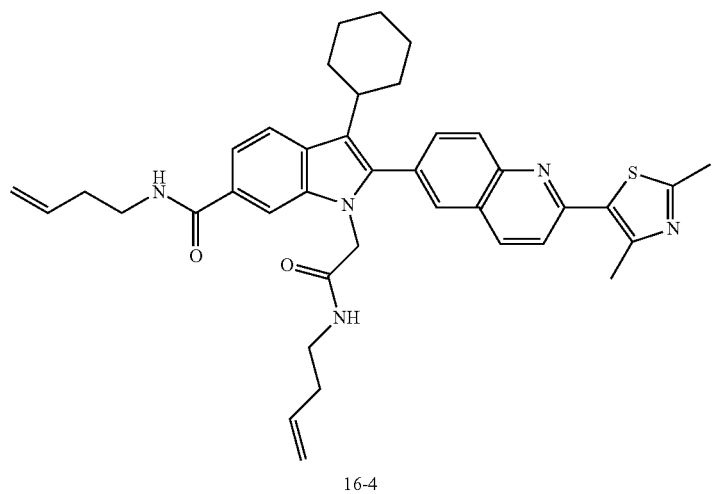
16-4

Intermediate 16-4 was synthesized following the procedure reported in step D of the synthesis of example 15, starting from 16-3 (0.52 g, 0.917 mmol) instead of 15-3 and yielding 0.5 g (69%) of the pure product 1-but-3-enylcarbamoylmethyl-3-cyclohexyl-2-[2-(2,4-dimethyl-thiazol-5-yl)-quinolin-6-yl]-1H-indole-6-carboxylic acid but-3-enylamide 16-4 as a yellow solid; m/z=646 (M+H$^+$).
Step D.
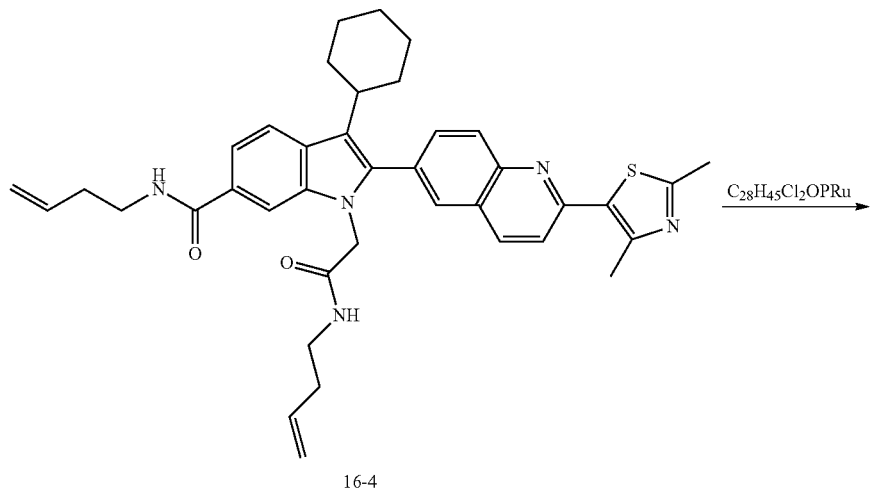
16-4
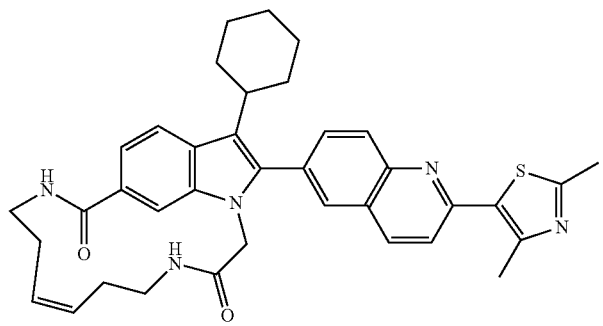
17

The final compound 17 was synthesized following the procedure reported in the step E of the synthesis of example 15, starting from 16-4 (0.41 g, 0.636 mmol) instead of 15-4 and yielding 0.162 g (41%) of the pure product 17; m/z=618 (M+H$^+$), NMR (DMSO-d6); δ (ppm) 1.03-1.27 (m, 3H), 1.64 (m, 1H), 1.074 (m, 4H), 1.88 (m, 2H), 2.19 (m, 1H), 2.34 (m, 3H), 2.61 (m, 1H), 2.64 (s, 3H, Me), 2.72 (s, 3H, Me), 3.24 (m, 2H), 3.39 (m, 2H), 4.48+4.51 (s, 2H, 0.3/0.7), 5.36 (m, 1H), 5.54 (m, 1H), 7.44+7.50 (d, J=8.4 Hz, 1H, 0.3/0.7), 7.45+7.57 (t, J=5.8 Hz, NH, 0.3/0.7 rotamers), 7.73+7.92 (s, 1H, 0.3/0.7), 7.84 (d, J=8.4 Hz, 1H), 7.92 (d, J=8.6 Hz, 1H), 7.92+7.98 (dd, J=1.5 Hz, 8.6 Hz, 1H, 0.3/0.7), 8.10 (d, J=8.6 Hz, 1H), 8.31+8.51 (m, 1H, 0.7/0.3), 8.54 (d, J=8.8 Hz, 1H).

Example 17

Synthesis of 17-cyclohexyl-18-[2-(2,4-dimethyl-thiazol-5-yl)-quinolin-6-yl]-10,10-dioxo-10λ$^6$-thia-1,4,11-triaza-tricyclo[11.5.2.0$^{16,19}$]icosa-7,13(20),14,16(19),17-pentaene-3,12-dione (18)

18

Step A.

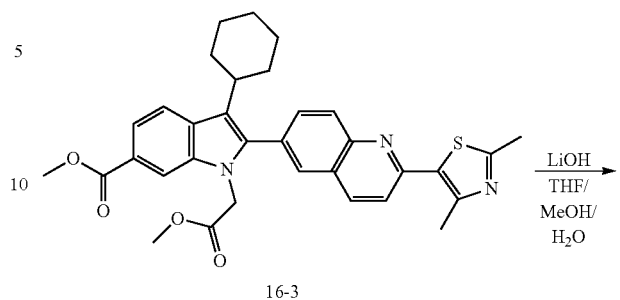

16-3

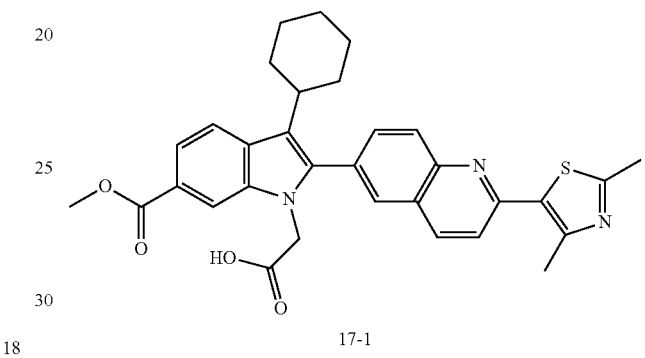

17-1

To a solution of intermediate 16-3 (1.17 g, 2.061 mmol) in THF (100 mL), cooled at 0° C. with an ice bath, was added a solution of LiOH (56%, 107 mg, 1.2 eq) in water (6 mL) dropwise. The reaction mixture was stirred at 0° C. until completion (30 h), next acidified to pH 4 with HCl 3 M and concentrated under reduced pressure. Water was then added to the residue and the yellow precipitate was filtered off and washed with petroleum ether, affording 1.09 g (95%) of [1-carboxymethyl-3-cyclohexyl-2-[2-(2,4-dimethyl-thiazol-5-yl)-quinolin-6-yl]-1H-indole]-6-carboxylic acid methyl ester 17-1, which was used without any further purification in the next step; m/z=554 (M+H$^+$).

Step B.

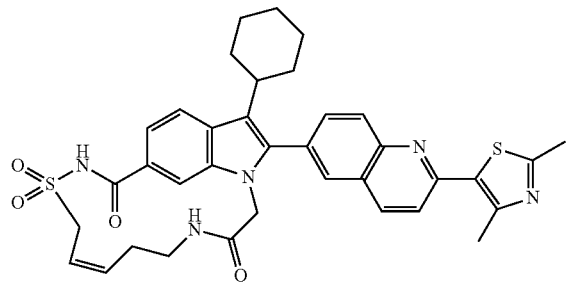

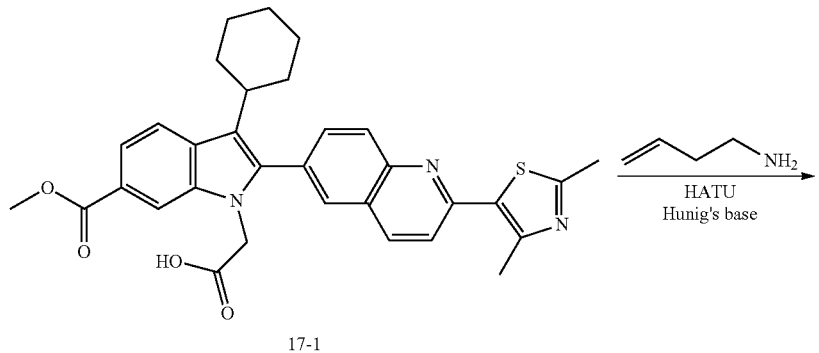

17-1

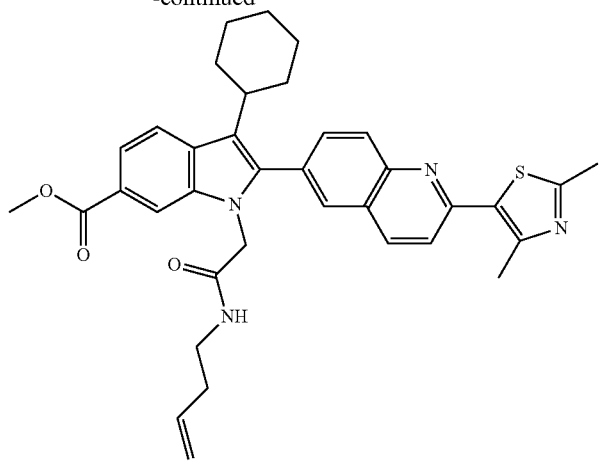

17-2

A mixture of the previous intermediate 17-1 (506 mg, 0.915 mmol), HATU (686 mg, 1.97 eq), but-3-enylamine (83 mg, 1.1 eq) and Hunig's base (352 mg, 3 eq) in dry DMF (5 mL) was stirred at room temperature under $N_2$. After 18 h, the reaction mixture was poured into water and the precipitate was filtered off, washed with water and heptane, affording 457 mg (82%) of the desired product 1-(3-butenyl-carbamoylmethyl)-3-cyclohexyl-2-[2-(2,4-dimethyl-thiazol-5-yl)-quinolin-6-yl]-1H-indole-6-carboxylic acid methyl ester 17-2 as a yellow solid, which was used without any further purification in the next step; m/z=607 (M+H$^+$).

Step C.

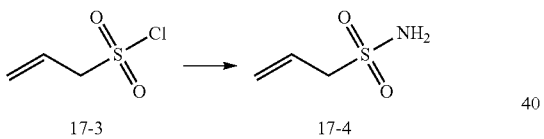

17-3    17-4

To a solution of prop-2-ene-1-sulfonyl chloride 17-3 (5 g, 35.56 mmol) in dry THF, at 0° C., was bubbled $NH_3$ gas during 30 min. The reaction mixture was then concentrated under reduced pressure, ethyl acetate was added and the reaction mixture was heated at 70° C., then filtered over silica (hot) and washed with hot ethyl acetate. The organic layers were concentrated and the residue was crystallized from pentane, to give 4 g (93%) of the desired product prop-2-ene-1-sulfonic acid amide 17-4 as a white solid; m/z=122 (M+H$^+$).

Step D.

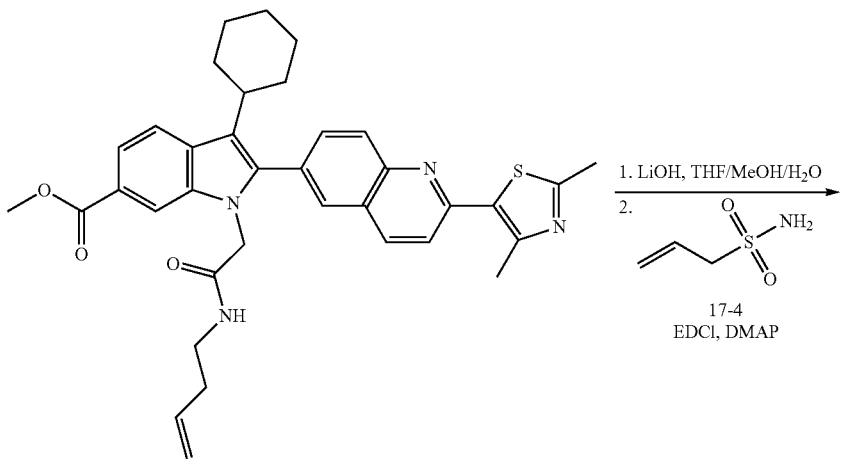

17-2

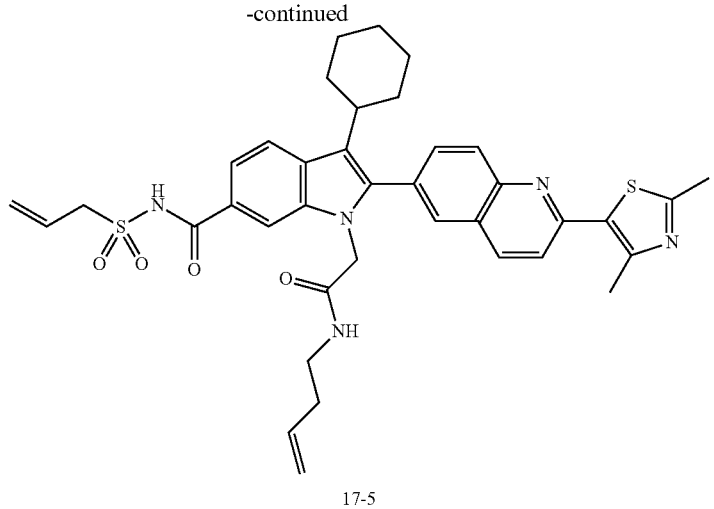

17-5

To a solution of intermediate 17-2 (457 mg, 0.754 mmol) in THF/methanol (1:1, 10 mL) was added a solution of NaOH (3.05 g, 100 eq) in water (5 mL) at room temperature. The reaction mixture was stirred at room temperature until completion (24 h), then concentrated under reduced pressure, diluted with water and acidified with HCl 6 M until pH 3 with a vigorous stirring. The resulting precipitate was filtered off and washed with petroleum ether, affording 409 mg (91%) of the desired intermediate as a yellow solid, which was used without any further purification in the next step; m/z=593 (M+H$^+$).

A mixture of the previous intermediate (404 mg, 0.682 mmol), EDCI (224 mg, 1.7 eq), 17-4 (167 mg, 2 eq) and DMAP (150 mg, 1.8 eq) in dry DMF (10 mL) was stirred at room temperature under N$_2$. After 18 h, the reaction mixture was poured into water and the product was extracted with a mixture of ethyl acetate and THF several times. The organic layers were combined, washed with water and brine, dried over Na$_2$SO$_4$, filtered and concentrated under reduced pressure. Recrystallization from CH$_2$Cl$_2$/diethylether afforded 268 mg (56%) of N-but-3-enyl-2-[3-cyclohexyl-2-[2-(2,4-dimethyl-thiazol-5-yl)-quinolin-6-yl]-6-(prop-2-ene-1-sulfonyl-aminocarbonyl)-indol-1-yl]-acetamide 17-5 as a yellow solid; m/z=696 (M+H$^+$).

Step E.

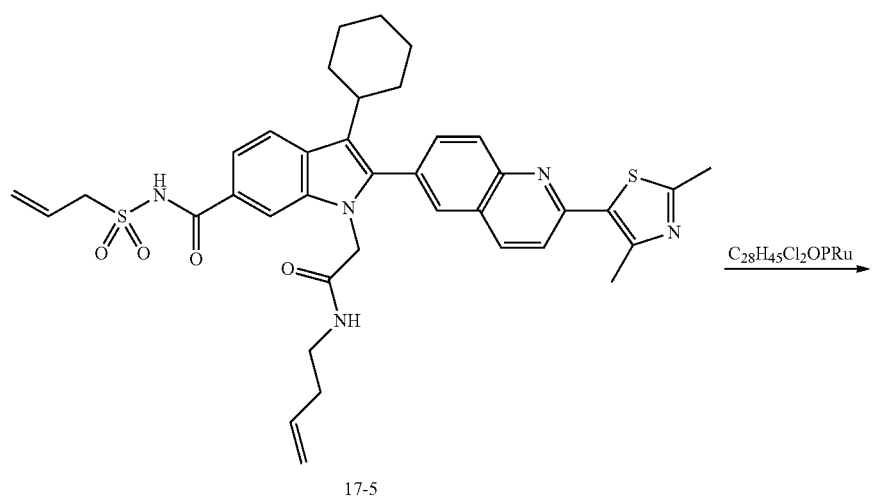

17-5

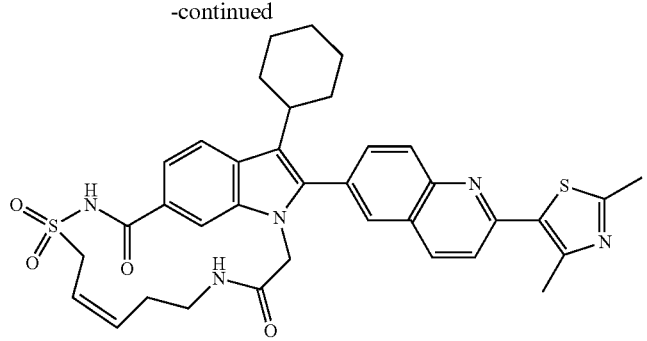

18

A solution of intermediate 17-5 (260 mg, 0.373 mmol) in DCE (400 mL) was bubbled through with $N_2$ during 2 h. Hoveyda-Grubbs $1^{st}$ generation catalyst (45 mg, 0.2 eq) was next added and the reaction mixture was heated at 80° C. under $N_2$ overnight. The reaction mixture was then concentrated under reduced pressure and purified by flash chromatography ($CH_2Cl_2$/methanol 95:5) to give the desired product 18 as a gray powder after recrystallization from $CH_2Cl_2$/isopropyl ether; m/z=668 (M+H+), NMR (DMSO-d6): δ (ppm) 1.20-1.30 (m, 3H), 1.63-1.93 (m, 9H), 2.34 (m, 2H), 2.66 (m, 1H), 2.67 (s, 3H), 2.73 (s, 3H), 3.23 (m, 2H), 4.50 (s, 2H), 5.64 (m, 2H), 7.45 (m, 1H), 7.73-8.12 (m, 6H), 8.47 (broad s, 1H, NHCO), 8.54 (d, J=8.4 Hz, 1H), 11.47 (broad s, 1H, $NHSO_2$).

Step A.

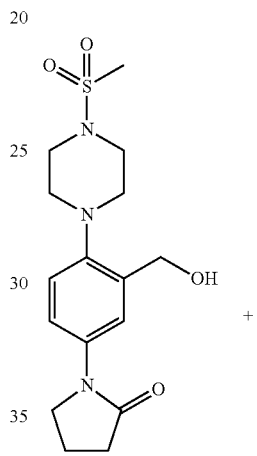

11-4

+

Example 18

Synthesis of 17-cyclohexyl-18-(2-fluoro-4-(2-(4-methanesulfonyl-piperazin-1-yl)-5-(2-oxo-pyrrolidin-1-yl)-benzyloxy)-phenyl)-9-methyl-10,10-dioxo-$10\lambda^6$-thia-1,4,9,11-tetraaza-tricyclo[11.5.2.0$^{16,19}$]icosa-6,13(20),14,16(19),17-pentaene-3,12-dione (19)

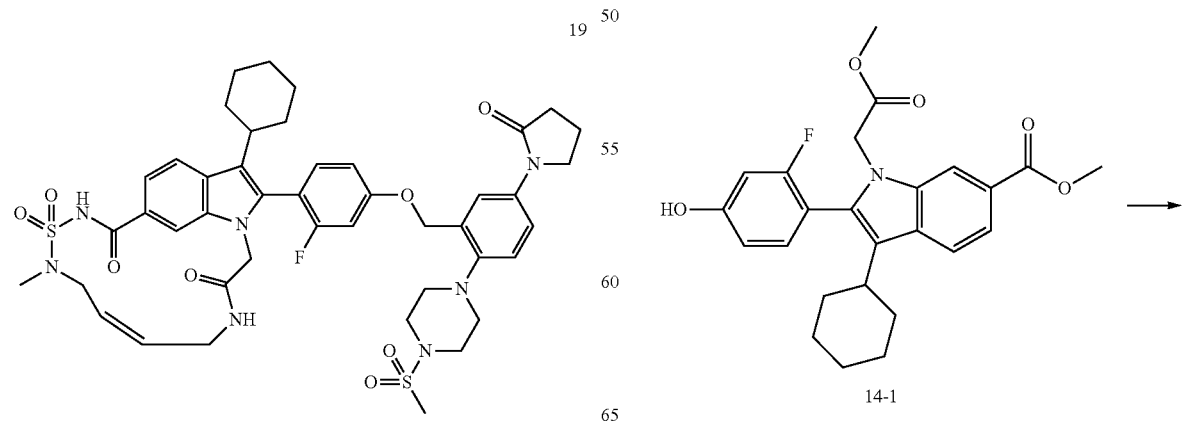

19

14-1

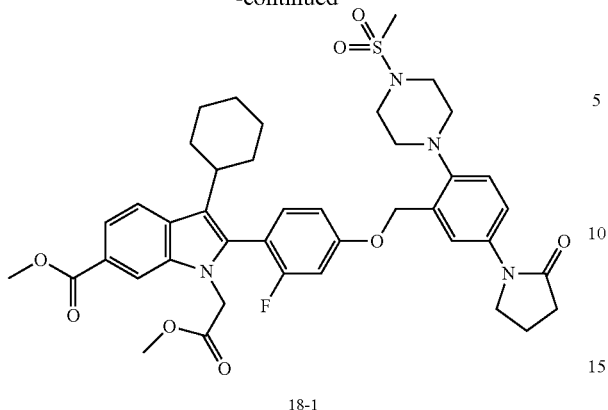

18-1

The intermediate 18-1 was synthesized following the step E of example 11, starting from 11-4 and 14-1 instead of intermediate 3-8, and was obtained in 68% yield; m/z=775 (M+H)⁺.

Step B

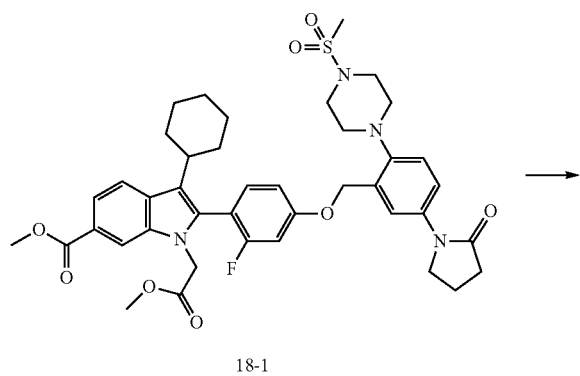

18-1

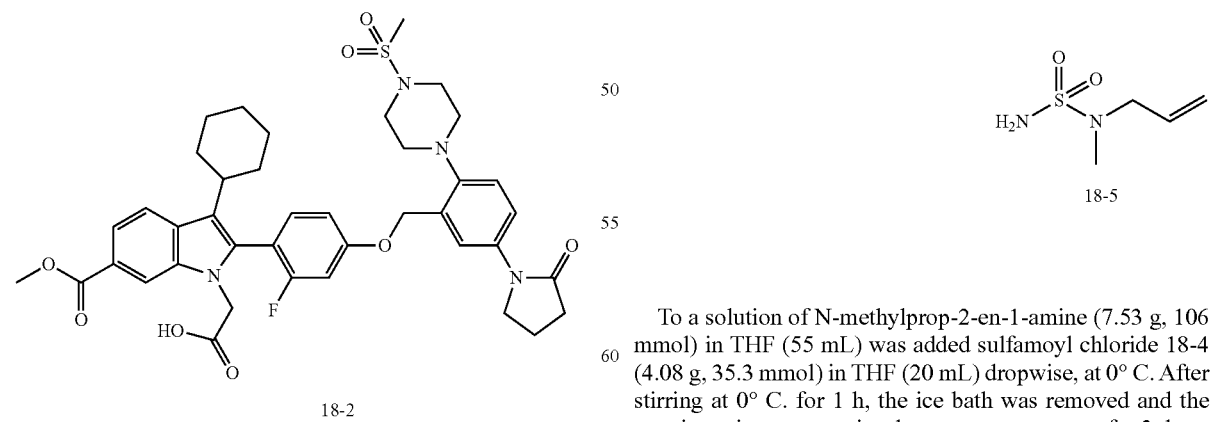

18-2

To a solution of intermediate 18-1 (1.19 g, 1.534 mmol) in THF/methanol 1:1, cooled at 0° C. with an ice bath, was added a solution of LiOH (40 mg, 1.1 eq) in water (6 mL) dropwise. The reaction mixture was stirred at 0° C. during 4 h then at room temperature, concentrated under reduced pressure to remove organic solvents, diluted with water, acidified to pH 4 with HCl 3 M and extracted with THF. The organic layer was separated, dried over magnesium sulfate, filtered and concentrated to give 1.04 g (89%) of the target product 18-2 as a yellow foam; m/z=761 (M+H⁺).

Step C

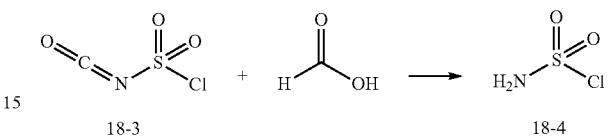

18-3    18-4

Formic acid (1.626 g, 35.3 mmol) was added to chlorosulfonyl isocyanate 18-3 (5 g, 1 eq) in a cooled stirred flask. Dry toluene (12 mL) was then added to the reaction mixture and the cooling bath was removed. The reaction mixture was stirred at room temperature overnight, then filtered and the filtrate was concentrated to dryness to afford 4.08 g of the target product 18-4 as a white solid.

Step D

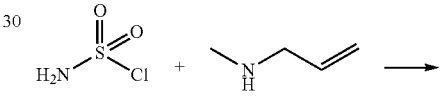

18-4

18-5

To a solution of N-methylprop-2-en-1-amine (7.53 g, 106 mmol) in THF (55 mL) was added sulfamoyl chloride 18-4 (4.08 g, 35.3 mmol) in THF (20 mL) dropwise, at 0° C. After stirring at 0° C. for 1 h, the ice bath was removed and the reaction mixture was stirred at room temperature for 3 days, then was concentrated under reduced pressure and the crude product was purified by flash chromatography using dichloromethane/methanol 9:1 as eluent to afford 2.64 g (50%) of the desired product 18-5 as a yellow solid; m/z=151 (M+H⁺).

Step E

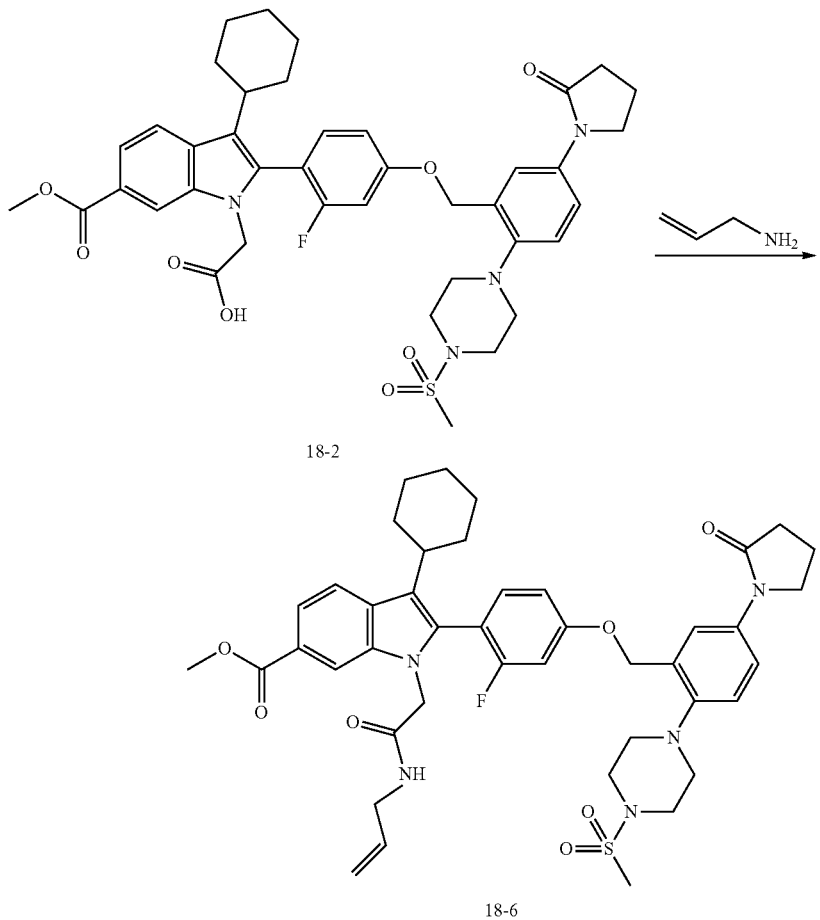

Intermediate 1-allylcarbamoylmethyl-3-cyclohexyl-2-(2-fluoro-4-(2-(4-methane-sulfonyl-piperazin-1-yl)-5-(2-oxo-pyrrolidin-1-yl)-benzyloxy)-phenyl)-1H-indole-6-carboxylic acid methyl ester 18-6 was obtained in 82% yield (351 mg) as a white powder, following the procedure reported for the synthesis of compound 12-3, using intermediate 18-2 (407 mg, 0.535 mmol) instead of intermediate 12-2 and allylamine (43 mg) instead of but-3-enylamine; m/z=800 (M+H)$^+$.

Step F

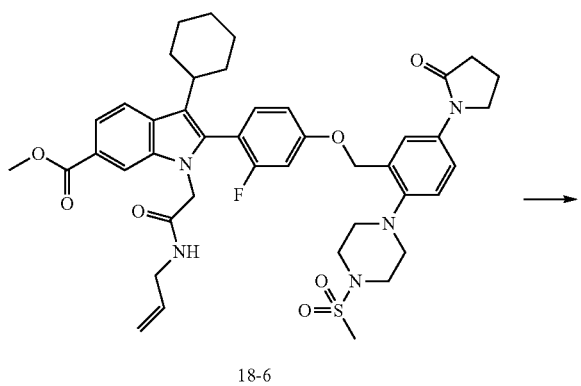

-continued

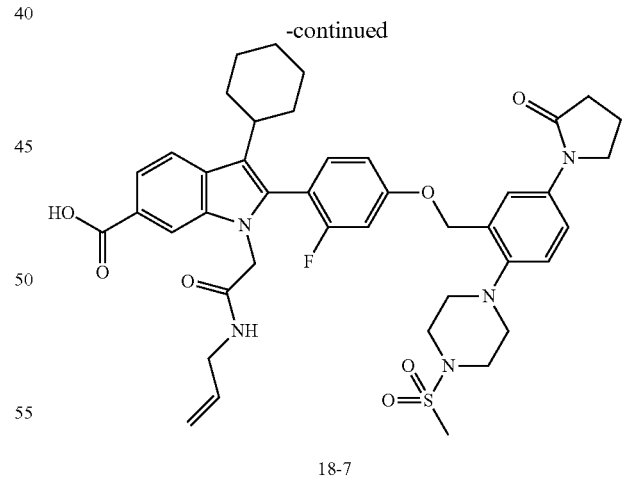

Intermediate 1-allylcarbamoylmethyl-3-cyclohexyl-2-(2-fluoro-4-(2-(4-methane-sulfonyl-piperazin-1-yl)-5-(2-oxo-pyrrolidin-1-yl)-benzyloxy)-phenyl)-1H-indole-6-carboxylic acid 18-7 was obtained in quantitative yield (351 mg), following the procedure reported for the synthesis of compound 12-4 and using intermediate 18-6 (351 mg, 0.439 mmol) instead of intermediate 12-3; m/z=786 (M+H)$^+$.

Step G
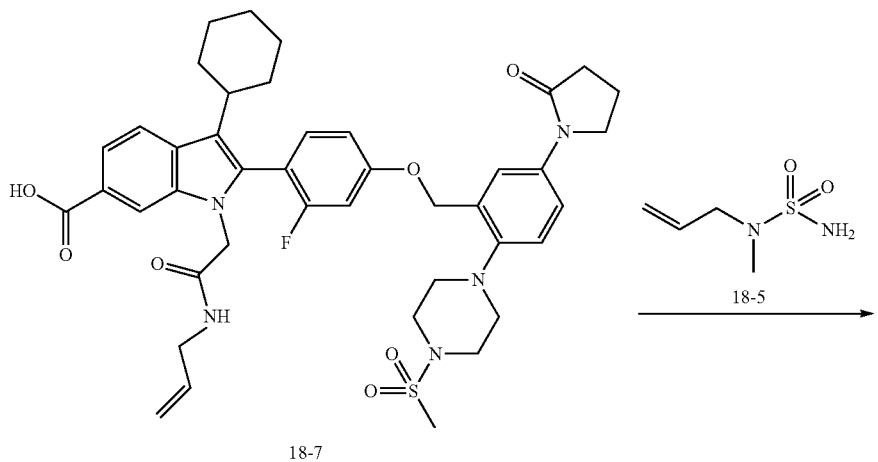
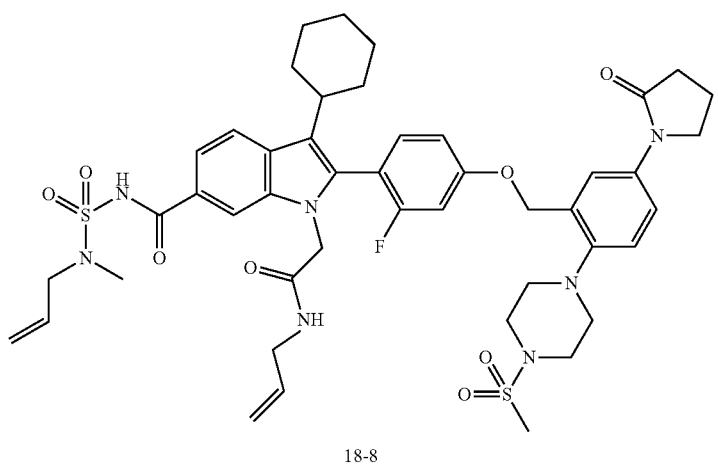
Intermediate 18-8 was synthesized in 69% yield (200 mg, 0.218 mmol) following the procedure reported for the synthesis of compound 12-5, using intermediate 18-7 instead of intermediate 12-4 and intermediate 18-5 instead of prop-2-en-1-sulfonamide; m/z=919 (M+H)$^+$.
Step H
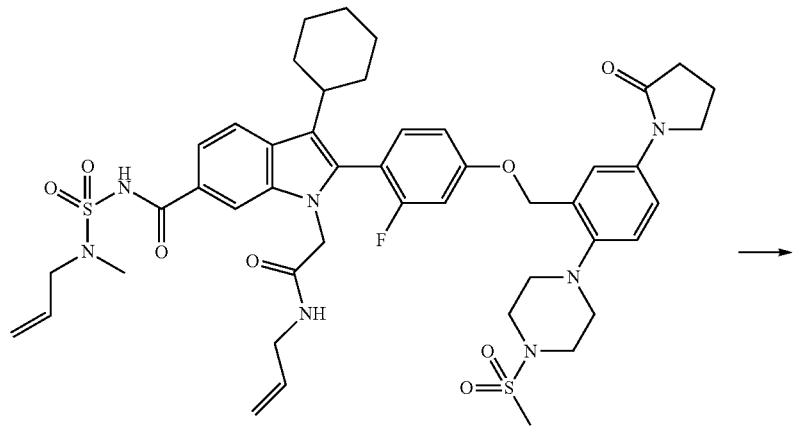

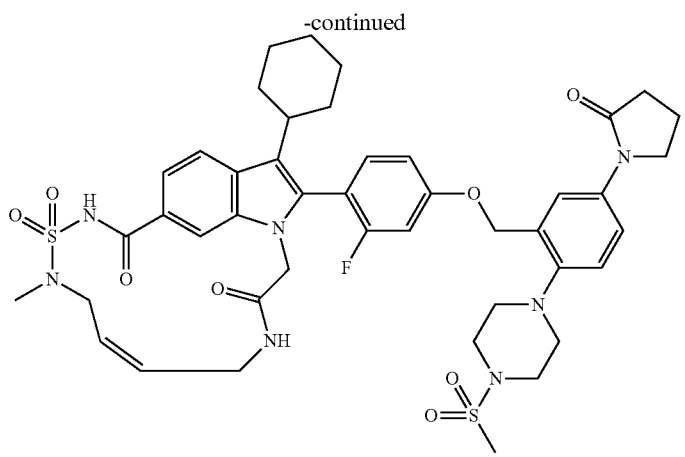

19

The target product 19 was synthesized from intermediate 18-8, following the procedure reported for the synthesis of compound 3 and using Hoveyda-Grubbs $2^{nd}$ generation catalyst instead of the $1^{st}$ generation catalyst; m/z=891 (M+H)$^+$.

Example 19

Synthesis of 19-(4-Chloro-phenyl)-18-cyclohexyl-10-methyl-11,11-dioxo-11$\lambda^6$-thia-1,4,10,12-tetraaza-tricyclo[12.5.2.0$^{17,20}$]henicosa-7,14(21),15,17(20),18-pentaene-3,13-dione (20)

(20)

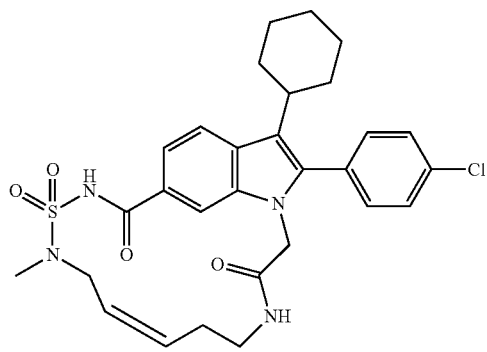

Step A

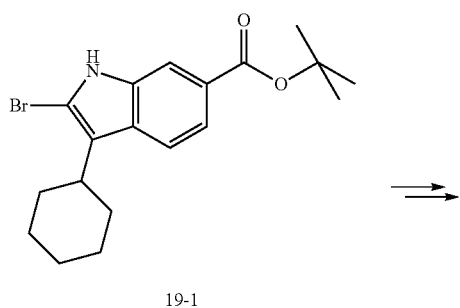

19-1

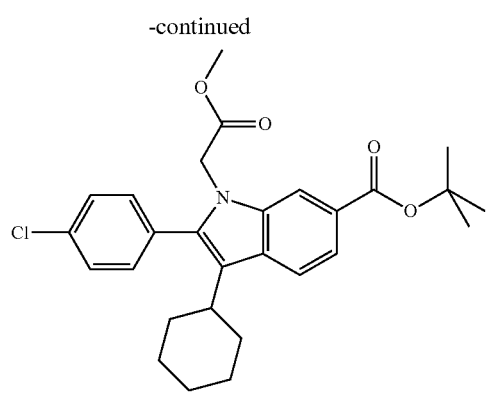

19-2

Compound 19-2 was synthesized following the steps E and F used in example 1, using the bromoindole 19-1 (synthesized as described in US2007270405 A1) instead of compound 1-5, and 4-chlorophenyl boronic acid instead of 3-furan boronic acid, and was obtained as a white powder, m/z=410 (M+H)$^+$ (yield 60%).

Step B

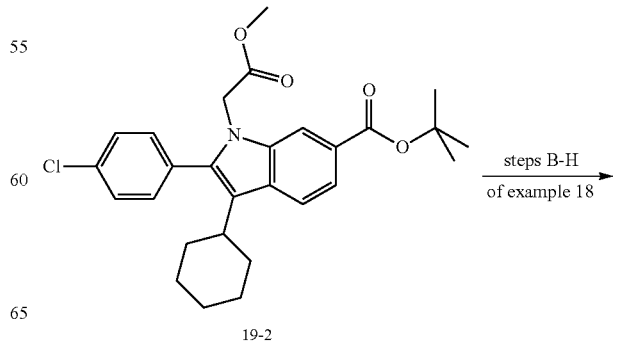

19-2 steps B-H of example 18

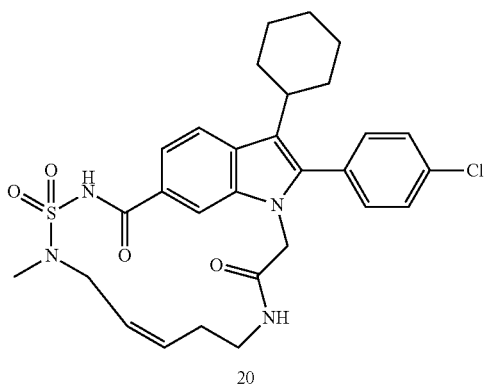

20

Compound 20 was synthesized in a similar way as compound 19, following the steps B to H of example 18, with the following modifications:

in step B, compound 19-2 was used instead of compound 18-1;

in step E, But-3-enylamine was used instead of allylamine;

in step F, a mixture of TFA and DCM was used instead of lithium hydroxide.

Compound 20 was obtained as a mixture of E/Z isomers with the ratio 14/86, m/z=570 (M+H)+. $^1$H NMR CDCl$_3$: 1.25-1.32 (m, 4H), 1.75-1.85 (m, 6H), 2.2 (s, 2H), 2.6-2.75 (m, 1H), 3.3 (s, 3H), 3.5 (s, 2H), 3.8 (s, 2H), 4.6 (s, 2H), 5.65-5.75 (m, 2H), 6.75 (s, 1H), 7.5-7.55 (m, 4H), 7.65-7.75 (m, 2H), 7.8 (d, J=8.44 Hz, 1H), 9.6 (s, 1H).

Example 20

Synthesis of 19-(4-Chloro-phenyl)-18-cyclohexyl-10-methyl-11,11-dioxo-11λ$^6$-thia-1,4,10,12-tetraaza-tricyclo[12.5.2.017,20]henicosa-14(21),15,17(20),18-tetraene-3,13-dione (21) and 18-Cyclohexyl-10-methyl-11,11-dioxo-19-phenyl-11λ$^6$-thia-1,4,10,12-tetraaza-tricyclo[12.5.2.017,20]henicosa-14(21),15,17(20),18-tetraene-3,13-dione (22)

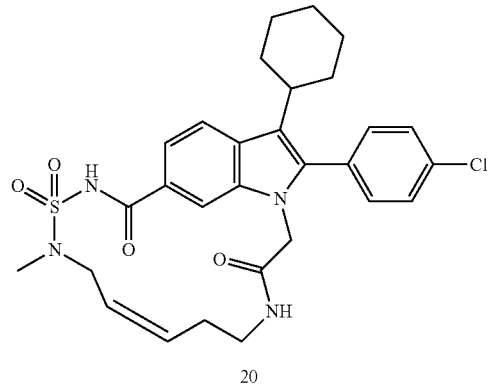

20

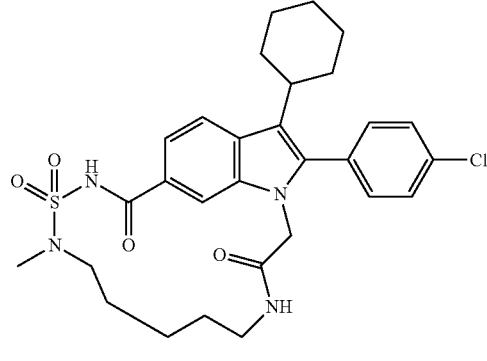

21

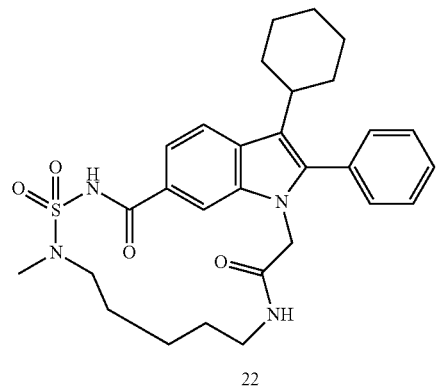

22

Compound (20) (140 mg, 0.246 mmol) was dissolved in ethyl acetate (20 mL) and was hydrogenated on Pd/C. The reaction mixture was then concentrated and the residue was purified by silica gel flash chromatography (mixture of DCM and ethyl acetate as eluent), then by preparative HPLC to yield 79 mg of compound (21), m/z=572 (M+H)+ $^1$H NMR CDCl$_3$: 1.25-1.32 (m, 4H), 1.4-1.5 (m, 4H), 1.75-1.85 (m, 8H), 2.5-2.6 (m, 1H), 3.2 (s, 3H), 3.25-3.3 (m, 4H), 4.6 (s, 2H), 6.25 (t, J=5.84 Hz, 1H), 7.3 (d, J=8.24 Hz, 2H), 7.4 (d, J=8.24 Hz, 2H), 7.6 (d, J=8.36 Hz, 1H), 7.8 (s, 1H), 7.88 (d, J=8.36 Hz, 1H), 10 (s, 1H), and 10 mg of compound (22), m/z=537 (M+H)+, $^1$H NMR CDCl$_3$: 1.25-1.32 (m, 4H), 1.4-1.5 (m, 4H), 1.75-1.85 (m, 8H), 2.5-2.6 (m, 1H), 3.2 (s, 3H), 3.25-3.3 (m, 4H), 4.6 (s, 2H), 6.25-6.3 (m, 1H), 7.3-7.5 (m, 3H), 7.4-7.5 (m, 2H), 7.6 (d, J=8.44 Hz, 1H), 7.8 (s, 1H), 7.88 (d, J=8.44 Hz, 1H), 9.7 (s, 1H).

Example 21

Synthesis of 18-(4-Chloro-phenyl)-17-cyclohexyl-4,9-dimethyl-10,10-dioxo-10λ$^6$-thia-1,4,9,11-tetraaza-tricyclo[11.5.2.016,19]icosa-6,13(20),14,16(19),17-pentaene-3,12-dione (23)

(23)

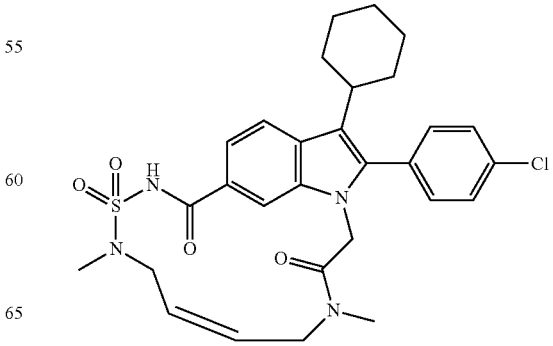

Compound 23 was synthesized in a similar way as compound 19, following the steps B to H of example 18, with the following modifications:

in step B, compound 19-2 was used instead of compound 18-1;

in step F, a mixture of TFA and DCM was used instead of lithium hydroxide.

Example 22

Synthesis of 18-(4-Chloro-phenyl)-17-cyclohexyl-4,9-dimethyl-10,10-dioxo-10λ$^6$-thia-1,4,9,11-tetraaza-tricyclo[11.5.2.0$^{16,19}$]icosa-13(20),14,16(19),17-tetraene-3,12-dione (24)

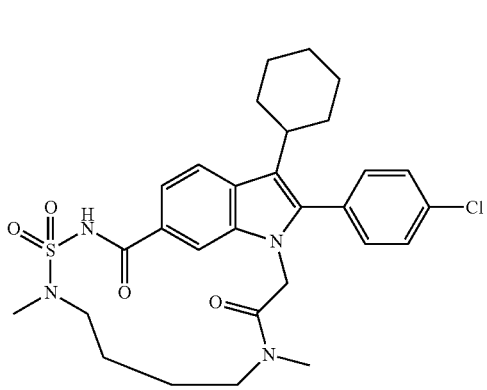

(24)

compound (24) was synthesized following the procedure reported in example 20 and was obtained in 12% yield, m/z=572 (M+H)$^+$.

Example 23

Synthesis of 17-Cyclohexyl-18-(4-methoxy-phenyl)-9-methyl-10,10-dioxo-10λ$^6$-thia-1,4,9,11-tetraaza-tricyclo[11.5.2.0$^{16,19}$]icosa-13(20),14,16(19),17-tetraene-3,12-dione (25)

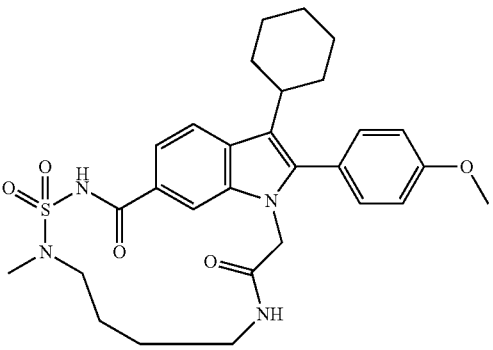

(25)

Step A

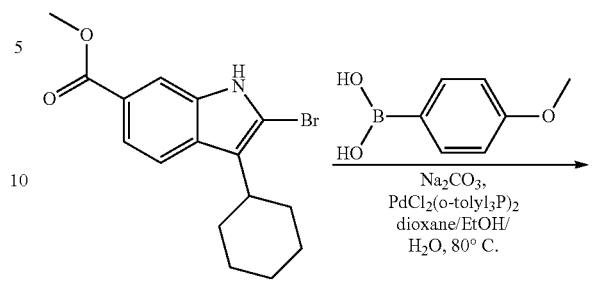

1-5

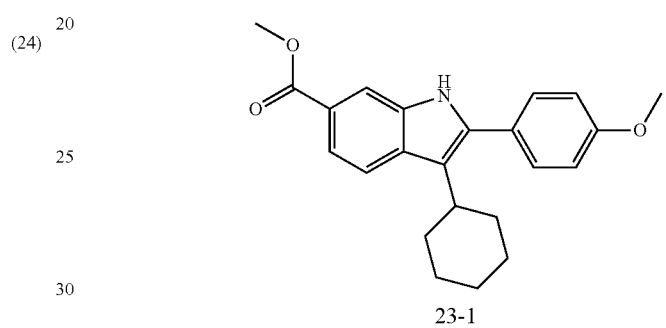

23-1

To a stirred solution of the indole derivative 1-5 (5 g, 14.87 mmoles) in a mixture of dioxane/ethanol/water 1/1/1 (75 mL) were added 4-methoxyphenyl boronic acid (3.39 g, 1.5 eq), sodium carbonate (4.73 g, 3 eq) and Bis(tri-o-tolylphosphine)palladium(II) Dichloride (1.172 g, 0.1 eq). The reaction mixture was stirred at 80° C. under nitrogen. After completion, the reaction mixture was concentrated under vacuum, then ethylacetate was added. The resulting precipitate and the filtrate were treated separately. The precipitate was filtered off, redissolved in hot ethylacetate. After filtration, the organic layer was dried over magnesium sulfate, filtered and concentrated to give 1.2 g of the target compound 23-1. The first filtrate was washed with a sodium bicarbonate aqueous solution, then dried over magnesium sulfate, filtered and concentrated. The residue was recrystallized from DCM to afford a second crop of the target compound 23-1 (3.33 g). In total, 4.53 g (84% yield) of the target compound was obtained, m/z=364 (M+H)$^+$.

Step B

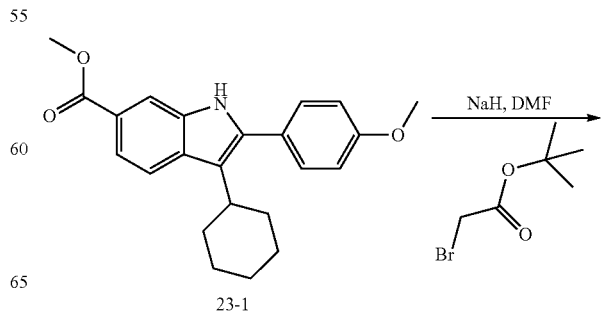

23-1

Step C

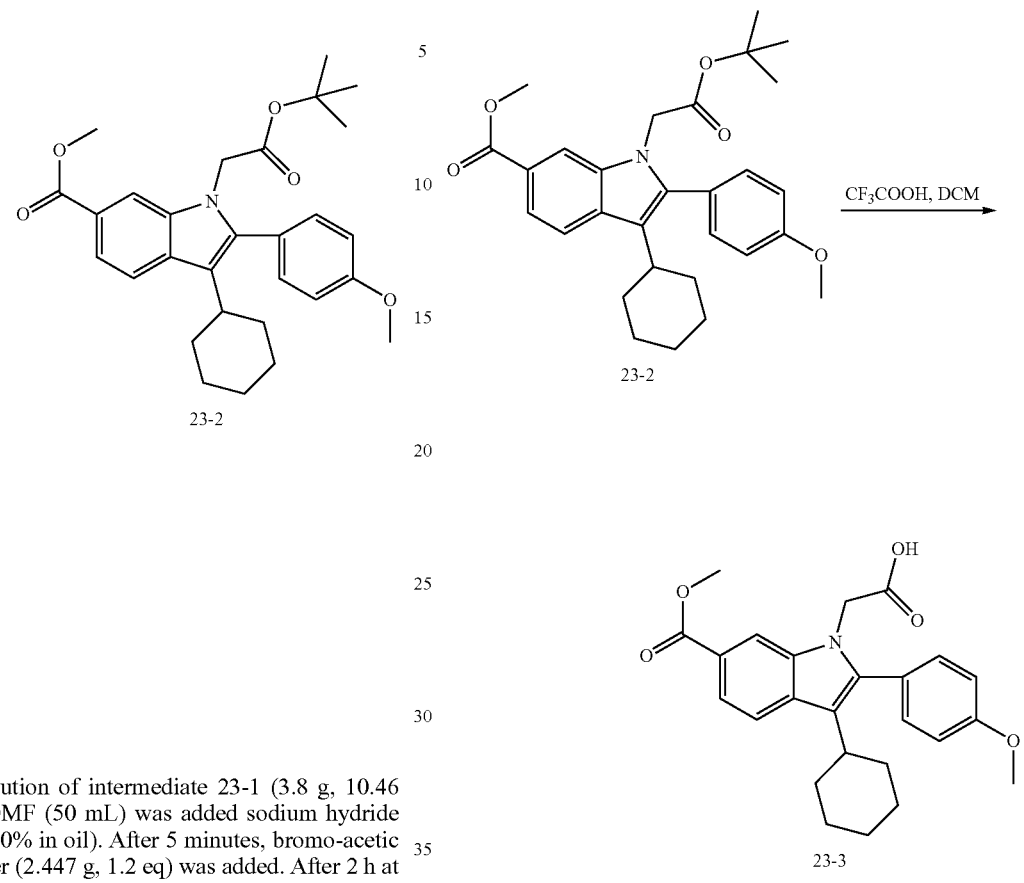

To a stirred solution of intermediate 23-1 (3.8 g, 10.46 mmoles) in dry DMF (50 mL) was added sodium hydride (0.502 g, 1.2 eq, 60% in oil). After 5 minutes, bromo-acetic acid tert-butyl ester (2.447 g, 1.2 eq) was added. After 2 h at room temperature, the reaction mixture was poured into 200 mL of cold water. The resulting precipitate was filtered off and washed with water, and the aqueous layer was extracted with ethylacetate. The organic layer was washed with water, dried over magnesium sulfate, filtered and concentrated to dryness. This residue and the former precipitate were combined to give 5 g of the target compound 23-2, which was used without further purification in the following step, m/z=478 (M+H)$^+$.

To a solution of intermediate 23-2 (5 g, 10.46 mmoles) was added trifluoroacetic acid (19.29 mL, 20 eq). After stirring overnight at room temperature, the reaction mixture was concentrated to dryness under vacuum. The residue was redissolved in DCM, washed with water, dried over magnesium sulphate, filtered and concentrated to give 4.49 g (82%) of the target compound 23-3, m/z=422 (M+H)$^+$.

Step D

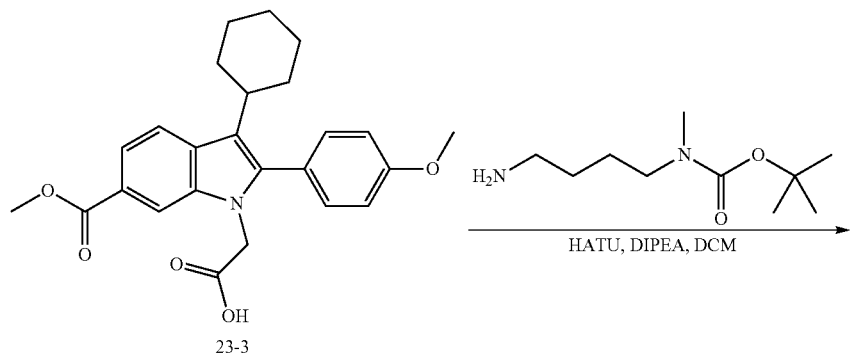

-continued

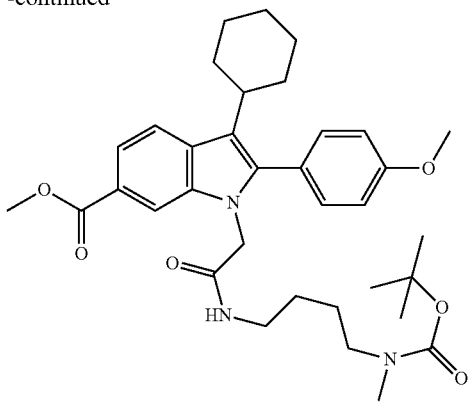

23-4

A solution of intermediate 23-3 (0.5 g, 1.186 mmole), (4-amino-butyl)-methyl-carbamic acid tert-butyl ester (0.312 g, 1.3 eq), HATU (0.677 g, 1.5 eq) and DIPEA (0.23 g, 1.5 eq) in DCM was stirred at room temperature. After completion, the reaction mixture was diluted with DCM, washed with water, dried over magnesium sulphate, filtered and concentrated. The crude was purified by silica gel flash chromatography (DCM to DCM/ethylacetate 1/1) to give 0.455 g (64% yield) of the target product 23-4, m/z=606 (M+H)$^+$.

Step E overnight at room temperature, the reaction mixture was concentrated to dryness under vacuum. The residue was redissolved in DCM, washed with a saturated sodium carbonate aqueous solution then water, dried over magnesium sulphate, filtered and concentrated to give 0.351 g (94%) of the target compound 23-5, m/z=506 (M+H)$^+$.

Step F

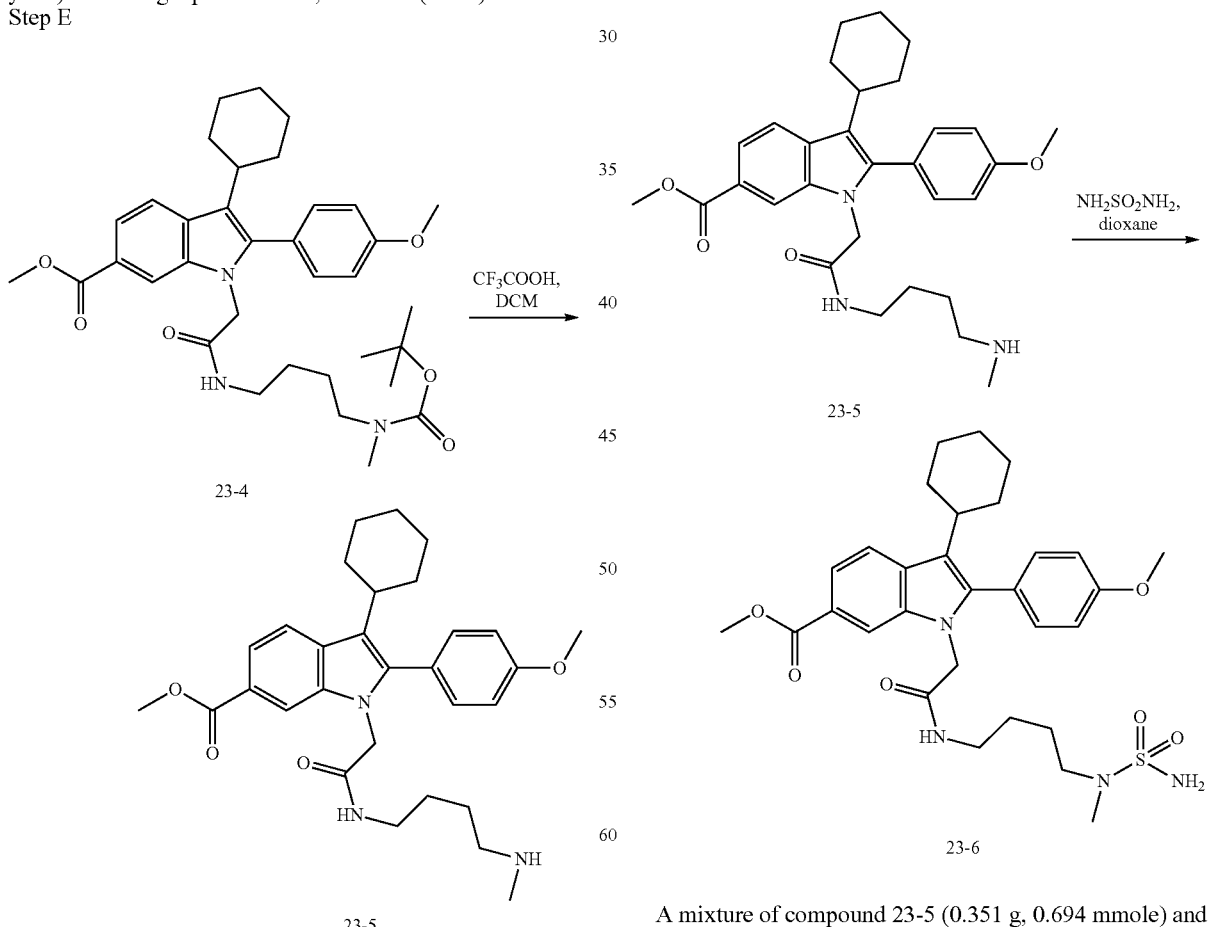

To a solution of compound 23-4 (0.455 g, 0.735 mmoles) was added trifluoroacetic acid (0.55 mL, 10 eq). After stirring A mixture of compound 23-5 (0.351 g, 0.694 mmole) and sulfamide (0.200 g, 3 eq) in dioxane (7 mL) was heated at 100° C. in a microwave oven during 40 minutes. The reaction mixture was then concentrated and redissolved in DCM. The precipitate of sulfamide in excess was filtered off and the filtrate was concentrated to dryness to give 0.335 g (83% yield) of the target product 23-6, which was used without any further purification in the next step, m/z=585 (M+H)+.

Step G

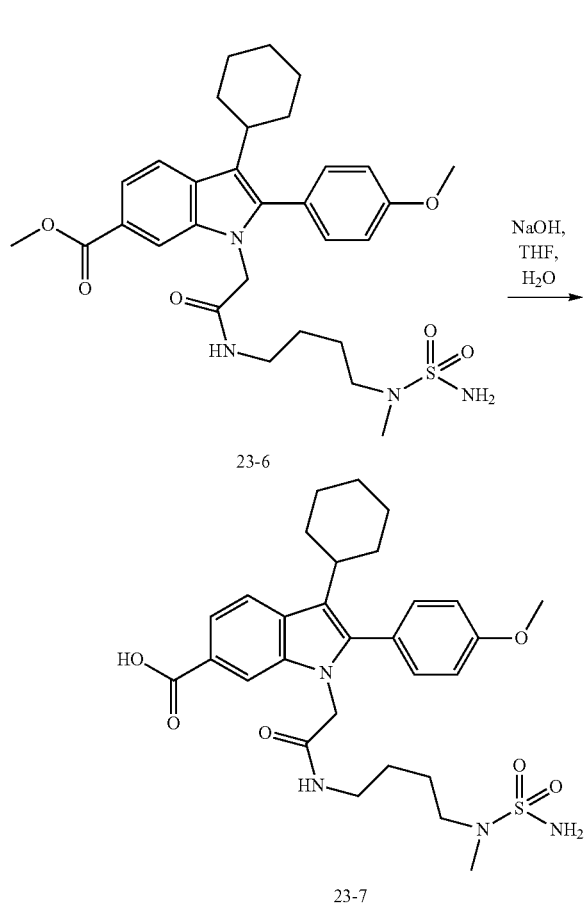

A mixture of methylester 23-6 (0.327 g, 0.559 mmole) and NaOH (2 mL, 50% w/w aqueous solution) in THF was stirred at room temperature overnight. The reaction mixture was then concentrated, acidified with HCl 3N until pH 0-1 and extracted with DCM. The organic layer was dried over magnesium sulphate, filtered and concentrated to give 0.28 g (88% yield) of the target product 23-7, m/z=571 (M+H)+.

Step H

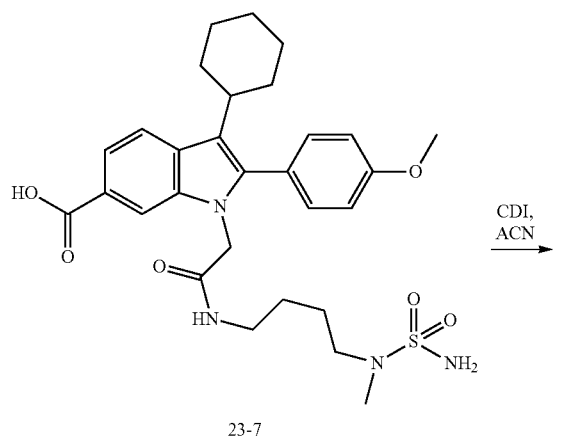

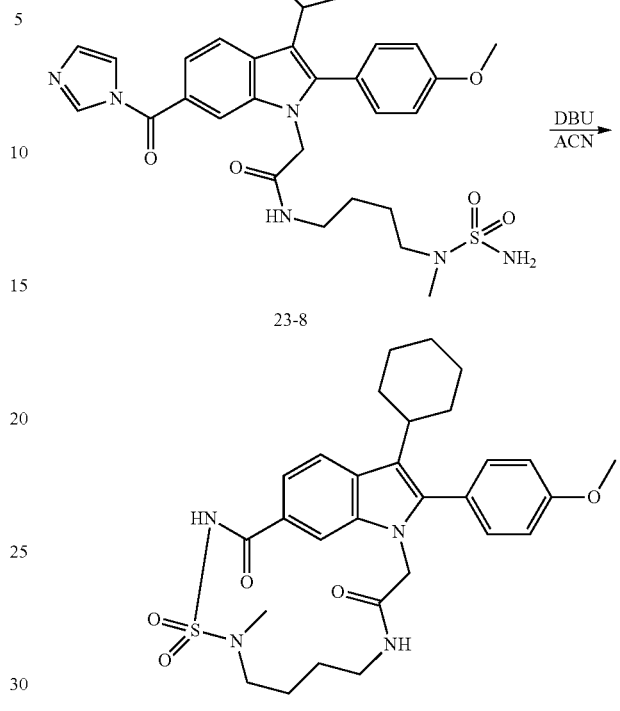

A solution of compound 23-7 (0.26 g, 0.456 mmole) and CDI (0.222 g, 3 eq) in CH$_3$CN was stirred at room temperature until complete conversion to the acylimidazole compound 23-8. The reaction mixture was then concentrated and the residue was purified by flash chromatography (gradient of ethylacetate to CH$_3$CN) to give 77 mg of 23-8. This intermediate was subsequently redissolved in CH$_3$CN (10 mL) and DBU (41.5 mg, 2.2 eq) was added. After 30 minutes at room temperature, acetic acid (2 drops) was added and the reaction mixture was concentrated. Purification by flash chromatography (gradient of ethylacetate to ethylacetate/CH3CN 7/3) afforded 16 mg of the target product 25, m/z=553 (M+H)+.
NMR (DMSO-d6): δ (ppm) 1.10-1.46 (5H, m), 1.59-1.82 (5H, m), 1.82-2.05 (4H, m), 2.63 (3H, s), 3.00-3.15 (2H, m), 3.15-3.24 (2H, m), 3.82 (3H, s), 4.39 (2H, s), 7.09 (2H, d, J=8.6 Hz), 7.39 (2H, d, J=8.6 Hz), 7.54 (1H, d, J=8.6 Hz), 7.67 (1H, d, J=8.6 Hz), 7.94 (1H, s), 8.43 (1H, s(br))

Example 24

Synthesis of 18-Cyclohexyl-19-(4-methoxy-phenyl)-10-methyl-11,11-dioxo-11λ$^6$-thia-1,4,10,12-tetraaza-tricyclo[12.5.2.0$^{17,20}$]henicosa-14(21),15,17(20), 18-tetraene-3,13-dione (26)

(26)

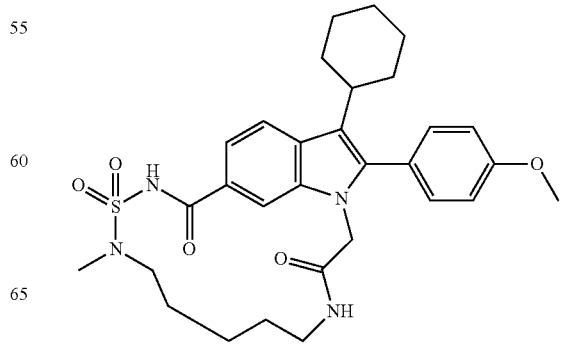

Step A

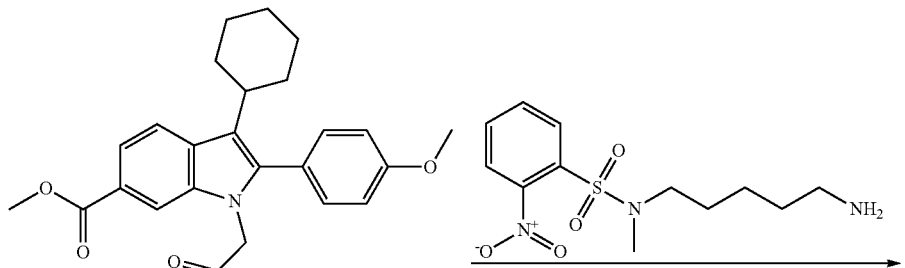

A solution of compound 23-3 (0.5 g, 1.186 mmole), N-(5-Amino-pentyl)-N-methyl-2-nitro-benzenesulfonamide (0.786 g, 2.2 eq), synthesized as described in example 29, HATU (1.128 g, 2.5 eq) and DIPEA (0.537 g, 3.5 eq) in DCM (5 mL) was stirred at room temperature. After completion, the reaction mixture was diluted with DCM, washed with water, dried over magnesium sulfate, filtered and concentrated. The crude was purified by silica gel flash chromatography (gradient of heptane to DCM to ethylacetate) to give 0.585 g (70% yield) of the target product 24-1, m/z=705 (M+H)$^+$.

Step B

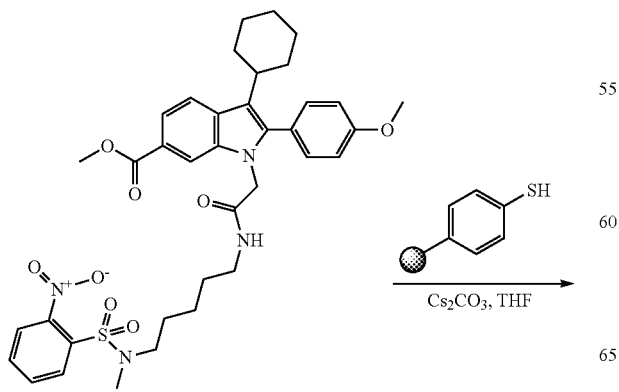

-continued

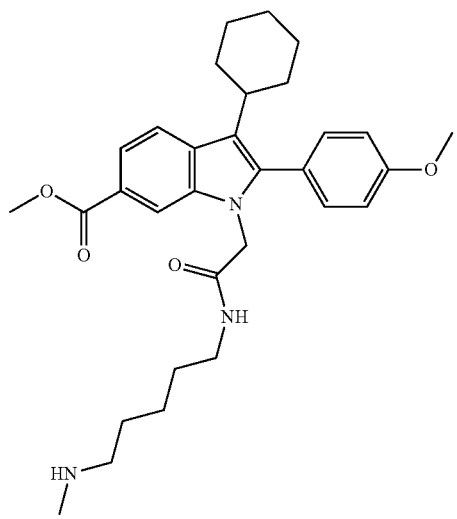

A mixture of compound 24-1 (0.58 g, 0.823 mmole), cesium carbonate (0.402 g, 1.5 eq) and a PS-thiophenol resin (1.3 eq, 1.4 mmol/g) in THF was shaken overnight. The resin was then filtered off and more cesium carbonate (0.402 g, 1.5 eq) and PS-thiophenol resin (1.3 eq, 1.4 mmol/g) were added. After completion, the reaction mixture was filtered off and the filtrate was concentrated. The obtained residue was purified by a catch and release method, using a MP-TsOH SPE column, to give 0.3 g (70% yield) of the target product 24-2, m/z=520 (M+H)$^+$.

Step C

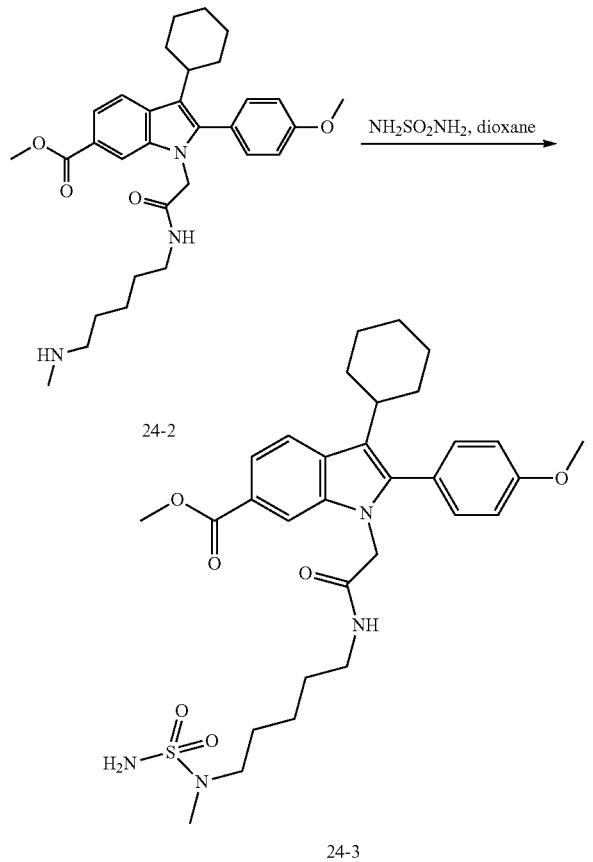

24-2

24-3

The target product 24-3 was obtained in 97% yield following the procedure reported in step F of example 23, using compound 24-2 (0.290 g, 0.558 mmole) instead of compound 23-5, m/z=599 (M+H)$^+$.

Step D

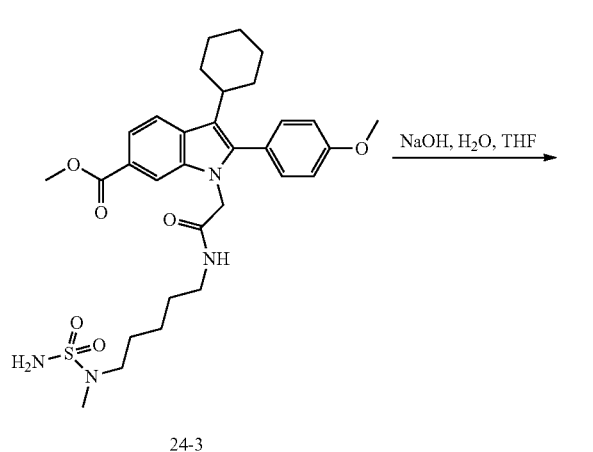

24-3

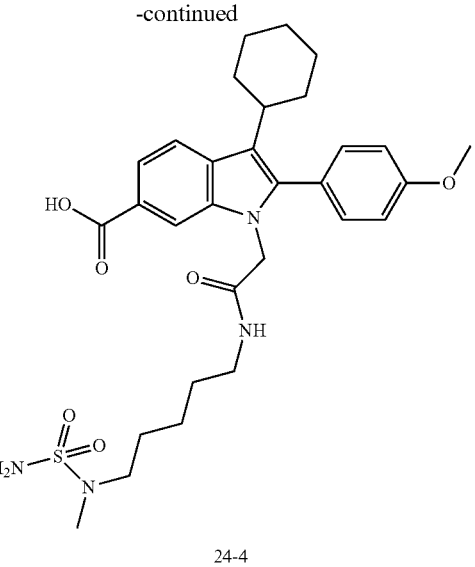

24-4

The target product 24-4 was obtained in 99% yield following the procedure reported in step G of example 23, using methyl ester 24-3 (0.340 g, 0.558 mmole) instead of methyl ester 23-6, m/z=585 (M+H)$^+$.

Step E

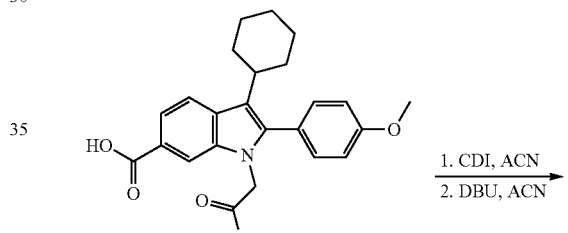

24-4

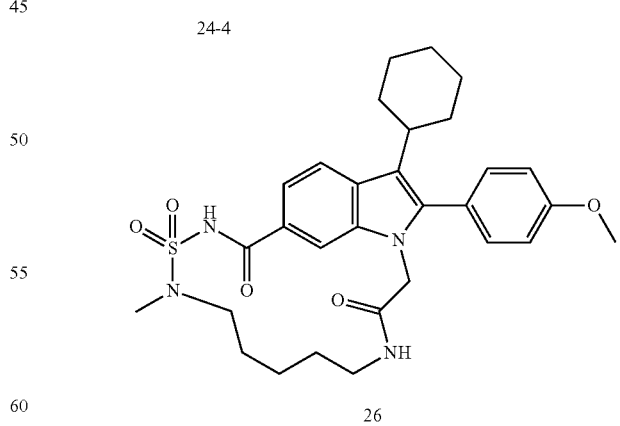

26

The target product 26 was obtained in 31% yield following the procedure reported in step H of example 23, using intermediate 24-4 (0.328 g, 0.558 mmole) instead of 23-7, m/z=567 (M+H)$^+$. $^1$H NMR (δ, DMSO-d6): 1.10-1.62 (9H, m), 1.62-1.82 (5H, m), 1.82-1.97 (2H, m), 2.75 (3H, s), 3.01-

3.20 (4H, m), 3.83 (3H, s), 4.42 (2H, s), 7.09 (2H, d, J=8.3 Hz), 7.40 (2H, d, J=8.3 Hz), 7.55 (1H, d, J≈8 Hz), 7.70 (1H, d, J≈8 Hz), 7.90 (1H, s), 8.36 (1H, s(br))

Example 25

Synthesis of 18-Cyclohexyl-19-(4-methoxy-phenyl)-7-methyl-11,11-dioxo-11λ⁶-thia-1,4,7,10,12-pentaaza-tricyclo[12.5.2.017,20]henicosa-14(21),15,17(20),18-tetraene-3,13-dione (27)

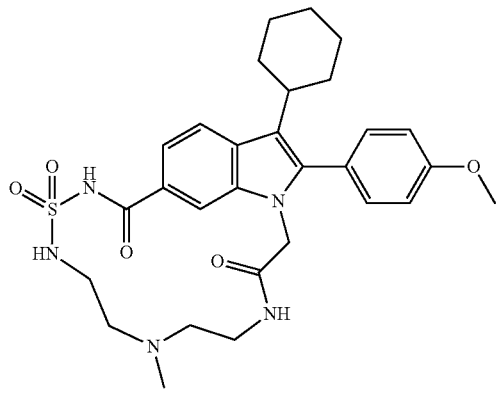

Step A

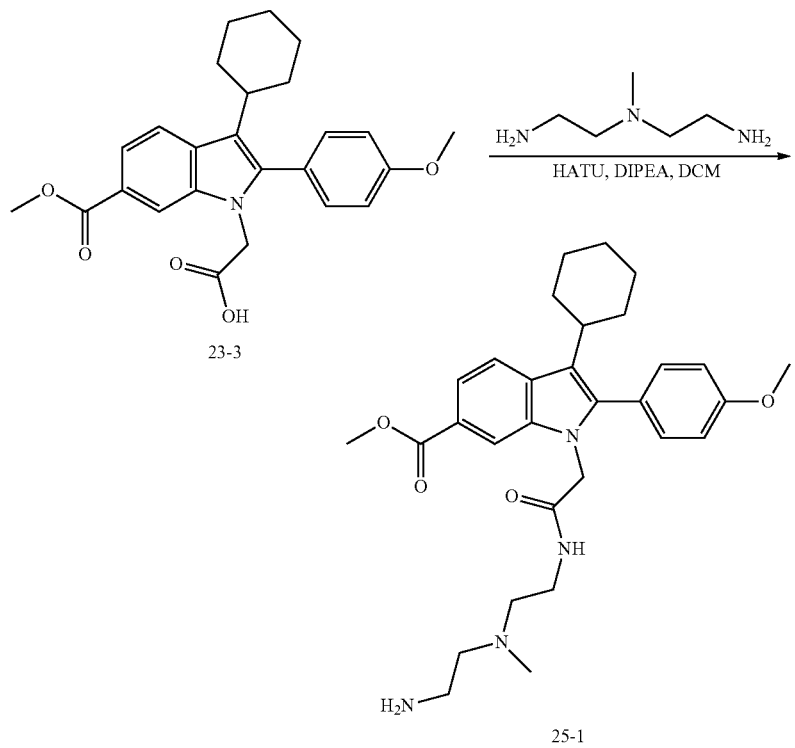

A solution of compound 23-3 (0.5 g, 1.186 mmole), N1-(2-Amino-ethyl)-N-1-methyl-ethane-1,2-diamine (0.695 g, 5 eq), HATU (0.677 g, 1.5 eq) and DIPEA (0.23 g, 1.5 eq) in DCM (5 mL) was stirred at room temperature. After 2 days at room temperature, the reaction mixture was diluted with DCM, washed with water, dried over magnesium sulphate, filtered and concentrated. The crude was purified by silica gel flash chromatography (gradient of ethylacetate to ethylacetate/NH₃ in MeOH 8/2) to give 0.120 g (19% yield) of the target product 25-1, m/z=521 (M+H)⁺.

Step B

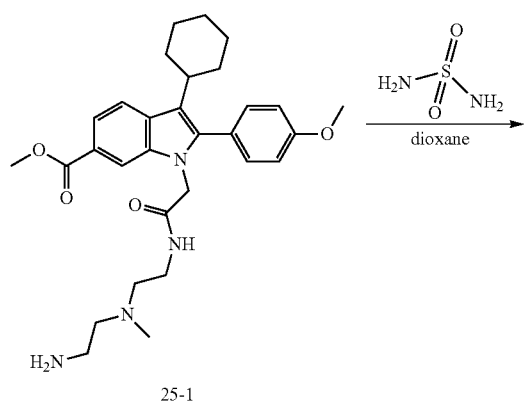

25-1

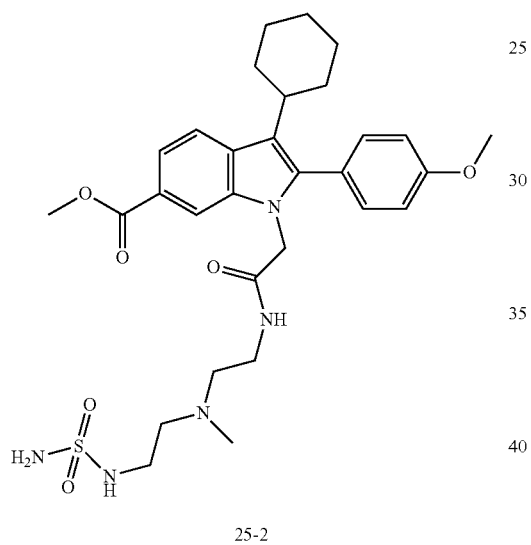

25-2

The target product 25-2 was obtained in 49% yield following the procedure reported in step F of example 23, using compound 25-1 (0.240 g, 0.461 mmole) instead of compound 23-5, m/z=600 (M+H)⁺.

Step C

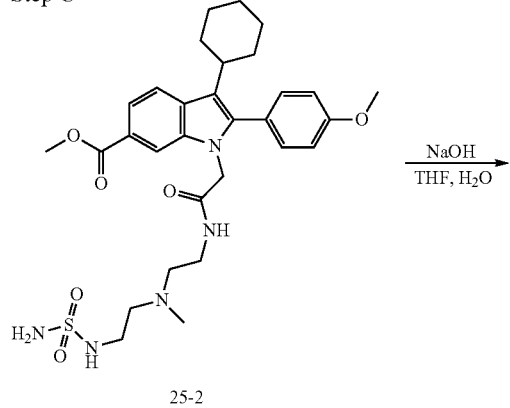

25-2

-continued

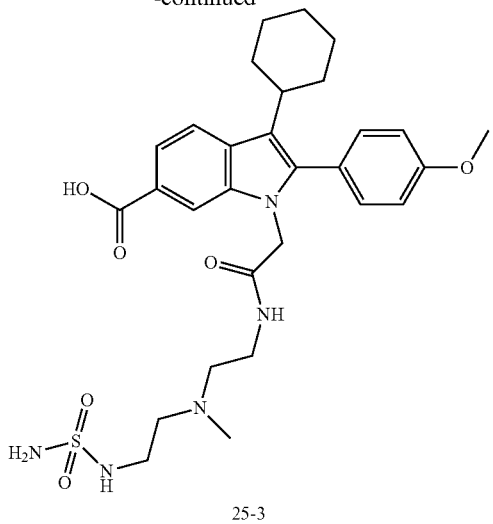

25-3

The target product 25-3 was obtained in 21% yield following the procedure reported in step G of example 23, using methyl ester 25-2 (0.060 g, 0.1 mmol) instead of methyl ester 23-6, m/z=586 (M+H)⁺.

Step D

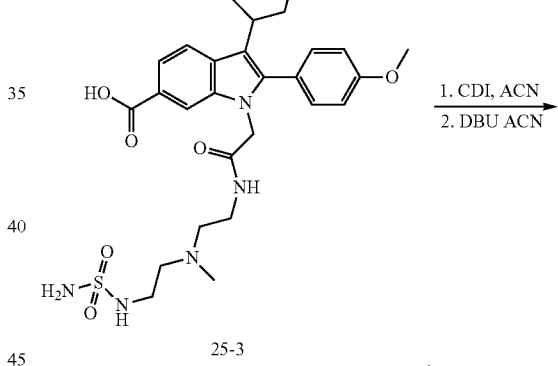

25-3

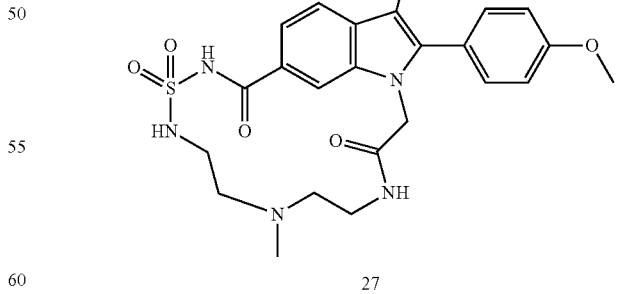

27

The target product (27) was obtained in 11% yield following the procedure reported in step H of example 23, using intermediate 25-3 instead of 23-7, m/z=568 (M+H)⁺. ¹H NMR (δ, DMSO-d6): 1.10-1.40 (4H, m), 1.54-1.82 (6H, m), 1.83-1.99 (2H, m), 2.19 (3H, s), 2.61-2.70 (2H, m), 2.96-3.10

(2H, m), 3.10-3.22 (2H, m), 3.57 (1H, s), 3.83 (3H, s), 4.40 (2H, s), 4.99-5.13 (1H, m), 7.08 (2H, d, J=8.1 Hz), 7.39 (2H, d, J=8.1 Hz), 7.53 (1H, d, J=8.1 Hz), 7.64 (1H, d, J=8.1 Hz), 7.96 (1H, s), 8.46-8.60 (1H, m)
Example 26
Synthesis of 17-Cyclohexyl-18-furan-3-yl-9-methyl-10,10-dioxo-10$\lambda^6$-thia-1,4,9,11-tetraaza-tricyclo[11.5.2.0$16,19$]icosa-13(20),14,16(19),17-tetraene-3,12-dione (28)
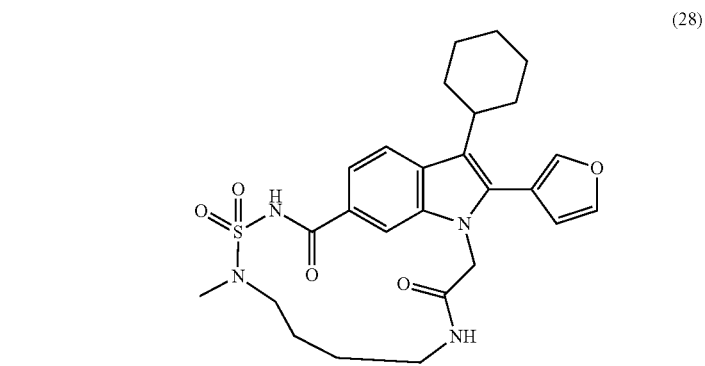 [SMILES: CN1CCCCNC(=O)Cn2c(-c3ccoc3)c(C3CCCCC3)c3ccc(cc32)C(=O)NS1(=O)=O]
Step A
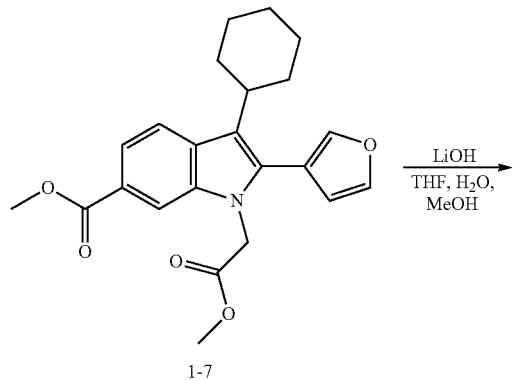
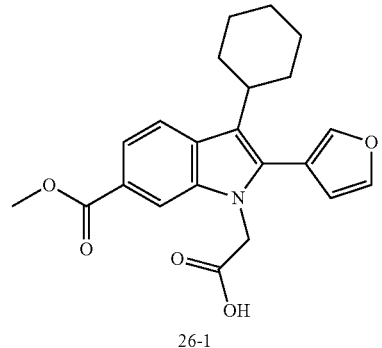
The target compound 26-1 was obtained in 82% yield following the procedure reported in step A of example 12, using intermediate 1-7 instead of 10-9, m/z=382 (M+H)$^+$.
Step B
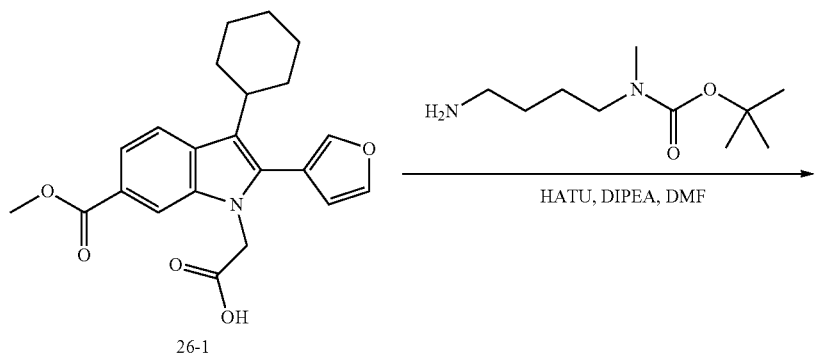

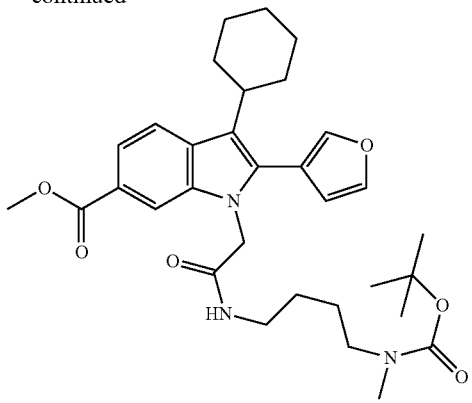

26-2

The target compound 26-2 was obtained following the procedure reported in step D of example 23, using intermediate 26-1 instead of intermediate 23-3, m/z=566 (M+H)⁺.

Step C

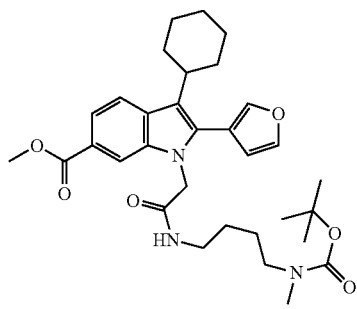

26-2

The target compound 26-3 was obtained following the procedures reported in steps E, F and G of example 23, using intermediate 26-2 instead of intermediate 23-4, m/z=531 (M+H)⁺.

Step D

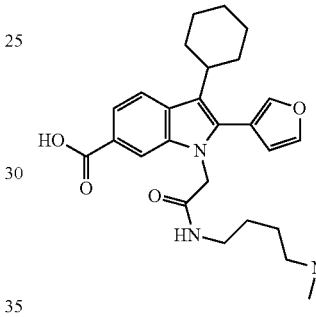

26-3

1. CDI, ACN
2. DBU, ACN

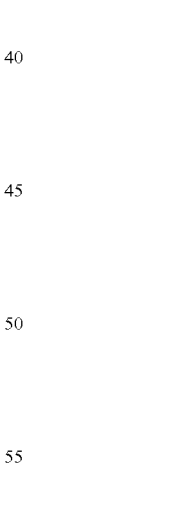

(28)

The target product (28) was obtained in 9% yield following the procedure reported in step H of example 23, using intermediate 26-3 instead of 23-7, m/z=513 (M+H)⁺. ¹H NMR, DMSO-d₆: δ 1.42-1.21 (m, 5H), 1.82-1.62 (m, 5H), 2.00-1.81 (m, 4H), 2.58 (s, 3H), 2.73-2.62 (m, 1H), 3.08 (t, J=7.5 Hz, 2H), 3.25-3.17 (m, 2H), 4.53 (s, 2H), 6.67 (s, 1H), 7.59 (d, J=8.3 Hz, 1H), 7.66 (d, J=8.3 Hz, 1H), 7.86 (s, 2H), 8.00 (s, 1H), 8.32 (s, 1H), 8.55 (br s, 1H)

Example 27

Synthesis of 18-Cyclohexyl-19-furan-3-yl-10-methyl-11,11-dioxo-11λ$^6$-thia-1,4,10,12-tetraaza-tricyclo[12.5.2.0$^{17,20}$]henicosa-7,14(21),15,17(20),18-pentaene-3,13-dione (29)

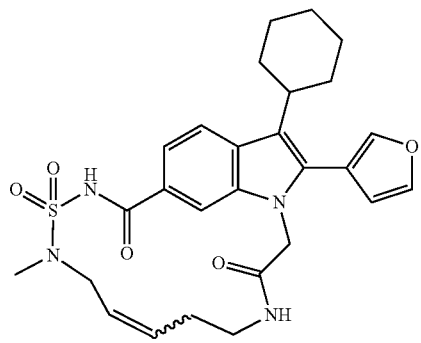

(29)

The target product (29) was synthesized in a similar way as compound 19, following the steps B to H of example 18, with the following modifications:
- in step B, intermediate 1-7 was used instead of compound 18-1
- in step E, but-3-enylamine was used instead of allylamine Compound (29) was obtained as a mixture of E/Z isomers, m/z=525 (M+H)$^+$.

Example 28

Synthesis of 18-Cyclohexyl-19-furan-3-yl-10-methyl-11,11-dioxo-11λ$^6$-thia-1,4,10,12-tetraaza-tricyclo[12.5.2.0$^{17,20}$]henicosa-14(21),15,17(20),18-tetraene-3,13-dione (30)

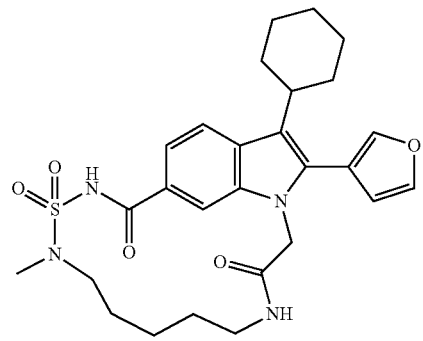

(30)

The target product (30) was obtained in 81% yield following the procedure reported in example 20, m/z=527 (M+H)⁺.

Example 29

Synthesis of N-(5-amino-pentyl)-N-methyl-2-nitro-benzenesulfonamide (31)

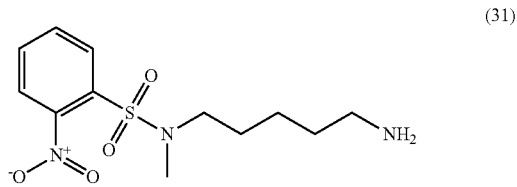

Step A

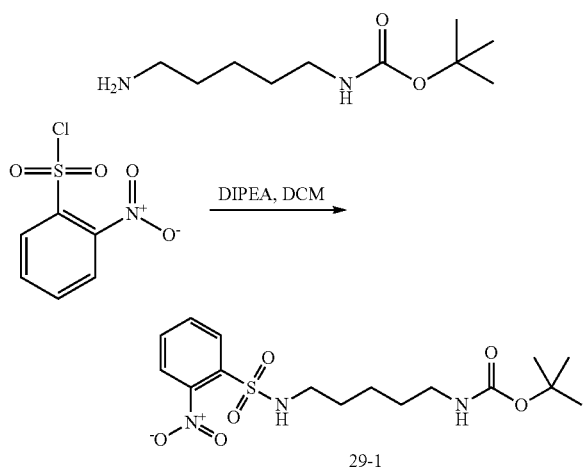

To a solution of (5-amino-pentyl)-carbamic acid tert-butyl ester (1 g, 4.94 mmol) in DCM (10 mL) were added 2-nitrobenzene sulfonyl chloride (1.15 g, 1.05 eq) and DIPEA (0.958 g, 1.5 eq) at room temperature. After 1 h, the reaction mixture was diluted with water, washed with a solution of aqueous citric acid, dried over magnesium sulphate, filtered and concentrated to give 1.91 g (quantitative yield) of the target product 29-1, which was used without any further purification in the next step, m/z=388 (M+H)⁺.

Step B

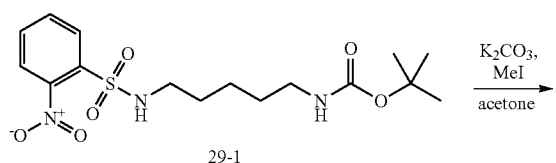

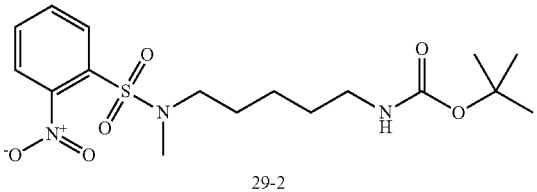

To a solution of intermediate 29-1 (1.91 g, 4.92 mmol) and potassium carbonate (0.816 g, 1.2 eq) in acetone (10 mL) was added methyl iodide (0.733 g, 1.05 eq) at room temperature. After completion, the reaction mixture was diluted with water and extracted with DCM. The organic layer was dried over magnesium sulfate, filtered and concentrated. Purification by flash chromatography on silica gel (eluent: DCM) afforded 1.29 g (65% yield) of the target product 29-2, m/z=402 (M+H)⁺.

Step C

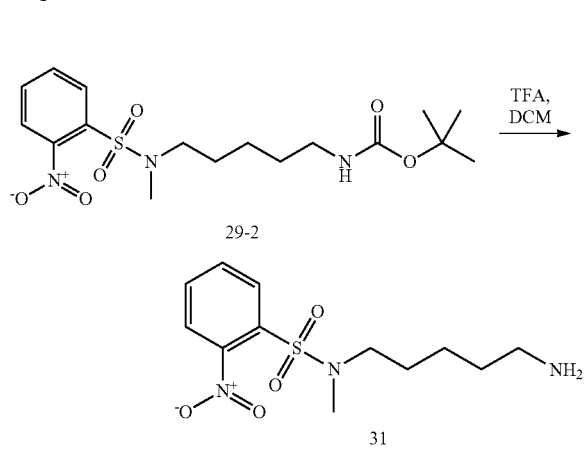

The target product 31 was obtained in a quantitative yield following the procedure reported in step E of example 23, using intermediate 29-2 (1.29 g, 3.21 mmoles) instead of intermediate 23-4, m/z=302 (M+H)⁺.

Example 30

Activity of Compounds of Formula (I)

a) Protein Purification

The cDNA encoding NS5B amino acid 1-570 (HC-J4, genotype 1b, pCV-J4L6S, genebank accession number AF054247) was subcloned into the Nhe I and Xho I restriction sites of pET-21b. Expression of the subsequent His-tagged C-terminal 21 amino acid deleted NS5B was performed as follows:

The NS5B expression construct was transformed into *E. coli* BL21(DE3) (Novagen, Madison, Wis.). Five milliliters of LB-medium supplemented with ampicillin (50 µg/mL) was inoculated with one colony. When the pre-culture reached an optical density of 0.6 measured at 600 nm, it was transferred to fresh LB-medium supplemented with ampicillin, at a ratio of 1:200. Cells were grown to an optical density at 600 nm of 0.6, after which the expression cultures were shifted to a growth temperature of 20° C. following induction with ispopropyl-1-thio-β-D-galactopyranoside and $MgCl_2$ at a final concentration of 0.4 mM and 10 µM, respectively. After ten hours of induction, cells were harvested by centrifugation and resuspended in 20 mM Tris-HCl, pH 7.5, 300 mM NaCl, 10% glycerol, 0.1% NP40, 4 mM $MgCl_2$, 5 mM DTT supplemented with EDTA-free Complete Protease Inhibitor (Roche, Basel, Switzerland). Cell suspensions were disrupted by sonication and incubated with 10-15 mg/L of DNase I (Roche, Basel, Switzerland) for 30 minutes. Cell debris was removed through ultracentrifugation at 30,000×g for 1 hour and clarified cell lysate was flash frozen and stored at −80° C. prior to purification.

Clarified cell lysate was thawed and subsequently loaded onto a 5 mL pre-packed HisTrap FF column equilibrated with 25 mM HEPES, pH 7.5, 500 mM NaCl, 10% glycerol and 5 mM DTT. Proteins were eluted with 500 mM imidazole at a flow rate of 1 mL/min. Fractions containing the protein of interest were applied onto a pre-packed 26/10 HiPrep Desalting Column equilibrated with 25 mM HEPES, pH 7.5, 150 mM NaCl, 10% glycerol and 5 mM DTT. The buffer-exchanged NS5B peak was then applied onto a 20 mL Poly-U Sepharose column. Protein was eluted with an increasing salt gradient and fractions collected. Protein purity was assessed on Nu-PAGE pre-cast gels (Invitrogen, Carlsbad, Calif.). Purified NS5B samples were concentrated using Centri-Prep concentrators (Millipore, Billerica, Mass., USA) and protein concentrations were determined by Bradford assay (Pierce, Rockford, Ill., USA).

b) Protein Sequence

PDB: 1nb4, Apo form

The protein sequence is as described in WO 2007/026024. Calc. Mol. Properties 64941.4 g/mol c) Inhibition Assay Measurement of HCV NS5B polymerization activity was performed by evaluating the amount of radiolabeled GTP incorporated by the enzyme in a newly synthesized RNA using heteropolymeric RNA template/primer. The high-throughput RNA dependent RNA polymerase (RdRp) assay was carried out in 384-well plates using 100 nM enzyme, 300 nM 5'-biotinylated oligo($rG_{13}$)/poly(rC) primer-template, 600 nM of GTP, and 0.1 µCi of [$^3$H]GTP in 25 mM Tris-HCl, pH 7.5, 5 mM $MgCl_2$, 25 mM KCl, 17 mM NaCl and 3 mM of dithiothreitol (DTT). Test compounds were dissolved in DMSO. The test compounds were added to the preformed polymerase-template complex, and incubated at room temperature for 15 min before the addition of nucleoside triphosphates (NTP). The 30 µl reaction was terminated after 2 h at 25° C. upon addition of 30 µl PVT-SPA beads (Amersham Biosciences RPNQ0009, 5 mg/ml in 0.5 M EDTA). After incubation at 25° C. for 30 min, the plate was counted using a Packard TopCount microplate reader (30 sec/well, 1 min count delay) and $IC_{50}$ values were calculated.

d) Replicon Assay

The compounds of formula (I) were examined for activity in the inhibition of HCV RNA replication in a cellular assay. The assay demonstrated that the compounds of formula (I) exhibited activity against HCV replicons functional in a cell culture. The cellular assay was based on a bicistronic expression construct, as described by Lohmann et al. (1999) Science vol. 285 pp. 110-113 with modifications described by Krieger et al. (2001) Journal of Virology 75: 4614-4624, in a multi-target screening strategy. In essence, the method was as follows.

The assay utilized the stably transfected cell line Huh-7 luc/neo (hereafter referred to as Huh-Luc). This cell line harbors an RNA encoding a bicistronic expression construct comprising the wild type NS3-NS5B regions of HCV type 1b translated from an Internal Ribosome Entry Site (IRES) from encephalomyocarditis virus (EMCV), preceded by a reporter portion (firefly luciferase), and a selectable marker portion ($neo^R$, neomycine phosphotransferase). The construct is bordered by 5' and 3' NTRs (non-translated regions) from HCV type 1b. Continued culture of the replicon cells in the presence of G418 ($neo^R$) is dependent on the replication of the HCV RNA. The stably transfected replicon cells that express HCV RNA, which replicates autonomously and to high levels, encoding inter alia luciferase, were used for screening the antiviral compounds.

The replicon cells were plated in 384 well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures have high luciferase expression in the absence of any inhibitor. The inhibitory activity of the compound on luciferase activity was monitored on the Huh-Luc cells, enabling a dose-response curve for each test compound. $EC_{50}$ values were then calculated, which value represents the amount of the compound required to decrease the level of detected luciferase activity by 50%, or more specifically, the ability of the genetically linked HCV replicon RNA to replicate.

TABLE 1

The following Table 1 lists compounds that
were prepared according to any one of the above examples.
The activities of the compounds tested are depicted in Table 3.

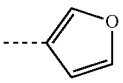

| Cpd. | Y | A=B | R⁴ |
|---|---|---|---|
| 1 | $CH_2$ | CH=CH | 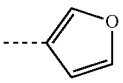 |
| 2 | $CH_2$ | $CH_2$—$CH_2$ | 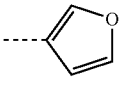 |
| 3 | $CH_2$ | CH=CH | 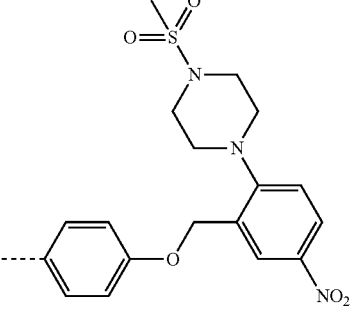 |
| 4 | $CH_2$ | CH=CH | 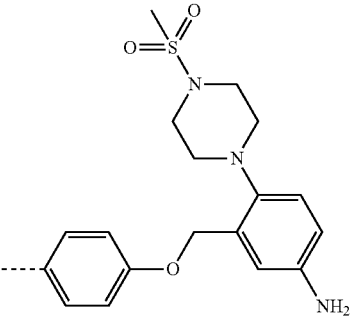 |

TABLE 1-continued

The following Table 1 lists compounds that
were prepared according to any one of the above examples.
The activities of the compounds tested are depicted in Table 3.

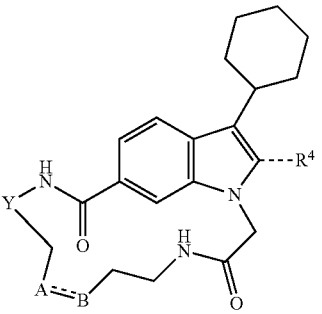

| Cpd. | Y | A=B | R⁴ |
|---|---|---|---|
| 5 | $CH_2$ | CH=CH | 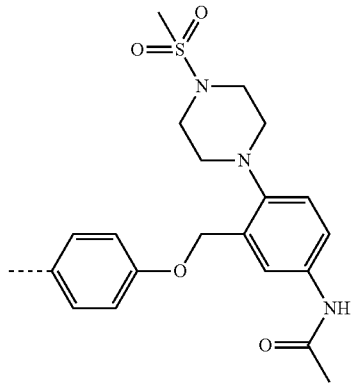 |
| 8 | $CH_2$ | $CH_2$—$CH_2$ |  |
| 9 | $CH_2$ | $CH_2$—$CH_2$ |  |
| 10 | $CH_2$ | $CH_2$—$CH_2$ |  |

TABLE 1-continued

The following Table 1 lists compounds that were prepared according to any one of the above examples. The activities of the compounds tested are depicted in Table 3.

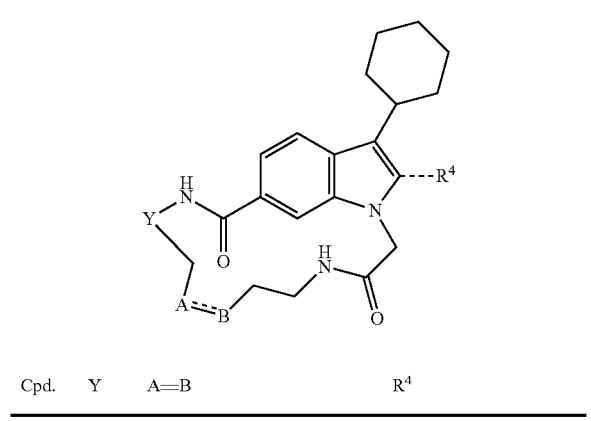

| Cpd. | Y | A=B | $R^4$ |
|---|---|---|---|
| 11 | $CH_2$ | CH=CH | 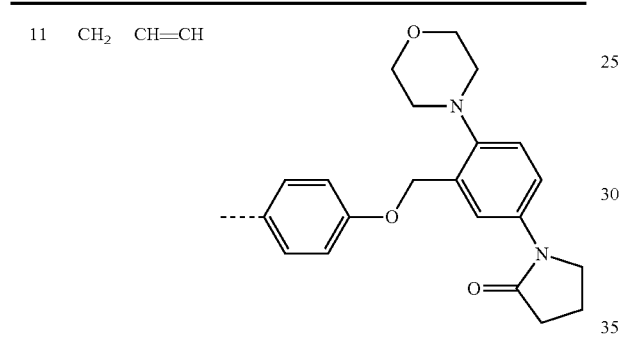 |
| 12 | $CH_2$ | CH=CH | 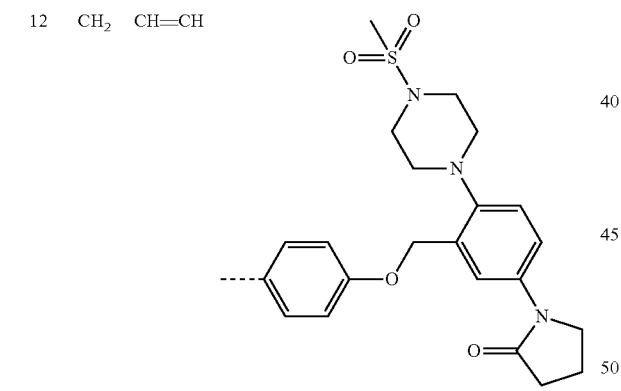 |
| 13 | $SO_2$ | CH=CH | 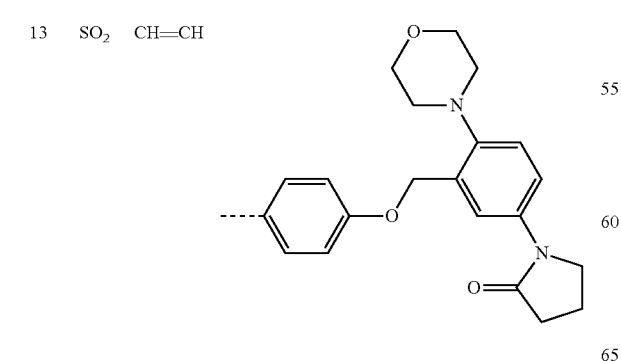 |

TABLE 1-continued

The following Table 1 lists compounds that were prepared according to any one of the above examples. The activities of the compounds tested are depicted in Table 3.

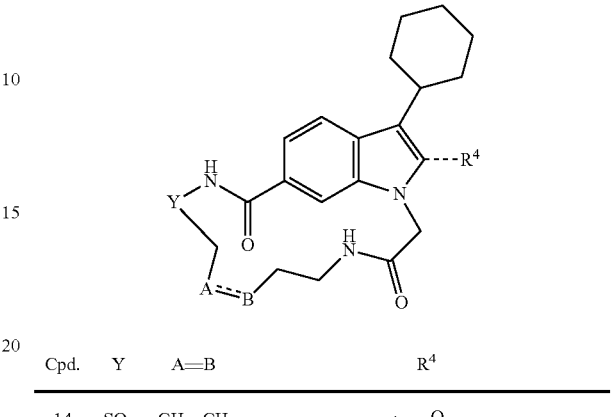

| Cpd. | Y | A=B | $R^4$ |
|---|---|---|---|
| 14 | $SO_2$ | CH=CH | 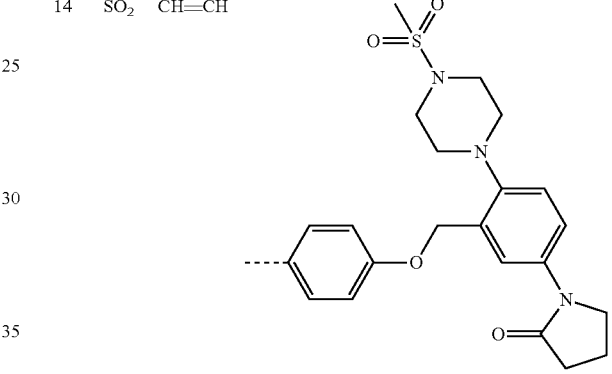 |
| 15 | $CH_2$ | CH=CH | 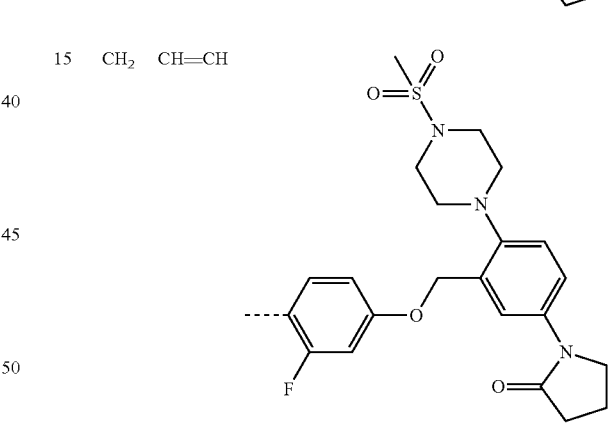 |
| 16 | $CH_2$ | CH=CH | 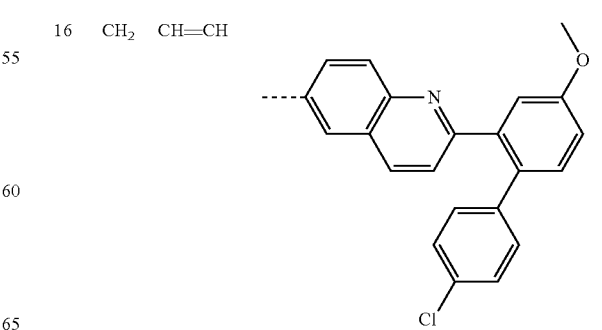 |

TABLE 1-continued

The following Table 1 lists compounds that
were prepared according to any one of the above examples.
The activities of the compounds tested are depicted in Table 3.

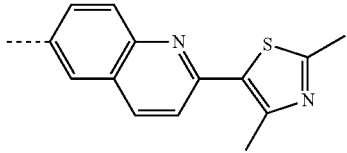

| Cpd. | Y | A=B | R⁴ |
|---|---|---|---|
| 17 | CH₂ | CH=CH | |

TABLE 1-continued

The following Table 1 lists compounds that
were prepared according to any one of the above examples.
The activities of the compounds tested are depicted in Table 3.

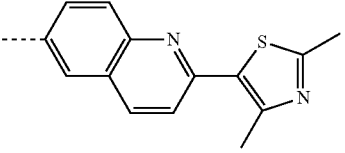

| Cpd. | Y | A=B | R⁴ |
|---|---|---|---|
| 18 | SO₂ | CH=CH | |

TABLE 2

The following Table 2 lists compounds that were prepared according to any one of the
above examples. The activities of the compounds tested are depicted in Table 3.

| Cpd | Structure |
|---|---|
| 19 | 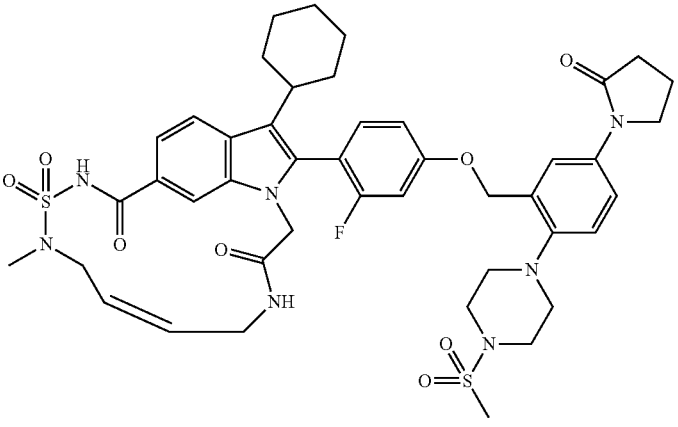 [SMILES: CN1C/C=C\CNC(=O)Cn2c(-c3ccc(OCc4cc(N5CCCC5=O)ccc4N4CCN(S(C)(=O)=O)CC4)cc3F)c(C3CCCCC3)c3ccc(cc32)C(=O)NS1(=O)=O] |
| 20 | 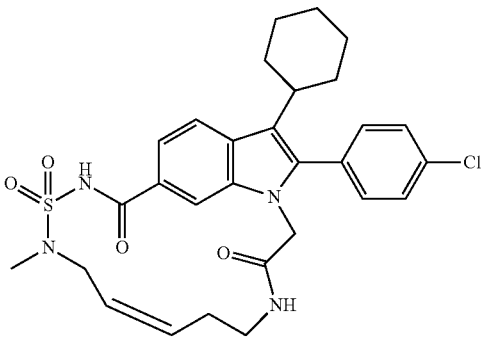 [SMILES: CN1C/C=C\CCNC(=O)Cn2c(-c3ccc(Cl)cc3)c(C3CCCCC3)c3ccc(cc32)C(=O)NS1(=O)=O] |

TABLE 2-continued
The following Table 2 lists compounds that were prepared according to any one of the above examples. The activities of the compounds tested are depicted in Table 3.
21
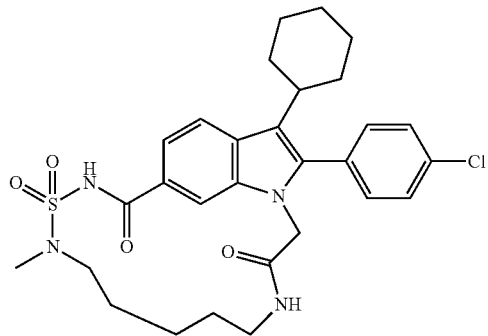 [SMILES: CN1CCCCCNC(=O)Cn2c(-c3ccc(Cl)cc3)c(C3CCCCC3)c3ccc(cc32)C(=O)NS1(=O)=O]
22
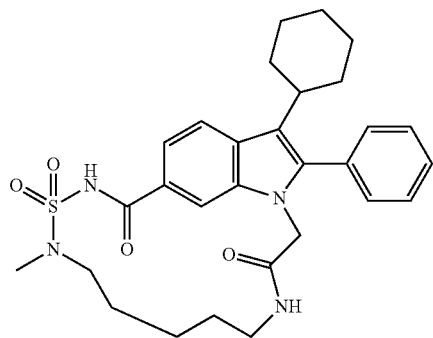 [SMILES: CN1CCCCCNC(=O)Cn2c(-c3ccccc3)c(C3CCCCC3)c3ccc(cc32)C(=O)NS1(=O)=O]
23
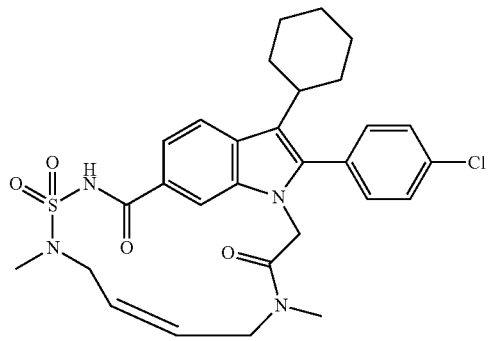 [SMILES: CN1C/C=C\CN(C)S(=O)(=O)NC(=O)c2ccc3c(C4CCCCC4)c(-c4ccc(Cl)cc4)n(c3c2)CC1=O]
24
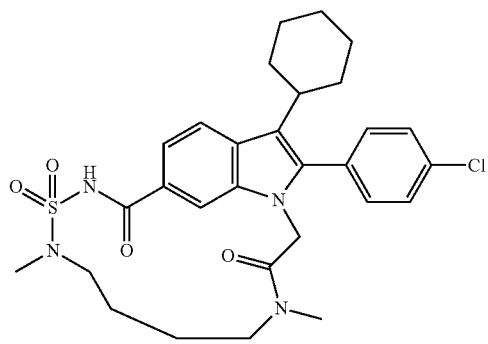 [SMILES: CN1CCCCN(C)S(=O)(=O)NC(=O)c2ccc3c(C4CCCCC4)c(-c4ccc(Cl)cc4)n(c3c2)CC1=O]

TABLE 2-continued
The following Table 2 lists compounds that were prepared according to any one of the above examples. The activities of the compounds tested are depicted in Table 3.
Cpd
25
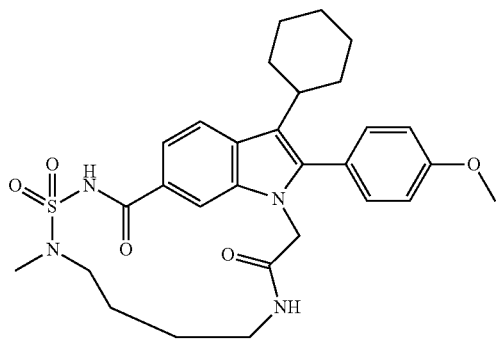 [SMILES: COc1ccc(-c2c(C3CCCCC3)c3ccc4cc3n2CC(=O)NCCCCN(C)S(=O)(=O)NC4=O)cc1]
26
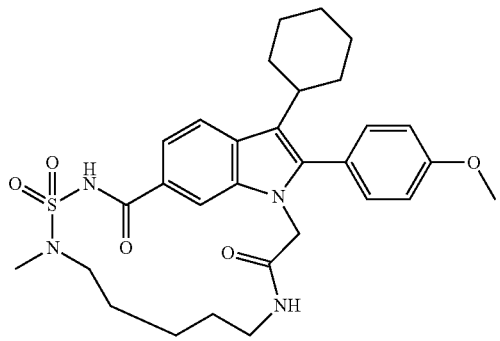 [SMILES: COc1ccc(-c2c(C3CCCCC3)c3ccc4cc3n2CC(=O)NCCCCCN(C)S(=O)(=O)NC4=O)cc1]
27
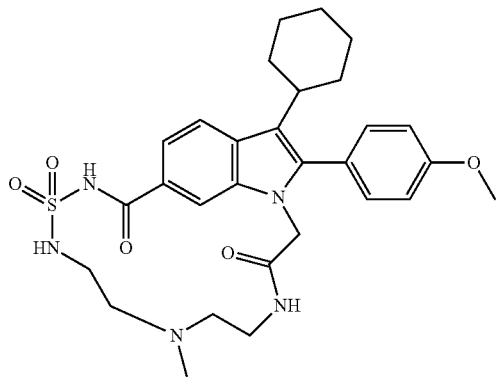 [SMILES: COc1ccc(-c2c(C3CCCCC3)c3ccc4cc3n2CC(=O)NCCN(C)CCNS(=O)(=O)NC4=O)cc1]
28
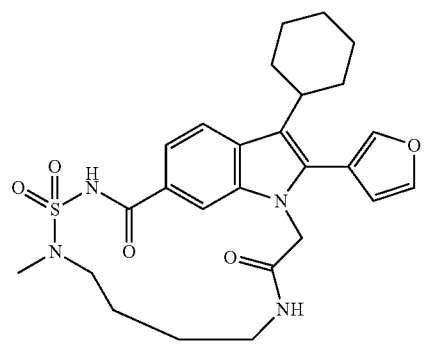 [SMILES: CN1CCCCNC(=O)Cn2c(-c3ccoc3)c(C3CCCCC3)c3ccc(cc32)C(=O)NS1(=O)=O]

TABLE 2-continued

The following Table 2 lists compounds that were prepared according to any one of the above examples. The activities of the compounds tested are depicted in Table 3.

29

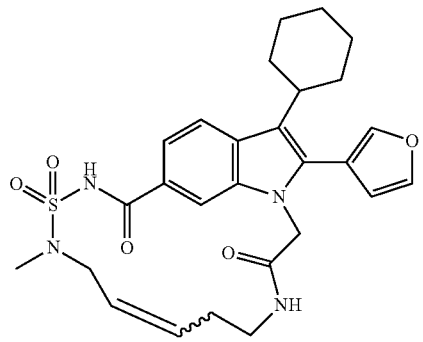 [SMILES: CN1CC=CCCNC(=O)Cn2c(-c3ccoc3)c(C3CCCCC3)c3ccc(cc32)C(=O)NS1(=O)=O]

30

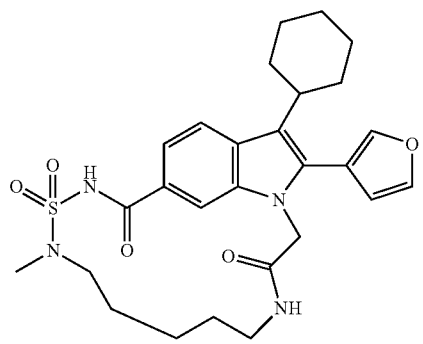 [SMILES: CN1CCCCCNC(=O)Cn2c(-c3ccoc3)c(C3CCCCC3)c3ccc(cc32)C(=O)NS1(=O)=O]

TABLE 3

The following Table 3 lists the activities of the tested compounds.

| Cpd | IC$_{50}$ (μM) Enzymatic assay | EC$_{50}$ (μM) Replicon assay |
|---|---|---|
| 1 | 2.2 | 3.4 |
| 2 | 9.5 | 4.3 |
| 3 | 1.1 | 0.72 |
| 4 | 0.27 | 0.24 |
| 5 | 0.29 | 0.58 |
| 8 | 2.79 | >32 |
| 9 | 13.0 | 4.8 |
| 10 | 6.9 | >32 |
| 11 | 0.45 | 0.69 |
| 12 | 0.36 | 0.27 |
| 13 | 0.04 | 2.36 |
| 14 | 0.88 | 2.04 |
| 15 | 1.58 | 0.27 |
| 16 | 1.44 | 17.61 |
| 17 | 2.70 | 5.39 |
| 18 | 0.04 | 12.85 |
| 19 | 0.042 | 2.36 |
| 20 | 0.17 | 0.61 |
| 21 | 0.19 | 0.59 |
| 22 | — | 0.43 |
| 23 | 0.45 | 1.08 |
| 24 | 0.44 | 0.53 |
| 25 | 0.18 | 1.76 |
| 26 | 0.19 | 0.35 |
| 27 | 0.44 | 3.47 |
| 28 | 0.11 | 1.58 |
| 29 | 0.051 | 0.65 |
| 30 | 0.11 | 0.79 |

The invention claimed is:

1. A compound having the formula (I) or an N-oxide, stereoisomer, tautomer, racemic or salt thereof, wherein

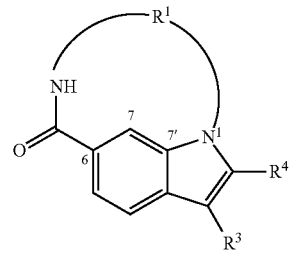

(I)

$R^1$ is a bivalent chain selected from

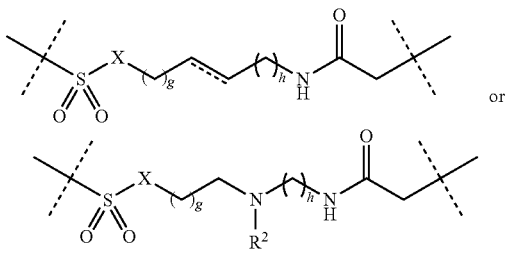

or wherein the sulfonyl group is attached to the remainder of the molecule via the nitrogen atom of the amide group, and the carbon atom of the acetamide moiety is attached to the remainder of the molecule via the nitrogen of the indole ring of the compound of formula (I);

X is selected from —CR$^{5a}$R$^{5b}$— or —NR$^{5a}$—;

each of g and h is, independently, an integer selected from 0, 1, 2, 3, 4, or 5, with the proviso that the macrocycle formed by the bivalent chain R$^1$, the —C(=O)—NH— moiety to which R$^1$ is attached and the nitrogen and carbon atoms N1, C6, C7, and C7' of the indole ring, has from 14 to 17 member atoms;

each parallel dashed line (represented by ===== ) represents an optional double bond;

R$^2$ is hydrogen or C$_{1-6}$alkyl;

R$^3$ is C$_{3-7}$cycloalkyl;

R$^4$ is a group selected from:

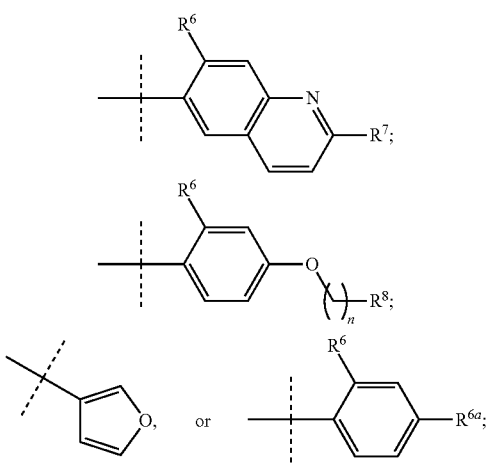

R$^{5a}$ and R$^{5b}$ are each independently selected from hydrogen; C$_{1-6}$alkyl; or haloC$_{1-6}$alkyl;

n is 0, 1, or 2;

R$^6$ is selected from hydrogen, halo, C$_{1-6}$alkyl, or C$_{3-7}$cycloalkyl;

R$^{6a}$ is selected from hydrogen, halo, C$_{1-6}$alkyl, or C$_{3-7}$cycloalkyl;

R$^7$ is phenyl or thiazolyl, wherein each phenyl is optionally substituted with one, two, or three substituents, wherein each thiazolyl is optionally substituted with one or two substituents; wherein the substituents on both phenyl and thiazolyl are each independently selected from halo; cyano; nitro; C$_{1-6}$alkyl; —OR$^{12}$; —C(=O)OR$^{12}$; —C(=O)R$^{13}$; —C(=O)NR$^{9a}$R$^{9b}$; —NR$^{9a}$R$^{9b}$; —NR$^{9a}$C(=O)R$^{13}$; —NR$^{9a}$C(=O)—CH$_2$—NR$^{9a}$R$^{9b}$; —SR$^{10}$; —SO$_2$R$^{11}$; —SO$_2$NR$^{9a}$R$^{9b}$; phenyl optionally substituted with one, two or three substituents each independently selected from halo, trifluoromethyl, cyano, C$_{1-6}$alkyl, C$_{1-6}$alkoxy, and —C(=O)NR$^{9a}$R$^{9b}$; and Het optionally substituted with one or two substituents each independently selected from oxo, C$_{1-6}$alkylsulfonyl, and C$_{1-6}$alkyl;

R$^8$ is hydrogen, phenyl, or thiazolyl, wherein each phenyl is optionally substituted with one, two, or three substituents, wherein each thiazolyl is optionally substituted with one or two substituents; wherein the substituents on both phenyl and thiazolyl are each independently selected from halo; cyano; nitro; C$_{1-6}$alkyl; —OR$^{12}$; —C(=O)OR$^{12}$; —C(=O)R$^{13}$; —C(=O)NR$^{9a}$R$^{9b}$; —NR$^{9a}$R$^{9b}$; —NR$^{9a}$C(=O)R$^{13}$; —NR$^{9a}$C(=O)—CH$_2$—NR$^{9a}$R$^{9b}$; —SR$^{10}$; —SO$_2$R$^{11}$; —SO$_2$NR$^{9a}$R$^{9b}$; phenyl optionally substituted with one, two or three substituents each independently selected from halo, trifluoromethyl, cyano, C$_{1-6}$alkyl, C$_{1-6}$alkoxy, and —C(=O)NR$^{9a}$R$^{9b}$; and Het optionally substituted with one or two substituents each independently selected from oxo, C$_{1-6}$alkylsulfonyl, and C$_{1-6}$alkyl;

R$^{9a}$ and R$^{9b}$ are each independently selected from hydrogen, C$_{1-6}$alkyl, or arylC$_{1-6}$alkyl; or R$^{9a}$ and R$^{9b}$, together with the nitrogen to which they are attached, form a saturated, partially unsaturated, or completely unsaturated 5-8 membered monocycle, wherein said monocycle optionally contains one additional heteroatom selected from the group consisting of oxygen, sulfur and nitrogen, and wherein the remaining monocycle members are carbon atoms;

wherein said monocycle is optionally substituted on any carbon atom with one or two substituents each independently selected from halo, C$_{1-6}$alkyl, hydroxy, or oxo, wherein aryl is phenyl or naphthyl;

R$^{10}$ is C$_{1-6}$alkyl or C$_{3-7}$cycloalkyl;

R$^{11}$ is C$_{1-6}$alkyl or C$_{3-7}$cycloalkyl;

R$^{12}$ is hydrogen, C$_{1-6}$alkyl, or benzyl;

R$^{13}$ is C$_{1-6}$alkyl;

Het is pyrrolidinyl, piperidinyl, morpholinyl, or piperazinyl.

2. A compound as claimed in claim 1 wherein R$^1$ is

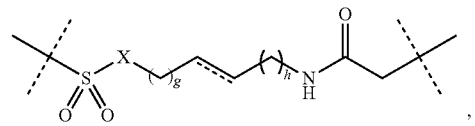

wherein the carbon atom carrying the R$^{5a}$ and R$^{5b}$ substituents (the left side of the depicted R$^1$ chains) is attached to the remainder of the molecule via the nitrogen atom of the amide group, and the carbon atom of the acetamide moiety (the right side of the depicted R$^1$ chains) is attached to the remainder of the molecule via the nitrogen of the indole ring of the compound of formula (I);

each parallel dashed line (represented by ===== ) represents an optional double bond; and R$^4$ is a group selected from:

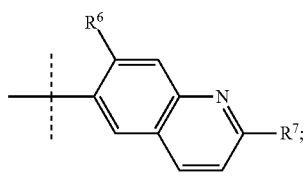

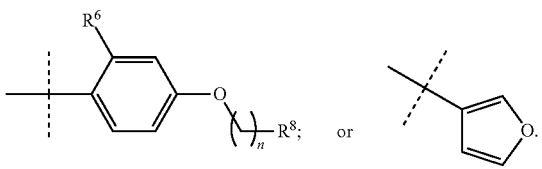

3. A compound according to claim 1, having the structural formula

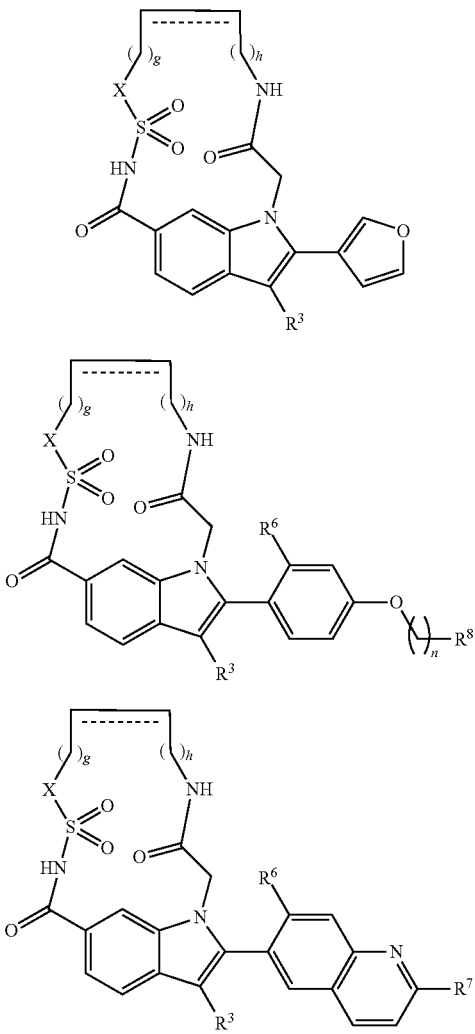

wherein the parallel dashed line, g, h, $R^3$, $R^6$, $R^7$, X, n, and $R^8$, have the same meaning as that defined in claim 1.

4. A compound according to claim 1 wherein $R^4$ is

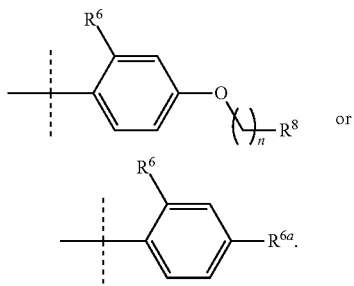

5. A compound according to claim 1, wherein $R^4$ is

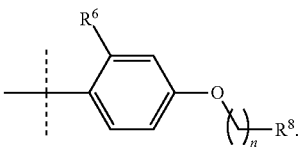

6. A compound according to claim 1, wherein $R^1$ is

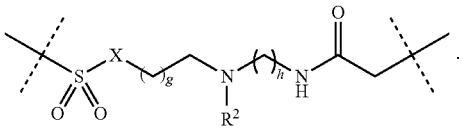

7. A compound according to claim 1, wherein each of g and h is, independently, 0, 1, 2, or 3, with the proviso that the macrocycle formed by the bivalent chain $R^1$, the —C(=O)—NH— moiety to which $R^1$ is attached and the nitrogen and carbon atoms N1, C6, C7, and C7' of the indole ring, has from 14 to 16 member atoms.

8. A compound according to claim 1, wherein $R^2$ is hydrogen or $C_{1-4}$alkyl.

9. A pharmaceutical composition comprising an anti-virally effective amount of a compound as claimed in claim 1 and a pharmaceutically acceptable carrier.

* * * * *